US009481670B2

(12) United States Patent
Dugar et al.

(10) Patent No.: US 9,481,670 B2
(45) Date of Patent: Nov. 1, 2016

(54) TRIAZINE COMPOUNDS

(75) Inventors: Sundeep Dugar, San Jose, CA (US); Dinesh Mahajan, Manesar (IN); Chandraban Rhushikesh Deokar, Manesar (IN); Frank Peter Hollinger, Wayne, PA (US); Kamal Kishore Kapoor, Jammu (IN)

(73) Assignee: Sphaera Pharma PTE. Ltd., Singapore (SG)

(*) Notice: Subject to any disclaimer, the term of this patent is extended or adjusted under 35 U.S.C. 154(b) by 0 days.

(21) Appl. No.: 13/981,579

(22) PCT Filed: Jan. 25, 2012

(86) PCT No.: PCT/IN2012/000055
§ 371 (c)(1),
(2), (4) Date: Jul. 24, 2013

(87) PCT Pub. No.: WO2012/101654
PCT Pub. Date: Aug. 2, 2012

(65) Prior Publication Data
US 2013/0303516 A1 Nov. 14, 2013

(30) Foreign Application Priority Data

Jan. 25, 2011 (IN) .............................. 179/DEL/2011

(51) Int. Cl.
*C07D 401/14* (2006.01)
*C07D 403/14* (2006.01)
*C07D 413/04* (2006.01)
*C07D 413/14* (2006.01)
*C07D 417/14* (2006.01)
*A61K 31/53* (2006.01)
*A61P 35/00* (2006.01)
*C07D 471/04* (2006.01)
*C07D 491/107* (2006.01)
*C07D 498/08* (2006.01)

(52) U.S. Cl.
CPC ........... *C07D 413/14* (2013.01); *C07D 401/14* (2013.01); *C07D 403/14* (2013.01); *C07D 413/04* (2013.01); *C07D 417/14* (2013.01); *C07D 471/04* (2013.01); *C07D 491/107* (2013.01); *C07D 498/08* (2013.01)

(58) Field of Classification Search
CPC C07D 401/04; C07D 401/14; C07D 403/04; C07D 403/14; C07D 413/04; C07D 413/14; C07D 417/04; C07D 417/14; C07D 471/04; C07D 471/14; A61K 31/53; A61K 31/496; A61K 31/4523; A61K 31/4427; A61K 31/5377
USPC .................. 544/180, 194, 216; 514/241, 245
See application file for complete search history.

(56) References Cited

U.S. PATENT DOCUMENTS

| | | | | |
|---|---|---|---|---|
| 5,488,108 A | * | 1/1996 | Leppard et al. | 544/216 |
| 6,242,598 B1 | * | 6/2001 | Stevenson et al. | 544/216 |
| 6,486,316 B1 | * | 11/2002 | Gupta et al. | 544/216 |
| 6,638,926 B2 | * | 10/2003 | Davies et al. | 514/217.05 |
| 2009/0291079 A1 | * | 11/2009 | Venkatesan et al. | 424/133.1 |
| 2010/0249099 A1 | * | 9/2010 | Rewcastle et al. | 514/210.21 |
| 2012/0165309 A1 | * | 6/2012 | Takahashi et al. | 514/210.21 |

FOREIGN PATENT DOCUMENTS

WO WO 2009125870 A1 * 10/2009
WO WO 2010092962 A1 * 8/2010

OTHER PUBLICATIONS

Fyffe et al., Cancer Manag Res. Aug. 23, 2013;5:271-80.*
Baselga J.,The Oncologist 2011, 16:12-19.*
Hulikal, V. Deuterium Labeled Compounds in Drug Discovery Process-Abstract, 2010. Also see www.hwb.gov.in/htmldocs/nahwd2010/L15.pdf.*
Fruman et al., Nat Rev Drug Discov. Feb. 2014 ; 13(2): 140-156.*
Klempner et al., Cancer Discov. Dec. 2013 ; 3(12):1-23.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Pyne et al. Cancer Res 2011 ;71:6576-6582.*
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Misawa et al., Heterocycles (2010), 81(6), 1419-1426; CA 153: 145456, 2010. CAPLUS Abstract provided.*
Hu et al., Journal of Combinatorial Chemistry (2009), 11(2), 267-273; CA 150: 214347, 2009. CAPLUS Abstract provided.*
Hulikal, V. Deuterium Labeled Compounds in Drug Discovery Process-Abstract, www.hwb.gov.in/htmldocs/nahwd2010/L15.pdf. ,National Conference on Non-Nuclear Applications of Heavy water and Deutrium, Jan. 28-29, 2010.*
Venkatasen et al. US 20090291079; CA 152;1475017,2009. CAPLUS Abstarct provided.*

* cited by examiner

*Primary Examiner* — Venkataraman Balasubramanian
(74) *Attorney, Agent, or Firm* — Schiff Hardin LLP

(57) ABSTRACT

The present invention relates to novel triazine compounds of formula (1), methods of their preparation, pharmaceutical compositions containing these compounds and the use of these compounds to treat proliferative disorders such as tumors and cancers and also other conditions and disorders related to or associated with dysregulation of PI3 Kinases, PI3 Kinase pathway, mTOR and/or the mTOR pathway.

3 Claims, No Drawings

TRIAZINE COMPOUNDS

FIELD

The present invention relates to novel triazine compounds that may be useful as kinase inhibitors. More particularly, the present invention relates to substituted triazine derivatives, methods for their preparation, pharmaceutical compositions containing these compounds and uses of these compounds in the treatment of certain PI3 kinase and/or mTOR related disorders.

BACKGROUND

Kinases, also known as phosphotransferases, are enzymes that transfer phosphate groups from high energy donor molecules (ATP) to specific target molecules (substrates). Kinases are involved in a variety of cellular processes including cell signaling. Certain cellular signaling processes have been implicated as important in a number of medical conditions and the effective inhibition of certain cell signaling processes, therefore they may provide the potential to stop these conditions from developing or treating medical conditions where such processes are up regulated or uncontrolled. Accordingly, kinases represent an attractive target and kinase inhibitors potentially affect signaling processes to be controlled leading to the control or treatment of certain medical conditions.

The phosphoinositide 3-kinase (PI3) family of kinases are a family of kinases which are involved in a wide range of cellular events such as cell migration, cell proliferation, oncogenic transformation, cell survival, signal transduction and intracellular trafficking of proteins, and have recently been the focus of much research aimed at developing therapies for a range of proliferative diseases, for example cancer, immune and inflammatory diseases, diseases supported by excessive neovascularization and transplant rejection.

The phosphoinositide 3-kinase (PI3K) family is a group of enzymes that generate lipids such as phosphatidylinositol. These lipids are involved in a wide range of physiological processes. In mammalian cells, the large PI3K family has been categorized into three classes, I, II, and III (Stephens et al., Curro Opin. Pharmacol. 2005, 5, 357). Class I PI3K convert phosphatidylinositol-4,5 bisphosphate (PIP2) to phosphatidylinositol-3,4,5 trisphosphate (PIP3). Class I PI3Ks are further comprised of Class IA and 1B PI3 kinases (PI3Ks).

Class I PI3Ks are key players of multiple intracellular signaling networks that integrate a variety of signals initiated by many growth factors. The Class IA enzymes are activated by tyrosine kinases (e.g. growth factor receptors), antigen receptors, and cytokine receptors, whilst the Class IB enzyme is activated by 'G Protein Coupled Receptors' (GPCRs). In response to activation, the PI3Ks generate lipid second messengers, which bind to, and activate, specific proteins in distinct signal transduction pathways. The signal transduction pathways remain active until phosphatase enzymes, in particular the oncogene PTEN, dephosphorylate the PI3K lipid second messengers. The PI3K signaling pathway is crucial to many aspects of cell growth and survival via its regulation of widely divergent physiological processes that include cell cycle progression, differentiation, transcription, translation and apoptosis. Constitutive activation of the PI3K pathway has been implicated in both the pathogenesis and progression of a large variety of cancers and there is now a body of evidence that demonstrates conclusively that PI3K signaling is frequently dysregulated in cancer.

A signaling pathway mediated by the PI3 kinases is the phosphatidylinositol 3-kinase (PI3K)/Akt pathway, which is critically involved in the mediation of cell survival and is a major signaling component downstream of growth factor receptor tyrosine kinases (RTKs). The PI3K-Akt signaling pathway regulates many cellular processes including cell proliferation, survival, growth, and motility-processes that are critical for tumorogenesis. The role of the PI3K/Akt pathway in oncogenesis has also been extensively investigated and mutations or altered expression of most of the pathway's components have been widely implicated in many cancers. Through a variety of mechanisms, many human cancers possess activated PI3K signaling.

These data provide strong validation for the development of novel anticancer strategies using inhibitors of PI3Ks. Interest in PI3K inhibitors has been intense with a number of compounds now in development having demonstrated anti-tumor activity in animal models. Compounds are also undergoing evaluation in clinical trials.

Since, PI3-kinase isoforms regulate different aspects of immune and inflammatory responses, there is great interest in the role of PI3-kinase signaling in a range of immune and inflammatory diseases as well as in transplant rejection.

PI3K isoforms also play a key role in the downstream signaling pathways of angiogenic growth factors such as VEGF, FGF and PDGF as well angiogenic cytokines. mTOR, another downstream serine/threonine kinase, is involved in the regulation of vascular endothelial growth factor (VEGF), hence PI3K and mTOR inhibitors also have potential to treat diseases supported by pathological neovascularization such as during tumorogenesis, inflammatory conditions such as rheumatoid arthritis and ocular neovascular diseases, e.g. age-related macular degeneration (AMD), retinal vascular diseases (vein occlusion and diabetic retinopathy) and other possible proliferative vascular disorders.

The p110 alpha isoform is selectively amplified and activated in a number of cancer types (Stephens et al., Curr. Opin. Pharmacol. 2005, 5, 357; Stauffer et al., Curr. Med. Chem.-Anti-Cancer Agents 2005, 5, 449). In addition, there is a high frequency of nonrandom mutations in specific sites, primarily in the C2 domain and or the activation loop, of the kinase in several human cancer cell lines, including colon, brain, breast, and stomach (Samuels et al., Science 2004, 304, 554). This results in a constitutively active enzyme (Ikenoue et al., Cancer Res. 2005, 65, 4562; Kang et al., Proc. Natl. Acad. Sci. USA 2005, 102, 802), making p110☐ one of the most highly mutated oncogenes found in human tumors. Structural studies have shown that many of the mutations occur at residues lying at the interfaces between p110☐ and p85☐ or between the kinase domain of p110☐ and other domains within the catalytic subunit (Miled et al., Science 2007, 317, 239; Huang et al., Science 2007, 318, 1744).

While PI3K isoenzymes play important roles in many cellular processes, published experimental studies in mice with human tumor xenografts show that the pan PI3K inhibitor LY294002 is well-tolerated, reduces signaling through the PI3K pathway, causes reduction of tumor volume, and is more active in cell lines over-expressing mutant forms than parental control cells (Semba et al., Clin. Cancer Res. 2002, 8, 1957; Hu et al., Cancer Res. 2002, 62, 1087).

Thus, PI3K, is an interesting target for drug intervention. Several classes of compounds have been identified as reversible inhibitors; for example, LY 294002 (Walker et al., *Mol Cell.* 2000, 6, 909), PI103 (Knight et al., *Cell* 2006, 125, 733; Hayakawa et al., *Bioorg. Med. Chem. Lett.* 2007, 17, 2438; Raynaud et al., *Cancer Res.* 2007, 67, 5840), ZSTK474 (Yaguchi et al., *J. Natl. Cancer Inst.* 2006, 98, 545; Kong et al., *Cancer Sci.* 2007, 98, 1639), TGX221 (Jackson et al., *Nat. Med.* 2005, 11, 507), oxazines (Lanni et al., *Bioorg. Med. Chem. Lett.* 2007, 17, 756), IC87114 (Sadhu et al. WO 2001/81346; Billottet et al., *Oncogene* 2006, 25, 6648), AS605240 (Camps et al., *Nat. Med.* 2005, 11, 936), the imidazo[1,2-a]pyridines (Hayakawa et al., *Bioorg. Med. Chem.* 2007, 15, 403; Hayakawa et al., *Bioorg. Med. Chem.* 2007, 15, 5837), and the imidazo[4,5-c]quinoline NVP-BEZ235 (Garcia-Echeverria, et al., WO 2006/122806).

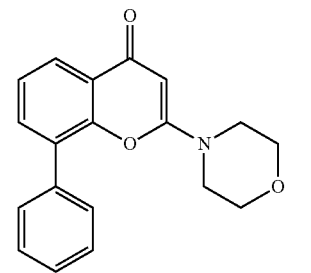

LY294002

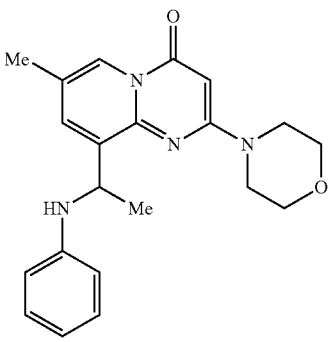

TGX221

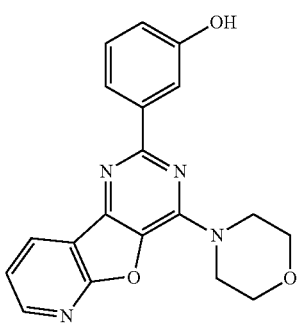

PI103

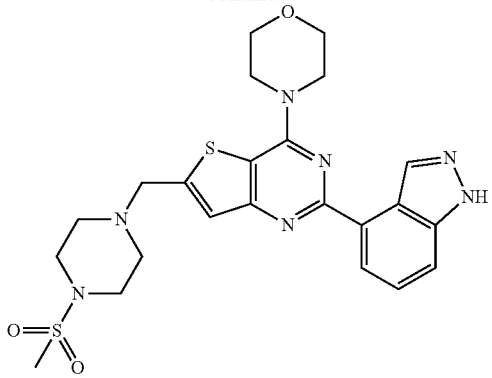

GDC0941

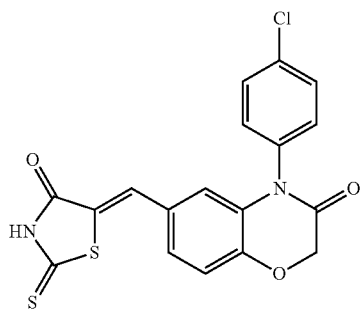

Oxazines

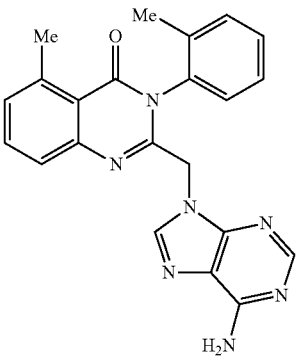

IC87114

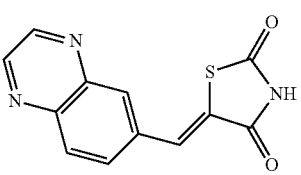

AS605240

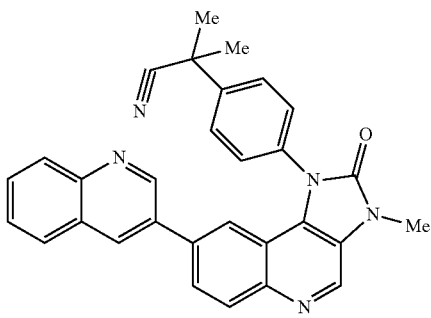

NVP-BEZ235

-continued

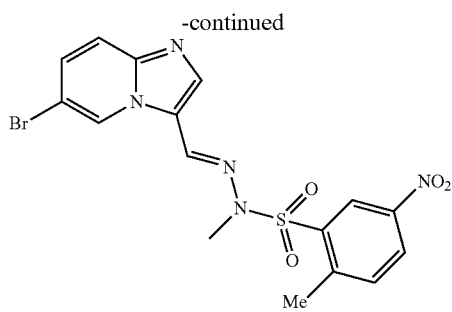
Imidazo[1,2-a]pyridine

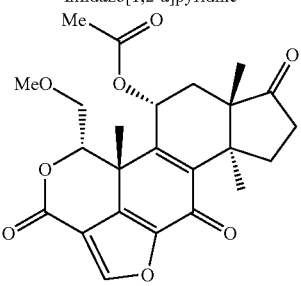
Wortmannin

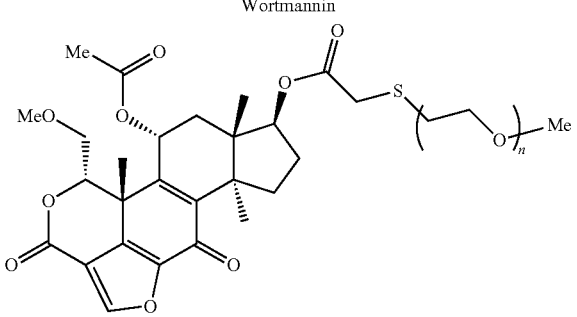
PWT-458 n = 103-110

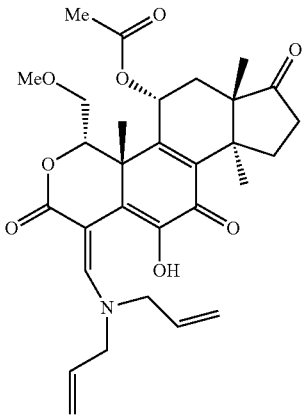
PX-866

All of the above mentioned compounds function as reversible inhibitors of the appropriate PI3K isoforms. Although irreversible activity is displayed by the fungal metabolite wortmannin and its analogues, such as PWT-458 (Zhu et al, *J. Med. Chem.*, 2006, 49, 1373) and PX-866 (Wipf et al., *Org. Biomol. Chem.* 2004, 2, 1911; Zask et al., *J. Med. Chem.* 2008, 51, 1319), these compounds are not selective for individual PI3K isoforms, undergoing reaction with a conserved lysine amino group (e.g., Lys-802 in P110☐, Lys-805 in P110☐, Lys-833 in P110γ, and Lys-799 in P110☐).

Despite the advances in developing PI3K inhibitors, there is an unmet need for PI3K inhibitors that are more potent and more selective, exhibit better pharmacokinetic properties, and/or produce fewer side effects than the existing PI3K inhibitors.

DETAILED DESCRIPTION OF THE INVENTION

The present invention relates to novel triazine compounds represented by Formula (I) their isomer, salt and solvate thereof;

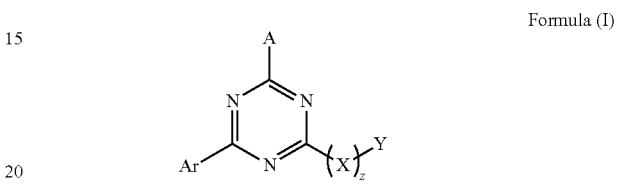

Formula (I)

Wherein:
A is selected from group consisting of:
(a) 3 to 8 membered saturated, mono-, fused-, spiro- or bridged carbocyclic or heterocyclic ring containing 1 to 3 O, N, S or $SO_2$ and optionally substituted with lower alkyl, =O, =$NOR^1$, F, Cl, Br, I, —$OR^1$, —COOH, —$COOR^1$, —$CON(R^1)_2$, —$SO_2N(R^1)_2$, —CN, —$CF_3$, —$CHF_2$, —$CFH_2$, —$OCF_3$, —$OCOR^1$, —$NR^1COR^1$, —$NR^1SO_2R^1$, —$OCON(R^1)_2$, —$NR^1COOR^1$, —$NR^1SO_2N(R^1)_2$, —$NR^1CO\ N(R^1)_2$, —$SO_2R^1$, —$SOR^1$, —$SR^1$; which is directly connected to the triazine ring or through C, O or N as a linker atom.

(b) monocyclic or bicyclic or fused $C_3$-$C_8$ cycloalkenyl, heterocycloalkenyl, aryl, heteroaryl; optionally substituted $C_3$-$C_8$ cycloalkenyloxy, heterocycloalkenyloxy; which is directly connected to the triazine ring or through C, O or N as a linker atom; these groups can be optionally substituted with 1 to 4 substituents which can be independently selected from F, Cl, Br, I, —$OR^1$, —COOH, —$COOR^1$, —$CON(R^1)_2$, —$SO_2N(R^1)_2$, —CN, —$CF_3$, —$CHF_2$, —$CFH_2$, —$OCF_3$, —$OCOR^1$, —$N(R^1)_2$, —$NR^1COR^1$, —$NR^1SO_2R^1$, —$OCON(R^1)_2$, —$NR^1COOR^1$, —$NR^1SO_2N(R^1)_2$, —$NR^1CO\ N(R^1)_2$, —$SO_2R^1$, —$SOR^1$, —$SR^1$.

(c) A can be selected from:

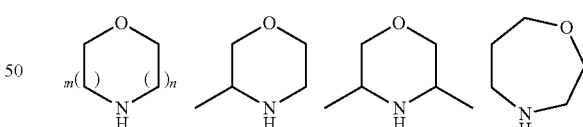

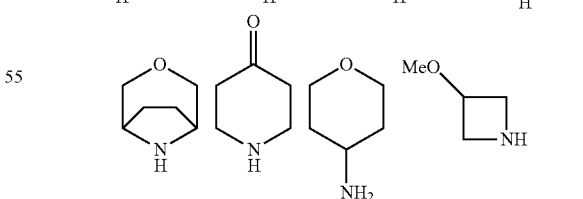

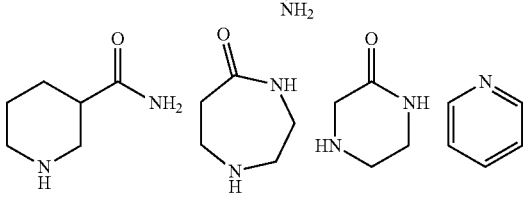

-continued

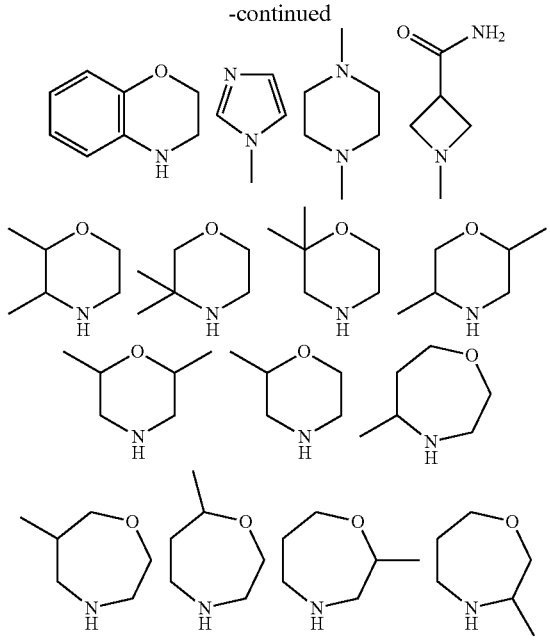

additionally, these can be optionally substituted with 2-5 substituents independently selected from lower alkyl ($C_1$-$C_4$), lower alkoxy, deuterium or F.

Ar is selected from group consisting of:

(a) a monocylic or bicyclic aryl or heteroaryl with 1-6 heteroatoms selected from O, N or S, with 1-4 substituents selected from with lower alkyl ($C_1$-$C_4$), D, F, Cl, Br, I, —$OR^1$, —COOH, —$COOR^1$, —$CON(R^1)_2$, —$SO_2N(R^1)_2$, —CN, —$CF_3$, —$CHF_2$, —$CFH_2$, —$OCF_3$, —$OCOR^1$, —$NR^1COR^1$, —$NR^1SO_2R^1$, —$OCON(R^1)_2$, —$NR^1COOR^1$, —$NR^1SO_2N(R^1)_2$, —$NR^1CO\ N(R^1)_2$, —$SO_2R^1$, —$SOR^1$, —$SR^1$;

(b) Ar can also be selected from:

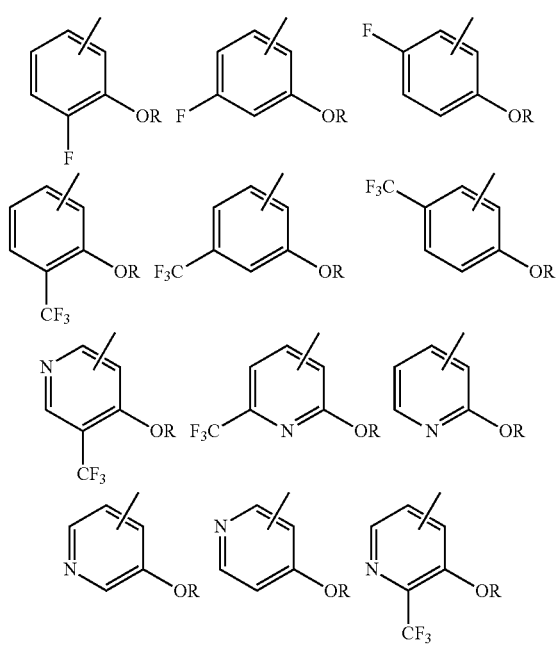

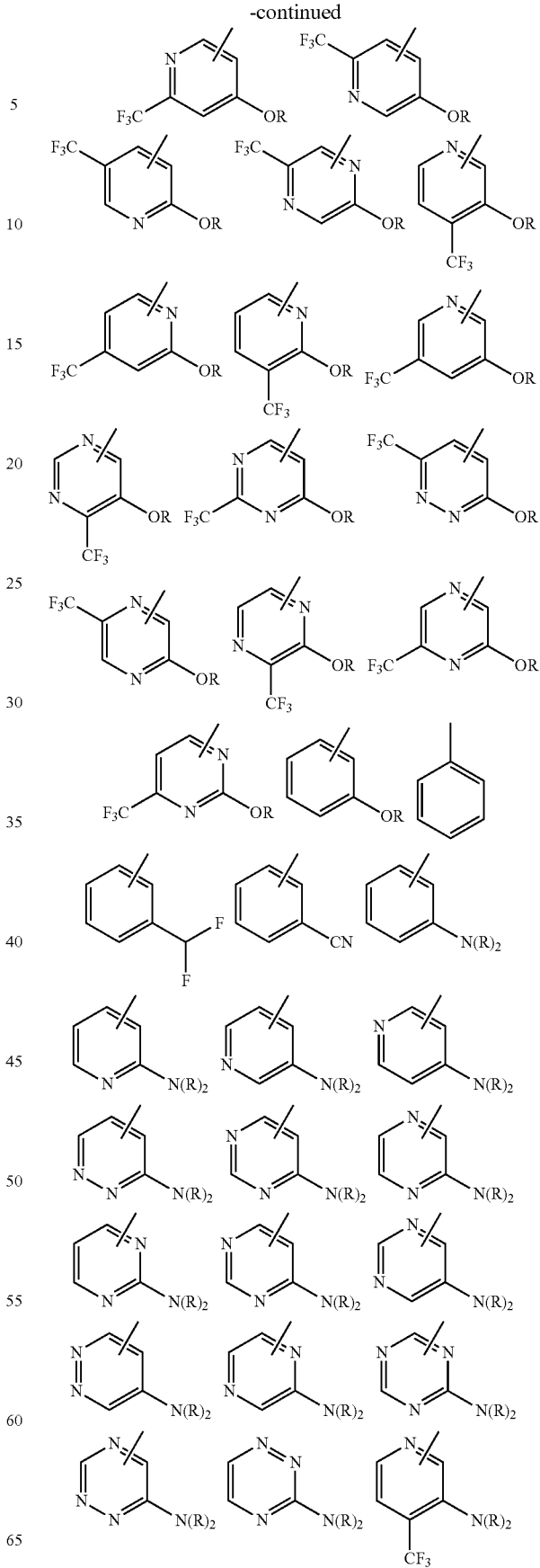

-continued
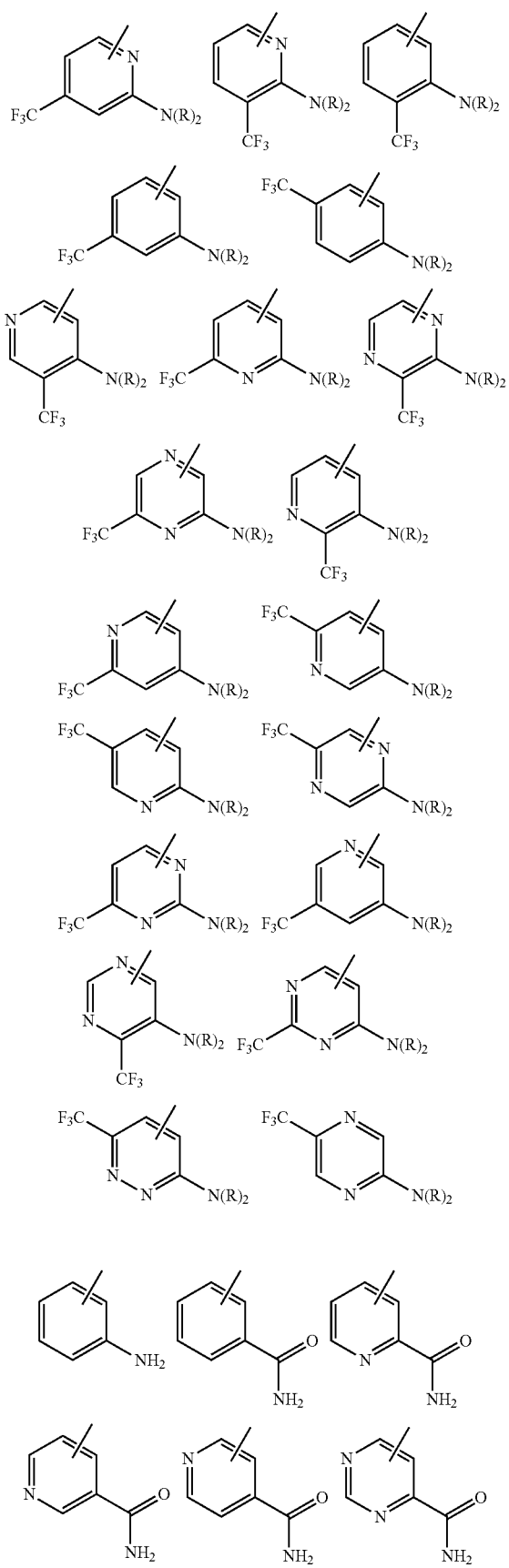
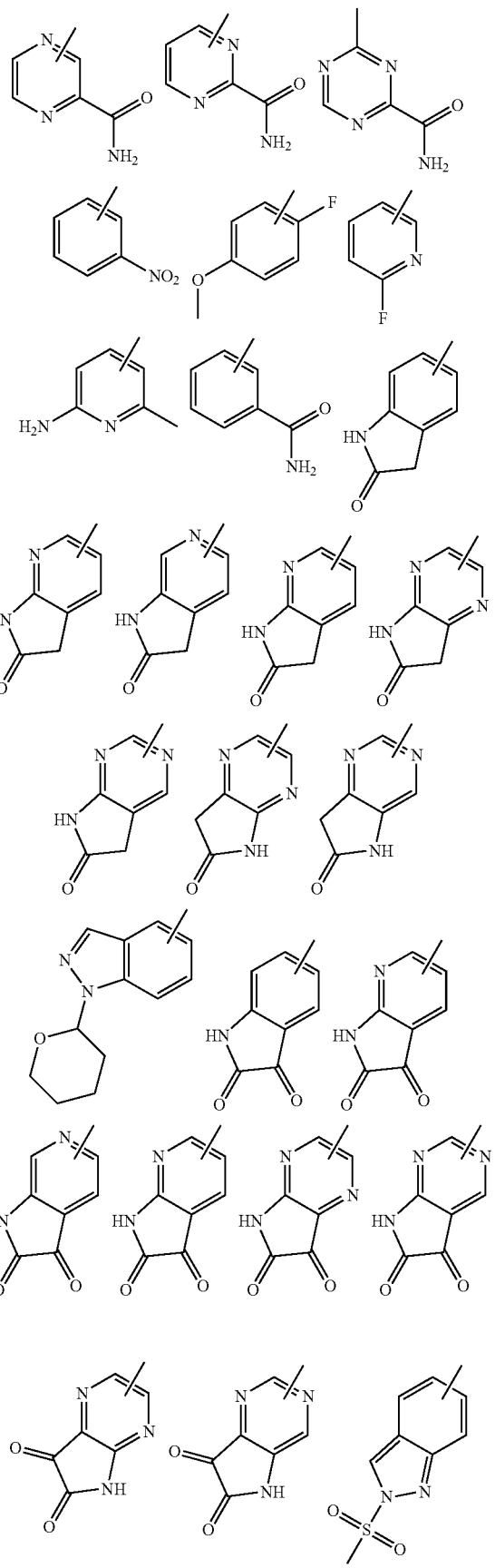

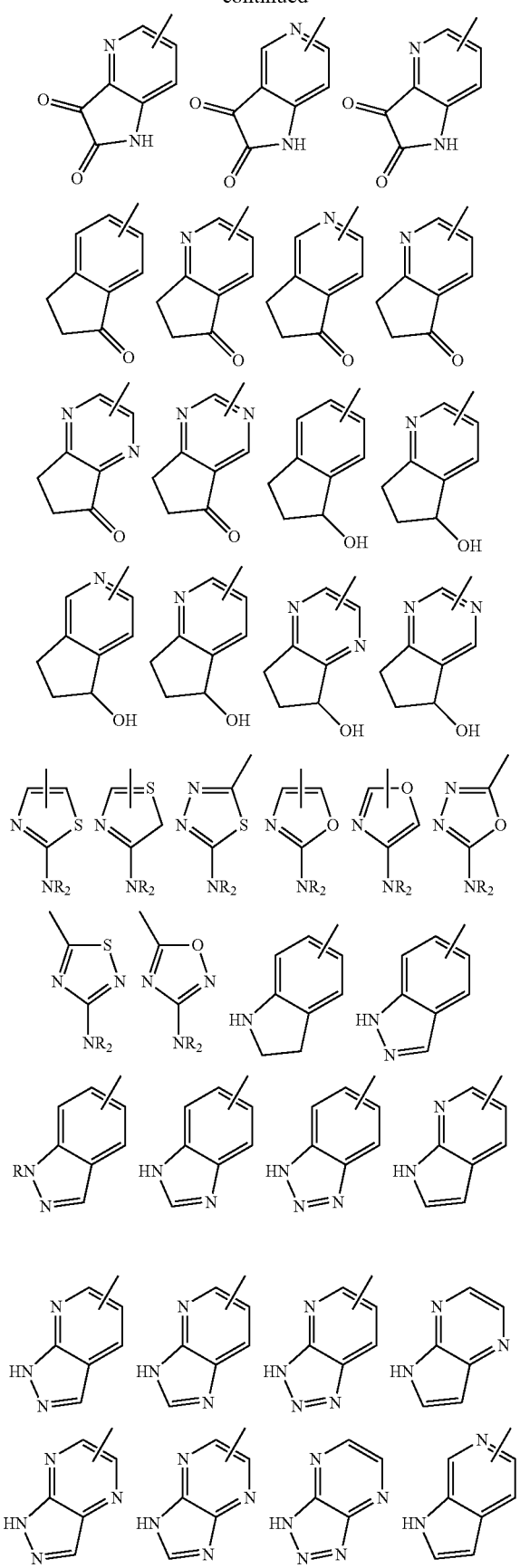
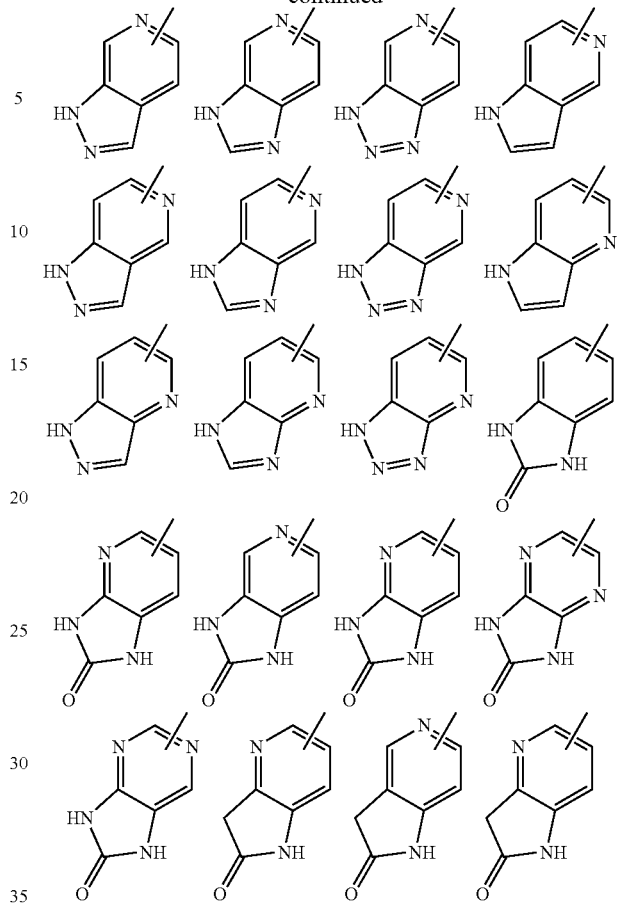

additionally, these can be optionally substituted with 2-5 substituents independently selected from lower alkyl ($C_1$-$C_4$), alkoxy, deuterium or F.

X is independently selected from group consisting of: O, S, SO, $SO_2$, NR or $C(R)_2$ wherein each R is independently selected;

Y is selected from group consisting of:

(a) an aromatic or a heteroaromatic ring optionally substituted with 1 to 4 substituents which can be independently selected from, F, Cl, Br, I, —$OR^1$, —COOH, —$COOR^1$, —$CON(R^1)_2$, —$SO_2N(R^1)_2$, —CN, —$CF_3$, —$CFH_2$, —$OCOR^1$, —$NR^1COR^1$, —$NR^1SO_2R^1$, —$OCON(R^1)_2$, —$NR^1COOR^1$, —$NR^1SO_2N(R^1)_2$, —$NR^1CON(R^1)_2$, —$SO_2R^1$, —$SOR^1$, —$SR^1$;

(b) 3 to 7 membered mono-, fused- or bridged saturated carbocyclic ring or heterocyclic ring containing 1 to 3 O, N, S or $SO_2$ and optionally substituted with lower alkyl ($C_1$-$C_4$), =O, =$NOR^1$, F, Cl, Br, I, —$OR^1$, —COOH, —$COOR^1$, —$CON(R^1)_2$, —$SO_2N(R^1)_2$, —CN, —$CF_3$, —$OCOR^1$, —$NR^1COR^1$, —$NR^1SO_2R^1$, —$OCON(R^1)_2$, —$NR^1COOR^1$, —$NR^1SO_2N(R^1)_2$, —$NR^1CO\ N(R^1)_2$, —$SO_2R^1$, —$SOR^1$, —$SR^1$; 1-4 deuterium;

and their isomers $R^1$ selected from the group consisting of: H, D, $C_1$-$C_6$ straight, branched, cycloalkyl optionally substituted $C_1$-$C_6$ alkyl, halo-$C_1$-$C_6$ alkyl, hydroxyl-$C_1$-$C_6$ alkyl, $C_1$-$C_6$ alkyloxy$C_1$-$C_6$ alkyl, cyano $C_1$-$C_6$ alkyl, amino $C_1$-$C_6$ alkyl, $C_1$-$C_6$ alkylamino $C_1$-$C_6$ alkyl, and di($C_1$-$C_6$ alkyl)amino$C_1$-$C_6$alkyl, optionally substituted $C_2$-$C_8$ alkenyl, optionally substituted $C_2$-$C_9$ alkynyl, optionally substituted $C_1$-$C_8$ heteroalkyl, optionally substituted $C_3$-$C_8$ cycloalkyl, optionally substituted $C_3$-$C_8$ cycloalkenyl, optionally substituted $C_3$-$C_8$ heterocycloalkyl, optionally substituted $C_3$-$C_8$ heterocycloalkenyl, optionally substituted aryl, and optionally substituted heteroaryl;

R is selected from the group consisting of: H, D, F, $OR^1$, $NO_2$, CN, $N(R^1)_2$, $COOR^1$, $CON(R^1)_2$, $N(R^1)CON(R^1)_2$, $N(R^1)COR^1$, $N(R^1)SO_2N(R^1)_2$, $SO_2N(R^1)_2$, $SO_2R^1$, $SOR^1$, $SR^1$, $N(R^1)$ $SO_2R^1$; optionally substituted straight or branched chain $C_1$-$C_6$ alkyl, alkenyl, fluoroalkyl, alkynyl, heteroalkyl; optionally substituted monocyclic, bicyclic, fused $C_3$-$C_8$ cycloalkyl, cycloalkenyl, heterocycloalkyl, heterocycloalkenyl; optionally substituted aryl, heteroaryl, arylalkyl; $(CH_2)_mCO_2R^1$; $(CH_2)_mCO_2N(R^1)_2$; optionally substituted $C_2$-$C_{12}$ alkenyloxy, alkynyloxy, heteroalkyloxy; optionally substituted $C_3$-$C_8$ cycloalkyloxy, cycloalkenyloxy, heterocycloalkyloxy, heterocycloalkenyloxy; optionally substituted $C_1$-$C_8$ alkylamino;

wherein $R^1$ can be independently selected;

Further any two R or $R^1$ when taken together with the atoms to which they are attached may form a cyclic moiety; m or n are independently an integer between 1, 2, 3, and 4. Z is 0, 1, or 2.

The present invention relates Novel triazine compounds represented by Formula (I), their isomer, salt and solvate thereof;

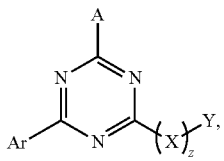

Formula (I)

Wherein:
A is selected from the group consisting of:

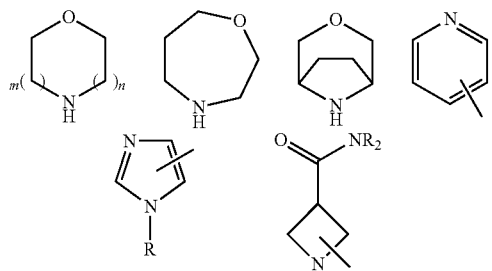

additionally, these can be optionally substituted with 2-5 substituents independently selected from lower alkyl ($C_1$-$C_4$), alkoxy, deuterium or F.

Ar is selected from group consisting of:

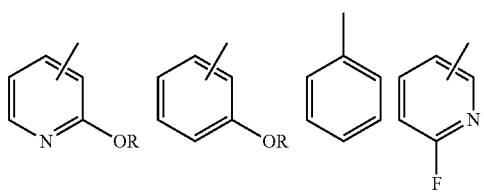

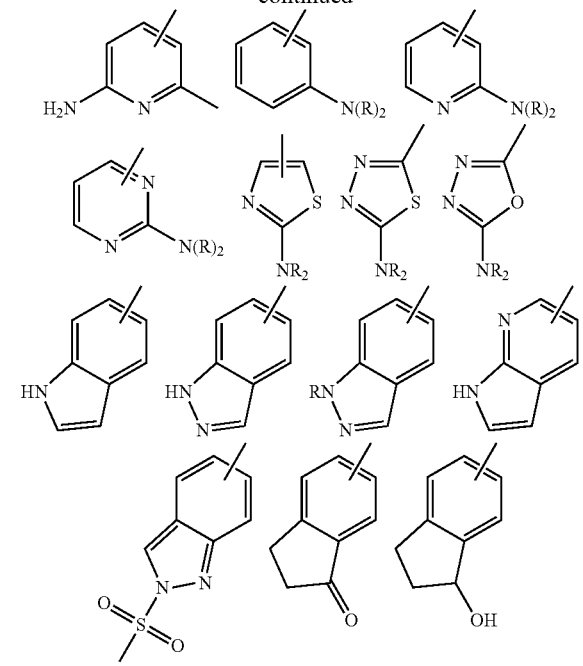

additionally, these can be optionally substituted with 2-5 substituents independently selected from lower alkyl ($C_1$-$C_4$), alkoxy, deuterium or F.

X is independently selected from group consisting of: O, S, SO, $SO_2$, NR or $C(R)_2$ wherein each R is independently selected;

Y is selected from group consisting of:

(a) an aromatic or a heteroaromatic ring optionally substituted with 1 to 4 substituents which can be independently selected from, F, Cl, Br, I, $-OR^1$, $-COOH$, $-COOR^1$, $-CON(R^1)_2$, $-SO_2N(R^1)_2$, $-CN$, $-CF_3$, $-CHF_2$, $-CFH_2$, $-OCF_3$, $-OCOR^1$, $-NR^1COR^1$, $-NR^1SO_2R^1$, $-OCON(R^1)_2$, $-NR^1COOR^1$, $-NR^1SO_2N(R^1)_2$, $-NR^1CO\ N(R^1)_2$, $-SO_2R^1$, $-SOR^1$, $-SR^1$;

(b) 3 to 7 membered mono-, fused- or bridged saturated carbocyclic ring or heterocyclic ring containing 1 to 3 O, N, S or $SO_2$ and optionally substituted with lower alkyl ($C_1$-$C_4$), =O, =$NOR^1$, F, Cl, Br, I, $-OR^1$, $-COOH$, $-COOR^1$, $-CON(R^1)_2$, $-SO_2N(R^1)_2$, $-CN$, $-CF_3$, $-CHF_2$, $-CFH_2$, $-OCF_3$, $-OCOR^1$, $-NR^1COR^1$, $-NR^1SO_2R^1$, $-OCON(R^1)_2$, $-NR^1COOR^1$, $-NR^1SO_2N(R^1)_2$, $-NR^1CO\ N(R^1)_2$, $-SO_2R^1$, $-SOR^1$, $-SR^1$; 1-4 deuterium;

and their isomers.

where R and $R^1$ are as defined above.

Further any two R or $R^1$ when taken together with the atoms to which they are attached may form a cyclic moiety; m or n are independently an integer between 1, 2, 3, and 4.

Z is 0, 1 or 2

The present invention relates to novel triazine compounds represented by Formula (I), their isomer, salt and solvate thereof;

Formula (I)
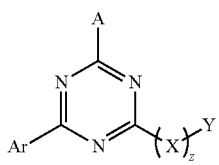
Wherein:
A is selected from the group consisting of:
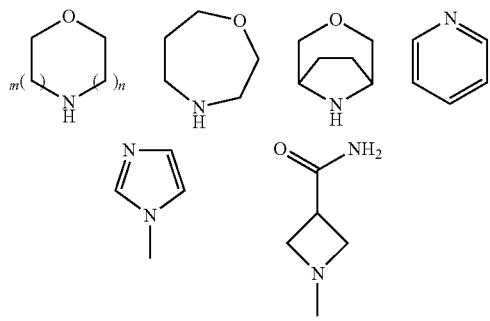
additionally, these can be optionally substituted with 2-5 substituents independently selected from lower alkyl ($C_1$-$C_4$), alkoxy, deuterium or F.
Ar is selected from group consisting of:
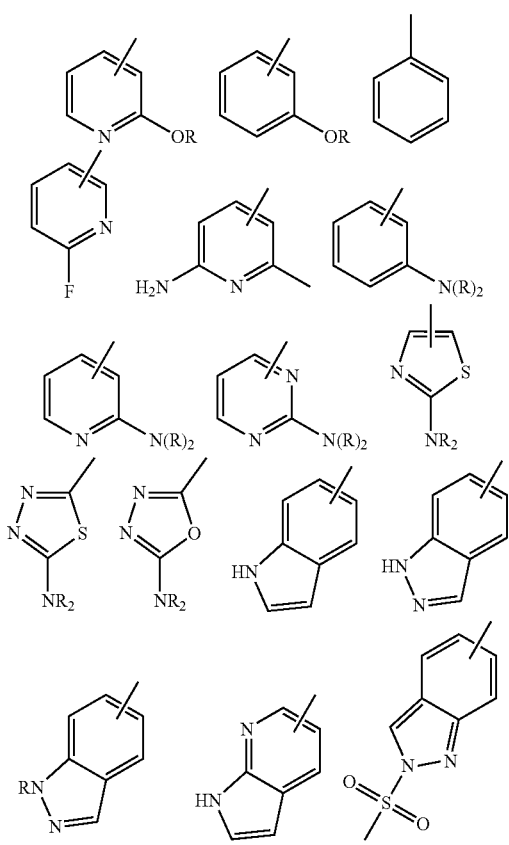
-continued
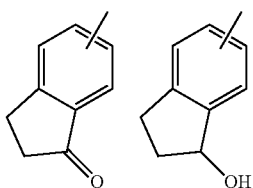
X is independently selected from group consisting of: O or NR;
Y is selected from group consisting of:
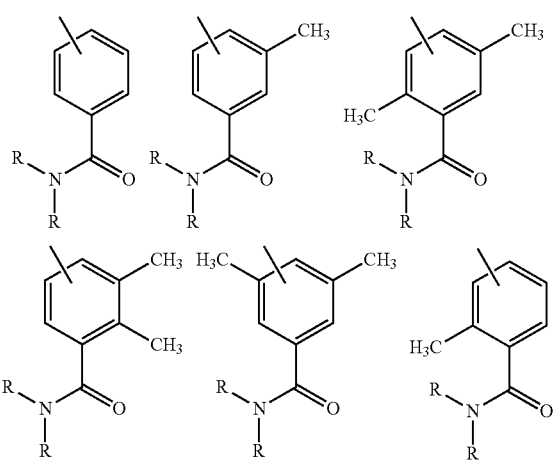
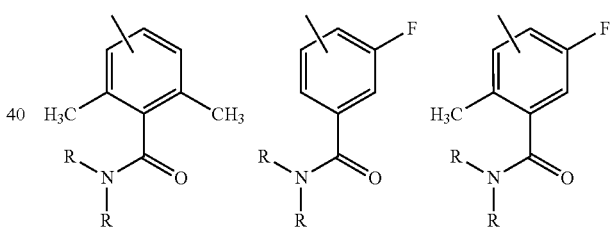
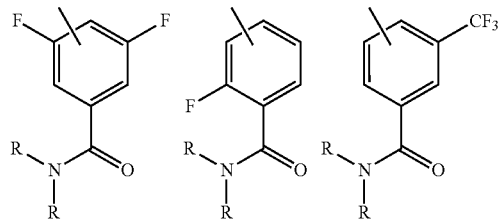
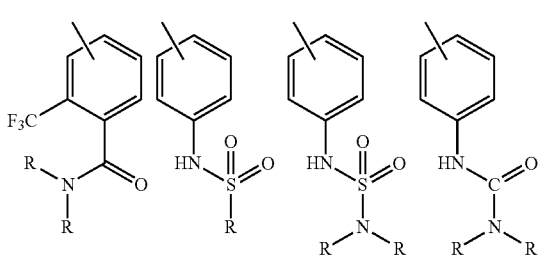

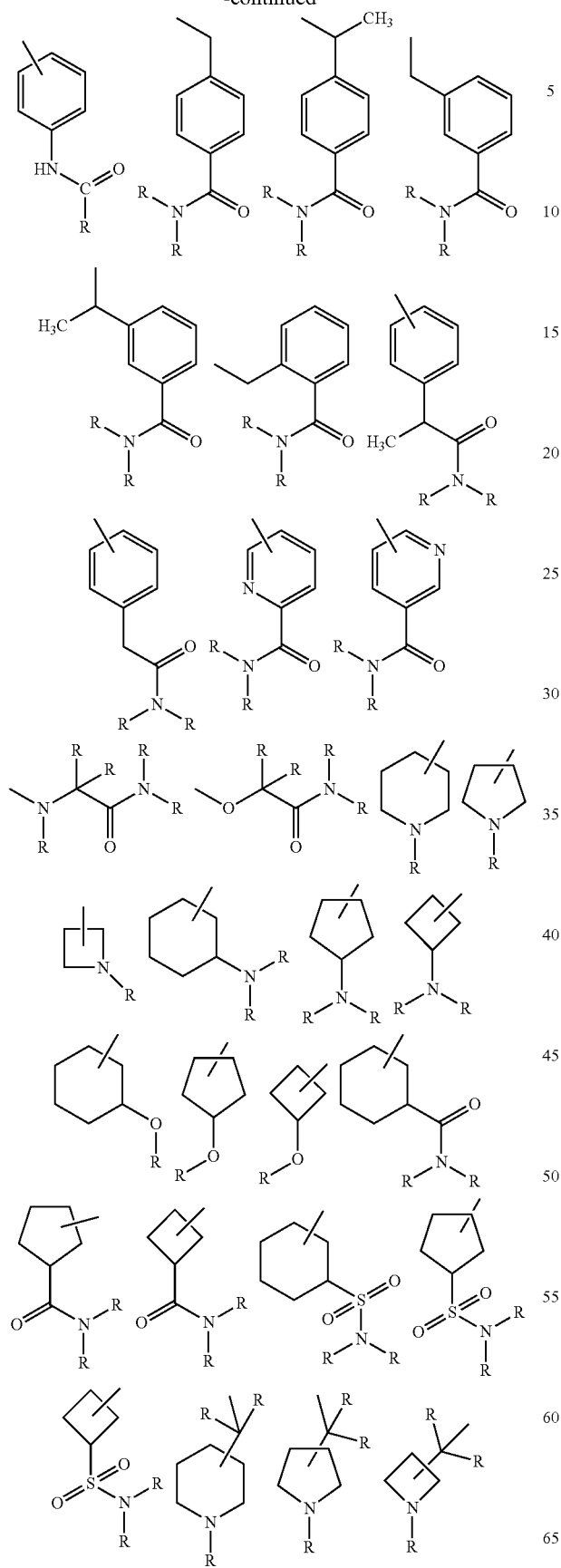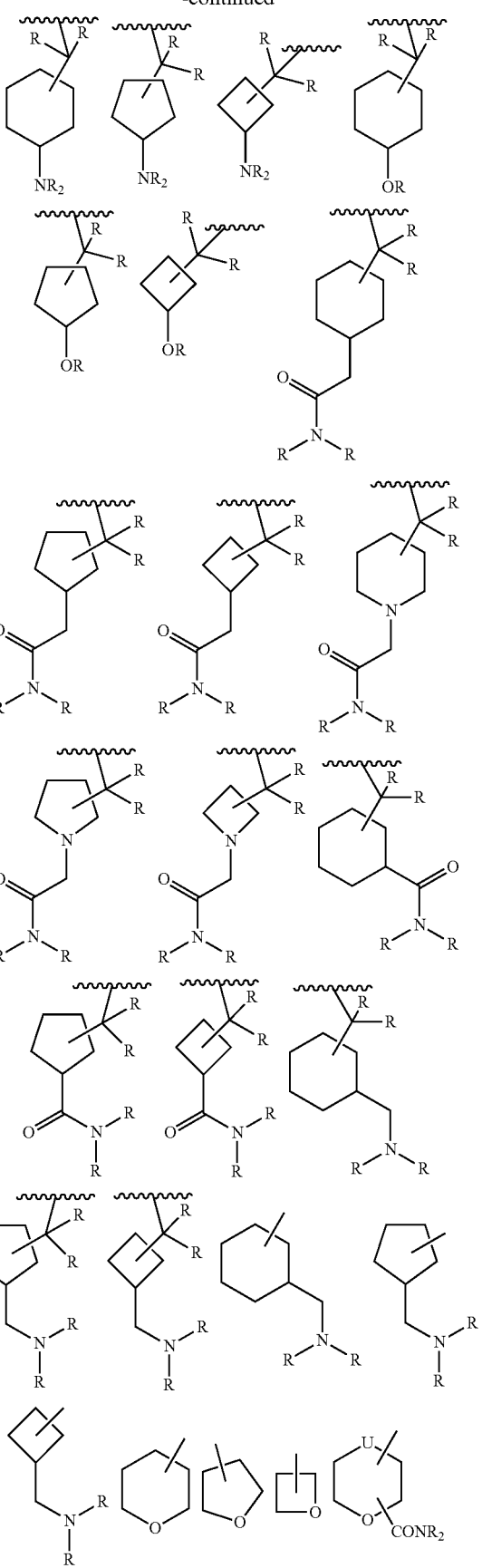

-continued

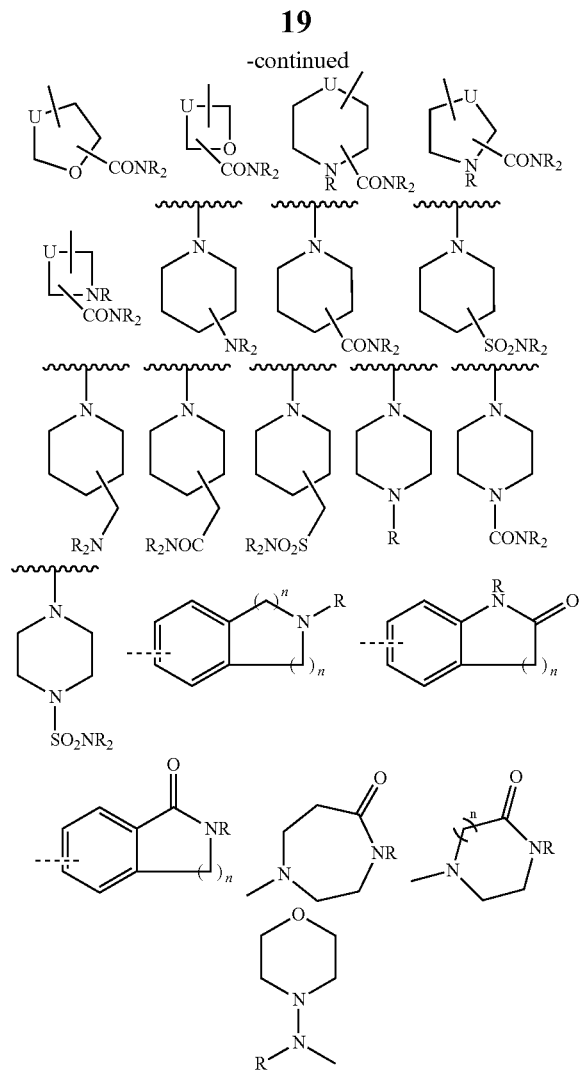

U = CH, O or NR wherein U can be optional CH, O or NR;
and their isomers;
additionally, these can be optionally substituted with 2-5 substituents independently selected from lower alkyl ($C_1$-$C_4$), alkoxy, deuterium or F;
where R and $R^1$ are as defined above.

Further any two R or $R^1$ when taken together with the atoms to which they are attached may form a cyclic moiety;
Further, each R is independently selected;
m or n are independently an integer between 1, 2, 3, and 4.
Z is 0, 1 or 2.

The present invention relates to novel triazine compounds represented by Formula (I), their isomer, salt and solvate thereof;

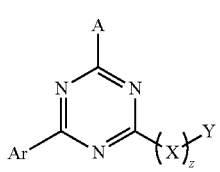

Formula (I)

wherein:
A is preferably

Ar is preferably

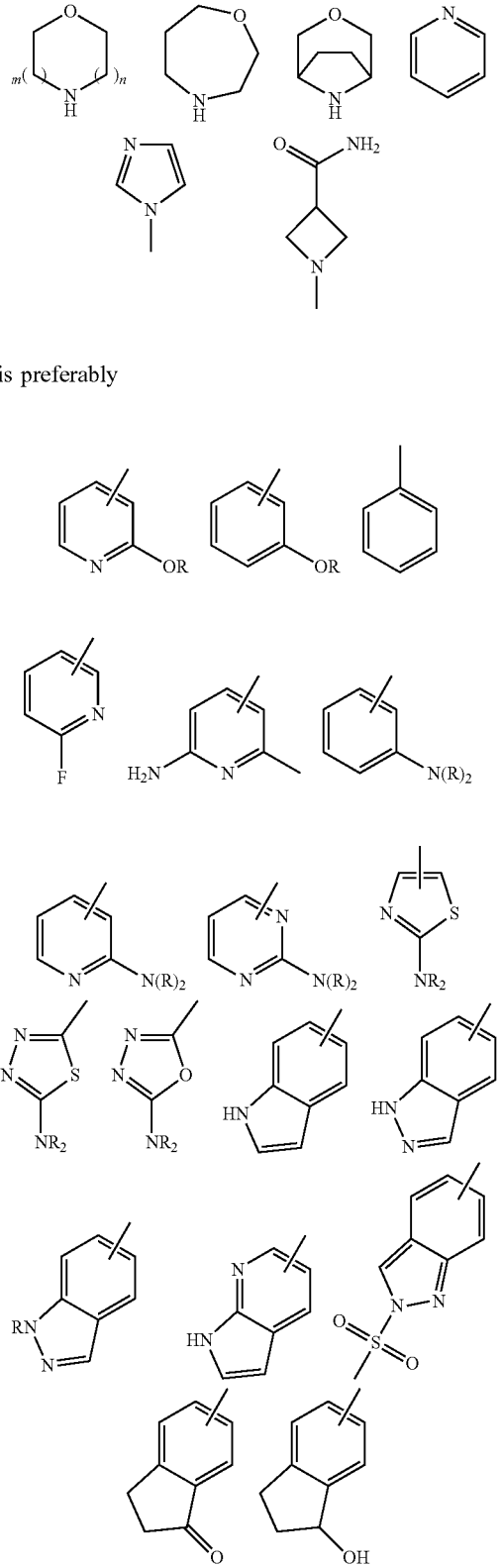

X is preferably O or NR

Y is preferably:
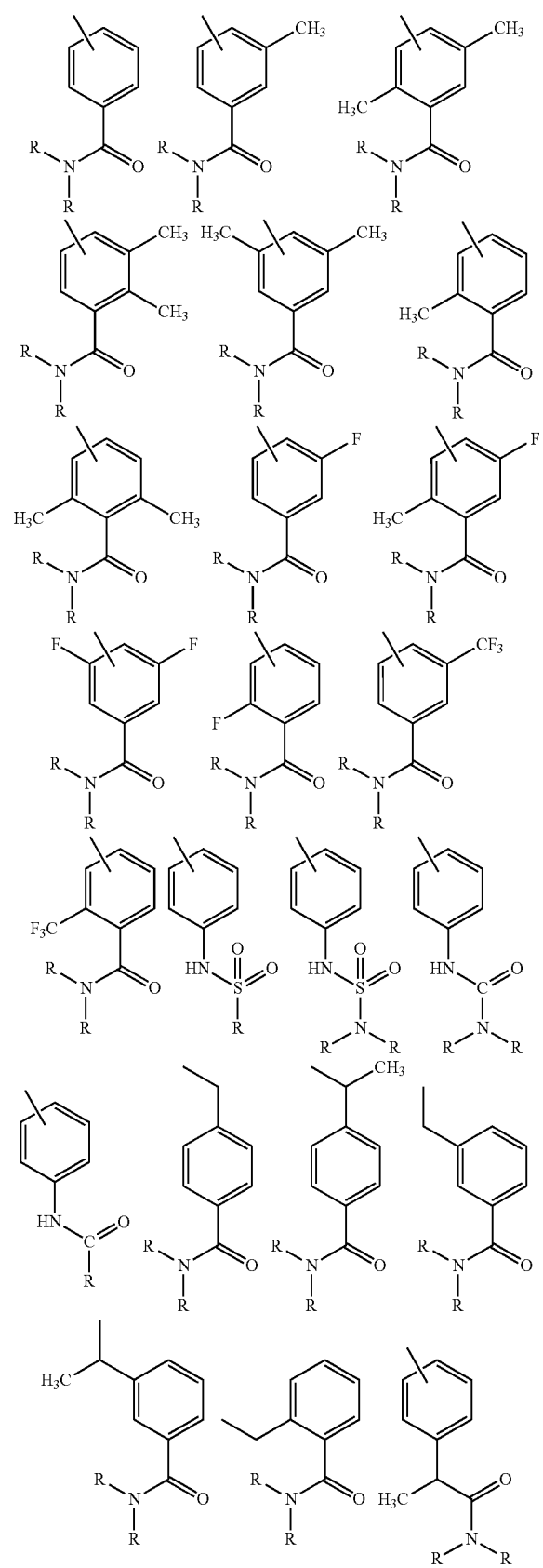
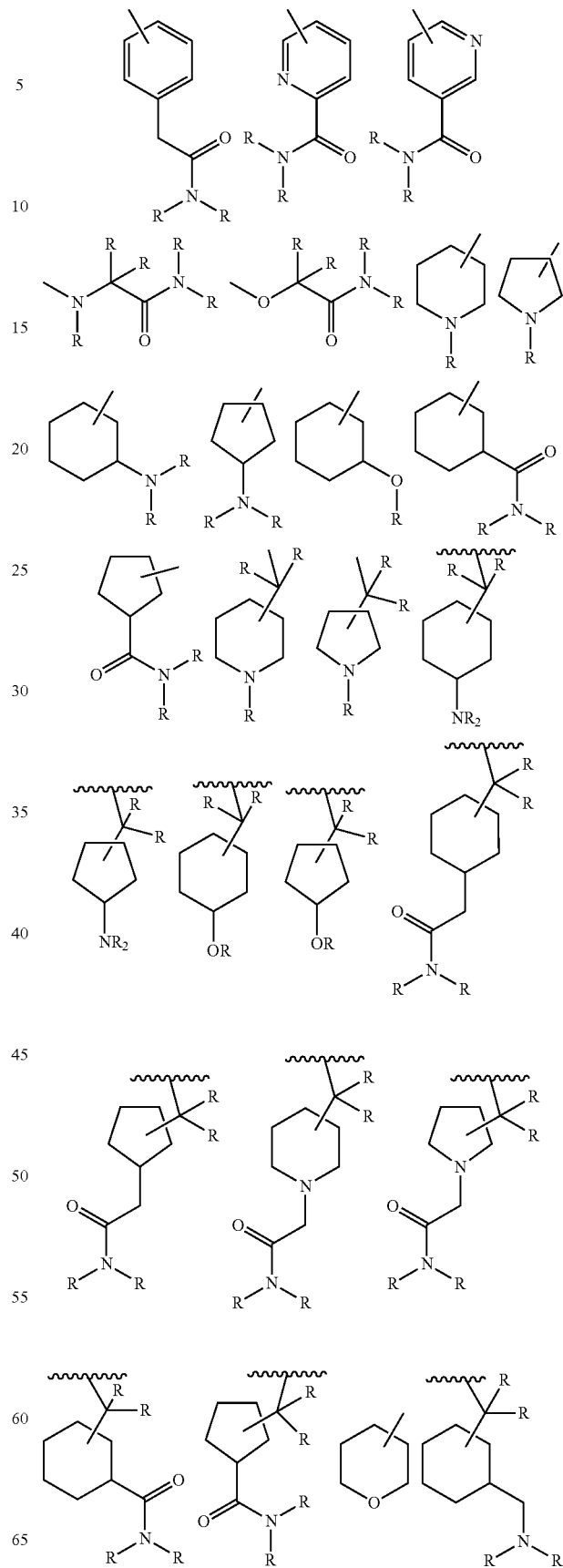

23

-continued

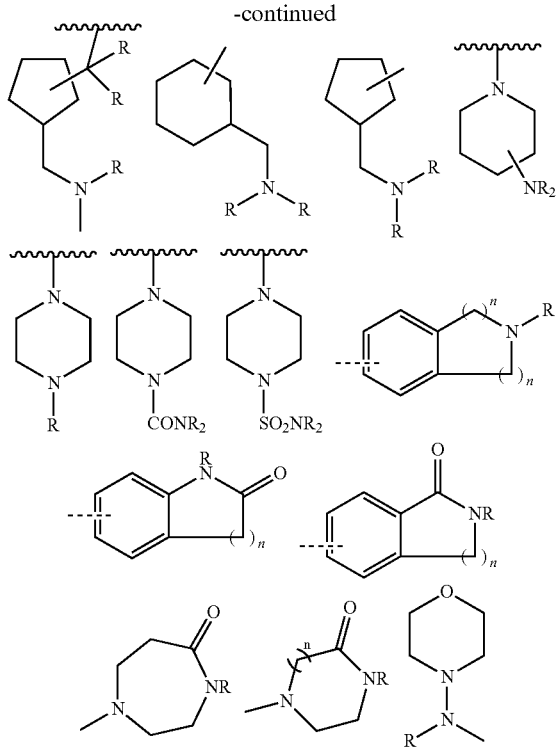

and their isomers;
additionally, these can be optionally substituted with 2-5 substituents independently selected from lower alkyl ($C_1$-$C_4$), alkoxy, deuterium or F.
m or n are independently an integer from 0 to 4.
Z is 0, 1 or 2
where R and $R^1$ are as defined above.

Further any two R or $R^1$ when taken together with the atoms to which they are attached may form a cyclic moiety;
Further, each R is independently selected;

The present invention relates to novel triazine compounds represented by Formula (I), their isomer, salt and solvate thereof;

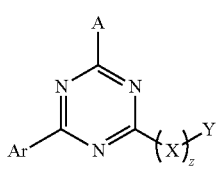

Formula (I)

wherein:
A is preferably morpholine
Ar is preferably

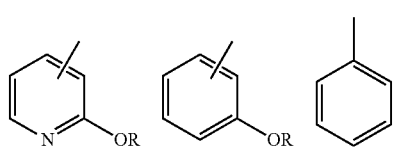

24

-continued

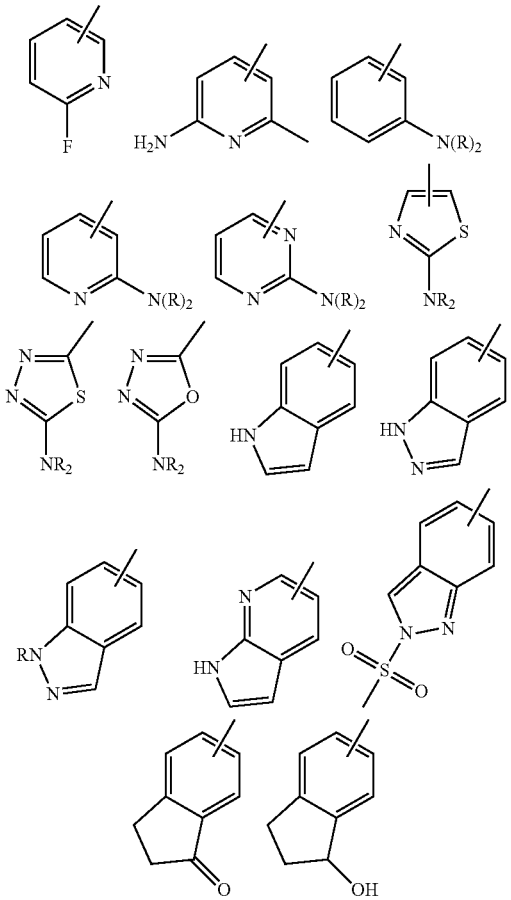

X is preferably O
Y is preferably:

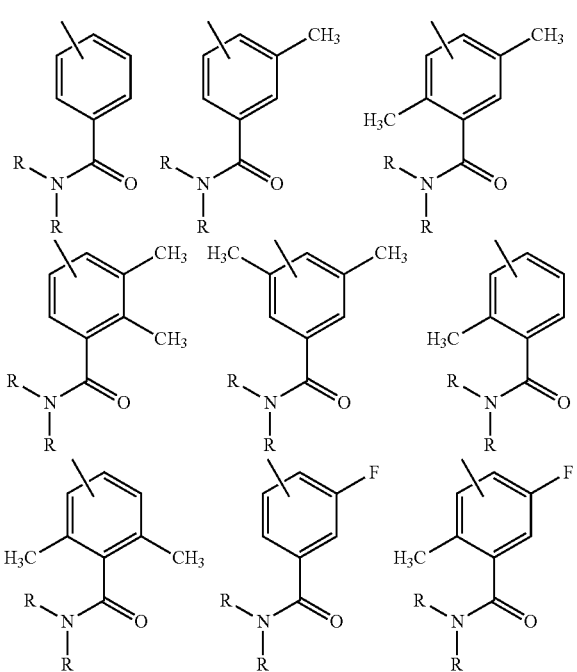

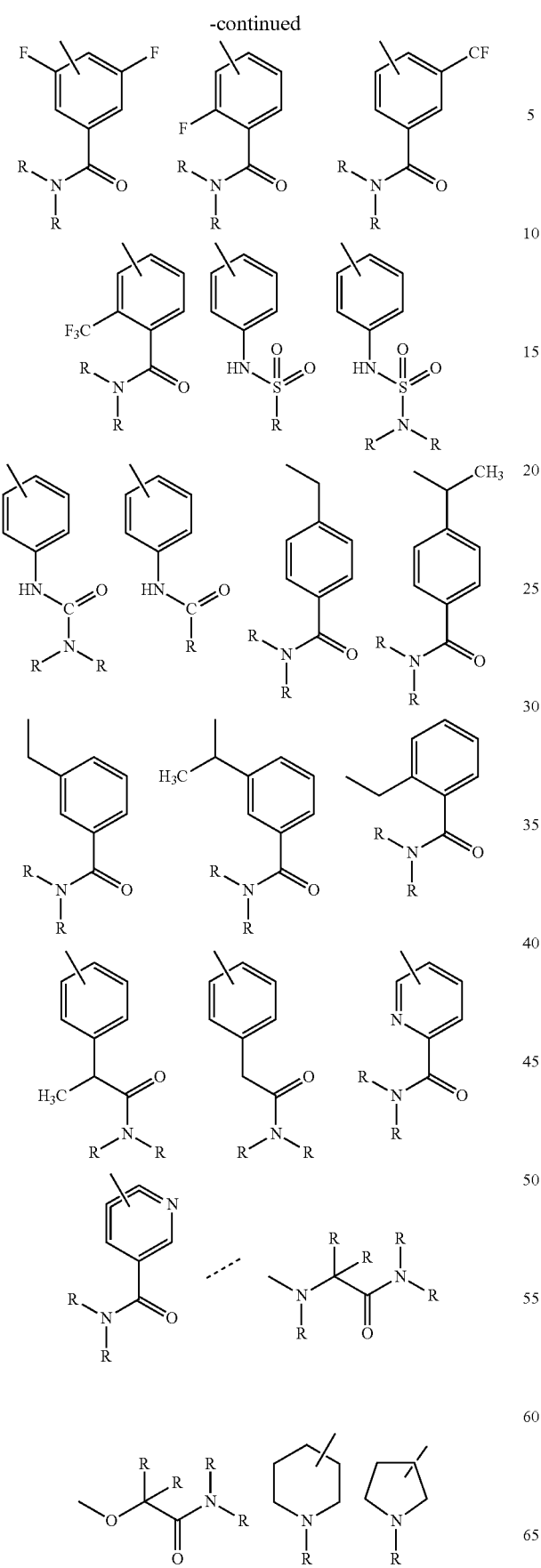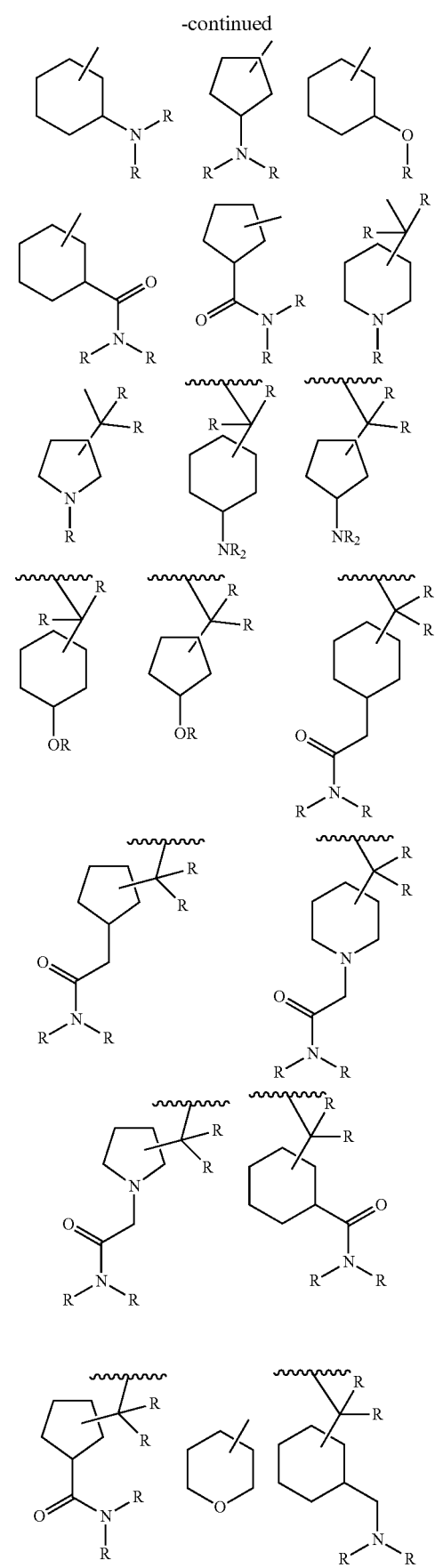

-continued

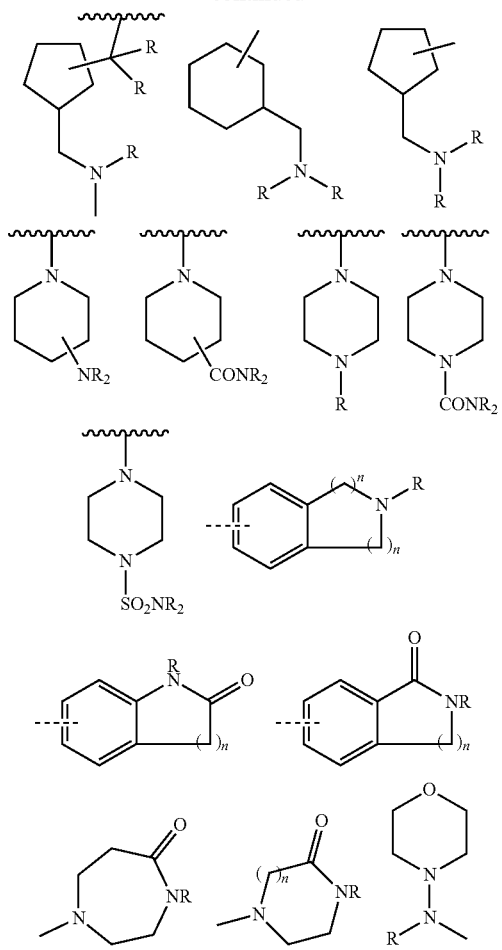

and their isomers;
additionally, these can be optionally substituted with 2-5 substituents independently selected from lower alkyl ($C_1$-$C_4$), alkoxy, deuterium or F;
m or n are independently an integer from 0 to 4.
Z is 0 or 1
where R and $R^1$ are as defined above.

Further any two R or $R^1$ when taken together with the atoms to which they are attached may form a cyclic moiety;

Further, each R is independently selected;

The present invention relates to novel triazine compounds represented by Formula (I), their isomer, salt and solvate thereof;

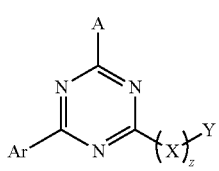

Formula (I)

wherein:
A is preferably morpholine

Ar is preferably

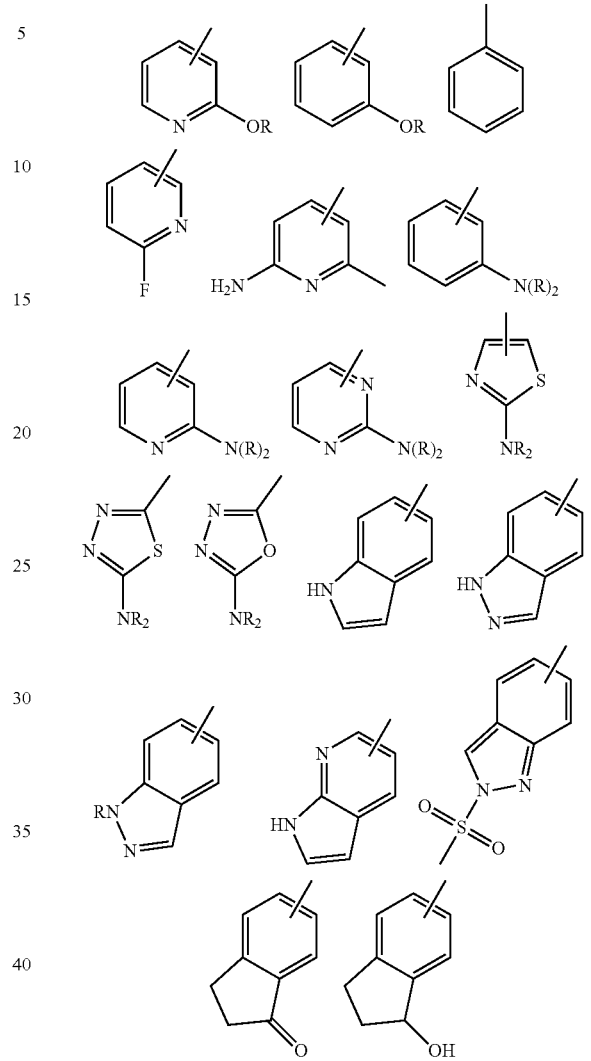

X is preferably NR
Y is preferably:

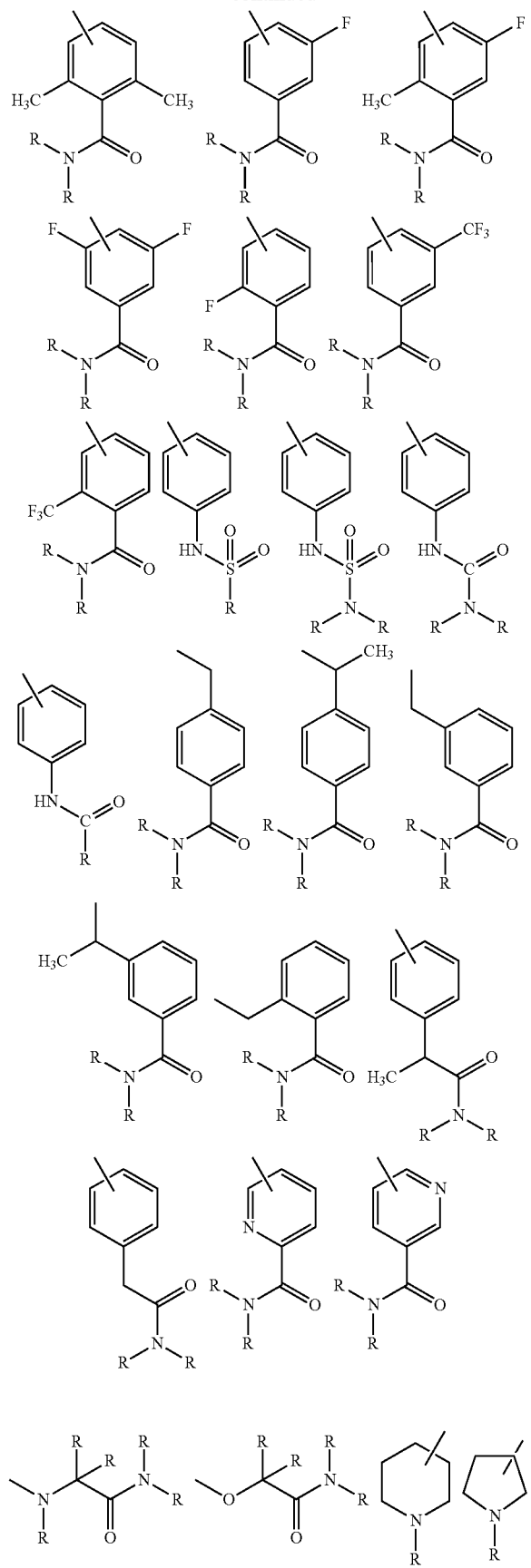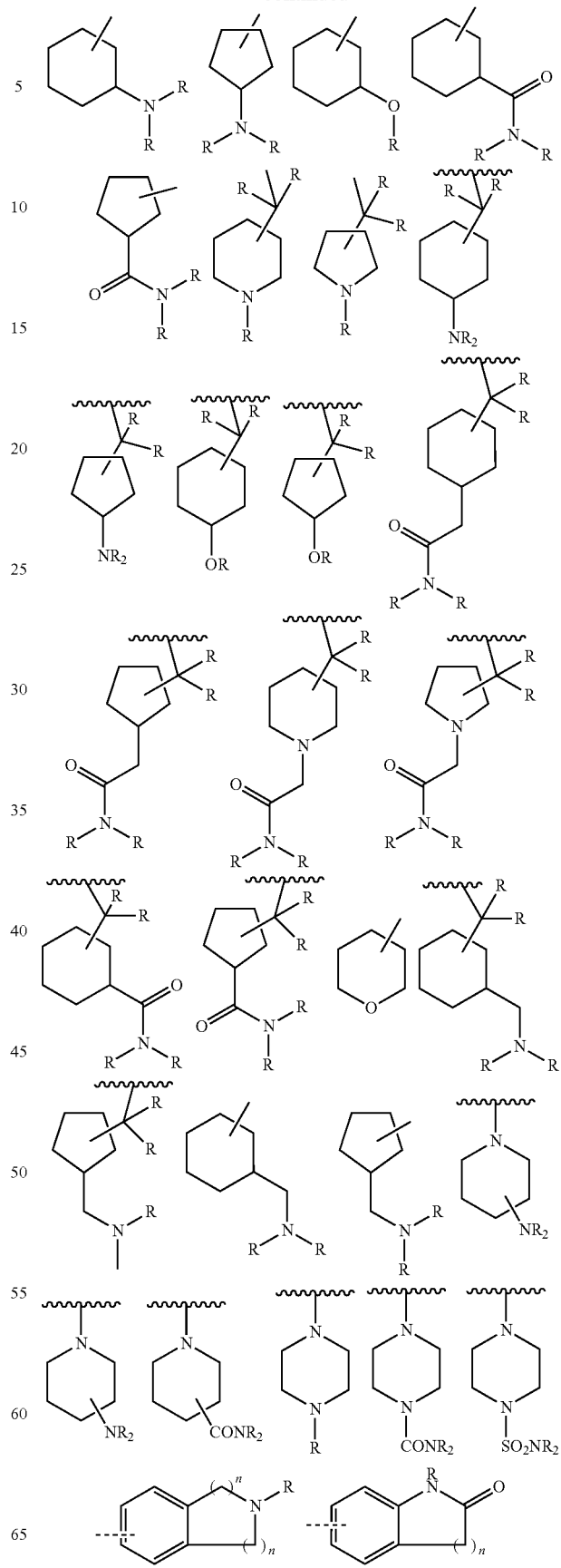

-continued

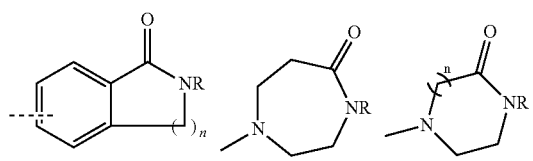

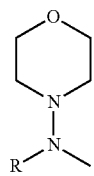

and their isomers;
additionally, these can be optionally substituted with 2-5 substituents independently selected from lower alkyl ($C_1$-$C_4$), alkoxy, deuterium or F;
m or n are independently an integer from 0 to 4.
Z is 0, 1 or 2
where R and $R^1$ are as defined above.

Further any two R or $R^1$ when taken together with the atoms to which they are attached may form a cyclic moiety;

Further, each R is independently selected;

The present invention relates to a novel triazine, of formula (I), their isomer, salt and solvate thereof,

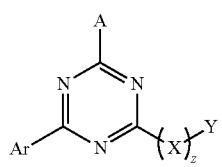

Formula (I)

Wherein
A is morpholino
X is O
Ar, Y, R and R1 are defined above.

The present invention relates to a novel triazine, of formula (I), their isomer, salt and solvate thereof,

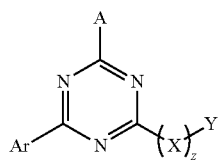

Formula (I)

Wherein
A is morpholino
X is NR
Ar, Y, R and R1 are as defined above.

The present invention relates to a novel triazine, of formula (I), their isomers, salt and solvate thereof

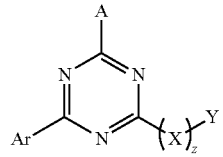

Formula (I)

wherein
X is O
Y is

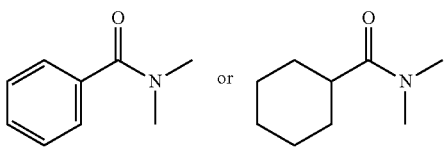

or their isomers
A and Ar, R and $R^1$ are as defined above.

Also provided herein are pharmaceutical compositions comprising a compound disclosed herein, e.g. a compound of Formula I, or a pharmaceutically acceptable salt, solvate, hydrate, or prodrug thereof; in combination with one or more pharmaceutically acceptable carriers.

Additionally provided herein is a method for treating, preventing, or ameliorating one or more symptoms of a PI3K-mediated disorder, disease, or condition in a subject, comprising administering to the subject a therapeutically effective amount of a compound disclosed herein, e.g. a compound of Formula I, or a pharmaceutically acceptable salt thereof or prodrug thereof.

Further provided herein is a method for modulating PI3K activity, comprising contacting a PI3K with a therapeutically effective amount of a compound disclosed herein, e.g. a compound of Formula I, or a pharmaceutically acceptable salt thereof.

The term "alkyl" refers to a linear or branched saturated monovalent hydrocarbon radical, wherein the alkylene may optionally be substituted as described herein.

The term "alkyl" also encompasses both linear and branched alkyl, unless otherwise specified. In certain embodiments, the alkyl is a linear saturated monovalent hydrocarbon radical that has the specified number of carbon atoms, or branched saturated monovalent hydrocarbon radical of specified number of carbon atoms. As used herein, linear $C_1$-$C_6$ and branched $C_3$-$C_6$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_1$-$C_6$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted as described herein.

The term "alkylene" encompasses both linear and branched alkylene, unless otherwise specified. In certain embodiments, the alkylene is a linear saturated divalent hydrocarbon radical that has the specified number of carbon atoms, or branched saturated divalent hydrocarbon radical of the specified number of carbon atoms. As used herein, linear $C_1$-$C_6$ and branched $C_3$-$C_6$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_1$-$C_6$ alkylene refers to a linear saturated divalent hydrocarbon radical of 1 to 6 carbon atoms or a branched saturated divalent hydrocarbon radical of 3 to 6 carbon atoms.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_2$-$C_6$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical that has the specified number of carbon atoms, or a branched monovalent hydrocarbon radical that has the specified number of carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, carbon-carbon double bonds. The alkenylene may be optionally substituted as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_2$-$C_6$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical that has the specified number of carbon atoms, or a branched divalent hydrocarbon radical that has the specified number of carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical that has the specified number of carbon atoms, or a branched monovalent hydrocarbon radical that has the specified number of carbon atoms. Examples of alkynyl groups include, but are not limited to, ethynyl (—C≡CH) and propargyl

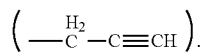

For example, $C_2$-$C_6$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more, in one embodiment, one to five, carbon-carbon triple bonds. The alkynylene may be optionally substituted as described herein. The term "alkynylene" also encompasses both linear and branched alkynylene, unless otherwise specified. In certain embodiments, the alkynylene is a linear divalent hydrocarbon radical that has the specified number of carbon atoms, or a branched divalent hydrocarbon radical that has the specified number of carbon atoms. Examples of alkynylene groups include, but are not limited to, ethynylene (—C≡C—) and propargylene (—CH$_2$C≡C—). For example, $C_2$—$C_6$ alkynylene refers to a linear unsaturated divalent hydrocarbon radical of 2 to 6 carbon atoms or a branched unsaturated divalent hydrocarbon radical of 3 to 6 carbon atoms.

The term "cycloalkyl" refers to a cyclic saturated bridged and/or non-bridged monovalent hydrocarbon radical, which may be optionally substituted as described herein. In certain embodiments, the cycloalkyl has from 3 to 20 ($C_3$-$C_{20}$), from 3 to 15 ($C_3$-$C_{15}$), from 3 to 10 ($C_3$-$C_{10}$), or from 3 to 7 ($C_3$-$C_7$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkylene" refers to a cyclic saturated bridged and/or nonbridged divalent hydrocarbon radical, which may be optionally substituted as described herein. In certain embodiments, the cycloalkylene has from 3 to 20 ($C_3$-$C_{20}$), from 3 to 15 ($C_3$-$C_{15}$), from 3 to 10 ($C_3$-$C_{10}$), or from 3 to 7 ($C_3$-$C_7$) carbon atoms. Examples of cycloalkylene groups include, but are not limited to, cyclopropylene, cyclobutylene, cyclopentylene, cyclohexylene, cycloheptylene, decalinylene, and adamantylene.

The term "aryl" refers to a monocyclic aromatic group and/or multicyclic monovalent aromatic group that contain at least one aromatic hydrocarbon ring. In certain embodiments, the aryl has from 6 to 20 ($C_6$-$C_{20}$), from 6 to 15 ($C_6$-$C_{15}$), or from 6 to 10 ($C_6$-$C_{10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "arylene" refers to a monocyclic and/or multicyclic divalent aromatic group that contains at least one aromatic hydrocarbon ring. In certain embodiments, the arylene has from 6 to 20 ($C_6$-$C_{20}$), from 6 to 15 ($C_6$-$C_{15}$), or from 6 to 10 ($C_6$-$C_{10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). In certain embodiments, arylene may also be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group may contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heteroarylene" refers to a divalent aromatic group and/or multicyclic aromatic group that contain at least one aromatic ring, wherein at least one aromatic ring contains one or more heteroatoms independently selected from O, S, and N. Each ring of a heteroarylene group may contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzothiophenylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroaryl groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroaryl may also be optionally substituted as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, p-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heterocyclylene" refers to a divalent non-aromatic ring system and/or multicyclic ring system that contain at least one non-aromatic ring, wherein one or more of the non-aromatic ring atoms are heteroatoms independently selected from O, S, or N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, p-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorphol inylene, thiazolidinylene, tetrahydroquinolinylene, and 1,3,5-trithianylene. In certain embodiments, heterocyclic may also be optionally substituted as described herein.

The term "halogen", "halide" or "halo" refers to fluorine, chlorine, bromine, and iodine.

The term "optionally substituted" is intended to mean that a group, such as an alkyl, alkylene, alkenyl, alkenylene, alkynyl, alkynylene, alkoxy, alkylamino, dialkylamino, carboxamido, cycloalkyl, cycloalkylene, aryl, arylene, heteroaryl, heteroarylene, heterocyclyl, or heterocyclylene, may be substituted with one or more substituents independently selected from, e.g., (a) $C_1$-$C_6$ alkyl, $C_2$-$C_6$ alkenyl, $C_2$-$C_6$ alkynyl, $C_3$-$C_7$ cycloalkyl, $C_6$-$C_{14}$ aryl, $C_7$-$C_{15}$ aralkyl, heteroaryl, and heterocyclyl, each optionally substituted with one or more substituents; and (b) halo, cyano (—CN), nitro (—$NO_2$), —C(O)$R_3$, —C(O)O$R_3$, —C(O)N$R_b$Rc, —C(N$R_3$)NR)RC, —O$R_3$, —OC(O)$R_3$, —OC(O)O$R_3$, —OC(O)N$R_b$RC, —OC(=N$R_3$)NR)RC, —OS(O)$R_3$, —OS(O)$_2$$R_3$, —OS(O)N$R_b$RC, —OS(O)$_2$N$R_b$Rc, —N$R_b$Rc, —N$R_3$C(O)$R_d$, —N$R_3$C(O)O$R_d$, —N$R_3$C(O)N$R_b$RC, —N$R_3$C(=N$R_d$)N$R_b$RC, —N$R_3$S(O)$R_d$, —N$R_3$S(O)$_2$$R_d$, —N$R_3$S(O)N$R_b$RC, —N$R_3$S(O)N$R_b$Rc, —S$R_3$, —S(O)$R_3$, —S(O)$_2$$R_3$, —S(O)N$R_b$RC, and —S(O)$_2$N$R_b$RC, wherein each $R_3$, $R_b$, $R_e$, and $R_d$ is independently (i) hydrogen; (ii) $C_1$-$C_6$ alkyl, $C_2$-$C_6$ alkenyl, $C_2$-$C_6$ alkynyl, $C_3$-$C_7$ cycloalkyl, $C_6$-$C_{14}$ aryl, $C_7$-$C_{15}$ aralkyl, heteroaryl, or heterocyclyl, each optionally substituted with one or more substituents; or (iii) $R_b$ and $R_e$ together with the N atom to which they are attached form heteroaryl or heterocyclyl, optionally substituted with one or more, in one embodiment, one, two, three, or four, substituents. As used herein, all groups that may be substituted are "optionally substituted," unless otherwise specified.

Pharmaceutical Compositions

In one embodiment, provided herein is a pharmaceutical composition comprising a compound of Formula I as defined herein, and a pharmaceutically acceptable excipient, adjuvant, carrier, buffer, or stabilizer. The pharmaceutically acceptable excipients, adjuvant, carrier, buffer, or stabilizer is non-toxic and does not interfere with the efficacy of the active ingredient. The precise nature of the carrier or other material will depend on the route of administration, which may be oral or by injection, such as cutaneous, subcutaneous, or intravenous injection.

The pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin. The pharmaceutical compositions are provided in a dosage form for parenteral administration, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilizers, buffers, antioxidants, and/or other additives may be included as required. The pharmaceutical compositions are provided in a dosage form for topical administration, which comprise a compound provided herein, and one or more pharmaceutically acceptable excipients or carriers. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms.

The pharmaceutical compositions provided herein may be provided in a unit dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time.

Methods of Use

The compounds of the present invention are designed to inhibit one or more isoform of PI3K and/or mTOR. Accordingly the inventors also provide method of cancer prevention or therapy for treating cancers, comprising administering a compound of Formula I as defined herein to a subject in need thereof which comprises the steps of selectively targeting a subunit of PI3K with a compound provided herein.

In one embodiment, provided is a method of treating, preventing, or ameliorating one or more symptoms of a disorder, disease, or condition associated with PI3K isoform and/or mTOR activity in a subject, which comprises administering to the subject a therapeutically effective amount of a compound provided herein, e.g., a compound of Formula I, or a pharmaceutically acceptable salt thereof.

In one embodiment, the subject is a mammal. In another embodiment, the subject is a human. In yet another embodiment, the subject is a primate other than a human, a farm animal such as cattle, a sport animal, or a pet such as a horse, dog, or cat.

The disorders, diseases, or conditions treatable with a compound provided herein, include, but are not limited to, inflammatory or allergic diseases, including cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system. In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal garnmopathy of undetermined signifimayce; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, non-seminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, denocarcinoma, and carcinosarcoma; and other cancer, including, not limited to, myxosarcoma, osteogenic arcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Depending on the disorder, disease, or condition to be treated, and the subject's condition, the compounds or pharmaceutical compositions provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally in the range of about 0.001 to 100 mg per kg subject body weight per day (mg/kg per day).

For oral administration, the pharmaceutical compositions provided herein may be formulated in the form of tablets containing from about 1.0 to about 1,000 mg of the active ingredient, for the symptomatic adjustment of the dosage to the patient to be treated. The pharmaceutical compositions may be administered on a regimen of 1 to 4 times per day, including once, twice, three times, and four times per day. The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); M (molar); mM (millimolar); uM (micromolar); RT or rt (room temperature), eq. (equivalent); Hz (Hertz); MHz (megahertz); mmol (millimoles); hr or hrs (hours); min (minutes); conc. (concentrated); mp (melting point); MS (mass spectrometry); MW (microwave reaction instrument); ESI (electrospray ionization); TLC (thin layer chromatography); DMF (dimethylormamide); DMSO (dimethylsulfoxide); DMSO-d6 (deuterated dimethylsulfoxide); EtOH (ethanol); EtOAc (ethyl acetate); i-PrOH (isopropanol); MeOH (methanol); THF (tetrahydrofuran); DIPEA (N,N-diisopropylethylamine); TFA (triethylacetic acid); TBDMSCI (tert-butylchlorodimethylsilane); TBAF, (tetra-n-butylammonium fluoride); PdCl$_2$(dppf), (1,1'-bis(diphenylphosphino) ferrocene) dichloropalladium (11)); EDTA, (ethylenediaminetetraacetic acid); Me (methyl); Et (ethyl); tBu (tert-butyl); and Boc (tertbutoxylcarbony). For all of the following examples, standard work-up and purification methods known to those skilled in the art may be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

General Experimental Information:

The agents of the various embodiments may be prepared using the reaction routes and synthesis schemes as described below, The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions.

The following examples are representative of the disclosure, and provide detailed methods for preparing the compounds of the disclosure, including the preparation of intermediate compounds. In these examples, melting points were determined on a melting point apparatus, Mel-Temp (Laboratory Devices). NMR spectra were obtained on a Bruker Biospin spectrometer at 300 MHz for $^1$H and 100 MHz for $^{13}$C spectra, referenced to TMS (Si(CH$_3$)$_4$). Mass spectra were determined either on API-3000 (Applied Biosystems) or 6120 quadrupole (Agilent technologies) mass spectrometer. Column chromatography was carried out on silica gel (Merck 230-400 mesh), unless otherwise stated.

General Synthetic Schemes

A wide range of trisubstituted triazines may be prepared as shown in synthetic Scheme 1-Scheme 4.

General Synthetic Scheme 1

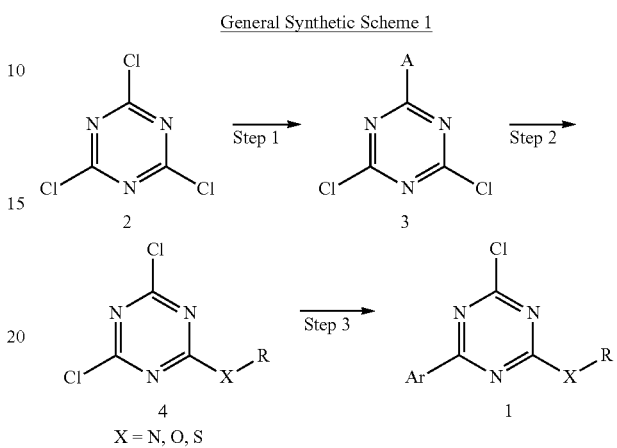

X = N, O, S

A general procedure involves initial reaction of a nucleophile such as morpholine with a slight excess of cyanuric chloride in a solvent such as acetone/THF and water in the presence of a suitable base to a trichloro triazine [2]. The base may be a non-reactive tertiary amine or an appropriate inorganic salt such as sodium bicarbonate. Although the mono addition product predominates, small quantities of 2-chloro-4,6-di-morpholin-4-yl-[1,3,5]-triazine, resulting from the addition of two molecules of morpholine, are generally formed but may be efficiently removed during purification in the final steps. Intermediate [3] is then treated with a nucleophilic reactant in the presence of a base such as a tertiary amine or sodium bicarbonate. Purification by chromatography at this stage will yield a very pure intermediate [4] for the final palladium catalyzed Suzuki or Stille coupling reactions. The boronic acids, esters and organotin employed were generally commercially available or could be prepared in a straightforward manner using procedures known to one versed in the art. In certain circumstances the substituent(s) on the rings of the compound(s) of formula [1] produced by this procedure were further elaborated using standard techniques to arrive at other members of the series.

General Synthetic Scheme 2

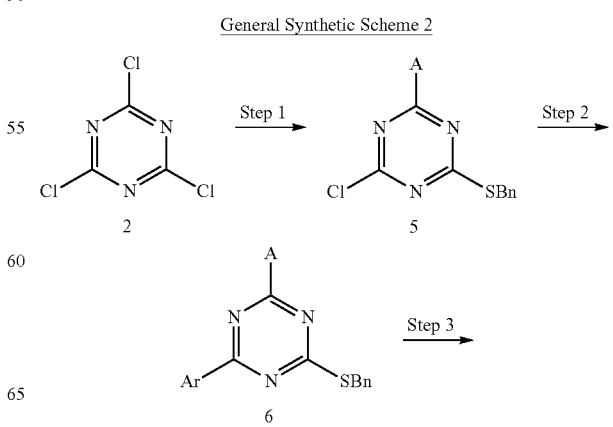

-continued

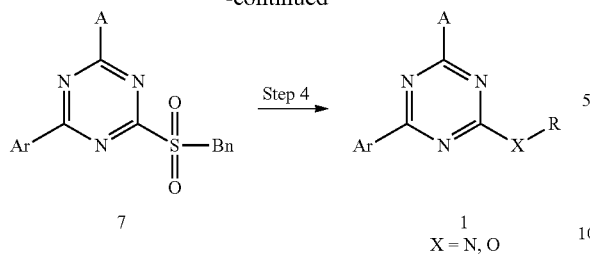

A general procedure involves initial reaction of a nucleophile such as morpholine with a slight excess of cyanuric chloride in a solvent such as acetone/THF and water in the presence of a suitable base followed by addition of thiol such as benzyl mercaptan. The base may be a non-reactive tertiary amine or an appropriate inorganic salt such as sodium bicarbonate. The desired product [5] may be further purified using standard lab purification methods such as column chromatography. Intermediate [5] under general Suzuki or Stille coupling conditions with an appropriate boronate or boronic acid or organotin reagent may provide [6]. Intermediate [6] may be converted to [7] under oxidation conditions with reagents such as oxone. The desire structure 1 may be obtained with attack of an appropriate nucleophile on [7]. In certain circumstances the substituent(s) on the rings of the compound(s) of formula [1] produced by this procedure were further elaborated using standard techniques to arrive at other members of the series.

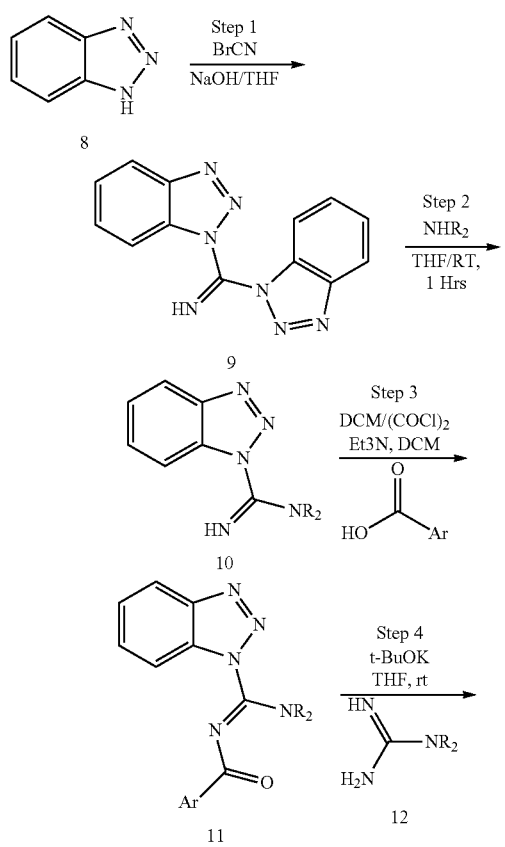

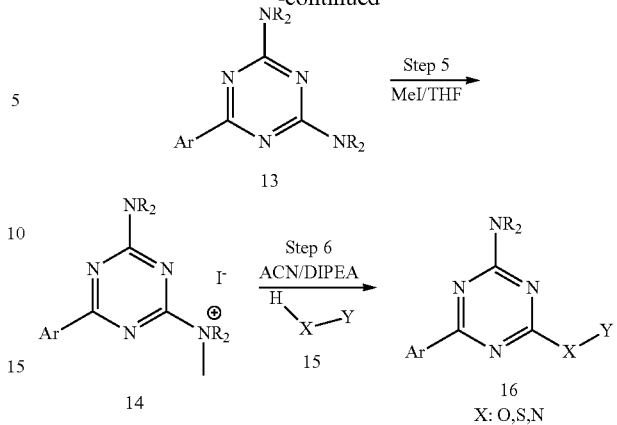

The structure of interest [16] may be synthesized starting from [9], that may be obtained from [8] as shown in scheme above. Compound [9] may be obtained from the reaction of 1,2,3-benzotriazole with cyanogen bromide. The displacement of the first benzotriazole moiety with a nucleophile such as morpholine in solvent such as DCM may yield compound [10], which may be converted to [11] using a base such as TEA and various acyl chloride in solvent such as DCM. Compound [13] may be synthesized by condensation of [11] and [12] in presence of base such as potassium tert.butoxide. Compound [13] may be converted to compound [16], through compound [14] by quaternization of morpholine nitrogen using alkylating reagents such as methyl iodide followed by displacements with a nucleophile [15] using neutral organic base such as DIPEA and solvent such as acetonitrile.

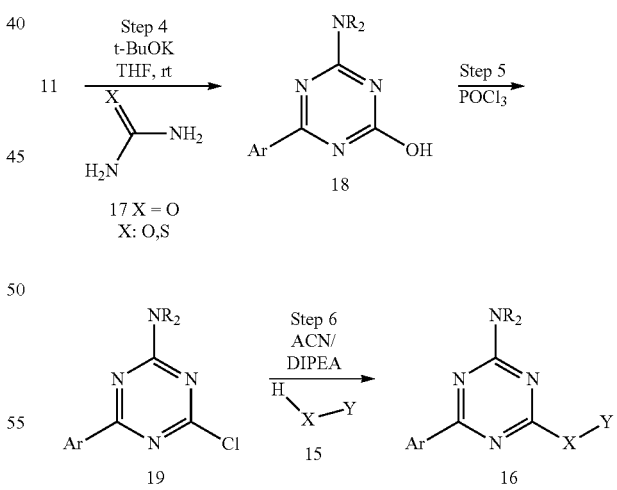

Compound [18] may be synthesized by condensation of [11] and [17] in presence of base such as potassium tert.butoxide. [18] on treatment with a chlorinating reagent such as phosphorous trichloride may afford [19]. Compound [19] may be converted to desire compound [16] by addition of a corresponding nucleophile using a base such as NaH and solvent such as DMF.

Scheme 5: Synthesis of 3-((4-(1H-indazol-4-yl)-6-morpholino-1,3,5-triazin-2-yl)amino)-N,N-dimethylbenzamide following Scheme 1

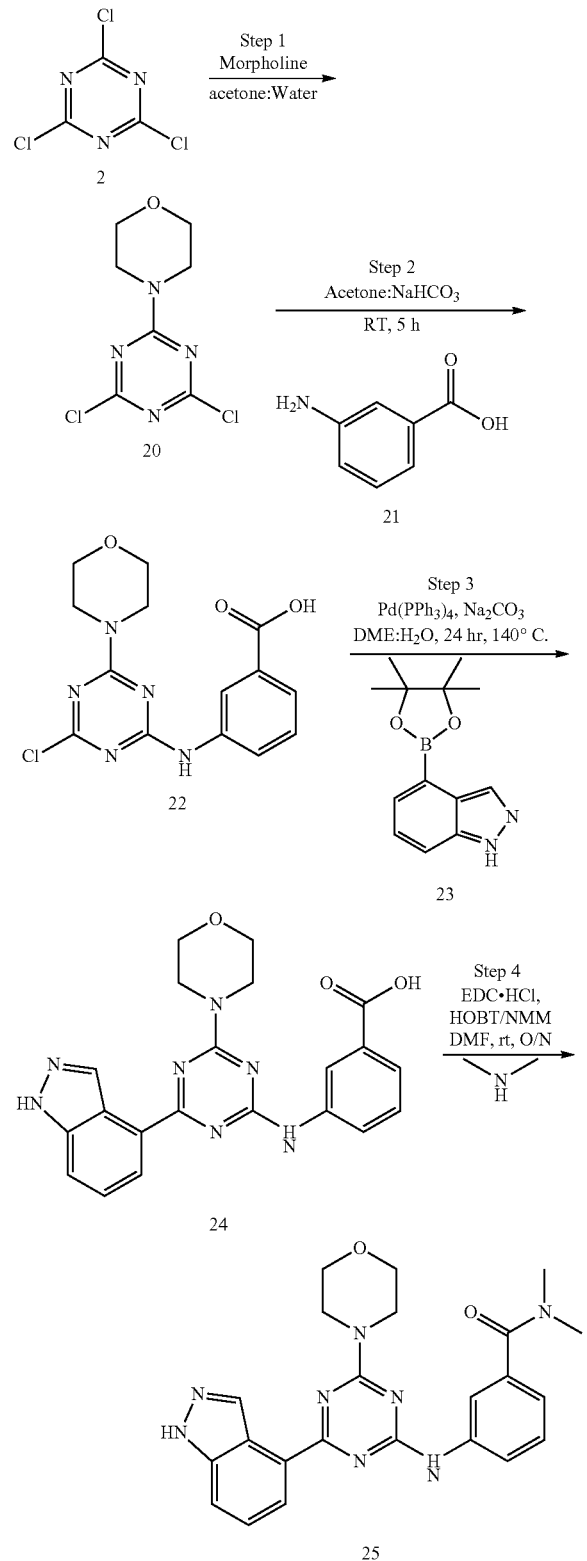

Step 1:
Compound [2] (20 g, 108.4 mmol, 1 eq) was dissolved in acetone (100 mL):water (30 mL). An acetone solution (10 mL) of morpholine (9.44 mL, 108.4 mmol, 1 eq) was added dropwise at 0° C. The reaction mass was stirred at 0° C. for 3 hrs; a solid formed during reaction and was filtered off. The filtrate was concentrated and again diluted with acetone: water::3:1; the precipitated solid was filtered again, both the solids were combined and dried to give compound [20] as white solid (14 g, 55%). (M+1=235)

Step 2:
Compound [20] (3.2 g, 13.6 mmol, 1 eq) was taken in a solution of acetone:NaHCO₃aq.::1:1 (30 mL). The reaction mass turned hazy and was stirred at RT until effervescence ceased. Compound [21] was added (1.49 g, 10.8 mmol, 0.8 eq) and the reaction mass was further stirred at RT for 2 hrs. The excess of acetone from the reaction mixture was evaporated to dryness. More water (20 mL) was added and the mixture was filtered through Buchner funnel. The filtrate was washed with DCM; the DCM layer was discarded and the water layer was acidified to pH=4. A ppt. formed, was filtered, washed with water and dried to give compound [22] (3.5 g, 76%) as white solid.

ESIMS: 336 (M$^+$+1)

Step 3:
To a solution of compound [22] (1.5 g, 4.47 mmol, 1 eq) in DME:H₂O::1:1 (30 mL) was added successively compound [23] (1.6 g, 6.71 mmol, 1.5 eq.) and Na₂CO₃ (1.42 g, 13.43 mmol, 5 eq). Degassing was done for 15 min, and then Pd(PPh₃)₄ (0.16 g, 0.14 mmol, 0.05 eq) was added under inert atmosphere. The reaction mass was refluxed at 110° C. for 24 hrs. Excess of solvent was evaporated. Reaction was diluted with water, acidified up to pH=4 and filtered through a Buchner funnel. Purification of solid residue was done by column chromatography with silica gel (100:200 mesh) in solvent system 2% MeOH in DCM to get compound 1241 (1.15 g, 62%) as pale white solid.

ESIMS: 418 (M$^+$+1)

Step 4:
To a solution of compound [24] (0.15 g, 0.35 mmol, 1 eq) in DMF (2 mL) was added successively EDC.HCl (0.10 g, 0.53 mmol, 1.5 eq.) and HOBT (0.13 g, 0.53 mmol, 1.5 eq). After that NMM (0.12 mL, 1.07 mmol, 3 eq) was added and reaction mass was stirred for 10 min. Finally 2 M dimethyl amine in THF (0.5 mL, 3 eq) was added and reaction mass was stirred overnight. The reaction mass was diluted with water; a ppt. formed which was filtered through a Buchner funnel. The solid was washed with diethyl ether, dried to get compound [25] (0.09 g, 56%).

ESIMS: 445 (M$^+$+1)

Scheme 6: Synthesis of 4-((4-(1H-indazol-4-yl)-6-morpholino-1,3,5-triazin-2-yl)oxy)-N,N-dimethylbenzamide following Scheme 2

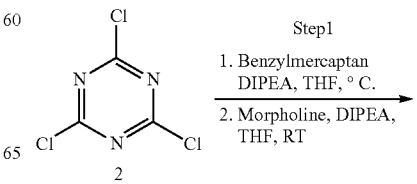

-continued

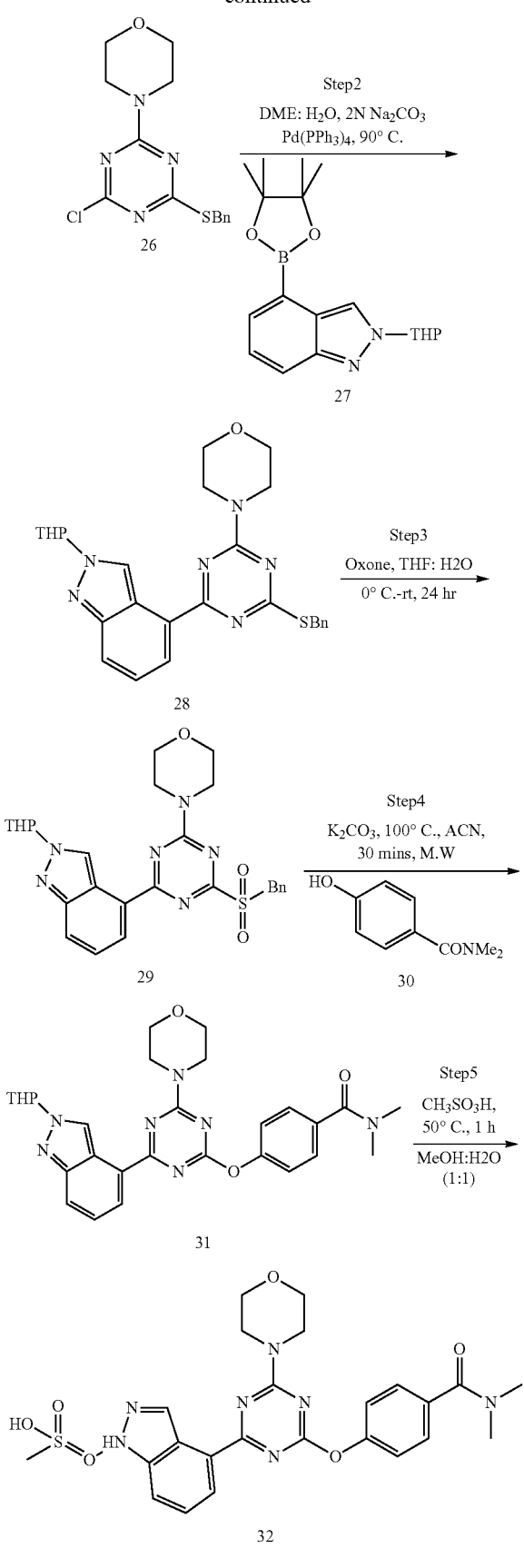

Step 1

Benzyl mercaptan (1.3 mL, 10.26 mmol, 0.94 eq) and DIPEA (1.7 mL, 10.37 mmol, 0.95 eq) were added to a solution of compound [2] (2 g, 10.92 mmol) in dry THF at 0° C. under a nitrogen atmosphere for 2 hrs. TLC was used to monitor for consumption of starting material [2]. Once the starting material was consumed, morpholine (0.95 mL, 10.92 mmol, 1 eq) and DIPEA (1.8 mL, 10.92 mmol, 1 eq) were added. The mixture was then stirred at RT for 3 h, followed by removal of the solvent under reduced pressure. Purification was done by silica gel column chromatography with 50% EtOAc/cyclohexane to give compound [26] as a white solid (2.5 g, 71%).

ESIMS: 323 (M$^+$+1)

Step 2

To a solution of compound [26] (2 g, 5.59 mmol, 1 eq) in DME:H$_2$O::4:1, 5 mL of 2 M Na$_2$CO$_3$ was added followed by addition of compound [27] (2.16 g, 6.78 mmol, 1.2 eq). After that, tetrakis palladium (323 mg, 0.279 mmol, 0.05 eq) was added and the reaction was heated under inert condition at 90° C. overnight. DME was removed under vacuum and the reaction mass was extracted with (2×200 ml of DCM. The DCM extracts were combined, washed with brine, dried over anhydrous sodium sulphate, and then evaporated to obtain a viscous dark brown material. This material was purified by silica gel chromatography with 40% EtOAC/Hexane to obtain compound [28] as a pale yellow solid (1.2 g, 45%).

ESIMS: 489 (M$^+$+1)

Step 3

To a solution of compound [28] (1 g, 2.04 mmol, 1 eq) in THF:water::1:1 (50 ml), was added portion wise oxone (3.14 g, 5.12 mmol, 2.5 eq) at 0° C. After stirring at 0° C. for 1 h, the reaction mixture was stirred at room temperature for additional 24 h. After completion of the reaction, 50 ml of water was added, and the reaction mass was extracted with 2×100 mL EtOAc. The EtOAc layers were combined, washed with brine, dried over anhydrous sodium sulphate and concentrated to get compound [29] as a pale yellow solid (0.9 g, 85%).

ESIMS: 521 (M$^+$+1)

Step 4

To a solution of compound [29] (0.25 g, 0.48 mmol, 1 eq) in acetonitrile (2 ml) in a microwave vial, were added successively compound [30] (0.053 g, 0.38 mmol, 0.8 eq) and potassium carbonate (0.132 g, 0.96 mmol, 2 eq). The sealed vial was then heated for 30 mins at 100° C. in MW, and after cooling, the solvent was evaporated under vacuum. The resulting crude solid was dissolved in water (10 ml) and was washed with ether (10 ml) followed by ethyl acetate (10 mL). The aqueous layer was acidified up to pH=4 to 5 using dilute HCl, and the off-white ppt. so obtained was filtered and dried at 50° C. to yield compound [31] as an off-white solid (0.105 g, 44%).

ESIMS: 503 (M$^+$+1)

Step 5

Compound [31] (0.82 g, 0.15 mmol, 1 eq.) was dissolved in MeOH:H$_2$O::2:1 (6 mL), then CH$_3$SO$_3$H (0.05 ml, 0.77 mmol, 5 eq) was added drop wise at RT. The reaction mass was refluxed at 50-55° C. for 1 h. TLC and mass spectra confirmed completion of the reaction. Afterward, the reaction mixture was evaporated to yield a brownish colored crude oil (0.075 g). The crude material was purified by prep-TLC with a mobile phase of 5% methanol in DCM to yield a colorless gum. The resulting gum was washed with diethyl ether (2×5 ml), to yield compound [32] as off-white solid (0.012 g, 13% yield).

ESIMS: 446 (M$^+$+1)

Scheme 7: Synthesis of 4-((4-(1,4-oxazepan-4-yl)-6-(1-(tetrahydro-2H-pyran-2-yl)-1H-indazol-4-yl)-1,3,5-triazin-2-yl)-N,N-dimethylbenzamide following Scheme 2

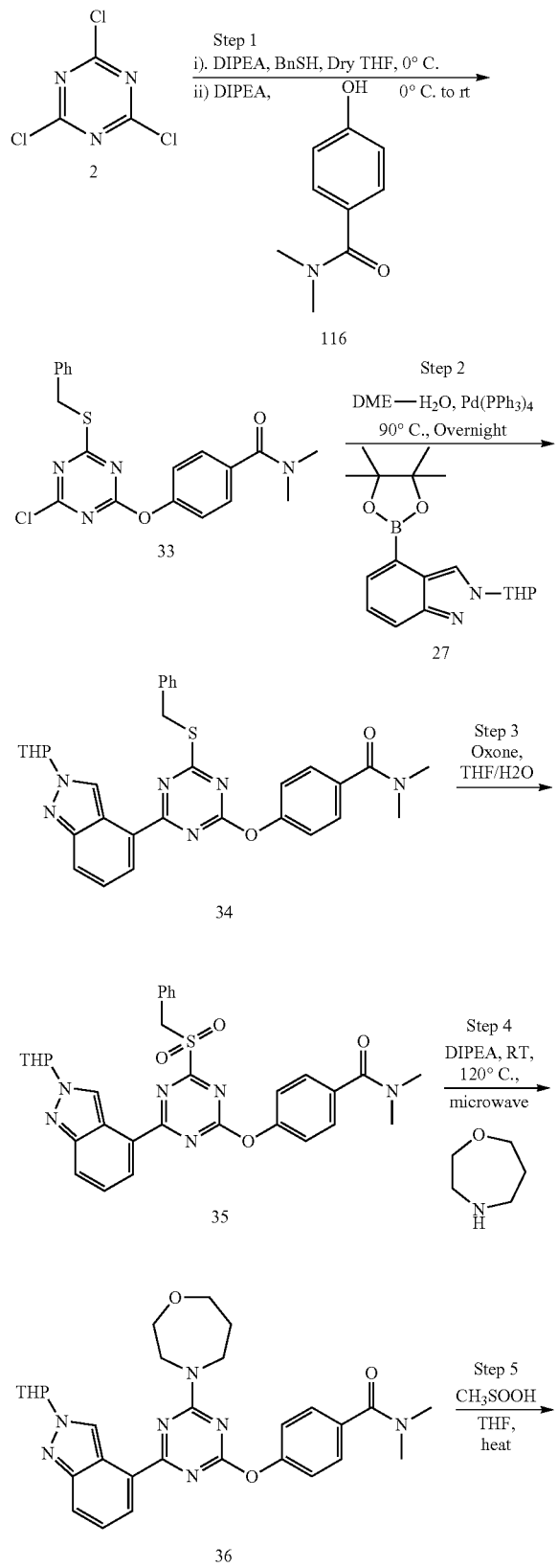

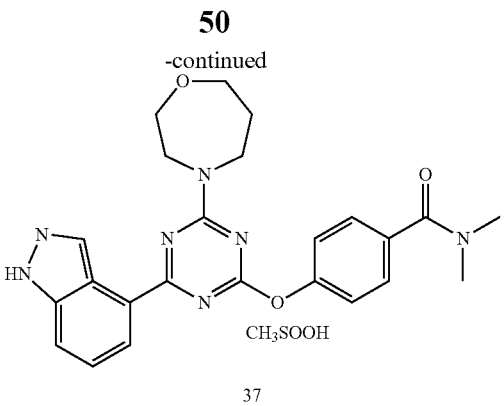

Step 1

Cyanuric chloride [2] (1.0 g, 5.4 mmol) was suspended in anhydrous THF (20 ml) in a three neck RB flask under inert atmosphere and cooled using ice-bath, followed by addition of DIPEA (5.16 mmol) and benzyl mercaptan (5.08 mmol). The reaction mixture was allowed to stir at 0-4° C. for 1 h and monitored by TLC examination (5% EtOAc/Hexane). A mixture of DIPEA (5.40 mmol) and 4-hydroxy-N,N-dimethylbenzamide [116] (5.40 mmol) was added to reaction mixture followed by an addition stirring for 3 h at RT. The excess solvent was evaporated under reduced pressure to obtained crude product which was purified using silica gel column chromatography (eluent, 25% EtOAc/Hexane) to obtain product [33] in 87% yield.

Step 2

Compound [33] (0.718 mmol) was dissolved it in 5 ml of DME in three neck round bottom flask followed by addition of [27] (0.914 mmol) and 2 ml of 2M $Na_2CO_3$ solution. The reaction mixture was degassed using nitrogen for 30 min followed by addition of palladium catalyst (0.0359 mmol). The reaction mixture was refluxed for 16 h and monitored by TLC (70% EtOAc/Hexane). After completion, the reaction mixture was diluted with DCM and washed with water, followed by brine. The organic layer was dried over $Na_2SO_4$ and evaporated under reduced pressure to obtained crude product which was purified using silica gel column chromatography using 50% EtOAc/Hexane affording product [34] in 30% yield.

Step 3

Compound [34] (0.23 mmol) was dissolved in 4 ml of $THF/H_2O$ (1:1) solution at 0-4° C. followed by addition of oxone (0.69 mmol) portion-wise. Reaction temperature was allowed to rise until reaching room temperature and stirred for 10 h. The reaction progress was monitored by TLC (70% EtOAc/hexane). After completion, the reaction mixture was diluted with EtOAc and washed successively with $H_2O$ and brine. The organic layer was dried over anhydrous $Na_2SO_4$, filtered and evaporated under reduced pressure. The product obtained [35] was pure enough to be used for next step without any further purification.

Step 4

Compound [35] (0.050 mmol), homomorpholine (0.20 mmol) was dissolved in acetonitrile in a microwave reaction vessel followed by addition of DIPEA (0.5 mmol). The reaction mixture was heated to 120° C. under microwave conditions for 30 min. Excess solvent was removed under reduced pressure yielding the crude product which was subjected to silica gel column chromatography to obtain pure product [36] in 30% yield.

Scheme 8: Synthesis of 4-((4-(2-aminothiazol-5-yl)-6-morpholino-1,3,5-triazin-2-yl)oxy)-N,N-dimethylbenzamide hydrochloride [41]

Scheme 9: Synthesis of 4-((4-(1H-indazol-4-yl)-6-morpholino-1,3,5-triazin-2-yl)oxy)-N,N-dimethylbenzamide [47] Following Scheme 3

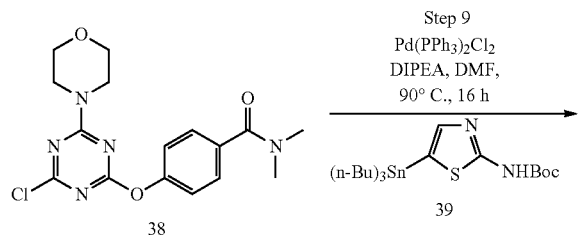

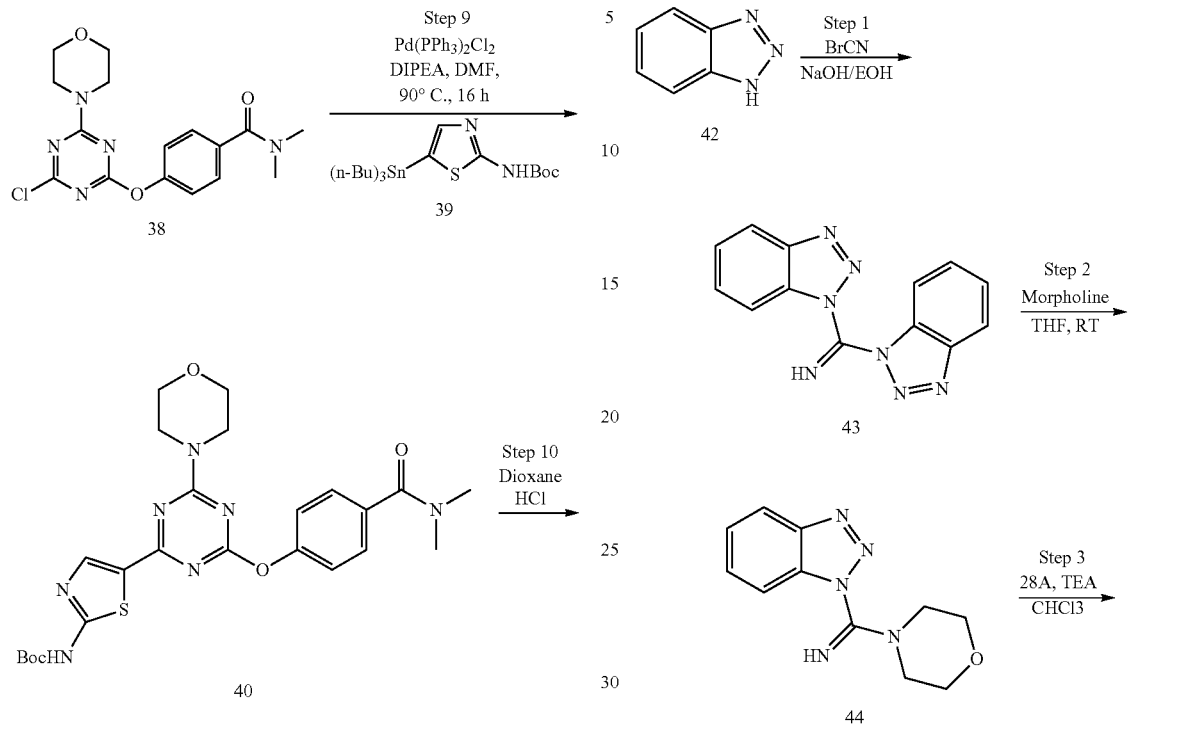

Step 9

Compound [38] (1.0 g, 2.7 mmol) was taken in DMF (10 ml). [39] (2.02 g, 4.05 mmol) (Pd(PPh$_3$)$_2$Cl$_2$ (0.193 g, 0.277 mmol), DIPEA (0.978 ml, 5.4 mmol) were added. The mixture was heated at 95° C. for 16 hrs. After completion, the mixture was cooled to RT, poured to ice-water mixture, the precipitate formed were filtered to obtain compound [40] (0.725 g, 50% yield) as off while solid.

ESIMS: 528 (M$^+$+1)

Step 10

Compound [40] (0.100 g, 0.189 mmol) was taken in dioxane HCl (4 M) and mixture was stirred for 24 h. at RT. The solvent was evaporated and crude was purified by washing with DCM, ether and pentane to obtain compound [41] (0.070 g, 86% yield) as white solid.

ESIMS: 428 (M$^+$+1)

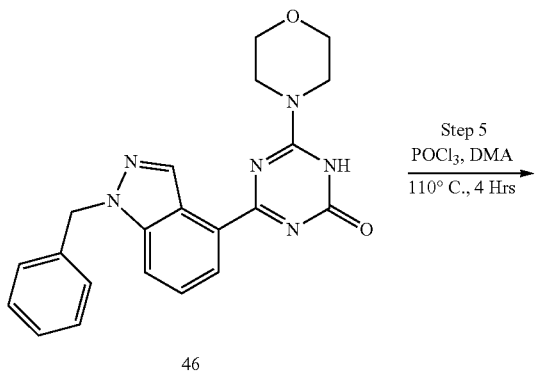

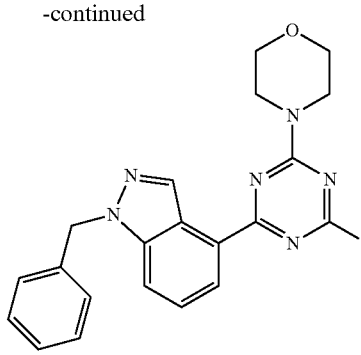

47

Step 1

Benzotriazole [42] (11.8 g, 0.05 mol) was dissolved in ethanol (200 ml). To this solution kept at 0° C. was added cyanogen bromide (5.0 g, 0.025 mol) in acetone (20 ml) followed by a 10% solution of NaOH (0.025 mol). The white precipitate was filtered off and washed with ice cold ethanol and recrystallized from benzene to give pure [43] as white micro needles in 23% yield.

ESIMS: 264 (M$^+$+1)

Step 2: Synthesis of (1H-benzo[d][1,2,3]triazol-1-yl)-(morpholino)methanimine [44]

Di(1,2,3-benzotriazol-1-yl)methanimine [43] (2 mmol) was dissolved under an inert atmosphere in dry THF (20 ml). The morpholine (2 mmol, 1 equiv) were added dropwise, and the resulting mixtures were allowed to react until complete conversion of [43], as monitored by TLC. The mixtures were then concentrated under vacuum and dissolved in CH2Cl2 (20 ml). The organic layers were washed twice with aqueous 10% Na2CO3 and dried (MgSO$_4$), and the solvent was removed under reduced pressure to afford compound [44] as a solid in 80% Yield.

ESIMS: 232 (M$^+$+1)

Step 3: Synthesis of (E)-N-((1H-benzo[d][1,2,3]triazol-1-yl)(morpholino)methylene)-1-benzyl-1H-indazole-4-carboxamide [45]

Compound [44] (1 equiv) was dissolved in chloroform, and 1-benzyl-1H-indazole-4-carbonyl chloride[28A] (1 equiv) was added followed by addition of triethylamine (1 equiv). The mixture was allowed to react for 2-4 h at ambient temperature. The completion of the reaction was monitored by TLC. The chloroform solution was washed with water to remove triethylamine hydrochloride. The chloroform layer was separated, dried, and concentrated under reduced pressure. The residue was purified by column chromatograph on silica gel with ethyl acetate/hexanes: 1/1 as an eluent to afford compound [45] as a white solid in 50% yield.

ESIMS: 46 (M$^+$+1)

Step 4: Synthesis of 4-(1-benzyl-1H-indazol-4-yl)-6-morpholino-1,3,5-triazin-2(1H)-one Compound [45] (1 mmol) and urea (1 mmol) was mixed in THF (10 ml). Potassium tert-butoxide (3 mmol) was added portionwise in 15 min. The reaction mixture was allowed to react for 6-8 h after which water (15 ml) was added to give a clear solution. The water solution was extracted with ethyl acetate (3×30 ml). Sodium bicarbonate was added to a water layer, and the water layer was additionally extracted with chloroform (2×50 ml). Extracts were combined, dried over MgSO4, and evaporated under reduced pressure. The residue obtained was triturated with DCM (10 ml) and n-Pentane (30 ml) to yield a white precipitate which was filtered and dried to afford compound [46] as a white solid in 87% yield.

ESIMS: 389 (M$^+$+1)

Step 5: Synthesis of 4-(4-(1-benzyl-1H-indazol-4-yl)-6-chloro-1,3,5-triazin-2-yl)morpholine [47]

A mixture of [46] (2.0 g) and phosphorous oxychloride (6 ml) was refluxed in The presence of N,N-dimethylaniline (0.6 ml) for 5 h. The reaction mixture was allowed to cool to room temperature and poured into ice cold water with stirring. The precipitate obtained was filtered, washed with distilled water and purified on silica gel column chromatography using hexane/ethyl acetate (40:1) as eluent to afford compound [47] as a white solid in 45% yield.

ESIMS: 407 (M$^+$+1)

Scheme 10: Synthesis of N,N-dimethyl-4-((4-morpholino-6-(1-(tetrahydro-2H-pyran-2-yl)-1H-indazol-4-yl)-1,3,5-triazin-2-yl)methyl)piperazine-1-carboxamide [58] following Scheme 4

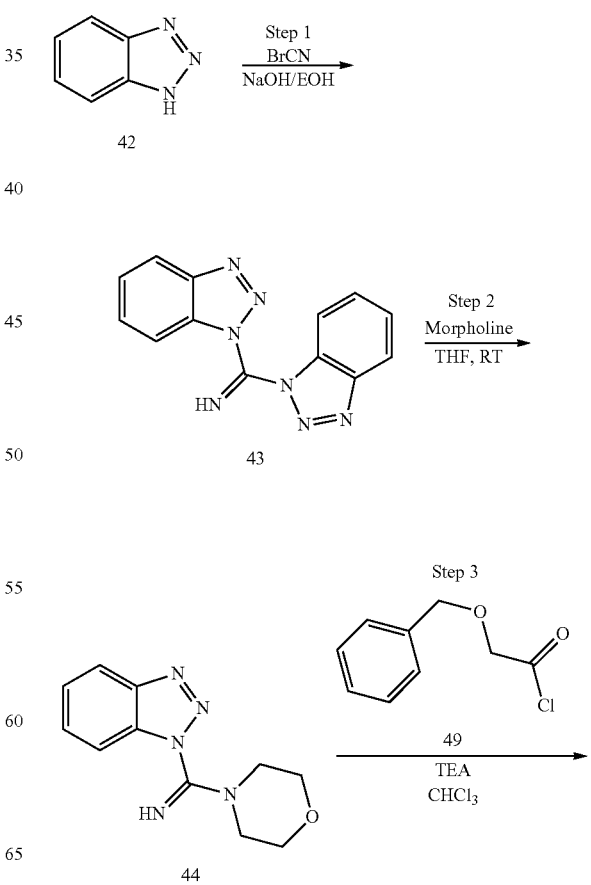

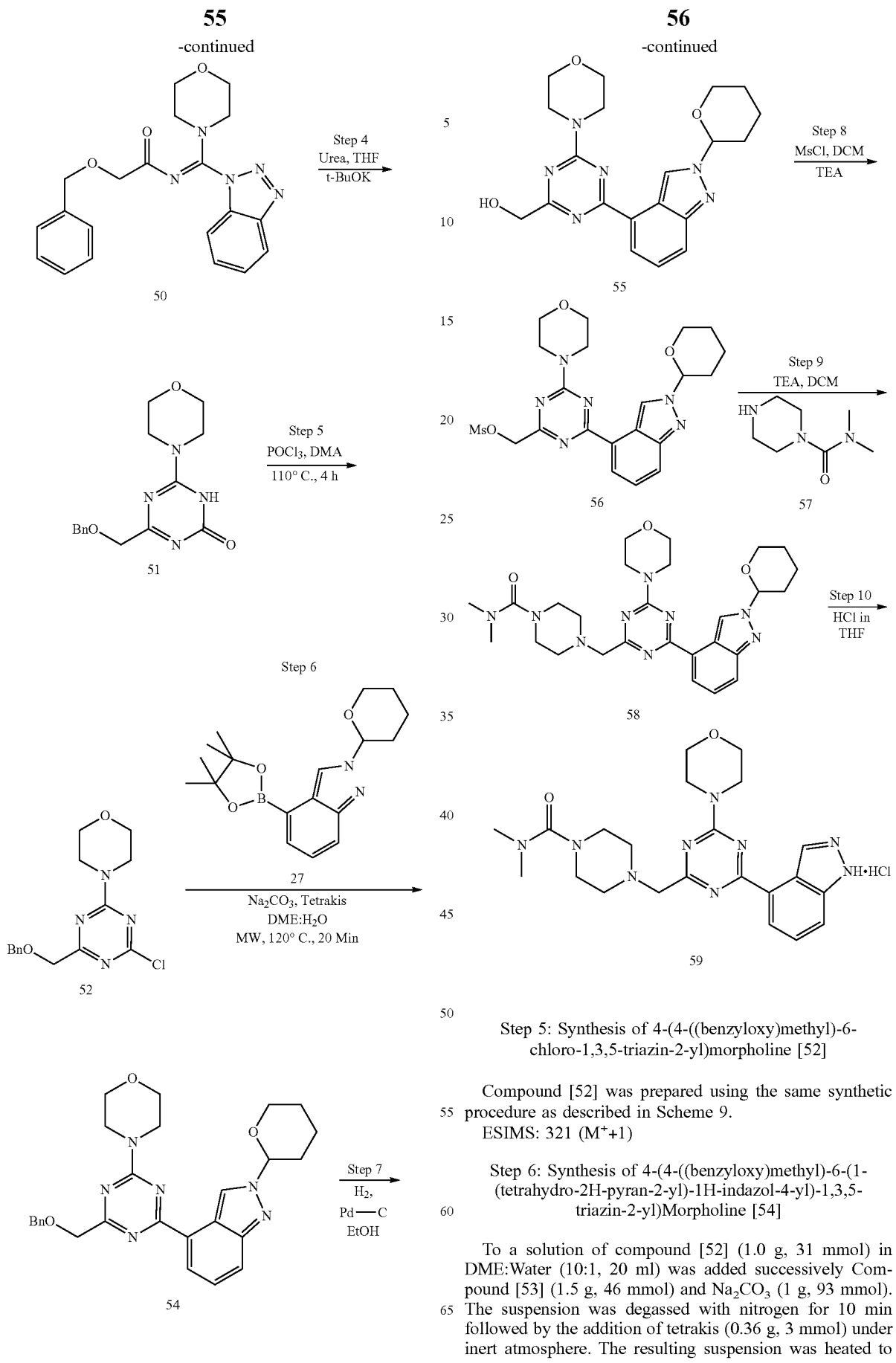

Step 5: Synthesis of 4-(4-((benzyloxy)methyl)-6-chloro-1,3,5-triazin-2-yl)morpholine [52]

Compound [52] was prepared using the same synthetic procedure as described in Scheme 9.
ESIMS: 321 (M⁺+1)

Step 6: Synthesis of 4-(4-((benzyloxy)methyl)-6-(1-(tetrahydro-2H-pyran-2-yl)-1H-indazol-4-yl)-1,3,5-triazin-2-yl)Morpholine [54]

To a solution of compound [52] (1.0 g, 31 mmol) in DME:Water (10:1, 20 ml) was added successively Compound [53] (1.5 g, 46 mmol) and Na₂CO₃ (1 g, 93 mmol). The suspension was degassed with nitrogen for 10 min followed by the addition of tetrakis (0.36 g, 3 mmol) under inert atmosphere. The resulting suspension was heated to 110° C. for 24 h. DME was removed under vacuum and extracted with 400 ml (200 ml×2) DCM, washed with brine and dried over sodium sulphate and evaporated to yield a viscous dark brown material which was purified on silica gel chromatography with 30% EtOAc:cyclohexane to afford compound [54] as a white solid in 46% yield.

ESIMS: 487 (M$^+$+1)

Step 7: Synthesis of (4-morpholino-6-(1-(tetra-hydro-2H-pyran-2-yl)-1H-indazol-4-yl)-1,3,5-tri-azin-2-yl)methanol [55]

To a solution of [54] in ethanol (10 ml) Pd—C was added under nitrogen atmosphere. The resulting black suspension was stirred at 45 psi for 4 h. The progress of the reaction was monitored by TLC. After complete conversion of starting material, the reaction mass was filtered through a celite bed and evaporated to afford crude compound [55] as a brown gel in 40% yield.

ESIMS: 398 (M$^+$+1)

Step 8: Synthesis of (4-morpholino-6-(1-(tetra-hydro-2H-pyran-2-yl)-1H-indazol-4-yl)-1,3,5-tri-azin-2-yl)methyl methanesulfonate [56]

To a cooled solution of compound [55] (70 mg, 17 mmol) in DCM (20 ml) at 0° C. TEA (0.1 ml, 68 mmol) was added dropwise and stirred it for 10 min followed by the addition of methane sulfonyl chloride (20 mg, 26 mmol). The reaction mixture was stirred at room temperature for 20 h. The progress of the reaction was monitored by TLC. The Reaction mixture was diluted with water (10 ml). The compound was extracted with DCM (50 ml). The DCM layer was washed with brine and dried over sodium sulphate and evaporated to get compound [56] as a viscous dark brown material in 8% yield.

ESIMS: 475 (M$^+$+1)

Step 9: Synthesis of N,N-dimethyl-4-((4-mor-pholino-6-(1-(tetrahydro-2H-pyran-2-yl)-1H-inda-zol-4-yl)-1,3,5-triazin-2-yl)methyl)piperazine-1-carboxamide [58]

To a cooled solution of compound [56] (30 mg, 6 mmol) in DCM (20 ml) at 0° C. TEA (0.25 ml, 18 mmol) was added dropwise and stirred for 10 min followed by the addition of compound [57] (20 mg, 12 mmol). The reaction mixture was stirred at room temperature for 20 h. The progress of the reaction was monitored by TLC. The reaction mixture was diluted with water (10 ml) and the compound was extracted by DCM (50 ml). The DCM layer was washed with brine and dried over sodium sulphate and evaporated to get viscous dark brown material which was purified on silica gel chromatography with 4% MeOH:DCM to afford compound [58] as a colorless gel in 80% yield.

ESIMS: 536 (M$^+$+1)

Step 10: Synthesis of 4-((4-(1H-indazol-4-yl)-6-morpholino-1,3,5-triazin-2-yl)methyl)-N,N-dimeth-ylpiperazine-1-carboxamide [59]

To a cooled solution of compound [58] (10 mg) in THF (5 ml) at 0° C. a stream of HCl gas was purged for 10 min. The resulting reaction mixture was stirred at RT for 1 h. The progress of the reaction was monitored by TLC. When completed, the reaction mass was evaporated to dryness. The residue was washed with diethyl ether (10 ml×2) to afford compound [59] as a white solid in 90% yield.

ESIMS: 452 (M$^+$+1)

General Schemes for the Synthesis of Aryl/heteroaryl boronates

The aryl/heteroaryl boronates may be synthesized by methods such as those represented in Scheme 11 or Scheme 12.

Scheme 11

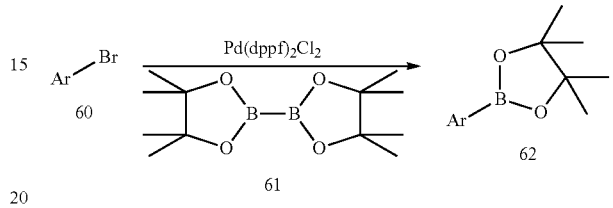

Aryl boronates [62] may be synthesized from corresponding aryl halides such as aryl bromides [60] using palladium catalysts such as [1,1'-bis(diphenylphosphino)ferrocene]palladium(II)chloride and a boronate source such as bis(pinacolato)-diboron [61] in a solvent such as DMSO at temperature varying from 40-100° C.

Scheme 12:

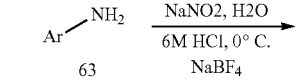

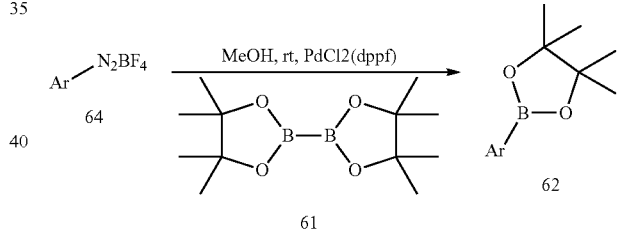

Aryl boronates [62] may also be synthesized from corresponding aryl amines [64] as shown in Scheme 12. An aryl amine [63] may be converted to corresponding diazonium tetrafluoroborate salt [64] by treating with reagents such as aqueous sodium nitrite and hydrochloric acid. The corresponding diazonium tetrafluoroborate salt when reacted with a boronate source such as bis(pinacolato)-diboron in presence of a suitable palladium catalyst such as [1,1'-bis(diphenylphosphino)ferrocene]palladium(II)chloride in a solvent such as methanol at RT may provide aryl boronate [62].

Scheme 13: Synthesis of indazole boronate [23]

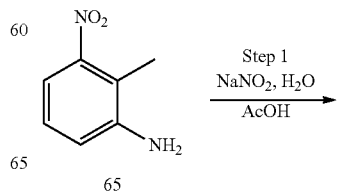

-continued

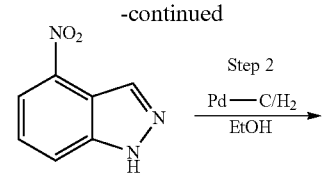

66

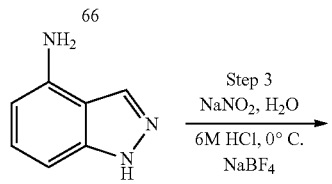

67

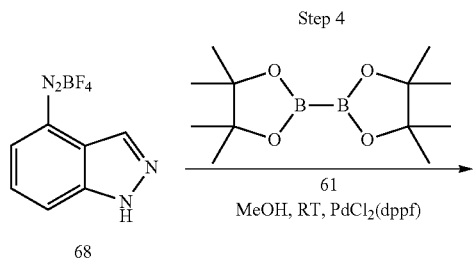

68

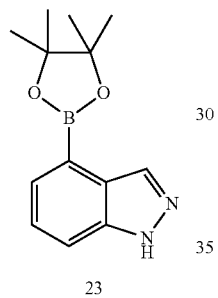

23

Step 1

Compound [65] (15.0 g, 0.099 mol) was dissolved in 375 ml glacial acetic acid in a 500 ml round bottom flask. An aqueous solution of sodium nitrite (8.16 g, 0.12 mol, in 35 ml of water) was added to it. The reaction mixture was stirred for 2 hrs at RT. TLC monitoring showed complete consumption of starting material. Reaction was ceased by the addition of ice-cold water, solid thus formed was filtered and dried well to afford yellowish solid [66] (10.0 g, 62%).

Step 2

Compound [66] (10.0 g) was suspended in ethyl alcohol (160 ml). The reaction mixture was charged with Pd—C (10%) (600 mg, 6% wt. by wt.) under nitrogen atmosphere. It was then allowed to stir at RT overnight under hydrogen atmosphere. TLC showed consumption of starting material. The reaction was worked up by filtering the reaction mass through celite and concentrated to afford [67] (7.9 g, 96%).

ESIMS: 134 ($M^+$+1)

Step 3

To compound [67] (6.0 g, 0.045 mol) was added 6 M HCl (70 ml) at −5° C. followed by drop wise addition of an aqueous solution of sodium nitrite (3.42 g, 0.049 mol, in 11 ml water). The reaction mixture was stirred at −5° C. for 30 min followed by addition of sodium tetrafluoroborate (7.4 g, 0.0675 mol). The reaction mixture was stirred for another 10 min and filtered using filter paper and dried well to yield crude [68] (6.0 g).

ESIMS: 163 ($M^+$+1)

Step 4

To a solution of compound [68] (6.0 g, 0.026 mol) in degassed MeOH (110 ml), bis(pinacolato)-diboron (6.604 g, 0.026 mol) was added followed by addition of [1,1′-bis (diphenylphosphino)ferrocene] palladium(II)chloride (546 mg). The reaction mixture was stirred at RT for overnight. After complete consumption of starting material, the reaction mixture was passed through celite and the organic layer obtained was concentrated to afford a crude product which was further purified using 100-200 mesh silica column and EtOAc-Cyclohexane as eluent to afford [23] (2.9 g, 40%).

ESIMS: 245 ($M^+$+1)

Scheme 14: Protection of Compound Indazole boronate [23]

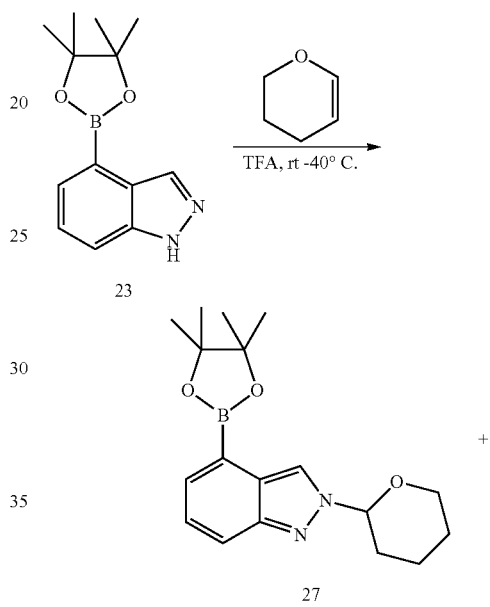

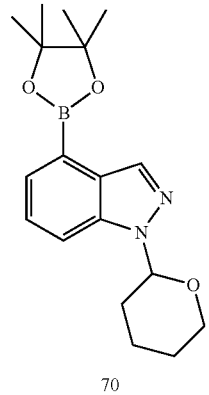

70

Compound [23] was dissolved in 25 ml of ethyl acetate in a two neck 100 ml round bottom flask followed by addition of 3,4-dihydro-2H-pyran. The reaction mixture was stirred for 10 min followed by addition of a catalytic addition of TFA. The reaction mixture was stirred overnight. Consumption of the starting material was monitored using TLC (20% ethyl acetate in hexane). After the complete addition of starting material, the reaction mixture was washed with water (2×25 ml). Organic layer was dried over anhydrous sodium sulfate and concentrated under reduced pressure to yield a crude product, which was a mixture of two regioisomers ([27] and [70]). Column purification of the crude product using silica gel column afforded a major regioisomer [27] as pure product (4.5 g, 85%).

ESIMS: 328 (M++1)

Scheme 15: Di-t-butyl(5-(4,4,5,5-tetramethyl-1,3,2-dioxaborolan-2-yl)pyridin-2-yl)dicarbamate [72]

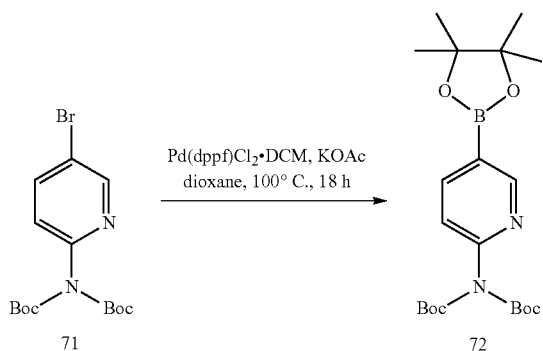

Compound [71] (1.0 g, 2.68 mmol) was dissolved in 1,4-dioxane (30 ml) in a clean oven-dried two necked RB flask (250 ml) and degassed with nitrogen. To this clear solution, bis(pinnacaloto)-diboron (0.82 g, 3.2 mmol) was added, followed by potassium acetate (0.79 g, 8.04 mmol) and [1,1'-bis(diphenylphosphino)ferrocene]palladium(II)chloride with dichloromethane (0.22 g, 2.6 mmol). The reaction mixture was stirred and heated at 100° C. for 18 h, under nitrogen atmosphere. The reaction was monitored by TLC. The reaction mixture was filtered through celite and was washed well with ethyl acetate. The filtrate was extracted with ethyl acetate (2×30 ml). The organic extracts were combined, washed with brine and dried using $Na_2SO_4$. The organic layer was evaporated to afford 5 as black oil (1.1 g) which was washed with ether to yield compound [72] (1 g, 89%) as a brown solid.

ESIMS: 421 (M++1)

Scheme 16: Synthesis of 4-(4,4,5,5-tetramethyl-1,3,2-dioxaborolan-2-yl)-1H-indole [74]

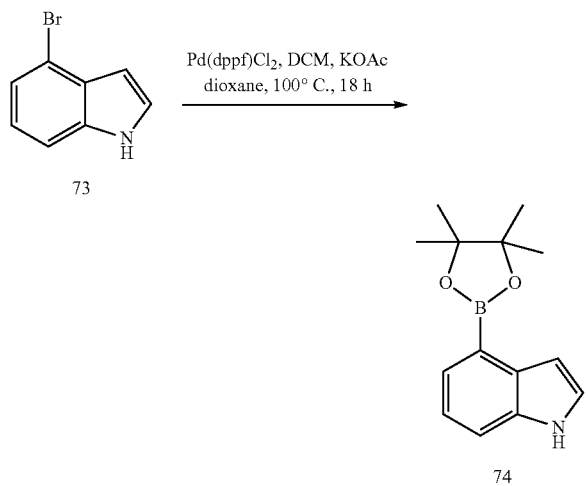

Compound [73] (1 g, 2.68 5.1 mmol) was dissolved in 1,4dioxane (30 ml) in a clean oven-dried two necked RB flask (250 ml) and degassed with nitrogen. To this clear solution, bis(pinnacaloto)-diboron (1.64 g, 6.12 mmol) was added, followed by potassium acetate (1.5 g, 15.3 mol) and [1,1'-bis(diphenylphosphino)ferrocene]palladium(II)chloride with dichloromethane (0.43 g, 0.51 mmol). The reaction mixture was stirred under a nitrogen atmosphere and heated at 100° C. for 18 h. The reaction was monitored by TLC. The reaction mixture was filtered through celite, washed well with ethyl acetate, the filtrate was then extracted with ethyl acetate (2×30 ml). The organic extracts were combined, washed with brine and dried over $Na_2SO_4$. The organic layer was then evaporated to give [74] as a crude black oil (1.2 g) which was washed with ether to yield [74] (0.9 g, 72%) as a brown solid.

ESIMS: 244 (M$^+$+1)

Scheme 17: Synthesis of tert-butyl 4-(4,4,5,5-tetramethyl-1,3,2-dioxaborolan-2-yl)-1H-pyrrolo[2,3-b]pyridine-1-carboxylate [77]

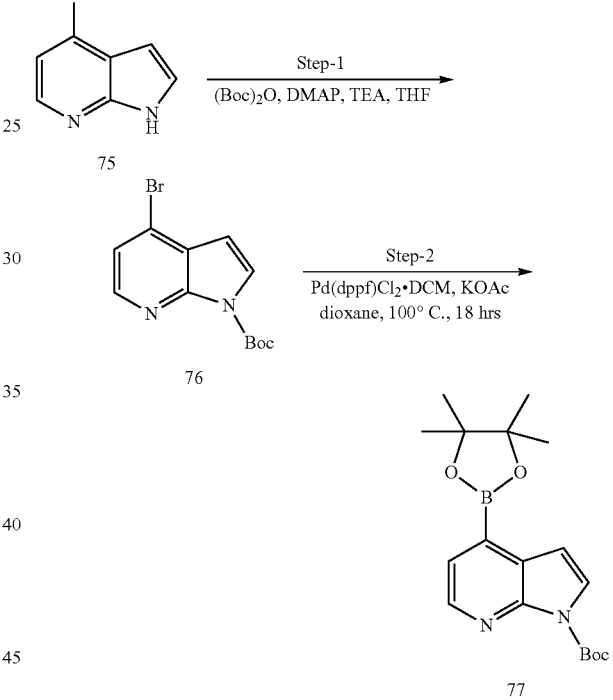

Step 1

Compound [75] (1.0 g, 5.1 mmol) was dissolved in THF (30 ml) and the temperature brought down to 0° C. with an ice bath. To this reaction mixture TEA (1.41 ml, 10.2 mmol), followed by BOC anhydride (1.33 g, 6.2 mmol) was added. A catalytic amount of DMAP (50 mg) was then added. This reaction mixture was then allowed to stirred and refluxed under nitrogen at 70° C. for 18 h. TLC and mass spectral analysis confirmed completion of the reaction. The reaction mixture was diluted with ethyl acetate (30 ml) which was washed with water and brine solution. The organic layers were combined, dried using anhydrous $Na_2SO_4$, filtered, and evaporated to yield [76] as a brown solid (1.3 g, 87%).

ESIMS: 298 (M$^+$+1)

Step 2

Compound [76] (1.3 g, 4.37 mmol) was dissolved in 1,4-dioxane (30 ml) in a clean oven-dried two necked RB flask (250 ml) and degassed with nitrogen. To this clear solution, bis(pinnacaloto)-diboron (1.3 g, 5.24 mmol) was added, followed by potassium acetate (1.28 g, 813.11 mmol) and [1,1'-bis(diphenylphosphino)ferrocene]palladium(II) chloride with dichloromethane (0.37 g, 0.437 mmol). The reaction mixture was stirred and heated at 100° C. for 18 h, under a nitrogen atmosphere. The reaction was monitored by TLC. Upon completion of the reaction, the reaction mixture was filtered through celite, washed well with ethyl acetate. The filtrate was extracted with ethyl acetate (2×30 ml). The organic extracts were combined, washed with brine and dried over Na$_2$SO$_4$, filtered and evaporated under vacuum to give [77] as dark brown solid (1.3 g), which upon further washing with ether yielded [77] as a brown solid (1.15 g, 76%).

ESIMS: 345 (M$^+$+1)

Scheme 18: Synthesis of heteroaryl organotin reagent [82,87,90]

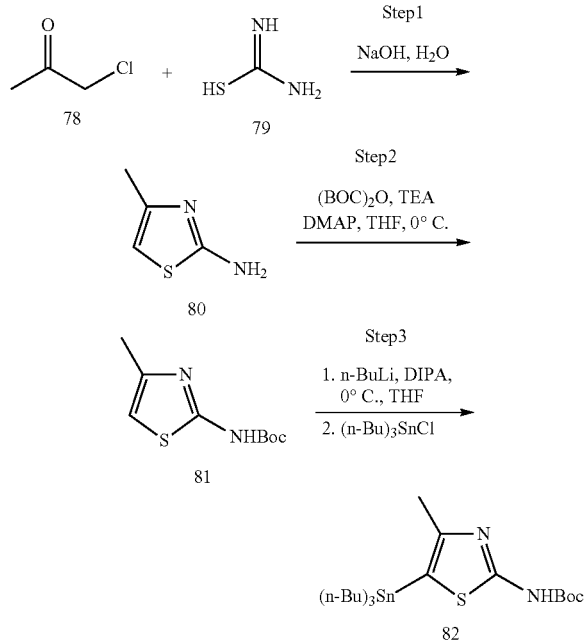

Step 1

To a solution of thiourea [79] (5.0 g, 0.065 mol, 1 eq.) in water (100 mL), chloroacetone [78] (6.08 g, 0.065 mol, 1 eq.) was added dropwise. The brown colored solution was refluxed for 2 hrs. then cooled in an ice bath. Afterward, NaOH (10 g, 0.25 mol) was added with cooling in an ice bath. The emulsion was extracted with ether (3×100 mL), to yield compound [80] (5.5 g, 73% yield) as brown solid.

ESIMS: 115 (M$^+$+1)

Step 2

Compound [80] (5.0 g, 0.044 mol, 1 eq.) was dissolved in THF (100 ml) and cooled to 0° C. TEA (7.32 ml, 0.052 mol, 1.2 eq.) was added dropwise followed by DMAP (0.100 g, 0.81 mmol). (BOC)$_2$O (10.50 g, 0.048 mol, 1.1 eq.) was added dropwise. The mixture was stirred at 0° C. for 16 hrs. After completion of the reaction, 100 ml of water was added, and the reaction mass was extracted with 3×100 ml EtOAc (3.×100 ml). The EtOAc layers were combined, washed with brine, dried over anhydrous and concentrated to give crude. The product was purified with column silica gel chromatography with DCM to obtain compound [81] as a pale yellow solid (5.60 g, 60% yield).

ESIMS: 215 (M$^+$+1)

Step 3

Compound [81] (1.0 g, 4.65 mmol) was dissolved in THF and cooled to −78° C. Freshly prepared LDA (2.1 eq.) was added to it and mixture was stirred for 1 hrs. (n-Bu)$_3$SnCl (1.51 g, 4.65 mmol, 1 eq.) was added dropwise and resulting mixture was stirred for 24 h. After completion of reaction 100 ml of aqueous saturated NH$_4$Cl was added and reaction was extracted with 3×100 ml EtOAc. The EtOAc layer was combined, washed with brine, dried over sodium sulphate and concentrated to obtain compound [82] as brown solid (2.02 g, 85% yield).

ESIMS: 504 (M$^+$+1)

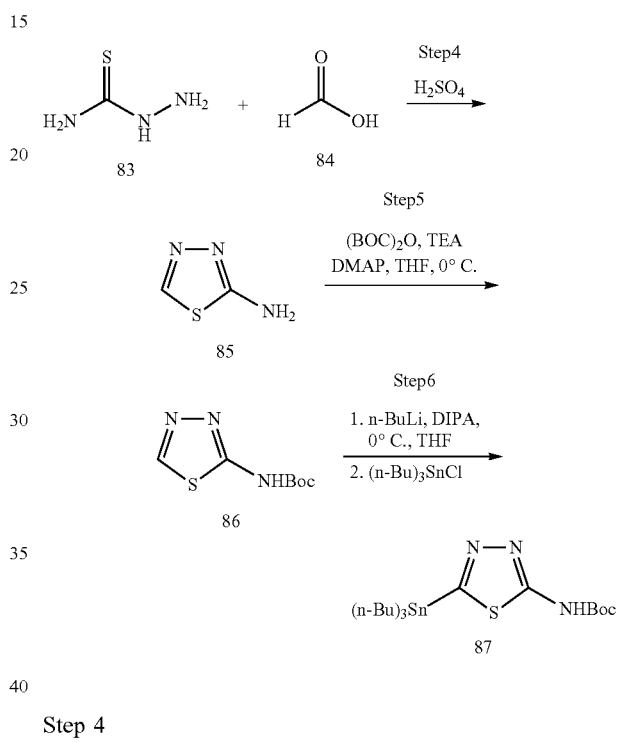

Step 4

To the sulfuric acid (24 ml) in a round bottom flask, formic acid [84] (14 ml) was added dropwise at 0° C. While effervescence occurred, the mixture was stirred for 30 min at 0° C. Temperature was then increased to 10-15° C. and thiosemicarbazide [83] (18.2 g, 0.2 mol) was added portionwise. The mixture was then heated at 95° C. for 4 h. The solution became transparent, shifted to RT, poured into ice-water mixture and basified (pH 8) with liq. Ammonia, while temperature should be maintained at 10° C. The reactions proceeds through compounds [85] and [86]. The product was obtained as white solid, filtered, dried and recrystallized from hot methanol to obtain compound [87] (5.74 g, 28% yield) as white solid.

ESIMS: 102 (M$^+$+1)

Step 5

Compound 1861 (white solid) was synthesized using the same procedure as for compound [81] (Step 2).

ESIMS: 202 (M$^+$+1)

Step 6

Compound [87] (brown solid) was synthesized using the same procedure as for compound [81] (Step 2).

ESIMS: 491 (M$^+$+1)

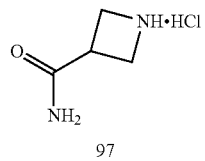

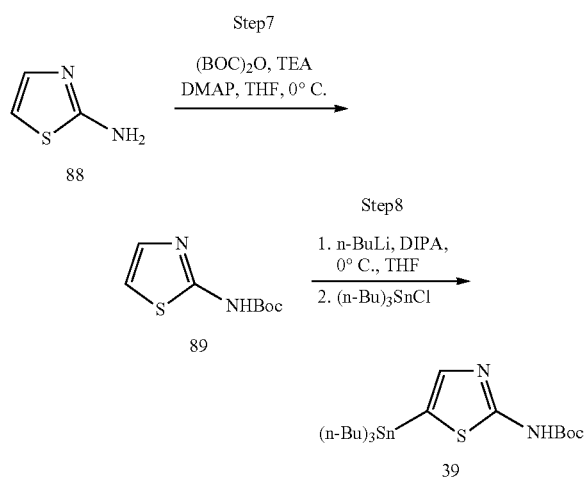

Step 7
Compound [89] (white solid) was synthesized using the same procedure as for compound [81] (Step 2).
ESIMS: 201 (M⁺+1)

Step 8
Compound [39] (brown solid) was synthesized using the same procedure as for compound [81] (Step 2).
ESIMS: 490 (M⁺+1)

Scheme 19: Synthesis of azetidine alcohol and azetidine-3-carboxamide

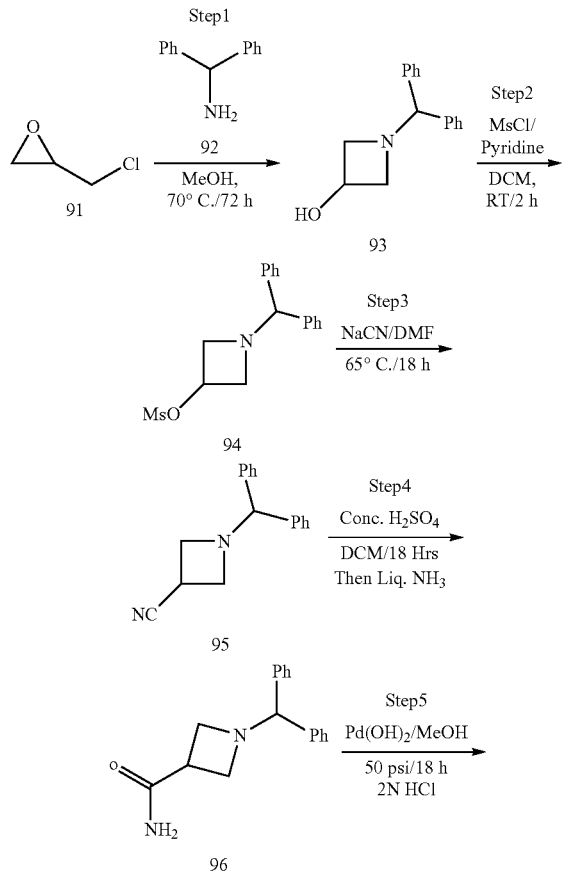

Step 1
To a stirred solution of epichlorohydrin [91] (11.3 g, 13.9 mmol) in methanol (50 ml), α-amino-diphenylmethane [92] (25 g, 13.9 mmol) was added dropwise under at room temperature. The resulting solution was refluxed at 70° C. for 72 h. The progress of the reaction was monitored by TLC. After 72 h, the solvent was evaporated under vacuum. The residual solid was washed with 1000 ml of diethyl ether. The resulting residue was purified by column chromatography over 100-200 mesh silica using 2% MeOH:DCM as eluent to gave 1-benzhydrylazetidin-3-ol [93] as a white solid (14.1 g, 41%).
ESIMS: 240 (M⁺+1)

Step 2
To a suspension of 1-benzhydrylazetidin-3-ol [93] (5.0 g, 2 mmol) in DCM (50 ml), pyridine (8.26 ml, 10 mmol) were slowly added at 0° C. under inert atmosphere. After the addition was complete, the suspension dissolved was stirred at 0° C. for 20 min, then methane sulphonyl chloride (2.5 ml, 15 mmol) was added to the solution and stirred at RT for 2 h. The progress of the reaction was monitored by TLC. Reaction mixture was quenched with water (150 ml) and extracted with DCM (500 ml×2). The DCM layer was washed with brine (100 ml×2), dried over anhydrous Na₂SO₄ and evaporated to yield a yellow gel. The product was purified by column chromatography over 100-200 silica mesh using 1% MeOH:DCM as eluent to give 1-benzhydrylazetidin-3-yl methane sulfonate [94] as a white solid (4.3 gm, 65%).
ESIMS: 318.1 (M⁺+1)

Step 3
To a solution of 1-benzhydrylazetidin-3-yl methanesulfonate [94] (3.5 g, 11 mmol) in DMF (50 ml), NaCN (1.35 g, 27.6 mmol) dissolved in 20 ml of water was added dropwise using a dropping funnel at RT under inert atmosphere. After the addition was complete, the solution was heated to 65° C. and kept at temperature for 16 h. The progress of the reaction was monitored by TLC. The reaction mass was quenched with water (150 ml) and extracted with EtOAc (400 ml×2). EtOAc layer was washed with brine (100 ml×1), dried over anhydrous Na₂SO₄ and evaporated to yield a yellow solid. The product was purified by column chromatography over 100-200 silica mesh using 10% EtOAc:cyclohexane as eluent to gave 1-benzhydrylazetidine-3-carbonitrile [95] as a white solid (2.02 g, 74%).
ESIMS: 249 (M⁺+1)

Step 4
To a solution of 1-benzhydrylazetidine-3-carbonitrile [95] (1.9 g, 7.7 mmol) in DCM (40 ml), concentrated H₂SO4 (4.9 ml, 91.0 mmol) was added drop wise using a dropping funnel at 0° C. under inert atmosphere. After the addition was complete, the solution was stirred at RT for 18 h, afterward the reaction mixture was cooled to 0° C. liquid ammonia was added dropwise while maintaining the reaction temperature below 20° C. at pH~10. The reaction mixture was extracted with DCM (100 ml×2). The DCM layer was then washed with brine (100 ml×1), dried over anhydrous Na$_2$SO$_4$ and evaporated under pressure to yield 1-benzhydrylazetidine-3-carboxamide [96] as a white solid (1.70 g, 85%).

ESIMS: 267 (M$^+$+1)

Step 5

To a solution of 1-benzhydrylazetidine-3-carboxamide [96] (1.5 g, 56 mmol) in MeOH (10 ml) was added Pd(OH)$_2$ (0.3 g, 30% by weight). The resulting mixture was hydrogenated under a hydrogen atmosphere in a Parr shaker at 50 psi for 18 h. The progress of the reaction was monitored by TLC. After completion of the reaction 2 N HCl (15 ml) was added and stirred the reaction mass for 10 min at RT. Pd(OH)$_2$ was removed using celite. The filtrate was diluted with diethyl ether (100 ml) and discarded. The aqueous layer was evaporated by azeotropic mixture with ethanol under reduced pressure to yield a brown gel. This brown gel was triturated with n-hexane to produce azetidine-3-carboxamide hydrochloride [97] as a white solid (0.73 g, 93%).

ESIMS: 101.3 (M$^+$+1)

hexane as eluent to yield 1-benzhydryl-3-methoxyazetidine [94A] as a white solid (2.37 g, 45%).

ESIMS: 254.37 (M$^+$+1)

Step 3

To a solution of 1-benzhydryl-3-methoxyazetidine [94] (1.0 g, 56 mmol) in MeOH (10 ml) was added Pd(OH)$_2$ (0.3 g, 30% by weight). The resulting mixture was hydrogenated under hydrogen atmosphere in a Parr shaker at 50 psi for 18 h. The progress of the reaction was monitored by TLC. After completion of the reaction, 2 N HCl (15 ml) was added and stirred for 10 min at RT. Pd(OH)$_2$ was filtered out using celite. The filtrate was diluted with diethyl ether (100 ml) which was subsequently separated out and discarded. The aqueous layer was evaporated under reduced pressure by making an azeotropic mixture with Ethanol to produce a brown gel. This brown gel was triturated with n-hexane to yield 3-methoxyazetidine hydrochloride [98] as a white solid (0.73 g, 93%).

ESIMS: 124.3 (M$^+$+1)

Scheme 20: Synthetic of 3-Methoxy-azetidine [98]

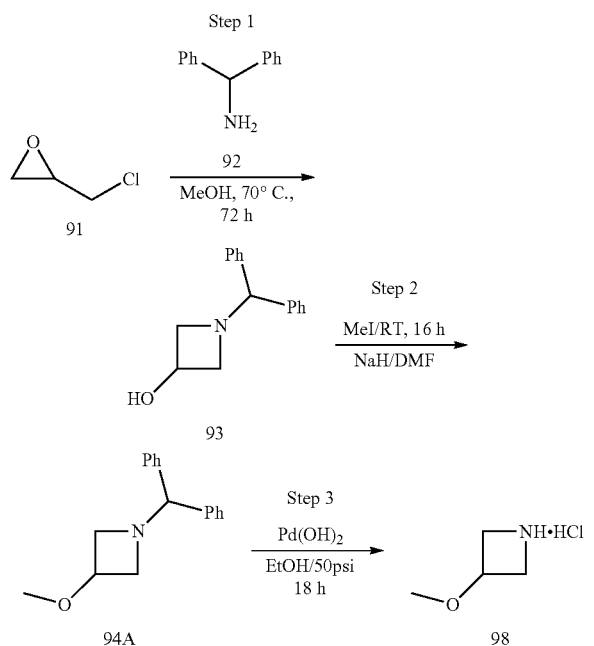

Step 1

[93] was synthesized using the procedure described in Scheme 19 [Step 1].

Step 2

To a suspension of 1-benzhydrylazetidin-3-ol [93] (5.0 g, 2 mmol) in DCM (50 ml), NaH (2.09 g, 5 mmol, 60% suspension) was slowly added at 0° C. under inert atmosphere. After the addition was complete, the suspension dissolved, was stirred at 0° C. for 20 min, then to this was added MeI (2.5 ml, 15 mmol) and the solution was stirred at RT for 12 h. The progress of the reaction was monitored by TLC. The reaction mixture was quenched with water (150 ml) and the compound was extracted with DCM (500 ml×2). The DCM layer was washed with brine (100 ml×2), dried over anhydrous Na$_2$SO$_4$, evaporated to produce a yellow gel. The product was purified by column chromatography over 100-200 silica mesh using 15% ethyl acetate:cyclo- Scheme 21: Synthesis of (1R,5S)-3-oxa-6-azabicyclo[3.1.0]hexane [103]

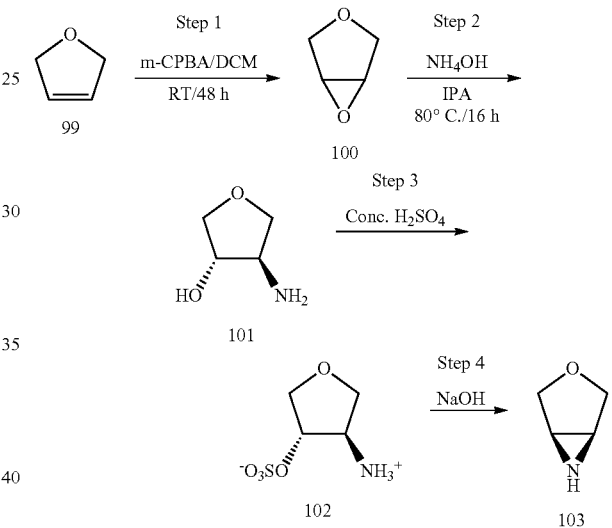

Step 1

To a stirred solution of 3,4-dihydro-2H-Pyrane 1991 (5.0 g, 72 mmol) in DCM (150 ml), m-CPBA (18.86 g, 93 mmol) was added portionwise under stirring at 0° C. The resulting white precipitate was stirred at RT for 72 h. The progress of the reaction was monitored by TLC. After 72 h, the precipitate was removed by filtration, and the organic layer was washed with saturated aqueous Na$_2$S$_2$O$_3$ (100 ml×2) followed by saturated aqueous NaHCO$_3$ solution (100 ml×1). The DCM layer was dried over anhydrous Na$_2$SO$_4$, evapourated to yield 3,6-dioxabicyclo[3.1.0]hexane [100] as a colorless gel (2.80 g, 43%) and used directly in the next step.

Step 2

Liquid NH$_3$ was added to a stirred solution of 3,6-dioxabicyclo[3.1.0]hexane [100] (1.0 g, 11 mmol) in IPA (10 ml) a sealed tube. The reaction mixture was heated 80° C. for 16 h. The progress of the reaction was monitored by TLC. After 16 h, the reaction vessel was cooled to RT and solvent was evaporated on vacuum to yield a brown gel. The crude gel product was washed with n-hexane (50 ml) followed by diethyl ether (50 ml), to yield (3S,4R)-4-aminotetrahydrofuran-3-ol [101] as a light brown gel (0.90 g, 75%).

ESIMS: 104.2 (M$^+$+1)

Step 3

A solution of 5.3 ml of concentrated sulfuric acid in 100 ml of water was added with cooling and stirring to a solution of (3S,4R)-4-aminotetrahydrofuran-3-ol [101] (10.1 g) in water (20.0 ml). The water was removed by distillation at reduced pressure and the residue was heated for 20 min at 100° C. and 2 mm Hg yielding [102] as a brown solid (17.60 g, 97.8% yield).

Step 4

To a solution of sodium hydroxide (50.0 g) in water (120 ml) was added (3S,4R)-4-ammoniotetrahydrofuran-3-yl sulfate [102] (100 g). The reaction mixture was stirred, gradually heated to boiling, and distilled. The distillate was collected in an ice-cooled flask containing ether (250 ml) and solid sodium hydroxide (25 g). The ether extract was separated and isolated. The aqueous phase was further extracted with two additional portions of ether (300 ml). The combined ether extracts were dried first over sodium hydroxide, then over sodium metal, and finally distilled yielding the product [103] as a colorless liquid (23.0 g, 49%).

Scheme 22: Synthesis of 1,4-oxazepane [108]

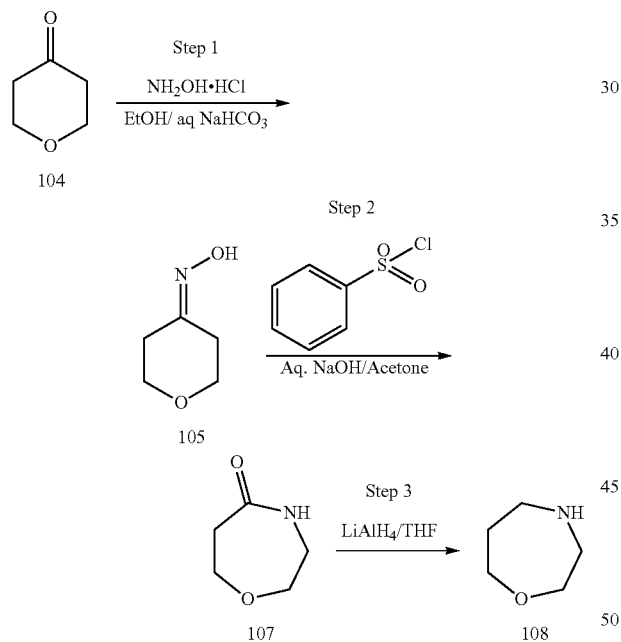

Step 1

Hydroxylamine hydrochloride (0.83 g, 0.012 mol) and sodium bicarbonate (2.52 g, 0.03 mol) were mixed together in a dried two neck round bottom flask followed by addition of ethanol (12 ml) and compound [104] (1.0 g, 0.009 mol) drop wisely at 0° C. The reaction mixture was stirred at RT for 2 h monitoring its progress by TLC. After complete consumption of starting material, the ethanol was evaporated followed by addition of water. The reaction mixture was extracted using EtOAc (3×50 ml), organic layers were combined dried over sodium sulphate and concentrated to gave dihydro-2H-pyran-4(3H)-one oxime [105] (700 mg, 61%).

ESIMS: 116 (M$^+$+1)

Step 2

Dihydro-2H-pyran-4(3H)-one oxime [105] (1 g, 8.7 mmol) was dissolved in acetone (20 ml) in a dry two neck round bottom flask. The reaction mixture was cooled to 0° C. followed by addition of benzene sulfonyl chloride[106] (9.6 mmol) and stirred for 15 min; after which was added dropwise 2.5 N NaOH (384 mg, 9.6 mmol). The reaction mixture was stirred at RT overnight. TLC showed complete consumption of starting material. The excess of solvent was removed under reduced pressure on rotary evaporator to yield a white solid. The product was purified by column chromatography over 100-200 silica mesh using 5% MeOH:DCM as eluent to gave 1,4-oxazepan-5-one [107] as a light yellow solid (0.4 g, 40%).

ESIMS: 116.2 (M$^+$+1)

Step 3

LAH powder (329 mg, 8.66 mmol) was placed in a clean and dried two necked round bottom flask and dry THF (7 ml) was added dropwise followed by addition of 1,4-oxazepan-5-one [107] (500 mg, 4.33 mmol pre-dissolved in 5 ml THF) at 0° C. under nitrogen atmosphere. The reaction mixture was stirred at RT for 5-6 h and quenched with a mixture of cold water (0.4 ml) and 10% aqueous NaOH (0.8 ml) followed by extraction with EtOAc (20 ml). The organic layer was passed through celite and concentrated under reduced pressure on a rotor evaporator to afford 1,4-oxazepane [108] as a colorless gel (0.35 g, 80%).

ESIMS: 102 (M$^+$+1)

Scheme 23: Synthesis of 3-hydroxy-N,N-dimethylbenzamide [112]

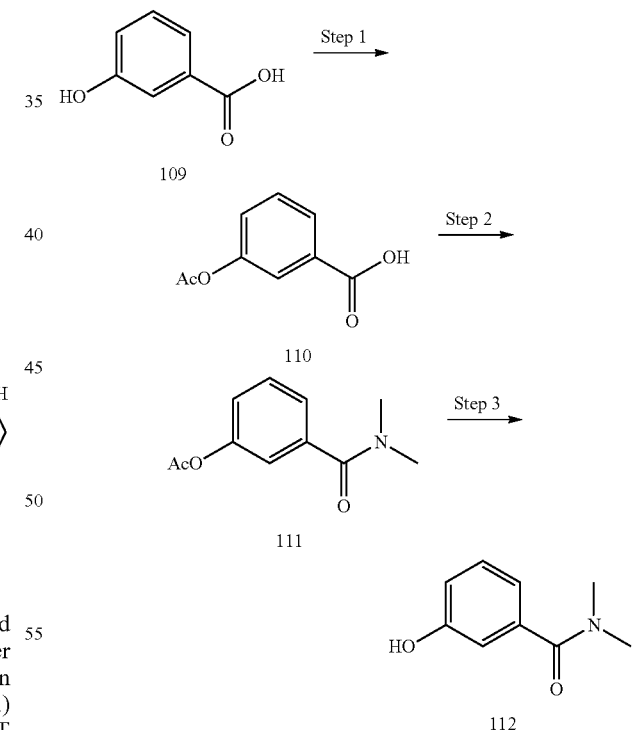

Step 1

Acetic anhydride (10 ml) was added dropwise to a cooled solution of [109] (2 g, 1 eq) in pyridine (20 ml), and stirred at RT for 4 h. The reaction mixture was cooled and poured over crushed ice. The white precipitate formed was collected by filtration, washed with diethyl ether (50 ml) and dried to afford [110] as a white solid (2.0 g, 77%).

ESIMS: 181 (M⁺+1)

Step 2

To a clean dried 100 ml two neck round bottom flask was added [110] (2.0 g, 1 eq) in DCM (25 ml). DMF (4 drops) was added to the solution and cooled to 0° C. followed by the addition of oxalyl chloride (3.0 ml, 3.0 eq). The resulting solution was stirred at RT for 4 h. After completion of the reaction, excess oxalyl chloride was evaporated on a rotary evaporator under nitrogen atmosphere to yield the corresponding acid chloride as a brown solid (2.16 gm, 100%). The resulting brown solid was dissolved in DCM (50 ml) and cooled to 0° C. followed by the addition of a 2.0 M solution of dimethyl amine in THF (11.2 ml, 2.0 eq) and stirred it for 20 h at RT. The progress of the reaction was monitored by TLC. The reaction was quenched with addition of a brine solution (50 ml) and extracted the compound by DCM (100 ml×2). The DCM layer was dried over Na₂SO₄ and evaporated to provide the product [111] as a white solid (1.6 g, 69%).

ESIMS: 208 (M⁺+1)

Step 3

[111] (1.5 g, 1.0 eq) was dissolved in MeOH (20 ml) to which K₂CO₃ (3.0 g, 3 eq) was added. The resulting suspension was stirred at RT for 5 h. The progress of the reaction was monitored by TLC. After complete conversion, the solvent was removed under reduced pressure. The resulting solid was then extracted with 10% MeOH:DCM (100 ml×2). The organic layer was evaporated to yield [112] as a white solid (0.8 g, 68%).

ESIMS: 165 (M⁺+1)

Scheme 24: Synthesis of 4-hydroxy-N,N-dimethylbenzamide [116]

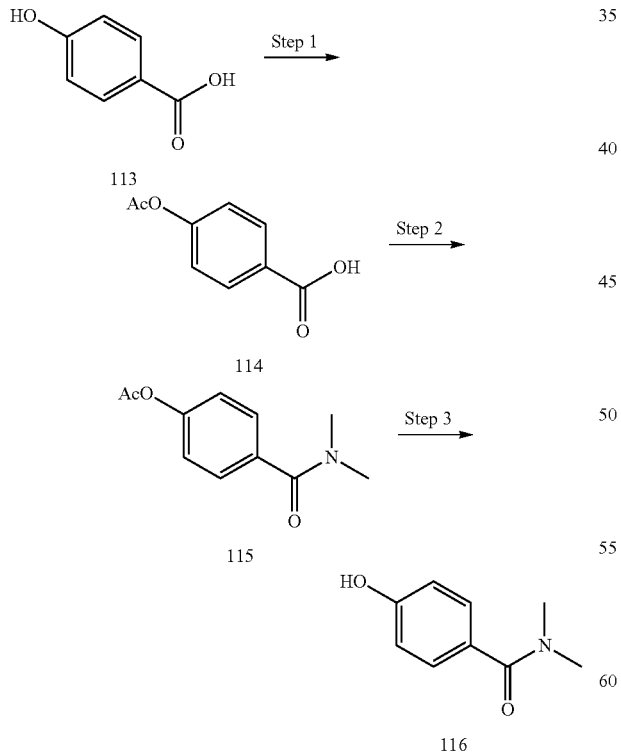

[116] was synthesized using the procedure described in Scheme 23.

ESIMS: 165 (M⁺+1)

Scheme 25: Synthesis of 2-(3-hydroxyphenyl)-N,N-dimethylbenzamide [120]

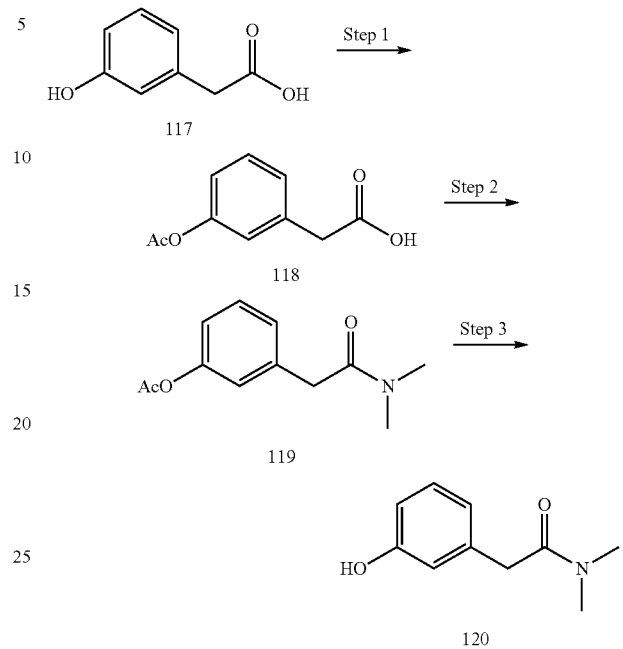

[120] was synthesized using procedure described in Scheme 23.

ESIMS: 180 (M⁺+1)

Scheme 26: Synthesis of 2-(4-hydroxyphenyl-N,N-dimethylacetamide [124]

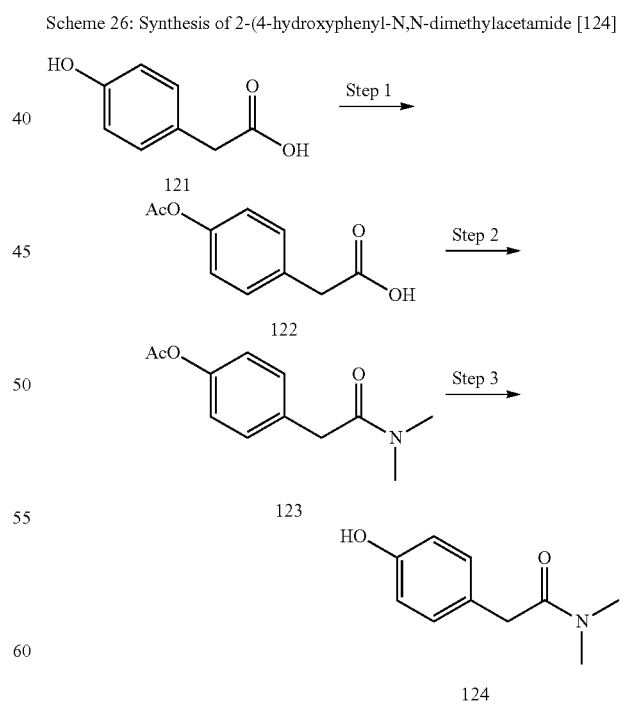

[124] was synthesized using procedure described in Scheme 23.

ESIMS: 180 (M⁺+1)

Scheme 27: Synthesis of (1s,4s)-4-hydroxy-N,N-dimethylcyclohexanecarboxamide [128]

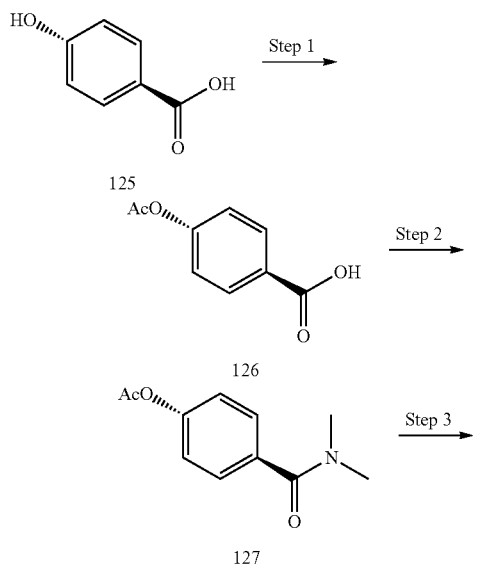

[128] was synthesized using procedure described in Scheme 23.
ESIMS: 172 (M$^+$+1)

Scheme 28: Synthesis of (1-methylsulfonyl)piperidin-4-yl)methanol [131]

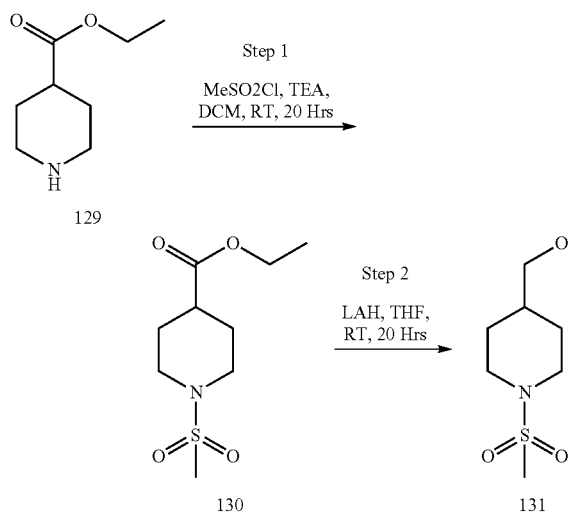

Step 1
To a cooled solution of compound [129] (10 g, 63 mmol) in DCM (120 ml) at 0° C., TEA (17.7 ml, 109 mol) was added dropwise and stirred it for 10 min followed by the addition of methane sulfonyl chloride (8.0 g, 70 mol). The reaction mixture was stirred at room temperature for 20 h. The progress of the reaction was monitored by TLC. The reaction mixture was diluted with water (100 ml) and extracted the compound with DCM (250 ml). The DCM layer was washed with brine, dried over sodium sulphate and evaporated to produce [130] as a white solid (60% yield).
ESIMS: 236 (M$^+$+1)

Step 2
Lithium aluminum hydride (0.8 g, 213 mmol) was dissolved in dry THF (60 ml) and cooled to 0° C. To this suspension [130] in 20 ml THF was added dropwise and stirred at RT for 20 h. The progress of the reaction was monitored by TLC. The reaction was quenched by ice cold water (10 ml) and passed through celite. The cellite bed was washed with methanol (15 ml×2). The filtrate was collected and evaporated to dryness. The resulting residue was dissolved in DCM (500 ml). The organic layer was washed with water (50 ml). The DCM layer was washed with brine, dried over sodium sulphate and evaporated to yield [131] as a white solid (76% yield).
ESIMS: 194 (M$^+$+1)

Scheme 29: Synthesis of 3-(hydroxymethyl)-N,N-dimethylpyrrolidine-1-carboxamide [134]

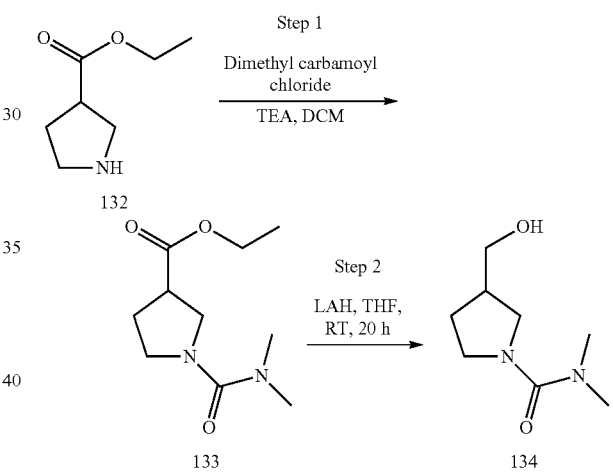

[134] was synthesized using procedure described in Scheme 28.
ESIMS: 173 (M$^+$+1)

Scheme 30: Synthesis of 3-(hydroxymethyl)-N,N-dimethylpyrrolidine-1-carboxamide [136]

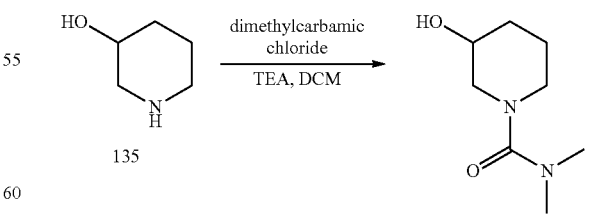

[136] was synthesized using procedure described in Scheme 28 (Step 1).
ESIMS: 173 (M$^+$+1)

Scheme 31: Synthesis of octahydro-1H-pyrrolo[3,4-c]pyridin-1-one [139]

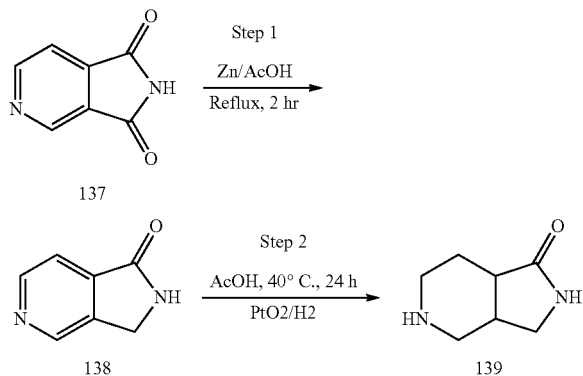

Step 1

To a solution of compound [137] (3 g, 20.2 mmol, 1 eq) in glacial acetic acid (30 ml), Zn dust (5.26 g, 81.0 mmol, 4 eq.) was added and the reaction mixture was refluxed at 100° C. for 4 h. The reaction mixture was cooled to room temperature and the solvent was evaporated. The reaction mass was made basic with aqueous NaHCO$_3$ to pH 8 and extracted with chloroform. The aqueous layer was concentrated and further extracted with chloroform. The combined organic layer was dried over Na$_2$SO$_4$ and evaporated to give [138] as a peach white solid (1.7 g, 62%).

ESIMS: 135 (M$^+$+1)

Step 2

[138] (2 g, 14.9 mmol, 1 eq) was placed in a Parr hydrogenation reactor with AcOH (20 ml) and PtO$_2$ (0.2 g). A hydrogen gas pressure of 60 PSI was applied and the reaction mixture was permitted to continue until a pressure of 26 PSI was measured. The reaction mixture was filtered, the solvent evaporated and dried to yield [139] (2 g, 96%).

ESIMS: 141 (M$^+$+1)

Scheme 31: Synthesis of 1,4-Diazepan-5-one

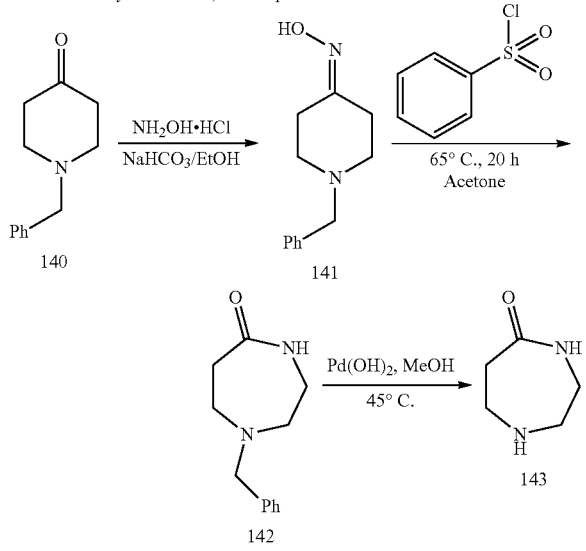

Step 1: Synthesis of 1-benzylpiperidin-4-one oxime [141]

To a clean and dried single necked round bottom flask was added hydroxylamine hydrochloride (3.08 g, 0.04 mol), sodium bicarbonate (9.32 g, 0.11 mol), and ethanol (120 ml) at 0° C. After 5 min compound [140] (7.0 g, 0.04 mol) was added dropwise at 0° C. The reaction mixture was brought to RT in 2 h. TLC analysis showed complete consumption of starting material. The reaction was worked up by removing the ethanol by distillation followed by addition of water (50 ml), extracted into EtOAc (3×150 ml), combined the organic layer which were dried over sodium sulphate and concentrated to yield [141] as a white solid (5.5 g, 72%).

ESIMS: 205 (M$^+$+1)

Step 2: Synthesis of 1-benzyl-1,4-diazepan-5-one [142]

To a clean and dried two necked round bottom flask [141] (2 g, 0.00976 mol) was dissolved in acetone (20 ml) and acetonitrile (20 ml). The reaction mixture was cooled to 0° C., and then to it 15% aqueous NaOH (1.2 ml) was added drop wise, followed by the addition of benzene sulphonyl chloride (1.49 ml, 0.011 mol). The reaction mixture was refluxed overnight. TLC showed complete consumption of SM. The reaction mixture was diluted with acetone, and passed through celite and concentrated. Saturated NaHCO$_3$ (50 ml) was added to the solid followed by extraction with EtOAc (3×150 ml), removal of the solvent under reduced pressure. The residue was purified by column chromatograph on silica gel with MeOH:DCM (1%) as an eluent to afford [142] as a white solid (600 mg, 30%).

ESIMS: 205 (M$^+$+1)

Step 3: Synthesis of 1,4-diazepan-5-one [143]

To a clean and dried two-necked RB flask taken compound [142] (600 mg, 2.93 mmol) was dissolved in MeOH (15 ml). Concentrated HCl (0.05 ml) and Pd(OH)$_2$ (120 mg) were added sequentially under a nitrogen atmosphere. The reaction mixture was heated to 45° C. under a hydrogen atmosphere and maintained at 45° C. overnight. The reaction was monitored by mass analysis. Crude compound [143] obtained was used as such for the next step (350 mg, crude).

ESIMS: 115 (M$^+$+1)

Scheme 33: Synthesis of (3aR,6aS)-tetrahydropyrrolo[3,4-c]pyrrole-1,3(2H,3aH)-dione [147]

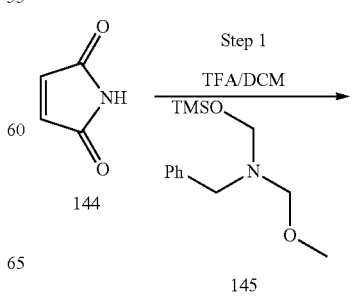

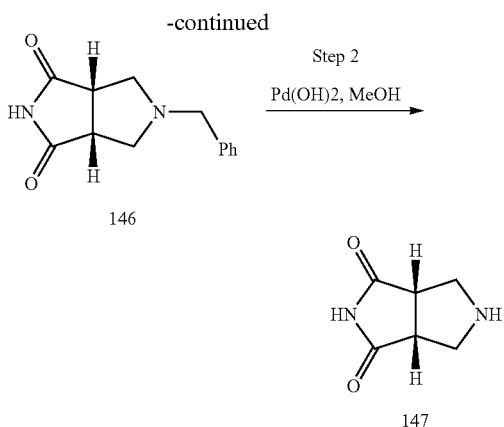

Step 1

A solution of N-(methoxymethyl)-N-(trimethylsilyl)benzylamine [145] (5 gm, 1 eq) in dichloromethane was added to an ice cooled mixture of maleimide [144] (1.7 gm, 0.9 eq.) and trifluoro acetic acid (0.1 eq) in dichloromethane dropwise over 30 min maintaining the reaction temperature between 0° C. to 5° C. The solution becomes yellow after complete addition of the reagents. The resulting bright yellow solution was allowed to warm gradually and stirred at room temperature for 24 h during which a solid precipitate forms. The mixture was diluted with dichloromethane and washed with saturated NaHCO$_3$ solution. The DCM layer was collected, dried over sodium sulphate and concentrated under vacuum to give a brownish oil. This residual oil was stirred with 10% EtOAc-heptane overnight (15 h). The resulting precipitate was filtered and washed by 10% EtOAc-heptane to provide [146] as a white solid in 40% yield.

Step 2

Pd(OH)$_2$ (0.3 gm, 30% by weight) was added to a solution of compound [146] in MeOH. The resulting mixture was kept under the pressure of a balloon filled with H$_2$. The reaction mixture was heated at 45° C. overnight. The reaction was monitored by TLC. After completion of reaction Pd(OH)$_2$ was filtered out by using celite pad. The filtrate was concentrated on buchi rotavapour under reduced pressure to afforded [147] as a white solid in 75% yield.

Certain Compounds of the Invention

Certain compounds of the invention that may be made using the schemes 1 to 33 or their equivalents thereof are presented at Table 1:

| Compound Number | IUPAC Name |
|---|---|
| 1001 | 4-8-{[4-1-(2-11-amino-1,3-thiazol-5-yl)-6-5-{3-oxa-8-azabicyclo[3.2.1]octan-8-yl}-1,3,5-triazin-2-yl]oxy}-N,N-dimethylbenzamide |
| 1002 | 4-9-{[4-1-(2-17-amino-1,3-thiazol-5-yl)-6-5-(1,4-oxazepan-4-yl)-1,3,5-triazin-2-yl]oxy}-N,N-dimethylbenzamide |
| 1003 | 4-9-{[4-1-(2-22-amino-1,3-thiazol-5-yl)-6-5-(3-25-methylmorpholin-4-yl)-1,3,5-triazin-2-yl]oxy}-N,N-dimethylbenzamide |
| 1004 | 4-14-{[4-1-(2-27-amino-1,3-thiazol-5-yl)-6-5-(morpholin-4-yl)-1,3,5-triazin-2-yl]oxy}-N,N-dimethylbenzamide |
| 1005 | 5-(4-(((1-(methylsulfonyl)piperidin-4-yl)methoxy)-6-morpholino-1,3,5-triazin-2-yl)pyrimidin-2-amine |
| 1006 | 2-26-(4-20-{[4-3-(2-15-aminopyrimidin-5-yl)-6-5-(morpholin-4-yl)-1,3,5-triazin-2-yl]oxy}phenyl)-N,N-dimethylacetamide |
| 1007 | N-(4-(2-aminothiazol-5-yl)-6-morpholino-1,3,5-triazin-2-yl)thiazol-2-amine |
| 1008 | 4-14-{[4-1-(2-17-aminopyrimidin-5-yl)-6-5-(morpholin-4-yl)-1,3,5-triazin-2-yl]oxy}-N,N-dimethylpiperidine-1-carboxamide |
| 1009 | 4-14-{[4-1-(5-17-aminopyrazin-2-yl)-6-5-(morpholin-4-yl)-1,3,5-triazin-2-yl]oxy}-N,N-dimethylbenzamide |
| 1010 | 6-20-{[4-1-(6-11-ammopyridin-3-yl)-6-5-(morpholin-4-yl)-1,3,5-triazin-2-yl]oxy}-1,2,3,4-tetrahydroquinolin-2-one |
| 1011 | 4-14-{[4-1-(2-27-aminopyrimidin-5-yl)-6-5-(morpholin-4-yl)-1,3,5-triazin-2-yl]oxy}-N,N-dimethylbenzamide |
| 1012 | 4-9-{[4-1-(6-12-aminopyridin-3-yl)-6-5-{3-oxa-8-azabicyclo[3.2.1]octan-8-yl}-1,3,5-triazin-2-yl]oxy}-N,N-dimethylbenzamide |
| 1013 | 2-26-(3-20-{[4-1-(6-11-aminopyridin-3-yl)-6-5-(morpholin-4-yl)-1,3,5-triazin-2-yl]oxy}phenyl)-N,N-dimethylacetamide |
| 1014 | 4-21-{[4-1-(6-9-aminopyridin-3-yl)-6-5-(1,4-oxazepan-4-yl)-1,3,5-triazin-2-yl]oxy}-N,N-dimethylbenzamide |
| 1015 | 3-20-{[4-1-(6-11-aminopyridin-3-yl)-6-5-(morpholin-4-yl)-1,3,5-triazin-2-yl]oxy}-N,N-dimethylbenzamide |
| 1016 | 4-9-{[4-5-(1H-imidazol-1-yl)-6-1-(1H-indazol-4-yl)-1,3,5-triazin-2-yl]oxy}-N,N-dimethylbenzamide |
| 1017 | 2-20-(4-9-{[4-1-(6-12-aminopyridin-3-yl)-6-5-(morpholin-4-yl)-1,3,5-triazin-2-yl]oxy}phenyl)-N,N-dimethylacetamide |
| 1018 | 4-14-{[4-1-(6-27-amino-5-26-methylpyridin-3-yl)-6-5-(morpholin-4-yl)-1,3,5-triazin-2-yl]oxy}-N,N-dimethylbenzamide |
| 1019 | 4-14-{[4-1-(6-26-hydrazinylpyridin-3-yl)-6-5-(morpholin-4-yl)-1,3,5-triazin-2-yl]oxy}-N,N-dimethylbenzamide |
| 1020 | 4-14-{[4-1-(6-17-amino-2-19-methylpyridin-3-yl)-6-5-(morpholin-4-yl)-1,3,5-triazin-2-yl]oxy}-N,N-dimethylbenzamide |
| 1021 | 4-20-{[4-1-(6-16-aminopyridin-3-yl)-6-5-(morpholin-4-yl)-1,3,5-triazin-2-yl]oxy}-N,2-trimethylbenzamide |
| 1022 | 4-14-{[4-1-(6-17-amino-4-15-methylpyridin-3-yl)-6-5-(morpholin-4-yl)-1,3,5-triazin-2-yl]ioxy}-N,N-dimethylbenzamide |
| 1023 | 5-(4-((1-(methylsulfonyl)piperidin-4-yl)methoxy)-6-morpholino-1,3,5-triazin-2-yl)pyridin-2-amine |
| 1024 | 4-9-{[4-1-(1H-indazol-4-yl)-6-5-(pyridin-4-yl)-1,3,5-triazin-2-yl]oxy}-N,N-dimethylbenzamide |
| 1025 | 3-21-({[4-3-(6-16-aminopyridin-3-yl)-6-5-(morpholin-4-yl)-1,3,5-triazin-2-yl]oxy}methyl)-N,N-dimethylpyrrolidine-1-carboxamide |
| 1026 | 3-19-{[4-3-(6-16-aminopyridin-3-yl)-6-5-(morpholin-4-yl)-1,3,5-triazin-2-yl]oxy}-N,N-dimethylpyrrolidine-1-carboxamide |
| 1027 | 4-14-{[4-1-(6-17-aminopyridin-3-yl)-6-5-(morpholin-4-yl)-1,3,5-triazin-2-yl]oxy}-N,N-dimethylbenzamide |
| 1028 | 4-20-{[4-1-(6-11-aminopyridin-3-yl)-6-5-(morpholin-4-yl)-1,3,5-triazin-2-yl]oxy}-N,N-dimethylpiperidine-1-carboxamide |
| 1029 | 4-14-{[4-1-(6-17-fluoropyridin-3-yl)-6-5-(morpholin-4-yl)-1,3,5-triazin-2-yl]oxy}-N,N-dimethylbenzamide |
| 1030 | 4-14-{[4-1-(3-21-hydroxyphenyl)-6-5-(morpholin-4-yl)-1,3,5-triazin-2-yl]oxy}-N,N-dimethylbenzamide |
| 1031 | 4-14-{[4-1-(4-17-aminophenyl)-6-5-(morpholin-4-yl)-1,3,5-triazin-2-yl]oxy}-N,N-dimethylbenzamide |
| 1032 | 4-14-{[4-1-(5-26-aminopyridin-3-yl)-6-5-(morpholin-4-yl)-1,3,5-triazin-2-yl]oxy}-N,N-dimethylbenzamide |
| 1033 | N,N-dimethyl-4-14-{[4-5-(morpholin-4-yl)-6-1-(1-30-oxo-1,2-dihydroisoquinolin-5-yl)-1,3,5-triazin-2-yl]oxy}benzamide |
| 1034 | N,N-dimethyl-4-14-{[4-5-(morpholin-4-yl)-6-1-(2-21-oxo-2,3-dihydro-1H-1,3-benzodiazol-4-yl)-1,3,5-triazin-2-yl]oxy}benzamide |
| 1035 | (1r,4r)-4-9-{[4-1-(6-12-aminopyridin-3-yl)-6-5-(morpholin-4-yl)-1,3,5-triazin-2-yl]oxy}-N,N-dimethylcyclohexane-1-carboxamide |
| 1036 | 4-14-{[4-1-(2-26-aminopyridin-4-yl)-6-5-(morpholin-4-yl)-1,3,5-triazin-2-yl]oxy}-N,N-dimethylbenzamide |
| 1037 | 5-(4-(benzylthio)-6-morpholino-1,3,5-triazin-2-yl)pyridin-2-amine |
| 1038 | 4-7-{[4-5-(1H-indazol-4-yl)-6-3-(5-31-oxo-1,4-diazepan-1-yl)-1,3,5-triazin-2-yl]oxy}-N,N-dimethylbenzamide |
| 1039 | 1-27-{4-1-[4-10-(dimethylcarbamoyl)phenoxy]-6-5-(1H-indazol-4-yl)-1,3,5-triazin-2-yl}piperidine-3-carboxamide |

| Compound Number | IUPAC Name |
|---|---|
| 1040 | 3-((4-(2-aminopyrimidin-5-yl)-6-morpholino-1,3,5-triazin-2-yl)amino)-N,N-dimethylbenzamide |
| 1041 | N,N-dimethyl-4-8-{[4-5-(morpholin-4-yl)-6-1-{1H-pyrrolo[2,3-b]pyridin-5-yl}-1,3,5-triazin-2-yl]oxy}benzamide |
| 1042 | 5-7-[4-3,6-5-bis(morpholin-4-yl)-1,3,5-triazin-2-yl]-1,3-thiazol-2-amine |
| 1043 | 4-9-{[4-5-(3,4-dihydro-2H-1,4-benzoxazin-4-yl)-6-1-(1H-indazol-4-yl)-1,3,5-triazin-2-yl]oxy}-N,N-dimethylbenzamide |
| 1044 | 4-8-{[4-5-(1H-indazol-4-yl)-6-3-(4-30-oxopiperidin-1-yl)-1,3,5-triazin-2-yl]oxy}-N,N-dimethylbenzamide |
| 1045 | 2-1-methyl-4-5,6-3-bis(morpholin-4-yl)-1,3,5-triazine |
| 1046 | 3-((4-(2-aminopyrimidin-5-yl)-6-morpholino-1,3,5-triazin-2-yl)amino)benzamide |
| 1047 | 1-7-{4-1-[4-11-(dimethylcarbamoyl)phenoxy]-6-5-(1H-indazol-4-yl)-1,3,5-triazin-2-yl}azetidine-3-carboxamide |
| 1048 | N-[(1S,3S)-3-14-{[4-1-(1-27-methanesulfonyl-1H-indazol-4-yl)-6-5-(morpholin-4-yl)-1,3,5-triazin-2-yl]oxy}cyclohexyl]methanesulfonamide |
| 1049 | 4-((4-(6-aminopyridin-3-yl)-6-morpholino-1,3,5-triazin-2-yl)methyl)-N,N-dimethylpiperazine-1-carboxamide |
| 1050 | 4-14-{[4-1-(1H-1,2,3-benzotriazol-4-yl)-6-5-(morpholin-4-yl)-1,3,5-triazin-2-yl]oxy}-N,N-dimethylbenzamide |
| 1051 | 1-6-[4-1-(2-22-aminopyrimidin-5-yl)-6-5-(morpholin-4-yl)-1,3,5-triazin-2-yl]-1,4-diazepan-5-one |
| 1052 | 4-14-{[4-1-(1H-indol-5-yl)-6-5-(morpholin-4-yl)-1,3,5-triazin-2-yl]oxy}-N,N-dimethylbenzamide |
| 1053 | 4-6-[4-1-(2-16-aminopyrimidin-5-yl)-6-5-(morpholin-4-yl)-1,3,5-triazin-2-yl]piperazine-1-sulfonamide |
| 1054 | 7-14-{[4-1-(1H-indazol-4-yl)-6-5-(morpholin-4-yl)-1,3,5-triazin-2-yl]oxy}-1,2,3,4-tetrahydroquinolin-2-one |
| 1055 | 4-8-{[4-5-(1H-indazol-4-yl)-6-3-{2-oxa-6-azaspiro[3.3]heptan-6-yl}-1,3,5-triazin-2-yl]oxy}-N,N-dimethylbenzamide |
| 1056 | 3-((4-(3-carbamoylcyclobutyl)-6-(1H-indazol-4-yl)-1,3,5-triazin-2-yl)amino)-N,N-dimethylbenzamide |
| 1057 | 4-((4-(1H-indazol-4-yl)-6-((tetrahydro-2H-pyran-4-yl)amino)-1,3,5-triazin-2-yl)oxy)-N,N-dimethylbenzamide |
| 1058 | N,N-dimethyl-4-14-{[4-5-(morpholin-4-yl)-6-1-{1H-pyrrolo[2,3-b]pyridin-4-yl}-1,3,5-triazin-2-yl]oxy}benzamide |
| 1059 | 4-7-{[4-5-(1H-indazol-4-yl)-6-3-(3-29-oxopiperazin-1-yl)-1,3,5-triazin-2-yl]oxy}-N,N-dimethylbenzamide |
| 1060 | 3-((4-(6-aminopyridin-3-yl)-6-morpholino-1,3,5-triazin-2-yl)amino)-N,N-dimethylbenzamide |
| 1061 | 4-9-{[4-1-(1H-indazol-4-yl)-6-5-(4-30-methylpiperazin-1-yl)-1,3,5-triazin-2-yl]oxy}-N,N-dimethylbenzamide |
| 1062 | 5-13-[4-3-(4-22-methanesulfonylpiperazin-1-yl)-6-5-(morpholin-4-yl)-1,3,5-triazin-2-yl]pyrimidin-2-amine |
| 1063 | 6-14-{[4-1-(1H-indazol-4-yl)-6-5-(morpholin-4-yl)-1,3,5-triazin-2-yl]oxy}-1,2,3,4-tetrahydroquinolin-2-one |
| 1064 | 4-14-{[4-1-(1H-indol-4-yl)-6-5-(morpholin-4-yl)-1,3,5-triazin-2-yl]oxy}-N,N-dimethylbenzamide |
| 1065 | 4-((4-(6-aminopyridin-3-yl)-6-morpholino-1,3,5-triazin-2-yl)amino)-N,N-dimethylbenzamide |
| 1066 | N-[3-16-(4-1-{[(2S)-1-(4-30-methanesulfonylpiperazin-1-yl)-1-oxopropan-2-yl]amino}-6-2-(morpholin-4-yl)-1,3,5-triazin-2-yl)phenyl]methanesulfonamide |
| 1067 | 4-14-{[4-1-(1H-indazol-4-yl)-6-5-(morpholin-4-yl)-1,3,5-triazin-2-yl]oxy}-N,N-dimethylthiophene-2-carboxamide |
| 1068 | 4-9-{[4-1-(1H-indazol-4-yl)-6-5-{3-oxa-8-azabicyclo[3.2.1]octan-8-yl}-1,3,5-triazin-2-yl]oxy}-N,N-dimethylbenzamide |
| 1069 | 1-{1-7-[4-3-(6-16-aminopyridin-3-yl)-6-5-(morpholin-4-yl)-1,3,5-triazin-2-yl]piperidin-4-yl}-3,3-dimethylurea |
| 1070 | 2-((4-(1-hydroxy-2,3-dihydro-1H-inden-4-yl)-6-morpholino-1,3,5-triazin-2-yl)amino)-N,N-dimethylacetamide |
| 1071 | 1-7-[4-3-(6-16-aminopyridin-3-yl)-6-5-(morpholin-4-yl)-1,3,5-triazin-2-yl]methanol |
| 1072 | 6-14-{[4-1-(1H-indazol-4-yl)-6-5-(morpholin-4-yl)-1,3,5-triazin-2-yl]oxy}-N,N-dimethylpyridine-3-carboxamide |
| 1073 | 4-7-{[4-5-(1H-indazol-4-yl)-6-3-(1,4-oxazepan-4-yl)-1,3,5-triazin-2-yl]oxy}-N,N-dimethylbenzamide |
| 1074 | 2-((4-(6-hydroxypyridin-3-yl)-6-morpholino-1,3,5-triazin-2-yl)amino)-1-(4-(methylsulfonyl)piperazin-1-yl)ethanone |
| 1075 | 4-9-{[4-1-(1H-indazol-4-yl)-6-5-(3-29-methoxyazetidin-1-yl)-1,3,5-triazin-2-yl]oxy}-N,N-dimethylbenzamide |
| 1076 | 2-((4-(3-hydroxyphenyl)-6-morpholino-1,3,5-triazin-2-yl)amino)-1-(4-(methylsulfonyl)piperazin-1-yl)propan-1-one |
| 1077 | 5-13-[4-5-(morpholin-4-yl)-6-3-(piperazin-1-yl)-1,3,5-triazin-2-yl]pyrimidin-2-amine |
| 1078 | 2-((4-morpholino-6-(1-oxo-2,3-dihydro-1H-inden-4-yl)-1,3,5-triazin-2-yl)amino)acetic acid |
| 1079 | 2-((4-(3-methoxyphenyl)-6-morpholino-1,3,5-triazin-2-yl)amino)-1-(4-(methylsulfonyl)piperazin-1-yl)ethanone |
| 1080 | 2-((4-(6-fluoropyridin-3-yl)-6-morpholino-1,3,5-triazin-2-yl)amino)-1-(4-(methylsulfonyl)piperazin-1-yl)ethanone |
| 1081 | 5-13-[4-3,6-5-bis(morpholin-4-yl)-1,3,5-triazin-2-yl]pyrimidin-2-amine |
| 1082 | 2-13-[4-1,6-6-bis(morpholin-4-yl)-1,3,5-triazin-2-yl]-2H-indazol-4-amine |
| 1083 | N-[(1R,3R)-3-14-{[4-1-(1H-indazol-4-yl)-6-5-(morpholin-4-yl)-1,3,5-triazin-2-yl]oxy}cyclopentyl]methanesulfonamide |
| 1084 | 4-morpholino-N-phenyl-6-(1-(tetrahydro-2H-pyran-2-yl)-1H-indazol-4-yl)-1,3,5-triazin-2-amine |
| 1085 | 2-27-(4-14-{[4-1-(1H-indazol-4-yl)-6-5-(morpholin-4-yl)-1,3,5-triazin-2-yl]oxy}phenyl)-N,N-dimethylacetamide |
| 1086 | 5-23-{[4-1-(1H-indazol-4-yl)-6-5-(morpholin-4-yl)-1,3,5-triazin-2-yl]oxy}-2,3-dihydro-1H-1,3-benzodiazol-2-one |
| 1087 | 4-14-{[4-1-(1H-indazol-4-yl)-6-5-(morpholin-4-yl)-1,3,5-triazin-2-yl]oxy}-N,N-dimethylazepane-1-carboxamide |
| 1088 | 3-22-{[4-1-(1H-indazol-4-yl)-6-5-(morpholin-4-yl)-1,3,5-triazin-2-yl]oxy}-N,N-dimethylbenzamide |
| 1089 | 2-((4-(3-hydroxyphenyl)-6-morpholino-1,3,5-triazin-2-yl)amino)-1-(4-(methylsulfonyl)piperazin-1-yl)ethanone |
| 1090 | 2-((4-(3-hydroxyphenyl)-6-morpholino-1,3,5-triazin-2-yl)amino)-3-phenylpropanamide |
| 1091 | 3-22-{[4-1-(1H-indazol-4-yl)-6-5-(morpholin-4-yl)-1,3,5-triazin-2-yl]oxy}-N,N-dimethylpiperidine-1-carboxamide |
| 1092 | N-(4-14-{[4-1-(1H-indazol-4-yl)-6-5-(morpholin-4-yl)-1,3,5-triazin-2-yl]oxy}phenyl)aminosulfonamide |
| 1093 | N-(4-14-{[4-1-(1H-indazol-4-yl)-6-5-(morpholin-4-yl)-1,3,5-triazin-2-yl]oxy}phenyl)methanesulfonamide |
| 1094 | N-[(1r,4r)-4-9-{[4-1-(1H-indazol-4-yl)-6-5-(morpholin-4-yl)-1,3,5-triazin-2-yl]oxy}cyclohexyl]aminosulfonamide |
| 1095 | N-[(1r,4r)-4-9-{[4-1-(1H-indazol-4-yl)-6-5-(morpholin-4-yl)-1,3,5-triazin-2-yl]oxy}cyclohexyl]methanesulfonamide |
| 1096 | 4-(4-(1H-indazol-4-yl)-6-((1-(methylsulfonyl)piperidin-4-yl)methoxy)-1,3,5-triazin-2-yl)morpholine |
| 1097 | 4-9-{[4-5-(3-28,5-32-dimethylmorpholin-4-yl)-6-1-(1H-indazol-4-yl)-1,3,5-triazin-2-yl]oxy}-N,N-dimethylbenzamide |
| 1098 | 4-9-{[4-1-(1H-indazol-4-yl)-6-5-(3-28-methylmorpholin-4-yl)-1,3,5-triazin-2-yl]oxy}-N,N-dimethylbenzamide |
| 1099 | (2R,4S)-4-14-{[4-1-(1H-indazol-4-yl)-6-5-(morpholin-4-yl)-1,3,5-triazin-2-yl]oxy}-N,N,1-trimethylpyrrolidine-2-carboxamide |
| 1100 | N-(4-14-{[4-1-(1H-indazol-4-yl)-6-5-(morpholin-4-yl)-1,3,5-triazin-2-yl]oxy}phenyl)-N'-methylethanediamide |
| 1101 | N-(4-14-{[4-1-(1H-indazol-4-yl)-6-5-(morpholin-4-yl)-1,3,5-triazin-2-yl]oxy}phenyl)-N',N'-dimethylethanediamide |
| 1102 | 4-7-{4-3-[(1-25-methanesulfonylpiperidin-4-yl)oxy]-6-5-(morpholin-4-yl)-1,3,5-triazin-2-yl}-1H-indazole |
| 1103 | (2R,4S)-4-14-{[4-1-(1H-indazol-4-yl)-6-5-(morpholin-4-yl)-1,3,5-triazin-2-yl]oxy}-N,N-dimethylpyrrolidine-2-carboxamide |
| 1104 | 3-((4-(6-aminopyridin-3-yl)-6-morpholino-1,3,5-triazin-2-yl)amino)-N,N-dimethylpropanamide |
| 1105 | 5-12-[4-5-(morpholin-4-yl)-6-3-(piperazin-1-yl)-1,3,5-triazin-2-yl]pyridin-2-ol |
| 1106 | 1-(4-14-{[4-1-(1H-indazol-4-yl)-6-5-(morpholin-4-yl)-1,3,5-triazin-2-yl]oxy}phenyl)-3,3-dimethylurea |
| 1107 | N-(4-14-{[4-1-(1H-indazol-4-yl)-6-5-(morpholin-4-yl)-1,3,5-triazin-2-yl]oxy}phenyl)-2-30-methylpropanamide |
| 1108 | 3-14-{[4-1-(1H-indazol-4-yl)-6-5-(morpholin-4-yl)-1,3,5-triazin-2-yl]oxy}-N,N-dimethylpyrrolidine-1-carboxamide |
| 1109 | 3-22-({[4-1-(1H-indazol-4-yl)-6-5-(morpholin-4-yl)-1,3,5-triazin-2-yl]oxy}methyl)-N,N-dimethylpyrrolidine-1-carboxamide |
| 1110 | 4-23-({[4-1-(1H-indazol-4-yl)-6-5-(morpholin-4-yl)-1,3,5-triazin-2-yl]oxy}methyl)-N,N-dimethylbenzamide |
| 1111 | 3-((4-(1H-indazol-4-yl)-6-(3-oxopiperazin-1-yl)-1,3,5-triazin-2-yl)amino)-N,N-dimethylbenzamide |

| Compound Number | IUPAC Name |
|---|---|
| 1112 | 2-8-[4-1,6-5-bis(morpholin-4-yl)-1,3,5-triazin-2-yl]-2H-indazole |
| 1113 | 4-14-{[4-1-(1H-indazol-4-yl)-6-5-(morpholin-4-yl)-1,3,5-triazin-2-yl]oxy}-N-methylbenzamide |
| 1114 | 4-14-{[4-1-(1H-indazol-4-yl)-6-5-(morpholin-4-yl)-1,3,5-triazin-2-yl]oxy}-N,N-dimethylbenzamide |
| 1115 | 4-(4-((1-benzylpiperidin-4-yl)oxy)-6-(1H-indazol-4-yl)-1,3,5-triazin-2-yl)morpholine |
| 1116 | tert-butyl 4-(3-((4-(1H-indazol-4-yl)-6-morpholino-1,3,5-triazin-2-yl)amino)benzamido)piperidine-1-carboxylate |
| 1117 | 1-(3-((4-(1H-indazol-4-yl)-6-morpholino-1,3,5-triazin-2-yl)amino)benzoyl)-1,4-diazepan-5-one |
| 1118 | 2-((4-(3-hydroxyphenyl)-6-morpholino-1,3,5-triazin-2-yl)amino)-3-phenylpropanoic acid |
| 1119 | 1-(4-((4-(1H-indazol-4-yl)-6-morpholino-1,3,5-triazin-2-yl)oxy)phenyl)-N,N-dimethylmethanamine |
| 1120 | 2-((4-(4-aminophenyl)-6-morpholino-1,3,5-triazin-2-yl)amino)-1-(4-(methylsulfonyl)piperazin-1-yl)ethanone |
| 1121 | 2-9-{N-[4-1-(3-14-acetamidophenyl)-6-5-(morpholin-4-yl)-1,3,5-triazin-2-yl]acetamido}acetic acid |
| 1122 | 3-12-(4-0-{[(dimethylcarbamoyl)methyl]amino}-6-4-(morpholin-4-yl)-1,3,5-triazin-2-yl)benzamide |
| 1123 | N-[(4E)-1-8-[4-1-(1-21-{4-24-[(4E)-4-37-(hydroxyimino)azepan-1-yl]-6-26-(morpholin-4-yl)-1,3,5-triazin-2-yl}-1H-indazol-4-yl)-6-5-(morpholin-4-yl)-1,3,5-triazin-2-yl]azepan-4-ylidene]hydroxylamine |
| 1124 | N-methyl-N'-[(1r,4r)-4-9-{[4-1-(1H-indazol-4-yl)-6-5-(morpholin-4-yl)-1,3,5-triazin-2-yl]oxy}cyclohexyl]ethanediamide |
| 1125 | N,N-dimethyl-N'-[(1r,4r)-4-9-{[4-1-(1H-indazol-4-yl)-6-5-(morpholin-4-yl)-1,3,5-triazin-2-yl]oxy}cyclohexyl]ethanediamide |
| 1126 | 4-14-{[4-1-(1H-indazol-4-yl)-6-5-(morpholin-4-yl)-1,3,5-triazin-2-yl]oxy}-N,N-dimethylpiperidine-1-carboxamide |
| 1127 | 2-1-(6-16-fluoropyridin-3-yl)-4-5-(morpholin-4-yl)-6-3-(piperazin-1-yl)-1,3,5-triazine |
| 1128 | 4-4-(3-13-methoxyphenyl)-6-0-(morpholin-4-yl)-1,3,5-triazin-2-amine |
| 1129 | 3-((4-(1H-indazol-4-yl)-6-morpholino-1,3,5-triazin-2-yl)amino)-N-(pyridin-2-yl)benzamide |
| 1130 | (3-((4-(1H-indazol-4-yl)-6-morpholino-1,3,5-triazin-2-yl)amino)phenyl)(4-(methylsulfonyl)piperazin-1-yl)methanone |
| 1131 | 3-22-{[4-1-(1H-indazol-4-yl)-6-5-(morpholin-4-yl)-1,3,5-triazin-2-yl]oxy}benzonitrile |
| 1132 | 3-((4-(1H-indazol-4-yl)-6-morpholino-1,3,5-triazin-2-yl)amino)-N,N-dimethylthiophene-2-carboxamide |
| 1133 | (1R,3R)-3-14-{[4-1-(1H-indazol-4-yl)-6-5-(morpholin-4-yl)-1,3,5-triazin-2-yl]oxy}-N,N-dimethylcyclohexane-1-carboxamide |
| 1134 | 5-18-[4-5-(morpholin-4-yl)-6-3-(piperazin-1-yl)-1,3,5-triazin-2-yl]pyridin-2-amine |
| 1135 | 3-6-{4-1-[(carbamoylmethyl)amino]-6-2-(morpholin-4-yl)-1,3,5-triazin-2-yl}benzamide |
| 1136 | 2-((4-(3-hydroxyphenyl)-6-morpholino-1,3,5-triazin-2-yl)amino)-4-(methylthio)butanoic acid |
| 1137 | 2-((4-(3-(difluoromethyl)phenyl)-6-morpholino-1,3,5-triazin-2-yl)-N,N-dimethylacetamide |
| 1138 | 2-((4-(3-(methylsulfonamido)phenyl)-6-morpholino-1,3,5-triazin-2-yl)amino)propanoic acid |
| 1139 | 3-8-[4-3-amino-6-5-(morpholin-4-yl)-1,3,5-triazin-2-yl]phenol |
| 1140 | (3-((4-(1H-indazol-4-yl)-6-morpholino-1,3,5-triazin-2-yl)amino)phenyl)(4-methoxypiperidin-1-yl)methanone |
| 1141 | 2-((4-(3-cyanophenyl)-6-morpholino-1,3,5-triazin-2-yl)amino)-N,N-dimethylacetamide |
| 1142 | (1r,4r)-4-21-{[4-1-(1H-indazol-4-yl)-6-5-(morpholin-4-yl)-1,3,5-triazin-2-yl]oxy}-N-methylcyclohexane-1-carboxamide |
| 1143 | (1s,4s)-4-21-{[4-1-(1H-indazol-4-yl)-6-5-(morpholin-4-yl)-1,3,5-triazin-2-yl]oxy}-N,N-dimethylcyclohexane-1-carboxamide |
| 1144 | (1r,4r)-4-21-{[4-1-(1H-indazol-4-yl)-6-5-(morpholin-4-yl)-1,3,5-triazin-2-yl]oxy}-N,N-dimethylcyclohexane-1-carboxamide |
| 1145 | 2-((4-(6-hydroxypyridin-3-yl)-6-morpholino-1,3,5-triazin-2-yl)amino)-N,N-dimethylacetamide |
| 1146 | 2-((4-(3-(methylsulfonamido)phenyl)-6-morpholino-1,3,5-triazin-2-yl)amino)acetic acid |
| 1147 | 1-(1-14-{[4-1-(1H-indazol-4-yl)-6-5-(morpholin-4-yl)-1,3,5-triazin-2-yl]oxy}-2-15-methylpropan-2-yl)-3,3-dimethylurea |
| 1148 | 3-((4-(1H-indol-4-yl)-6-morpholino-1,3,5-triazin-2-yl)amino)benzamide |
| 1149 | 4-7-{4-3-[(1-25-ethylpiperidin-4-yl)oxy]-6-5-(morpholin-4-yl)-1,3,5-triazin-2-yl}-1H-indazole |
| 1150 | 2-((4-(5-hydroxypyridin-3-yl)-6-morpholino-1,3,5-triazin-2-yl)amino)-N,N-dimethylacetamide |
| 1151 | 4-7-[4-5-(morpholin-4-yl)-6-3-(piperidin-4-yloxy)-1,3,5-triazin-2-yl]-1H-indazole |
| 1152 | (1r,4r)-4-9-{[4-1-(1H-indazol-4-yl)-6-5-(morpholin-4-yl)-1,3,5-triazin-2-yl]oxy}cyclohexan-1-amine |
| 1153 | 1-((4-(3-hydroxyphenyl)-6-morpholino-1,3,5-triazin-2-yl)amino)cyclopentanecarboxylic acid |
| 1154 | 1-(3-((4-(1H-indazol-4-yl)-6-morpholino-1,3,5-triazin-2-yl)amino)benzoyl)azetidine-3-carboxamide |
| 1155 | 3-6-{4-3-[(1-hydroxy-2-methylpropan-2-yl)amino]-6-5-(morpholin-4-yl)-1,3,5-triazin-2-yl}phenol |
| 1156 | 2-((4-(2-fluoro-5-methoxyphenyl)-6-morpholino-1,3,5-triazin-2-yl)amino)acetic acid |
| 1157 | 3-((4-(1H-indazol-4-yl)-6-morpholino-1,3,5-triazin-2-yl)amino)-N-(piperidin-4-yl)benzamide |
| 1158 | 3-((4-(1H-indazol-4-yl)-6-morpholino-1,3,5-triazin-2-yl)amino)thiophene-2-carboxamide |
| 1159 | 5-13-[4-0,6-8-bis(morpholin-4-yl)-1,3,5-triazin-2-yl]pyridin-2-amine |
| 1160 | 3-6-[4-1,6-2-bis(morpholin-4-yl)-1,3,5-triazin-2-yl]phenol |
| 1161 | 3-6-{4-1-[(carboxymethyl)amino]-6-2-(morpholin-4-yl)-1,3,5-triazin-2-yl}benzoic acid |
| 1162 | 4-0-(morpholin-4-yl)-6-4-phenyl-1,3,5-triazin-2-amine |
| 1163 | 4-(3-((4-(1H-indazol-4-yl)-6-morpholino-1,3,5-triazin-2-yl)amino)benzoyl)piperazin-2-one |
| 1164 | (3-((4-(1H-indazol-4-yl)-6-morpholino-1,3,5-triazin-2-yl)amino)phenyl)(3-methoxyazetidin-1-yl)methanone |
| 1165 | 2-((4-(6-aminopyridin-3-yl)-6-morpholino-1,3,5-triazin-2-yl)amino)-N,N-dimethylpropanamide |
| 1166 | 4-(4-(benzylthio)-6-(1H-indazol-4-yl)-1,3,5-triazin-2-yl)morpholine |
| 1167 | 2-((4-(3-hydroxyphenyl)-6-morpholino-1,3,5-triazin-2-yl)amino)-N,N-dimethylacetamide |
| 1168 | 2-((4-(3-hydroxyphenyl)-6-morpholino-1,3,5-triazin-2-yl)amino)-N-methylacetamide |
| 1169 | 2-((4-morpholino-6-(3-nitrophenyl)-1,3,5-triazin-2-yl)amino)acetic acid |
| 1170 | 2-((4-(6-aminopyridin-3-yl)-6-morpholino-1,3,5-triazin-2-yl)amino)-N,N-dimethylacetamide |
| 1171 | (3-((4-(1H-indazol-4-yl)-6-morpholino-1,3,5-triazin-2-yl)amino)phenyl)(piperazin-1-yl)methanone |
| 1172 | (3-((4-(1H-indazol-4-yl)-6-morpholino-1,3,5-triazin-2-yl)amino)phenyl)(4-methylpiperazin-1-yl)methanone |
| 1173 | (3-((4-(1H-indazol-4-yl)-6-morpholino-1,3,5-triazin-2-yl)amino)phenyl)(morpholino)methanone |
| 1174 | N-(4-23-ethoxyphenyl)-1-12-[4-1-(1H-indazol-4-yl)-6-5-(morpholin-4-yl)-1,3,5-triazin-2-yl]pyrrolidine-3-carboxamide |
| 1175 | 2-((4-(3-hydroxyphenyl)-6-morpholino-1,3,5-triazin-2-yl)amino)-3-methylbutanoic acid |
| 1176 | 2-((4-(6-hydroxypyridin-3-yl)-6-morpholino-1,3,5-triazin-2-yl)amino)acetic acid |
| 1177 | 3-((4-(1H-indazol-4-yl)-6-morpholino-1,3,5-triazin-2-yl)amino)-N,4-dimethylbenzamide |
| 1178 | 3-((4-(1H-indazol-4-yl)-6-morpholino-1,3,5-triazin-2-yl)amino)-N,N,4-trimethylbenzamide |
| 1179 | 2-((4-(6-fluoropyridin-3-yl)-6-morpholino-1,3,5-triazin-2-yl)amino)acetic acid |
| 1180 | 4-(4-(1H-1-indazol-4-yl)-6-morpholino-1,3,5-triazin-2-yl)methyl)-N,N-dimethylpiperazine-1-carboxamide |
| 1181 | 2-((4-(3-hydroxyphenyl)-6-morpholino-1,3,5-triazin-2-yl)amino)acetamide |
| 1182 | 1-8-[4-1-(1H-indazol-4-yl)-6-5-(morpholin-4-yl)-1,3,5-triazin-2-yl]-1H-pyrrole-2-carboxamide |
| 1183 | 2-((4-(3-methoxyphenyl)-6-morpholino-1,3,5-triazin-2-yl)amino)acetic acid |
| 1184 | 2-((4-(3-(hydroxyamino)phenyl)-6-morpholino-1,3,5-triazin-2-yl)amino)acetic acid |

| Compound Number | IUPAC Name |
|---|---|
| 1185 | 2-((4-(4-aminophenyl)-6-morpholino-1,3,5-triazin-2-yl)amino)-N,N-dimethylacetamide |
| 1186 | 3-((4-(1H-indazol-4-yl)-6-morpholino-1,3,5-triazin-2-yl)amino)-2-methylbenzamide |
| 1187 | 2-((4-(3-hydroxyphenyl)-6-morpholino-1,3,5-triazin-2-yl)amino)propanoic acid |
| 1188 | 2-((4-(3-hydroxyphenyl)-6-morpholino-1,3,5-triazin-2-yl)amino)-2-methylpropanoic acid |
| 1189 | 3-((4-(1H-indazol-4-yl)-6-morpholino-1,3,5-triazin-2-yl)amino)-N-methylbenzamide |
| 1190 | 3-((4-(1H-indazol-4-yl)-6-morpholino-1,3,5-triazin-2-yl)amino)-N,N-dimethylbenzamide |
| 1191 | 3-((4-(1H-indazol-4-yl)-6-morpholino-1,3,5-triazin-2-yl)amino)-1-(4-(methylsulfonyl)piperazin-1-yl)propan-1-one |
| 1192 | 2-((4-(3-hydroxyphenyl)-6-morpholino-1,3,5-triazin-2-yl)(methyl)amino)acetic acid |
| 1193 | 2-((4-(3-hydroxyphenyl)-6-morpholino-1,3,5-triazin-2-yl)amino)acetic acid |
| 1194 | 2-(2-((4-(1H-indazol-4-yl)-6-morpholino-1,3,5-triazin-2-yl)amino)phenyl)acetamide |
| 1195 | 2-(3-((4-(1H-indazol-4-yl)-6-morpholino-1,3,5-triazin-2-yl)amino)phenyl)acetamide |
| 1196 | 5-8-[4-1-(1H-indazol-4-yl)-6-5-(morpholin-4-yl)-1,3,5-triazin-2-yl]-octahydro-1H-pyrrolo[3,4-c]pyridin-1-one |
| 1197 | methyl 2-((4-(3-aminophenyl)-6-morpholino-1,3,5-triazin-2-yl)amino)acetate |
| 1198 | 2-((4-(1H-indazol-4-yl)-6-morpholino-1,3,5-triazin-2-yl)amino)benzamide |
| 1199 | 2-((4-(3-aminophenyl)-6-morpholino-1,3,5-triazin-2-yl)amino)acetic acid |
| 1200 | 3-((4-(1H-indazol-4-yl)-6-morpholino-1,3,5-triazin-2-yl)(methyl)amino)benzamide |
| 1201 | 3-((4-(1H-indazol-4-yl)-6-morpholino-1,3,5-triazin-2-yl)amino)benzamide |
| 1202 | 3-((4-(1H-indazol-4-yl)-6-morpholino-1,3,5-triazin-2-yl)amino)benzoic acid |
| 1203 | 2-((4-morpholino-6-phenyl-1,3,5-triazin-2-yl)amino)acetic acid |
| 1204 | 4-((4-(1H-indazol-4-yl)-6-morpholino-1,3,5-triazin-2-yl)amino)-N,N-dimethylbenzamide |
| 1205 | N-(4-(1H-indazol-4-yl)-6-morpholino-1,3,5-triazin-2-yl)-1H-indazol-4-amine |
| 1206 | 1-21-[4-1-(1H-indazol-4-yl)-6-5-(morpholin-4-yl)-1,3,5-triazin-2-yl]-1,4-diazepan-5-one |
| 1207 | methyl 1-12-[4-1-(1H-indazol-4-yl)-6-5-(morpholin-4-yl)-1,3,5-triazin-2-yl]pyrrolidine-3-carboxylate |
| 1208 | N-{1-8-[4-1-(1H-indazol-4-yl)-6-5-(morpholin-4-yl)-1,3,5-triazin-2-yl]piperidin-4-ylidene}hydroxylamine |
| 1209 | 2-((4-(1H-indazol-4-yl)-6-morpholino-1,3,5-triazin-2-yl)amino)-N,N-dimethyl-3-phenylpropanamide |
| 1210 | 2-((4-(1H-indazol-4-yl)-6-morpholino-1,3,5-triazin-2-yl)amino)-N,N-dimethyl-4-(methylsulfonyl)butanamide |
| 1211 | 4-7-[4-3-(4-16 methanesulfonylpiperazin-1-yl)-6-5-(morpholin-4-yl)-1,3,5-triazin-2-yl]-1H-indazole |
| 1212 | 4-1-(1H-indazol-4-yl)-6-5-(morpholin-4-yl)-1,3,5-triazin-2-ol |
| 1213 | 4-12-[4-3-(1,4-diazepan-1-yl)-6-5-(morpholin-4-yl)-1,3,5-triazin-2-yl]-1H-indazole |
| 1214 | (1r,4r)-4-((4-(1H-indazol-4-yl)-6-morpholino-1,3,5-triazin-2-yl)amino)-N,N-dimethylcyclohexanecarboxamide |
| 1215 | 4-((4-(1H-indazol-4-yl)-6-morpholino-1,3,5-triazin-2-yl)amino)-N-methylcyclohexanecarboxamide |
| 1216 | 4-((4-(1H-indazol-4-yl)-6-morpholino-1,3,5-triazin-2-yl)amino)-N,N-dimethylcyclohexanecarboxamide |
| 1217 | (2R)-1-7-[4-1-(1H-indazol-4-yl)-6-5-(morpholin-4-yl)-1,3,5-triazin-2-yl]-N,N-dimethylpyrrolidine-2-carboxamide |
| 1218 | 4-7-[4-1-(1H-indazol-4-yl)-6-5-(morpholin-4-yl)-1,3,5-triazin-2-yl]-N-methylpiperazine-1-carboxamide |
| 1219 | 4-(1H-indazol-4-yl)-6-morpholino-N-phenyl-1,3,5-triazin-2-amine |
| 1220 | 1-8-[4-1-(1H-indazol-4-yl)-6-5-(morpholin-4-yl)-1,3,5-triazin-2-yl]piperidin-4-ol |
| 1221 | 1-8-[4-1-(1H-indazol-4-yl)-6-5-(morpholin-4-yl)-1,3,5-triazin-2-yl]piperidin-4-one |
| 1222 | 1-8-[4-1-(1H-indazol-4-yl)-6-5-(morpholin-4-yl)-1,3,5-triazin-2-yl]piperidin-4-amine |
| 1223 | 3-((4-(1H-indazol-4-yl)-6-morpholino-1,3,5-triazin-2-yl)amino)-N,N-dimethylpropanamide |
| 1224 | 4-12-[4-3-(1H-indazol-4-yl)-6-5-(morpholin-4-yl)-1,3,5-triazin-2-yl]-1H-indazole |
| 1225 | 4-(1H-indazol-4-yl)-6-morpholino-N-(tetrahydro-2H-pyran-4-yl)-1,3,5-triazin-2-amine |
| 1226 | 4-7-[4-3-methyl-6-5-(morpholin-4-yl)-1,3,5-triazin-2-yl]-1H-indazole |
| 1227 | 3-((4-(1H-indazol-4-yl)-6-morpholino-1,3,5-triazin-2-yl)amino)propanoic acid |
| 1228 | 4-18-[4-3-(4-15 methylpiperazin-1-yl)-6-5-(morpholin-4-yl)-1,3,5-triazin-2-yl]-1H-indazole |
| 1229 | 4-17-[4-5-(morpholin-4-yl)-6-3-(piperazin-1-yl)-1,3,5-triazin-2-yl]-1H-indazole |
| 1230 | 4-7-[4-1-(1H-indazol-4-yl)-6-5-(morpholin-4-yl)-1,3,5-triazin-2-yl]piperazin-2-one |
| 1231 | 4-2-(1H-indazol-4-yl)-6-0-(morpholin-4-yl)-1,3,5-triazin-2-amine |
| 1232 | 2-((4-(1H-indazol-4-yl)-6-morpholino-1,3,5-triazin-2-yl)amino)-2-methylpropan-1-ol |
| 1233 | 4-8-[4,3,6-5-bis(morpholin-4-yl)-1,3,5-triazin-2-yl]-1H-indazole |
| 1234 | 2-((4-(1H-indazol-4-yl)-6-morpholino-1,3,5-triazin-2-yl)amino)propanamide |
| 1235 | 2-((4-(1H-indazol-4-yl)-6-morpholino-1,3,5-triazin-2-yl)amino)-2-methylpropanoic acid |
| 1236 | 2-((4-(1H-indazol-4-yl)-6-morpholino-1,3,5-triazin-2-yl)amino)acetic acid |
| 1301 | (S)-4-((4-(2-aminothiazol-5-yl)-6-(3-methylmorpholino)-1,3,5-triazin-2-yl)oxy)-N,N-dimethylbenzamide |
| 1302 | 4-((4-(2-aminothiazol-5-yl)-6-morpholino-1,3,5-triazin-2-yl)oxy)benzamide |
| 1303 | 4-((4-(2-aminothiazol-5-yl)-6-morpholino-1,3,5-triazin-2-yl)oxy)-N-methylbenzamide |
| 1304 | 3-((4-(2-aminothiazol-5-yl)-6-morpholino-1,3,5-triazin-2-yl)oxy)-N,N-dimethylbenzamide |
| 1305 | 4-((4-(2-aminothiazol-4-yl)-6-morpholino-1,3,5-triazin-2-yl)oxy)-N,N-dimethylbenzamide |
| 1306 | 4-((4-(5-amino-1,3,4-thiadiazol-2-yl)-6-morpholino-1,3,5-triazin-2-yl)oxy)-N,N-dimethylbenzamide |
| 1307 | 4-((4-(2-aminooxazol-5-yl)-6-morpholino-1,3,5-triazin-2-yl)oxy)-N,N-dimethylbenzamide |
| 1308 | 4-((4-(2-amino-1H-imidazol-5-yl)-6-morpholino-1,3,5-triazin-2-yl)oxy)-N,N-dimethylbenzamide |
| 1309 | N,N-dimethyl-4-((4-(2-(methylamino)thiazol-5-yl)-6-morpholino-1,3,5-triazin-2-yl)oxy)benzamide |
| 1310 | 4-((4-(2-aminothiazol-5-yl)-6-morpholino-1,3,5-triazin-2-yl)amino)-N,N-dimethylbenzamide |
| 1311 | 3-((4-(2-aminothiazol-5-yl)-6-morpholino-1,3,5-triazin-2-yl)amino)-N,N-dimethylbenzamide |
| 1312 | 4-((4-(2-aminothiazol-5-yl)-6-morpholino-1,3,5-triazin-2-yl)oxy)-3-fluoro-N,N-dimethylbenzamide |
| 1313 | 4-((4-(2-aminothiazol-5-yl)-6-(1,4-oxazepan-4-yl)-1,3,5-triazin-2-yl)oxy)-N,N-dimethylbenzamide |
| 1314 | (R)-2-(4-((4-(2-aminothiazol-5-yl)-6-morpholino-1,3,5-triazin-2-yl)oxy)phenyl)-N,N-dimethylpropanamide |
| 1315 | 4-((4-(2-amino-4-methylthiazol-5-yl)-6-morpholino-1,3,5-triazin-2-yl)oxy)-N,N-dimethylbenzamide |
| 1316 | 5-(4-((2-(methylsulfonyl)-1,2,3,4-tetrahydroisoquinolin-5-yl)oxy)-6-morpholino-1,3,5-triazin-2-yl)thiazol-2-amine |
| 1317 | 4-((4-(2-aminothiazol-5-yl)-6-morpholino-1,3,5-triazin-2-yl)oxy)-N,N-dimethylpiperidine-1-carboxamide |
| 1318 | 5-(4-((1-(methylsulfonyl)piperidin-4-yl)methoxy)-6-morpholino-1,3,5-triazin-2-yl)thiazol-2-amine |
| 1319 | 5-(4-(1-(1-(methylsulfonyl)piperidin-4-yl)ethoxy)-6-morpholino-1,3,5-triazin-2-yl)thiazol-2-amine |
| 1320 | (1s,4s)-4-((4-(2-aminothiazol-5-yl)-6-morpholino-1,3,5-triazin-2-yl)oxy)-N,N-dimethylcyclohexanecarboxamide |
| 1321 | 5-(4-((1-(methylsulfonyl)pyrrolidin-3-yl)methoxy)-6-morpholino-1,3,5-triazin-2-yl)thiazol-2-amine |
| 1322 | 5-(4-(((1-(methylsulfonyl)piperidin-3-yl)oxy)methyl)-6-morpholino-1,3,5-triazin-2-yl)thiazol-2-amine |
| 1323 | 5-(4-(((1-(methylsulfonyl)piperidin-4-yl)oxy)methyl)-6-morpholino-1,3,5-triazin-2-yl)thiazol-2-amine |

-continued

| Compound Number | IUPAC Name |
|---|---|
| 1324 | 5-(4-morpholino-6-(piperazin-1-yl)-1,3,5-triazin-2-yl)thiazol-2-amine |
| 1325 | 5-(4-morpholino-6-(1,4-oxazepan-4-yl)-1,3,5-triazin-2-yl)thiazol-2-amine |
| 1326 | 5-(4-morpholino-6-(piperazin-1-yl)-1,3,5-triazin-2-yl)-4-(trifluoromethyl)pyridin-2-amine |
| 1327 | 4-(4-(6-amino-4-(trifluoromethyl)pyridin-3-yl)-6-morpholino-1,3,5-triazin-2-yl)piperazine-1-sulfonamide |
| 1328 | 5-(4-(4-(methylsulfonyl)piperazin-1-yl)-6-morpholino-1,3,5-triazin-2-yl)-4-(trifluoromethyl)pyridin-2-amine |
| 1329 | 5-(4-(4-methylpiperazin-1-yl)-6-morpholino-1,3,5-triazin-2-yl)-4-(trifluoromethyl)pyridin-2-amine |
| 1330 | 5-(4,6-dimorpholino-1,3,5-triazin-2-yl)-4-(trifluoromethyl)pyridin-2-amine |
| 1331 | 5-(4-(4-methylpiperazin-1-yl)-6-morpholino-1,3,5-triazin-2-yl)pyrimidin-2-amine |

In another aspect the present invention is drawn to the compounds, their isomers, salts and solvates thereof.

(1) 4-9-{[4-1-(2-22-amino-1,3-thiazol-5-yl)-6-5-(3-25-methylmorpholin-4-yl)-1,3,5-triazin-2-yl]oxy}-N,N-dimethylbenzamide (2) 2-26-(4-20-{[4-3-(2-15-aminopyrimidin-5-yl)-6-5-(morpholin-4-yl)-1,3,5-triazin-2-yl]oxy}phenyl)-N,N-dimethylacetamide (3) 5-(4-((1-(methylsulfonyl)piperidin-4-yl)methoxy)-6-morpholino-1,3,5-triazin-2-yl)pyridin-2-amine (4) 4-14-{[4-1-(2-27-amino-1,3-thiazol-5-yl)-6-5-(morpholin-4-yl)-1,3,5-triazin-2-yl]oxy}-N,N-dimethylbenzamide (5) 4-14-{[4-1-(1H-indol-5-yl)-6-5-(morpholin-4-yl)-1,3,5-triazin-2-yl]oxy}-N,N-dimethylbenzamide (6) N,N-dimethyl-4-8-{[4-5-(morpholin-4-yl)-6-1-{1H-pyrrolo[2,3-b]pyridin-5-yl}-1,3,5-triazin-2-yl]oxy}benzamide (7) 4-14-{[4-1-(6-17-aminopyridin-3-yl)-6-5-(morpholin-4-yl)-1,3,5-triazin-2-yl]oxy}-N,N-dimethylbenzamide (8) (1r,4r)-4-21-{[4-1-(1H-indazol-4-yl)-6-5-(morpholin-4-yl)-1,3,5-triazin-2-yl]oxy}-N,N-dimethylcyclohexane-1-carboxamide (9) 4-14-{[4-1-(1H-indazol-4-yl)-6-5-(morpholin-4-yl)-1,3,5-triazin-2-yl]oxy}-N,N-dimethylpiperidine-1-carboxamide

(10) 4-14-{[4-1-(2-27-aminopyrimidin-5-yl)-6-5-(morpholin-4-yl)-1,3,5-triazin-2-yl]oxy}-N,N-dimethylbenzamide

(11) 1-6-[4-1-(2-22-aminopyrimidin-5-yl)-6-5-(morpholin-4-yl)-1,3,5-triazin-2-yl]-1,4-diazepan-5-one

(12) 4-14-{[4-1-(1H-indazol-4-yl)-6-5-(morpholin-4-yl)-1,3,5-triazin-2-yl]oxy}-N,N-dimethylbenzamide

(13) 3-((4-(2-aminopyrimidin-5-yl)-6-morpholino-1,3,5-triazin-2-yl)amino)benzamide

(14) 3-((4-(6-aminopyridin-3-yl)-6-morpholino-1,3,5-triazin-2-yl)amino)-N,N-dimethylbenzamide Biological Assay P110 Alpha TR-FRET Assay PI3K alpha kinase assay may be done using HTRF Transcreener ADP Assay (Cisbio).

Methodology:

Composition of the reaction buffer was as follows 50 mM HEPES, pH 7.5, 5 mM MgCl2, 1 mM DTT, 30 μM Na$_3$VO$_4$. PI3 Kinase was procured from Millipore Upstate. PIP2 Substrate (diC8, EchelonP-4508) was diluted from 1 mM Stock. ATP was used at final concentration of 10 μM. Corning 384 well white plates were used for the assay.

2 μl of diluted enzyme (50 ng), 3 μl of diluted compound and 5 μl of buffer were added, mixed then incubated for 20 minutes with shaking at 400 rpm. 3 μl of substrate (10 μM of ATP and 5 μM PIP2) were added to initiate the reaction. The samples were incubated for 20 min. At the end of the reaction time 10 μl of the Detection mix (5 μl of ADP-D2 and 5 μl of Anti-ADP-Cryptate) was added and the contents were incubated for 1 h. The reaction plate was directly read in an Envision Multilabel Plate Reader.

Relative fluorescence units (RFU) at 665 nm was plotted against the concentration of inhibitor and the IC$_{50}$ was calculated using Graph Pad Prism using non-linear regression fit method. The data of certain compounds are provided in Table 1 below by way of illustration.

Screening Compounds for Anti Proliferation Activity Using MTT Method

Proliferation inhibitory activity on ovarian cancer cells (A2780) was done using standard protocols. Cells were seeded into 96-well plates at 10000 cells per well overnight and then incubated with three concentrations (20, 2 and 0.2 μM) of compounds in triplicate wells per treatment. After culturing the cells for 48 h, MTT dye solution was added to each well and samples were incubated at 37° C. for 4 h. The formazan product formed during this reaction process was dissolved by adding 100 μl of DMSO to each well and the resultant colored solution in plates were read at 550 nm. Each treatment included nine wells. The % inhibition was calculated from the % formazan formation compared with a control in which no compound was added. The data obtained for a few compounds are provided in Table 1 below by way of illustration.

Pharmacokinetic Study

For pharmacokinetic study female swiss mice were used. The swiss mice weighing 25-30 g, fasted overnight, were orally dosed at 3 mg/kg body weight of compound in PEG 400. Blood samples (40 μl) were collected from each mouse by retro-orbital bleeding at 0, 0.16, 0.5, 1, 2, 4, 6 and 8 h after dosing into the tubes containing heparin as an anticoagulant. The samples were stored in ice and within 1 h after collection samples were centrifuged at 10000 RPM at 4° C. Plasma was collected and stored at −80° C. until analyis. The concentration of compounds in plasma were determined by liquid chromatography-tandem mass spectrometry (LC-MS/MS).

The protein precipitation method was used to extract the compounds. Acetonitrile was added to plasma, vortexed and centrifuged at 10000 RPM at 4° C. The supenatent was collected and injected onto the column. A CTC HTC PAL auto sampler (LEAP Technologies) linked to a Shimadzu SCL-10A VP HTC controller with LC-10AD pumps (Shimadzu), coupled with a Sciex API 3000 triple quadrupole mass spectrometer were used for the LC-MS/MS analysis. Some compounds as per the present invention are represented in the table below, were tested and their PK values are reported in Table 2.

TABLE 2

PK parameters of three exemplary compounds

| | PK Parameters | | |
|---|---|---|---|
| | 1113 | 1126 | 1144 |
| Tmax (hr) | 1.00 | 0.83 | 1.33 |
| Cmax (nM) | 1244 | 535 | 1664 |

TABLE 2-continued

| PK parameters of three exemplary compounds | | | |
|---|---|---|---|
| | PK Parameters | | |
| | 1113 | 1126 | 1144 |
| AUC (nM-hr) | 5246 | 1618 | 5849 |
| Elimination $t_{1/2}$ (hr) | 4.86 | 3.15 | 4.34 |

Compounds

Certain compounds envisaged within the scope of this invention are illustrated in Table 3. The compounds only serve as a means of exemplification and are not meant to limit the scope and spirit of the invention.

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1001 | 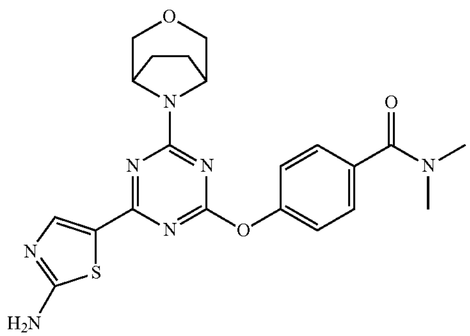 [SMILES: CN(C)C(=O)c1ccc(Oc2nc(-c3cnc(N)s3)nc(N3C4CCC3COC4)n2)cc1] | | | | C21H23N7O3S | 453.5 | 454.0 | <5 |
| 1002 | 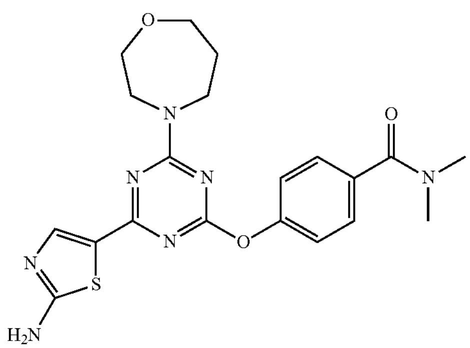 [SMILES: CN(C)C(=O)c1ccc(Oc2nc(-c3cnc(N)s3)nc(N3CCCOCC3)n2)cc1] | | | | C20H23N7O3S | 441.5 | 443.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1003 | 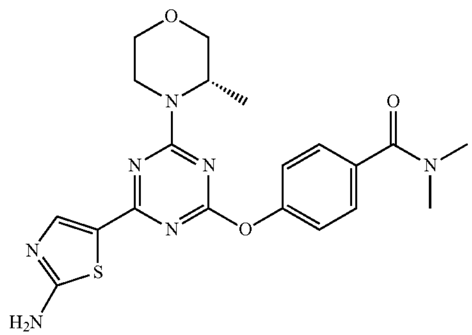 [SMILES: C[C@H]1COCCN1c1nc(Oc2ccc(C(=O)N(C)C)cc2)nc(-c2cnc(N)s2)n1] | | | | C20H23N7O3S | 441.5 | 443.0 | <5 |
| 1004 | 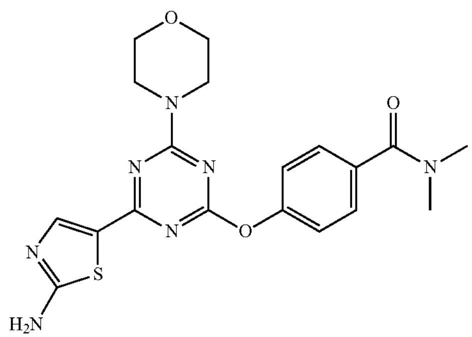 | | | | C19H21N7O3S | 427.5 | 428.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1005 | 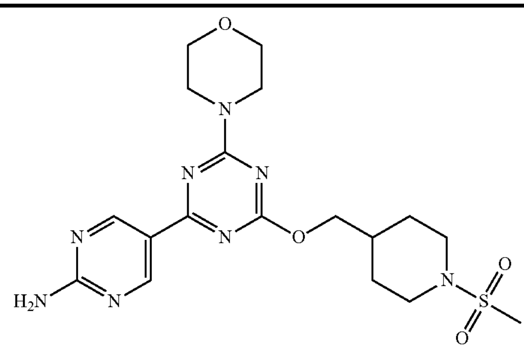 | S₁—O—CH₂—(piperidine-N-SO₂CH₃) | morpholine-N-S₃ | 2-aminopyrimidin-5-yl-S₂ | C18H26N8O4S | 450.5 | 452.0 | <5 |
| 1006 | 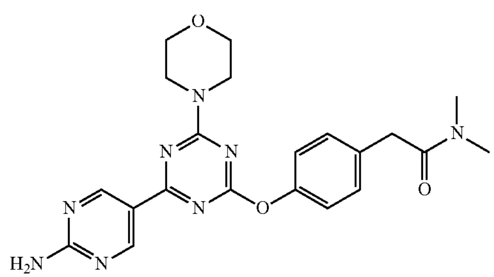 [SMILES: CN(C)C(=O)Cc1ccc(Oc2nc(-c3cnc(N)nc3)nc(N3CCOCC3)n2)cc1] | S₁—O—(phenyl)—CH₂—C(=O)—N(CH₃)₂ | morpholine-N-S₃ | 2-aminopyrimidin-5-yl-S₂ | C21H24N8O3 | 436.5 | 438.0 | <5 |
| 1007 | 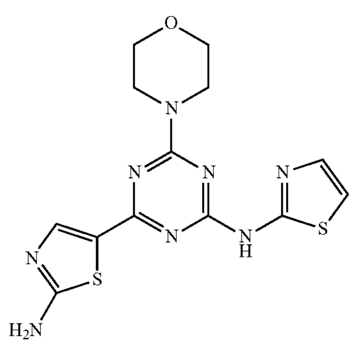 | thiazol-2-yl-NH—S₁ | morpholine-N-S₃ | 2-aminothiazol-5-yl-S₂ | C22H22N6O3 | 362.4 | 419 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1008 | [structure] | [structure] | [structure] | [structure] | C19H27N9O3 | 429.5 | 431.0 | <5 |
| 1009 | [structure] | [structure] | [structure] | [structure] | C20H22N8O3 | 422.4 | 423.0 | <5 |
| 1010 | [structure] | [structure] | [structure] | [structure] | C21H21N7O3 | 419.4 | 421.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1011 | 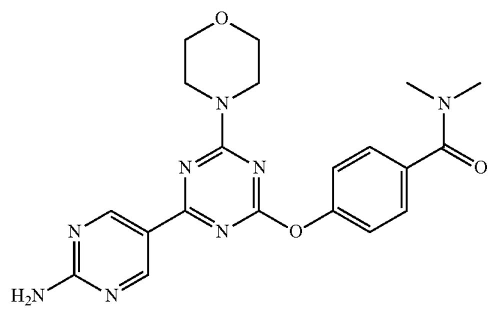 [SMILES: CN(C)C(=O)c1ccc(Oc2nc(-c3cnc(N)nc3)nc(N3CCOCC3)n2)cc1] | N,N-dimethylbenzamide with O-S1 (para) | morpholine-N-S3 | 2-aminopyrimidin-5-yl-S2 | C20H22N8O3 | 422.5 | 429.0 | <5 |
| 1012 | 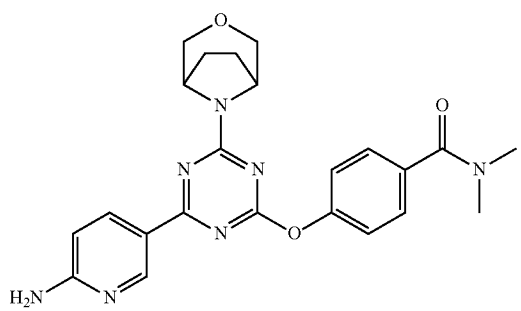 [SMILES: CN(C)C(=O)c1ccc(Oc2nc(-c3ccc(N)nc3)nc(N3C4CCC3COC4)n2)cc1] | N,N-dimethylbenzamide with O-S1 (para) | 8-oxa-3-azabicyclo[3.2.1]octane-N-S3 | 6-aminopyridin-3-yl-S2 | C23H25N7O3 | 447.5 | 448.0 | <5 |
| 1013 | 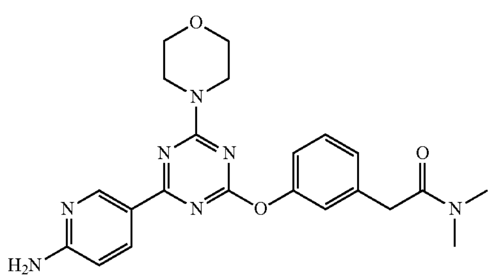 [SMILES: CN(C)C(=O)Cc1cccc(Oc2nc(-c3ccc(N)nc3)nc(N3CCOCC3)n2)c1] | N,N-dimethylphenylacetamide with O-S1 (meta) | morpholine-N-S3 | 6-aminopyridin-3-yl-S2 | C22H25N7O3 | 435.5 | 437.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1014 | 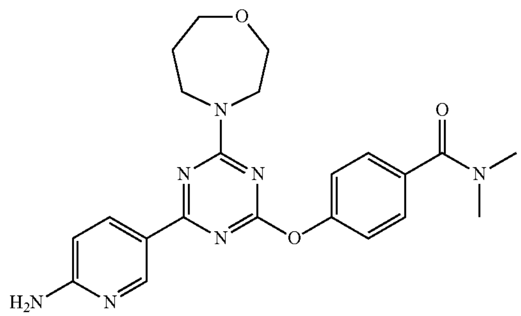 [SMILES: CN(C)C(=O)c1ccc(Oc2nc(-c3ccc(N)nc3)nc(N3CCCOCC3)n2)cc1] | | | | C22H25N7O3 | 435.5 | 436.0 | <5 |
| 1015 | 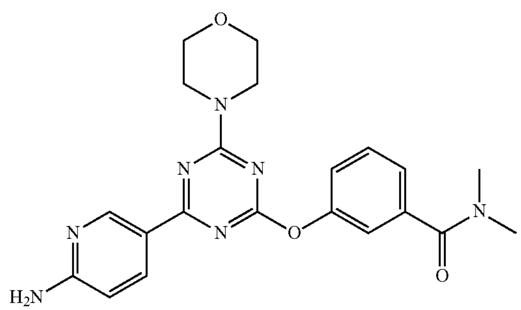 [SMILES: CN(C)C(=O)c1cccc(Oc2nc(-c3ccc(N)nc3)nc(N3CCOCC3)n2)c1] | | | | C21H23N7O3 | 421.5 | 458.0 | <5 |
| 1016 | 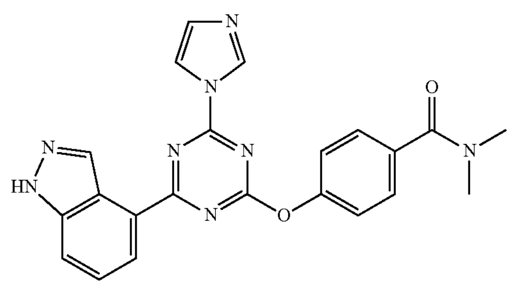 [SMILES: CN(C)C(=O)c1ccc(Oc2nc(-c3cccc4[nH]ncc34)nc(-n3ccnc3)n2)cc1] | | | | C22H18N8O2 | 426.4 | 427.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1017 | 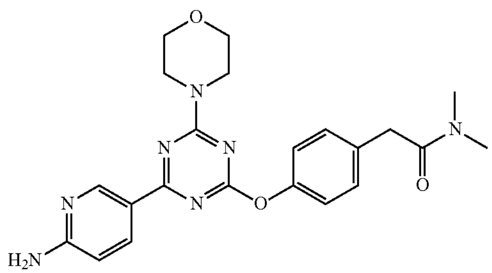 [SMILES: CN(C)C(=O)Cc1ccc(Oc2nc(-c3ccc(N)nc3)nc(N3CCOCC3)n2)cc1] | | | | C22H25N7O3 | 435.5 | 436.0 | <5 |
| 1018 | 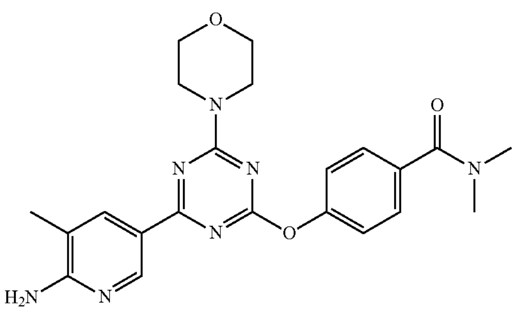 [SMILES: Cc1cc(-c2nc(Oc3ccc(C(=O)N(C)C)cc3)nc(N3CCOCC3)n2)cnc1N] | | | | C22H25N7O3 | 435.5 | 437.0 | <5 |
| 1019 | 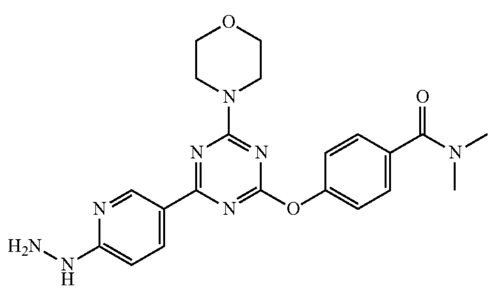 [SMILES: CN(C)C(=O)c1ccc(Oc2nc(-c3ccc(NN)nc3)nc(N3CCOCC3)n2)cc1] | | | | C21H24N8O3 | 436.5 | 438.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1020 | 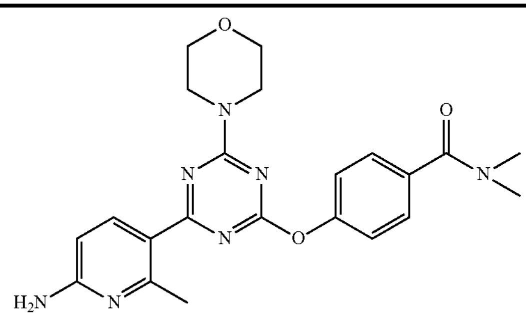 | | | | C22H25N7O3 | 435.5 | 437.0 | <5 |
| 1021 | 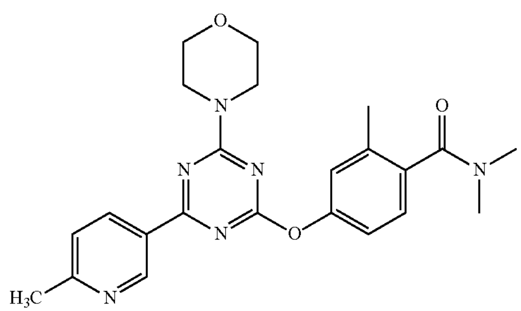 | | | | C22H25N7O3 | 435.2 | 436.0 | <5 |
| 1022 | 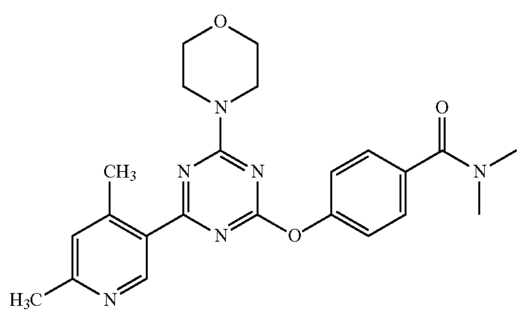 | | | | C22H25N7O3 | 435.5 | 437.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1023 | 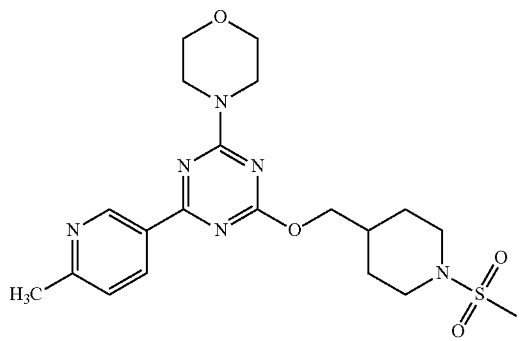 | | | | C19H27N7O4S | 449.5 | 451.0 | <5 |
| 1024 | 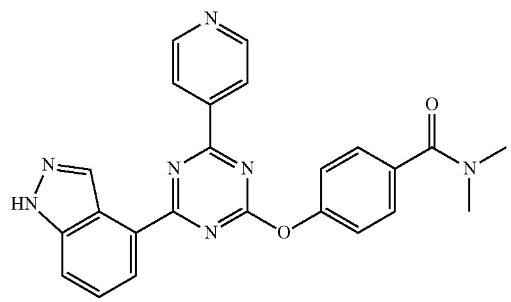 [SMILES: CN(C)C(=O)c1ccc(Oc2nc(-c3ccncc3)nc(-c3cccc4[nH]ncc34)n2)cc1] | | | | C24H19N7O2 | 437.5 | 438.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1025 | 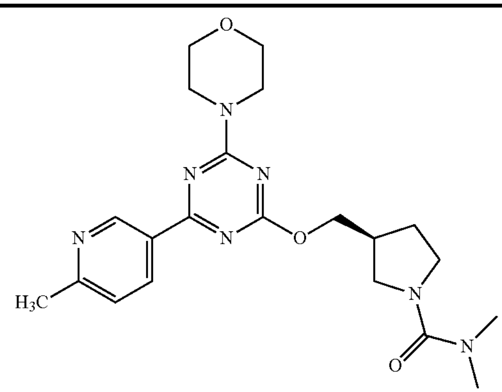 | | | | C20H28N8O3 | 428.5 | 429.0 | <5 |
| 1026 | 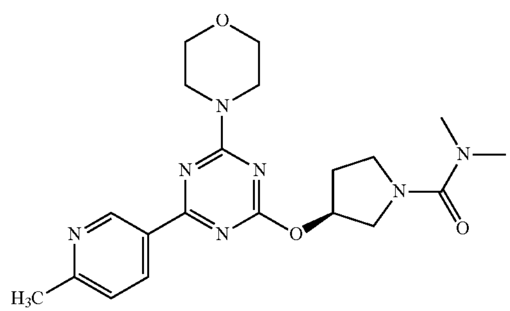 | | | | C19H26N8O3 | 414.5 | 415.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1027 | 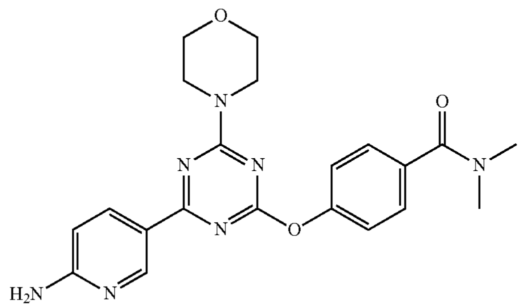 [SMILES: CN(C)C(=O)c1ccc(Oc2nc(-c3ccc(N)nc3)nc(N3CCOCC3)n2)cc1] | | | | C21H23N7O3 | 421.5 | 422.0 | <5 |
| 1028 | 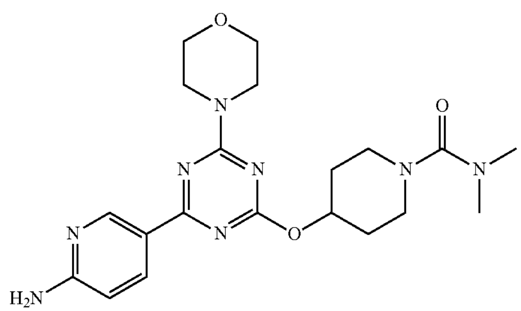 [SMILES: CN(C)C(=O)N1CCC(Oc2nc(-c3ccc(N)nc3)nc(N3CCOCC3)n2)CC1] | | | | C20H28N8O3 | 428.5 | 429.0 | <5 |
| 1029 | 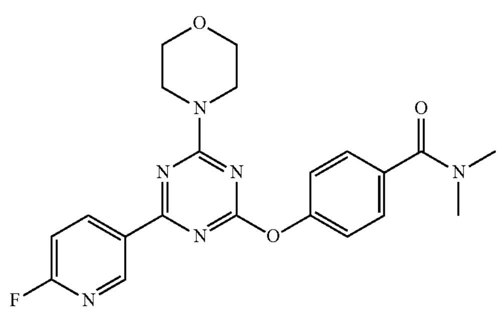 [SMILES: CN(C)C(=O)c1ccc(Oc2nc(-c3ccc(F)nc3)nc(N3CCOCC3)n2)cc1] | | | | C21H21FN6O3 | 424.4 | 425.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1030 | (structure with morpholine-triazine-O-phenyl-C(O)N(CH3)2 and 3-hydroxyphenyl) | 4-(O-S1)phenyl-C(O)N(CH3)(CH3) | morpholine-N-S3 | 3-hydroxyphenyl-S2 | C22H23N5O4 | 421.5 | 422.0 | <5 |
| 1031 | (structure with morpholine-triazine-O-phenyl-C(O)N(CH3)2 and 4-aminophenyl) | 4-(O-S1)phenyl-C(O)N(CH3)(CH3) | morpholine-N-S3 | 4-aminophenyl-S2 | C22H24N6O3 | 420.5 | 421.0 | <5 |
| 1032 | (structure with morpholine-triazine-O-phenyl-C(O)N(CH3)2 and 5-aminopyridin-3-yl) | 4-(O-S1)phenyl-C(O)N(CH3)(CH3) | morpholine-N-S3 | 5-aminopyridin-3-yl-S2 | C21H23N7O3 | 421.5 | 422.0 | <5 |

-continued

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1033 | 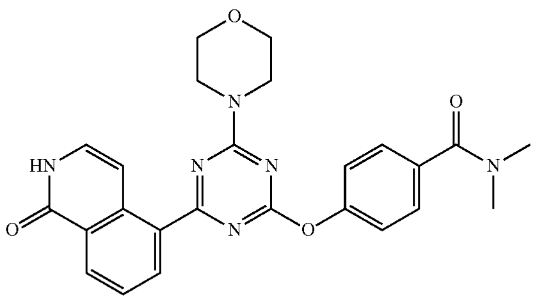 [SMILES: CN(C)C(=O)c1ccc(Oc2nc(-c3cccc4c(=O)[nH]ccc34)nc(N3CCOCC3)n2)cc1] | | | | C25H24N6O4 | 472.5 | 473.0 | >5 |
| 1034 | 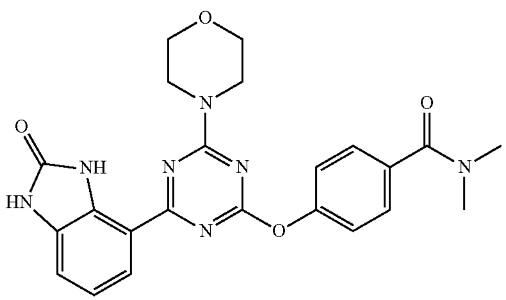 [SMILES: CN(C)C(=O)c1ccc(Oc2nc(-c3cccc4[nH]c(=O)[nH]c34)nc(N3CCOCC3)n2)cc1] | | | | C23H23N7O4 | 461.5 | 462.0 | >5 |
| 1035 | 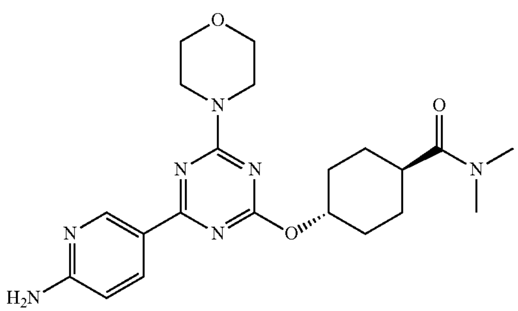 [SMILES: CN(C)C(=O)[C@H]1CC[C@H](Oc2nc(-c3ccc(N)nc3)nc(N3CCOCC3)n2)CC1] | | | | C21H29N7O3 | 427.5 | 464.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1036 | 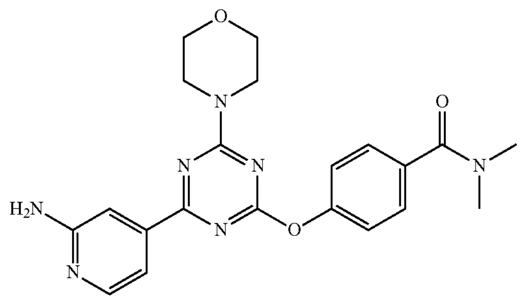 [SMILES: CN(C)C(=O)c1ccc(Oc2nc(-c3ccnc(N)c3)nc(N3CCOCC3)n2)cc1] | | | | C21H23N7O3 | 421.5 | 423.0 | <5 |
| 1037 | 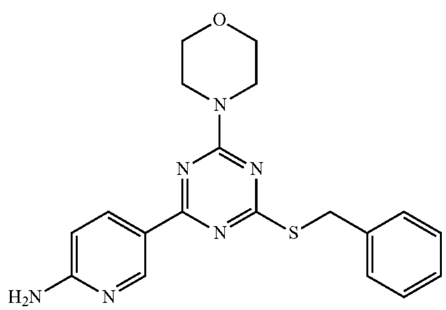 [SMILES: Nc1ccc(-c2nc(SCc3ccccc3)nc(N3CCOCC3)n2)cn1] | | | | C19H20N6OS | 380.5 | 382.0 | <5 |
| 1038 | 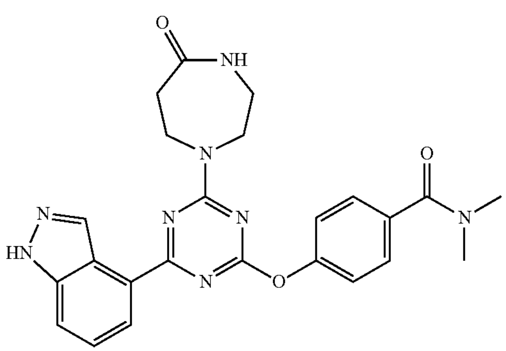 [SMILES: CN(C)C(=O)c1ccc(Oc2nc(-c3cccc4[nH]ncc34)nc(N3CCNC(=O)CC3)n2)cc1] | | | | C24H24N8O3 | 472.5 | 473.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1039 | ![structure] | 4-(dimethylcarbamoyl)phenyl ether with S1-O | piperidine-3-carboxamide with N-S3 | 1H-indazol-4-yl with S2 | C25H26N8O3 | 486.5 | 488.0 | >5 |
| 1040 | ![structure] | 3-(dimethylcarbamoyl)phenyl amine with S1-NH | morpholine with N-S3 | 2-aminopyrimidin-5-yl with S2 | C20H23N9O2 | 421.5 | 423.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1041 | 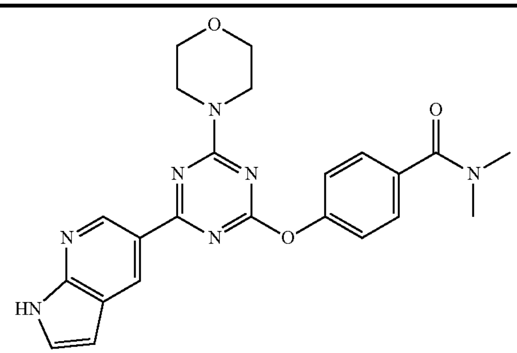 | | | | C23H23N7O3 | 445.5 | 447.0 | <5 |
| 1042 | 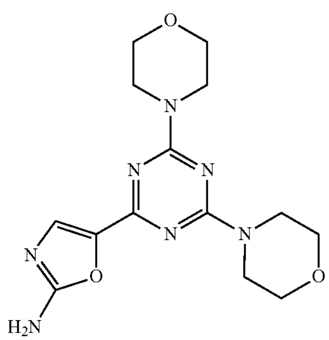 [SMILES: Nc1ncc(-c2nc(N3CCOCC3)nc(N3CCOCC3)n2)o1] | | | | C14H19N7O2S | 349.4 | 351.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1043 | 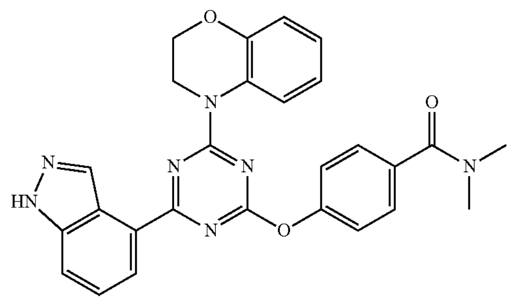 [SMILES: CN(C)C(=O)c1ccc(Oc2nc(-c3cccc4[nH]ncc34)nc(N3CCOc4ccccc43)n2)cc1] | | | | C27H23N7O3 | 493.5 | 494.0 | >5 |
| 1044 | 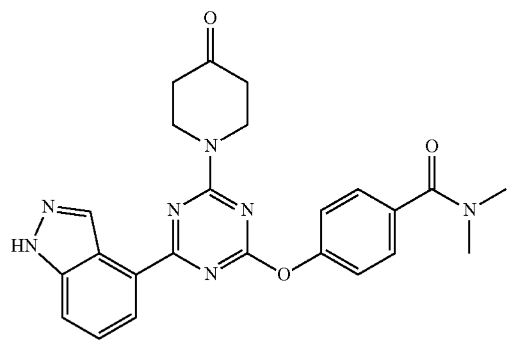 [SMILES: CN(C)C(=O)c1ccc(Oc2nc(-c3cccc4[nH]ncc34)nc(N3CCC(=O)CC3)n2)cc1] | | | | C24H23N7O3 | 457.5 | 459.0 | >5 |
| 1045 | 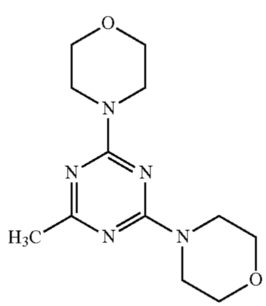 [SMILES: Cc1nc(N2CCOCC2)nc(N2CCOCC2)n1] | | | | C12H19N5O2 | 265.3 | 266.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1046 | 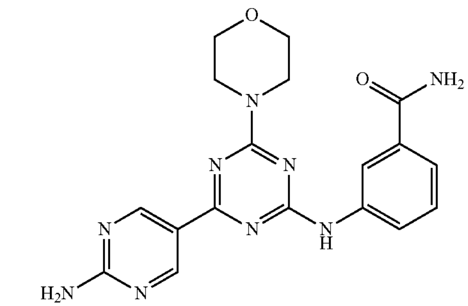 [SMILES: NC(=O)c1cccc(Nc2nc(-c3cnc(N)nc3)nc(N3CCOCC3)n2)c1] | | | | C18H19N9O2 | 393.4 | 394.0 | <5 |
| 1047 | 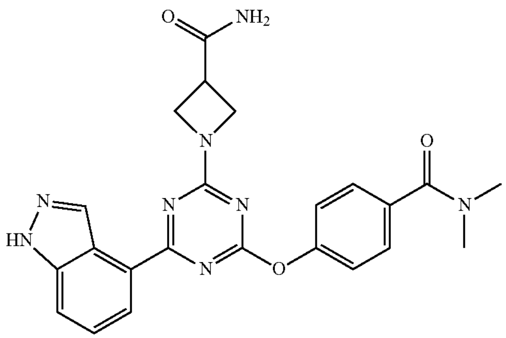 [SMILES: CN(C)C(=O)c1ccc(Oc2nc(-c3cccc4[nH]ncc34)nc(N3CC(C(N)=O)C3)n2)cc1] | | | | C23H22N8O3 | 458.5 | 460.0 | >5 |
| 1048 | 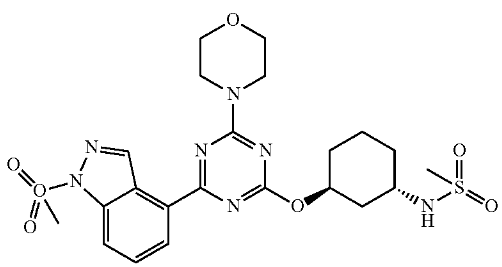 | | | | C22H29N7O6S2 | 551.6 | 553.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1049 | 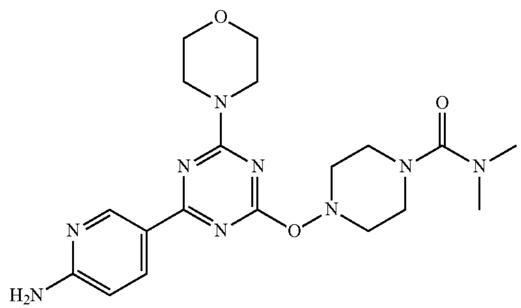 [SMILES: CN(C)C(=O)N1CCN(Oc2nc(-c3ccc(N)nc3)nc(N3CCOCC3)n2)CC1] | | | | C20H29N9O2 | 427.5 | 429.0 | <5 |
| 1050 | 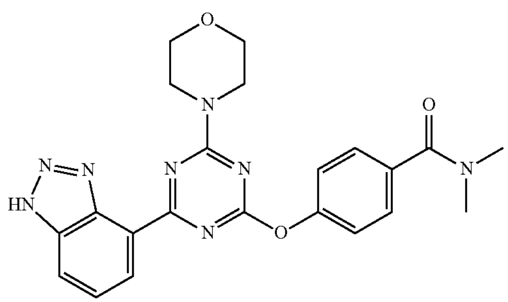 [SMILES: CN(C)C(=O)c1ccc(Oc2nc(-c3cccc4[nH]nnc34)nc(N3CCOCC3)n2)cc1] | | | | C22H22N8O3 | 446.5 | 447.0 | >5 |
| 1051 | 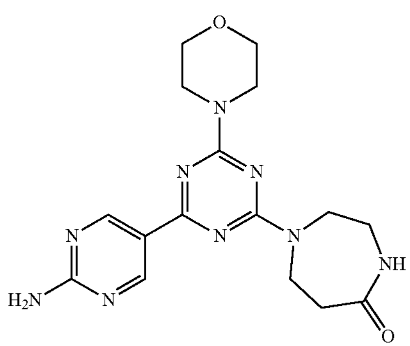 [SMILES: Nc1ncc(-c2nc(N3CCOCC3)nc(N3CCNC(=O)CC3)n2)cn1] | | | | C16H21N9O2 | 371.4 | 372.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1052 | 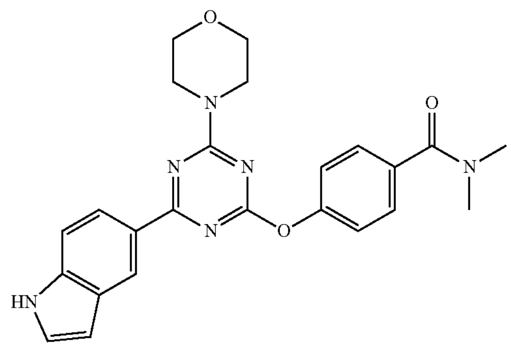 [SMILES: CN(C)C(=O)c1ccc(Oc2nc(-c3ccc4[nH]ccc4c3)nc(N3CCOCC3)n2)cc1] | | | | C24H24N6O3 | 444.5 | 446.0 | <5 |
| 1053 | 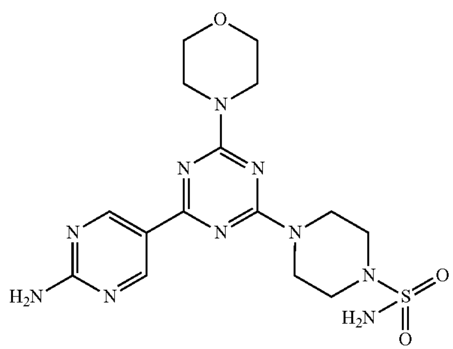 [SMILES: Nc1ncc(-c2nc(N3CCOCC3)nc(N3CCN(S(N)(=O)=O)CC3)n2)cn1] | | | | C15H22N10O3S | 422.5 | 423.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1054 | 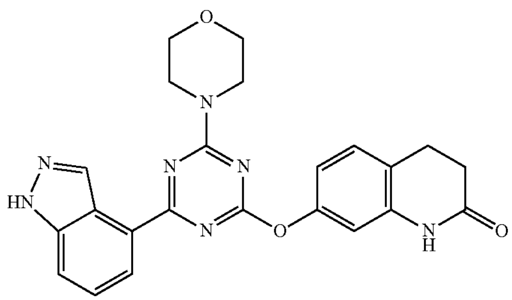 [SMILES: O=C1CCc2ccc(Oc3nc(-c4cccc5[nH]ncc45)nc(N4CCOCC4)n3)cc2N1] | | | | C23H21N7O3 | 443.5 | 445.0 | <5 |
| 1055 | 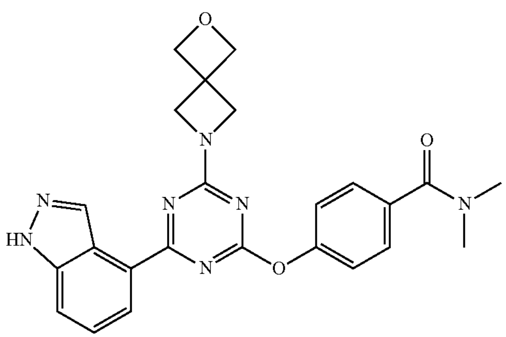 [SMILES: CN(C)C(=O)c1ccc(Oc2nc(-c3cccc4[nH]ncc34)nc(N3CC4(COC4)C3)n2)cc1] | | | | C24H23N7O3 | 457.5 | 459.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1056 | 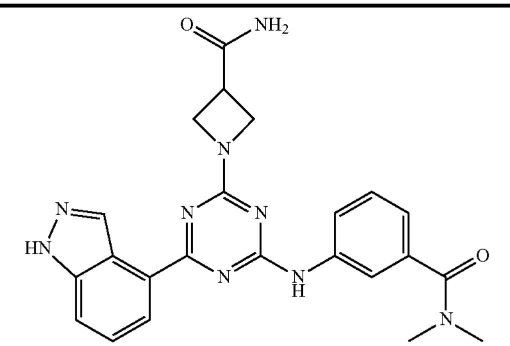 | | | | C23H23N9O2 | 457.5 | 458.0 | >5 |
| 1057 | 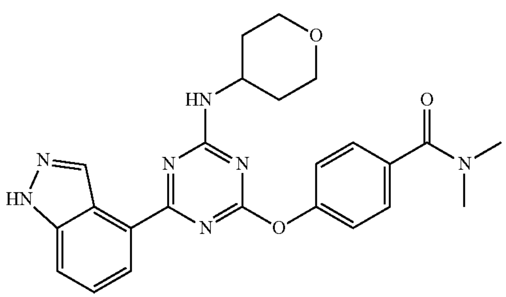 [SMILES: CN(C)C(=O)c1ccc(Oc2nc(NC3CCOCC3)nc(-c3cccc4[nH]ncc34)n2)cc1] | | | | C24H25N7O3 | 459.5 | 461.0 | >5 |
| 1058 | 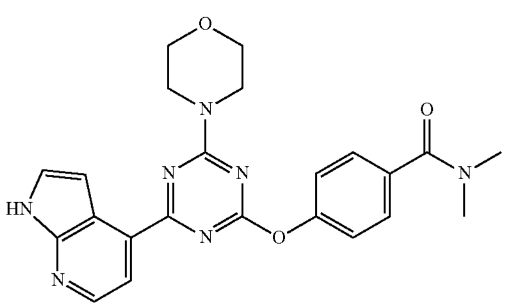 [SMILES: CN(C)C(=O)c1ccc(Oc2nc(-c3ccnc4[nH]ccc34)nc(N3CCOCC3)n2)cc1] | | | | C23H23N7O3 | 445.5 | 447.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1059 | 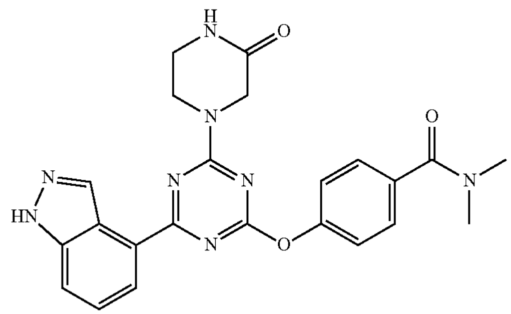 [SMILES: CN(C)C(=O)c1ccc(Oc2nc(-c3cccc4[nH]ncc34)nc(N3CCNC(=O)C3)n2)cc1] | | | | C23H22N8O3 | 458.5 | 460.0 | >5 |
| 1060 | 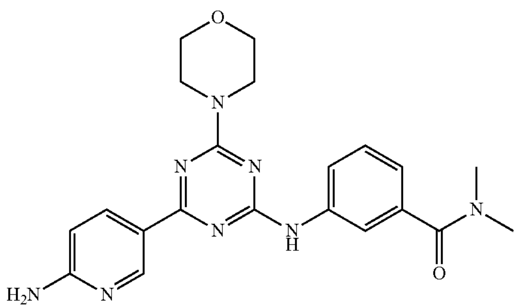 [SMILES: CN(C)C(=O)c1cccc(Nc2nc(-c3ccc(N)nc3)nc(N3CCOCC3)n2)c1] | | | | C21H24N8O2 | 420.5 | 421.0 | <5 |
| 1061 | 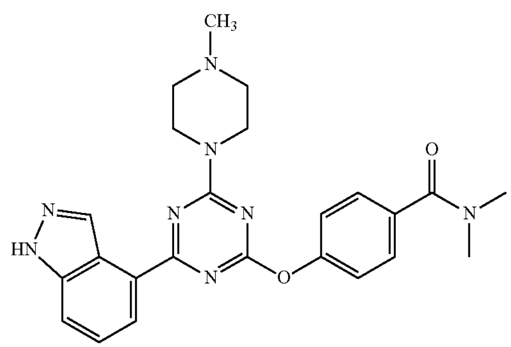 [SMILES: CN1CCN(c2nc(Oc3ccc(C(=O)N(C)C)cc3)nc(-c3cccc4[nH]ncc34)n2)CC1] | | | | C24H26N8O2 | 458.5 | 460.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1062 | 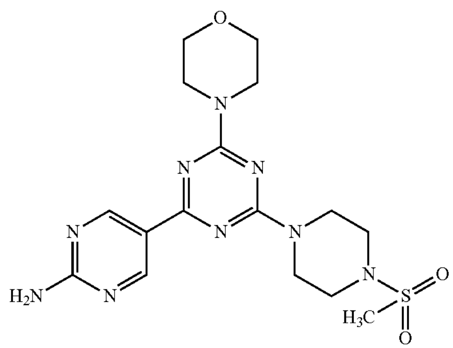 [SMILES: CS(=O)(=O)N1CCN(c2nc(-c3cnc(N)nc3)nc(N3CCOCC3)n2)CC1] | | | | C16H23N9O3S | 421.5 | 423.0 | <5 |
| 1063 | 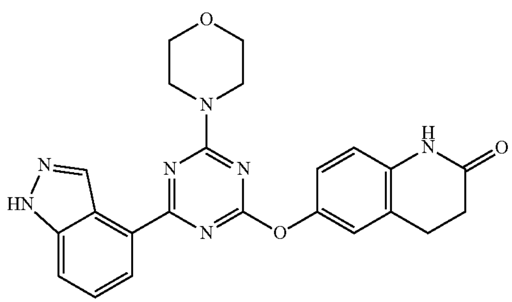 [SMILES: O=C1CCc2cc(Oc3nc(-c4cccc5[nH]ncc45)nc(N4CCOCC4)n3)ccc2N1] | | | | C23H21N7O3 | 443.5 | 445.0 | <5 |
| 1064 | 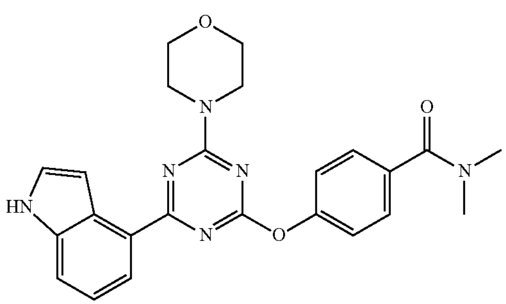 [SMILES: CN(C)C(=O)c1ccc(Oc2nc(-c3cccc4[nH]ccc34)nc(N3CCOCC3)n2)cc1] | | | | C24H24N6O3 | 444.5 | 445.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1065 | 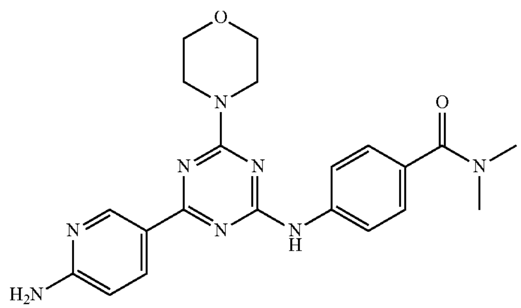 [SMILES: CN(C)C(=O)c1ccc(Nc2nc(-c3ccc(N)nc3)nc(N3CCOCC3)n2)cc1] | | | | C21H24N8O2 | 420.5 | 457.0 | <5 |
| 1066 | 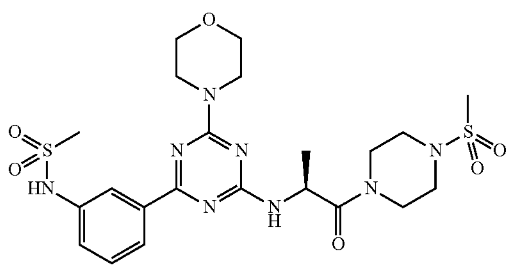 [SMILES: C[C@H](Nc1nc(-c2cccc(NS(C)(=O)=O)c2)nc(N2CCOCC2)n1)C(=O)N1CCN(S(C)(=O)=O)CC1] | | | | C22H32N8O6S2 | 568.6 | 570.0 | >5 |
| 1067 | 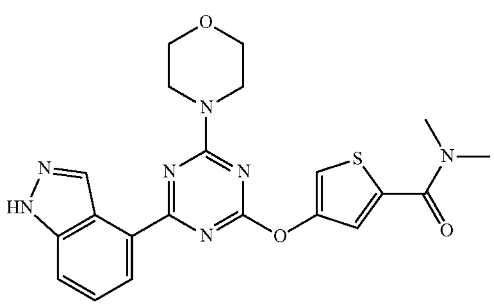 [SMILES: CN(C)C(=O)c1cc(Oc2nc(-c3cccc4[nH]ncc34)nc(N3CCOCC3)n2)cs1] | | | | C21H21N7O3S | 451.5 | 452.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1068 | 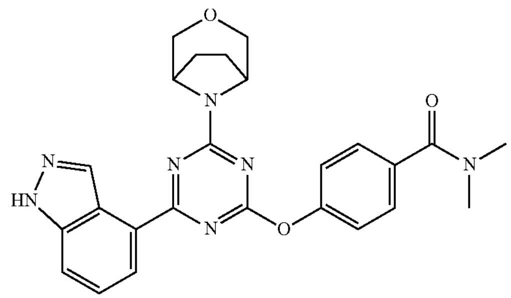 [SMILES: CN(C)C(=O)c1ccc(Oc2nc(-c3cccc4[nH]ncc34)nc(N3C4CCC3COC4)n2)cc1] | | | | C25H25N7O3 | 471.5 | 473.0 | >5 |
| 1069 | 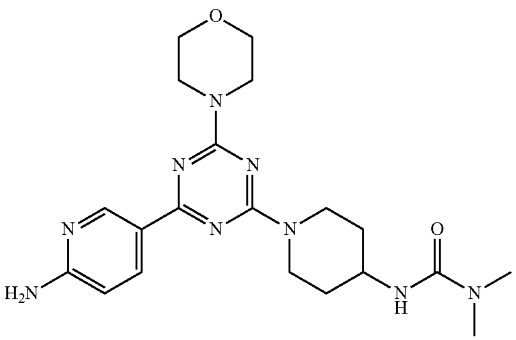 [SMILES: CN(C)C(=O)NC1CCN(c2nc(-c3ccc(N)nc3)nc(N3CCOCC3)n2)CC1] | | | | C20H29N9O2 | 427.5 | 428.0 | <5 |
| 1070 | 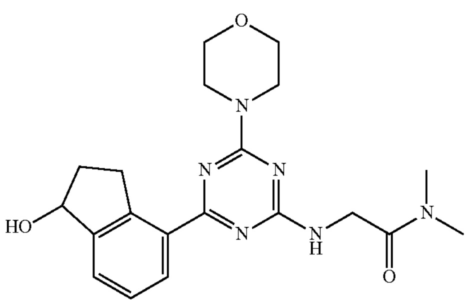 [SMILES: CN(C)C(=O)CNc1nc(-c2cccc3c2CCC3O)nc(N2CCOCC2)n1] | | | | C20H26N6O3 | 398.5 | 399.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1071 | 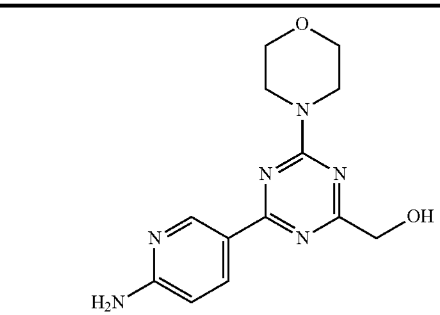 | | | | C13H16N6O2 | 288.3 | 290.0 | <5 |
| 1072 | 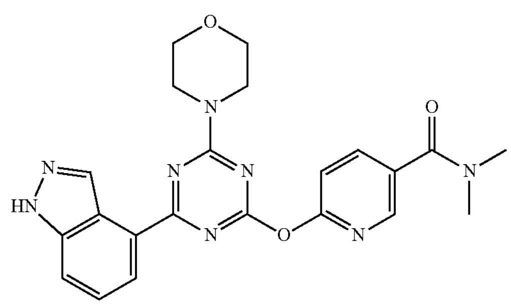 [SMILES: CN(C)C(=O)c1ccc(Oc2nc(-c3cccc4[nH]ncc34)nc(N3CCOCC3)n2)nc1] | | | | C22H22N8O3 | 446.5 | 448.0 | >5 |
| 1073 | 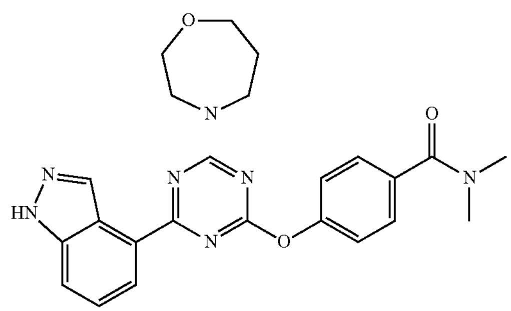 | | | | C24H25N7O3 | 459.5 | 461.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1074 | 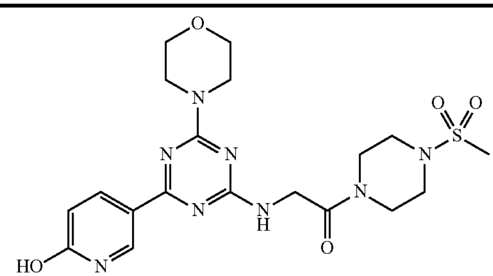 | | | | C19H26N8O5S | 478.5 | 479.0 | <5 |
| 1075 | 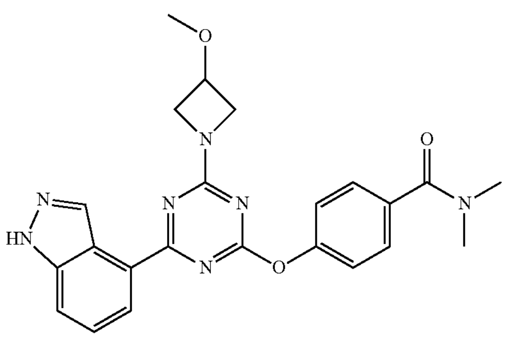 [SMILES: COC1CN(c2nc(Oc3ccc(C(=O)N(C)C)cc3)nc(-c3cccc4[nH]ncc34)n2)C1] | | | | C23H23N7O3 | 445.5 | 446.0 | >5 |
| 1076 | 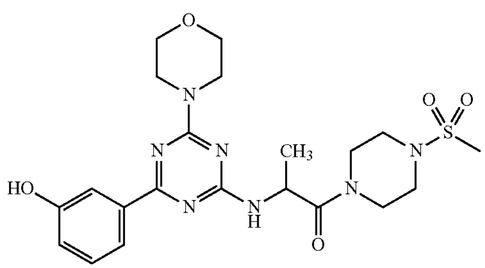 [SMILES: CC(Nc1nc(-c2cccc(O)c2)nc(N2CCOCC2)n1)C(=O)N1CCN(S(C)(=O)=O)CC1] | | | | C21H29N7O5S | 491.6 | 358.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1077 | 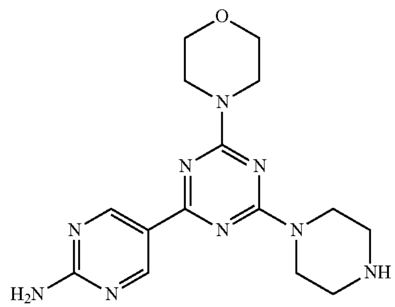 [SMILES: Nc1ncc(-c2nc(N3CCNCC3)nc(N3CCOCC3)n2)cn1] | | | | C15H21N9O | 343.4 | 344.0 | <5 |
| 1078 | 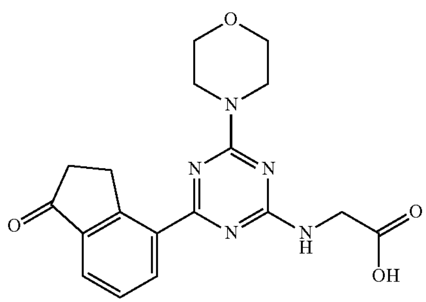 [SMILES: O=C(O)CNc1nc(-c2cccc3c2CCC3=O)nc(N2CCOCC2)n1] | | | | C18H19N5O4 | 369.4 | 370.0 | >5 |
| 1079 | 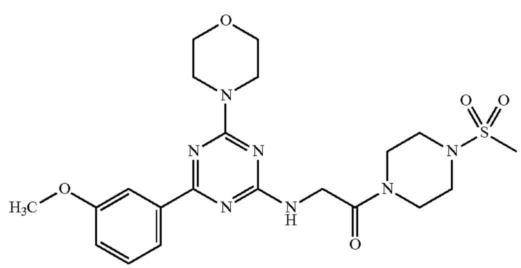 | | | | C21H29N7O5S | 491.6 | 493.0 | >5 |

-continued

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1080 | 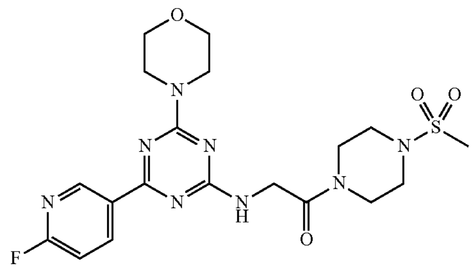 [SMILES: CS(=O)(=O)N1CCN(C(=O)CNc2nc(-c3ccc(F)nc3)nc(N3CCOCC3)n2)CC1] | | | | C19H25FN8O4S | 480.5 | 482.0 | >5 |
| 1081 | 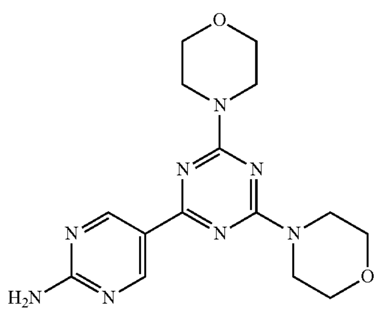 [SMILES: Nc1ncc(-c2nc(N3CCOCC3)nc(N3CCOCC3)n2)cn1] | | | | C15H20N8O2 | 344.4 | 345.0 | <5 |
| 1082 | 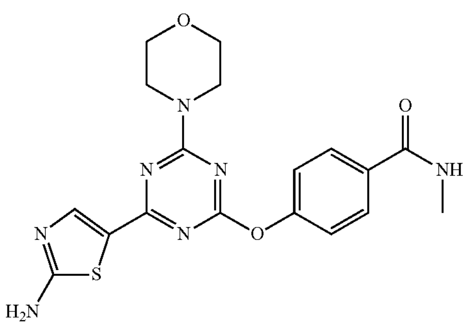 [SMILES: CNC(=O)c1ccc(Oc2nc(-c3cnc(N)s3)nc(N3CCOCC3)n2)cc1] | | | | C18H19N7O3S | 413.5 | 414.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1083 | 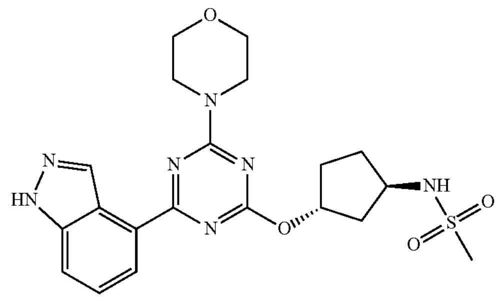 [SMILES: CS(=O)(=O)N[C@@H]1CC[C@@H](Oc2nc(-c3cccc4[nH]ncc34)nc(N3CCOCC3)n2)C1] | | | | C20H25N7O4S | 459.5 | 461.0 | <5 |
| 1084 | 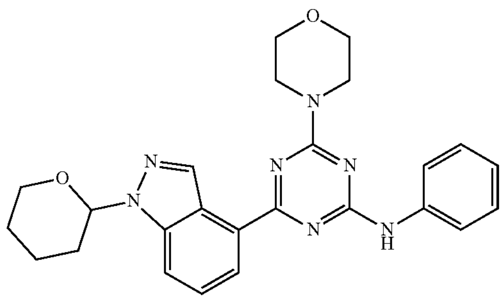 [SMILES: c1ccc(Nc2nc(-c3cccc4c3cnn4C3CCCCO3)nc(N3CCOCC3)n2)cc1] | | | | C25H27N7O2 | 457.5 | 458.0 | >5 |
| 1085 | 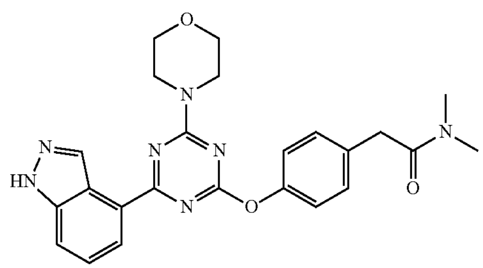 [SMILES: CN(C)C(=O)Cc1ccc(Oc2nc(-c3cccc4[nH]ncc34)nc(N3CCOCC3)n2)cc1] | | | | C24H25N7O3 | 459.5 | 461.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1086 | 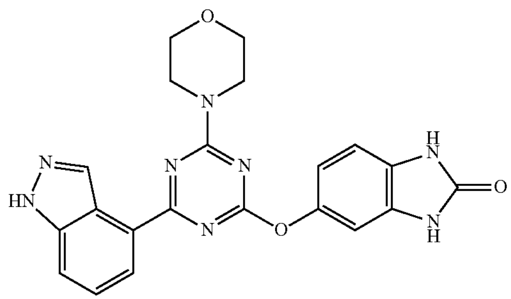 [SMILES: O=c1[nH]c2ccc(Oc3nc(-c4cccc5[nH]ncc45)nc(N4CCOCC4)n3)cc2[nH]1] | | | | C21H18N8O3 | 430.4 | 431.0 | <5 |
| 1087 | 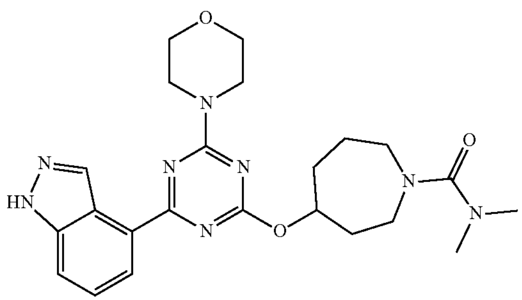 [SMILES: CN(C)C(=O)N1CCCC(Oc2nc(-c3cccc4[nH]ncc34)nc(N3CCOCC3)n2)CC1] | | | | C23H30N8O3 | 466.5 | 468.0 | <5 |
| 1088 | 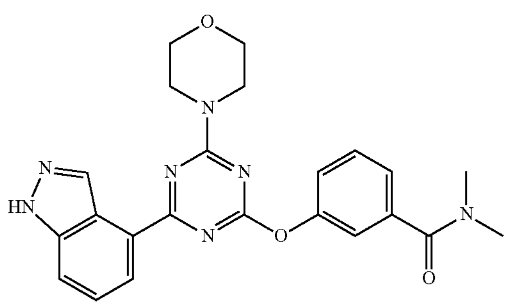 [SMILES: CN(C)C(=O)c1cccc(Oc2nc(-c3cccc4[nH]ncc34)nc(N3CCOCC3)n2)c1] | | | | C23H23N7O3 | 445.5 | 446.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1089 | 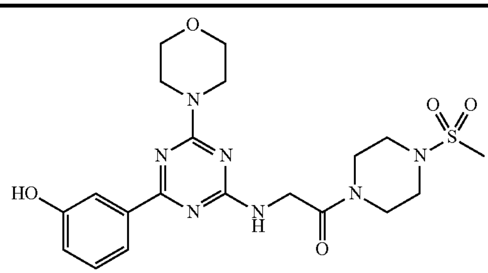 | | | | C20H27N7O5S | 477.5 | 478.0 | <5 |
| 1090 | 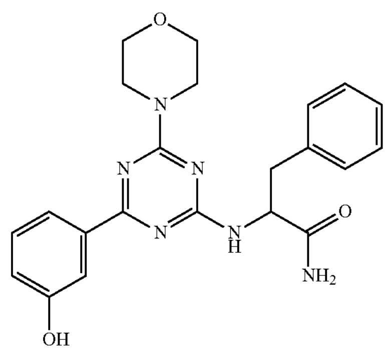 [SMILES: NC(=O)C(Cc1ccccc1)Nc1nc(-c2cccc(O)c2)nc(N2CCOCC2)n1] | | | | C22H24N6O3 | 420.5 | 421.0 | <5 |
| 1091 | 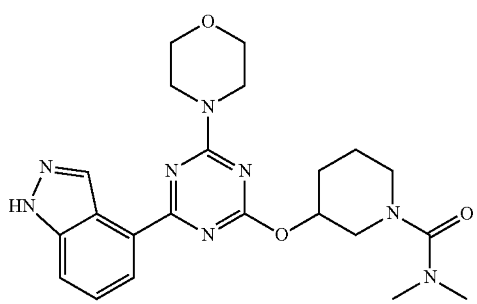 [SMILES: CN(C)C(=O)N1CCCC(Oc2nc(-c3cccc4[nH]ncc34)nc(N3CCOCC3)n2)C1] | | | | C22H28N8O3 | 452.5 | 453.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1092 | 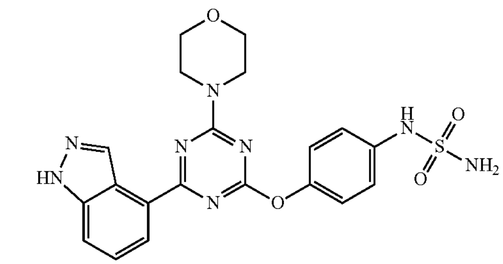 [SMILES: NS(=O)(=O)Nc1ccc(Oc2nc(-c3cccc4[nH]ncc34)nc(N3CCOCC3)n2)cc1] | | | | C20H20N8O4S | 468.5 | 470.0 | <5 |
| 1093 | 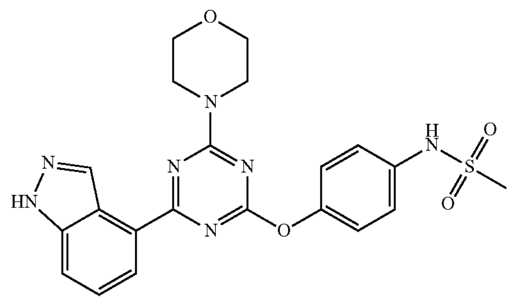 [SMILES: CS(=O)(=O)Nc1ccc(Oc2nc(-c3cccc4[nH]ncc34)nc(N3CCOCC3)n2)cc1] | | | | C21H21N7O4S | 467.5 | 468.0 | <5 |
| 1094 | 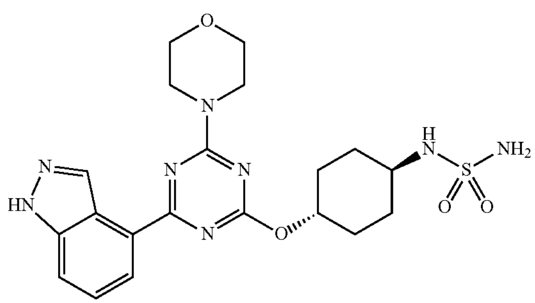 [SMILES: NS(=O)(=O)N[C@H]1CC[C@H](Oc2nc(-c3cccc4[nH]ncc34)nc(N3CCOCC3)n2)CC1] | | | | C20H26N8O4S | 474.5 | 475.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1095 | 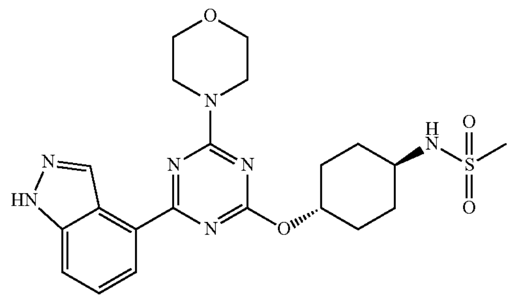 [SMILES: CS(=O)(=O)N[C@H]1CC[C@H](Oc2nc(-c3cccc4[nH]ncc34)nc(N3CCOCC3)n2)CC1] | | | | C21H27N7O4S | 473.6 | 475.0 | <5 |
| 1096 | 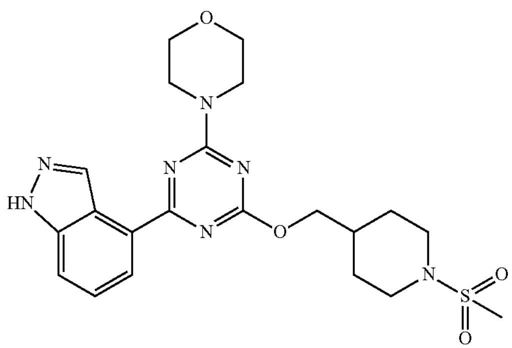 [SMILES: CS(=O)(=O)N1CCC(COc2nc(-c3cccc4[nH]ncc34)nc(N3CCOCC3)n2)CC1] | | | | C21H27N7O4S | 473.6 | 474.0 | <5 |
| 1097 | 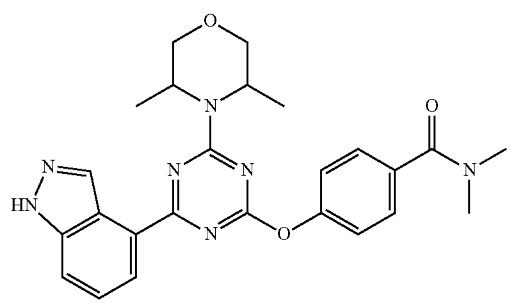 [SMILES: CC1COCC(C)N1c1nc(Oc2ccc(C(=O)N(C)C)cc2)nc(-c2cccc3[nH]ncc23)n1] | | | | C25H27N7O3 | 473.5 | 474.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1098 | 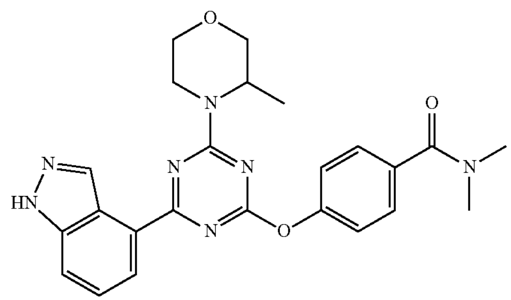 [SMILES: CC1COCCN1c1nc(Oc2ccc(C(=O)N(C)C)cc2)nc(-c2cccc3[nH]ncc23)n1] | | | | C24H25N7O3 | 459.5 | 461.0 | <5 |
| 1099 | 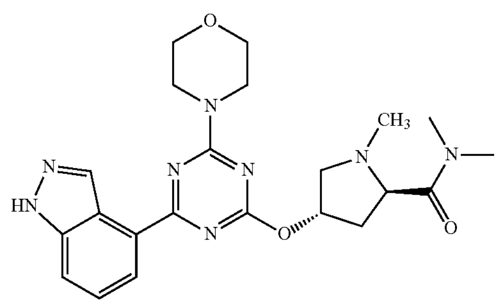 [SMILES: CN(C)C(=O)[C@H]1C[C@H](Oc2nc(-c3cccc4[nH]ncc34)nc(N3CCOCC3)n2)CN1C] | | | | C22H28N8O3 | 452.5 | 453.0 | <5 |
| 1100 | 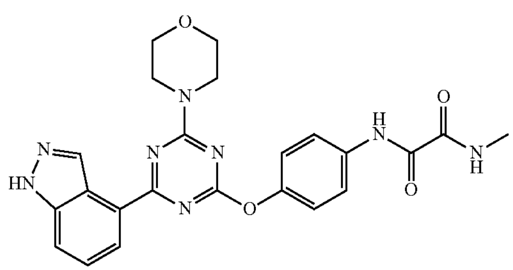 [SMILES: CNC(=O)C(=O)Nc1ccc(Oc2nc(-c3cccc4[nH]ncc34)nc(N3CCOCC3)n2)cc1] | | | | C23H22N8O4 | 474.5 | 478.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1101 | 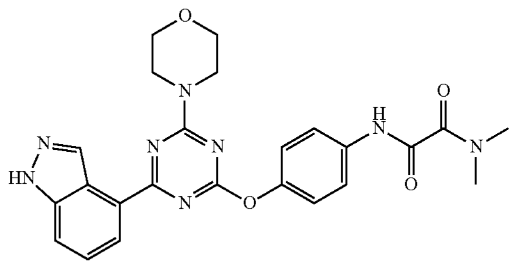 [SMILES: CN(C)C(=O)C(=O)Nc1ccc(Oc2nc(-c3cccc4[nH]ncc34)nc(N3CCOCC3)n2)cc1] | | | | C24H24N8O4 | 488.5 | 489.0 | <5 |
| 1102 | 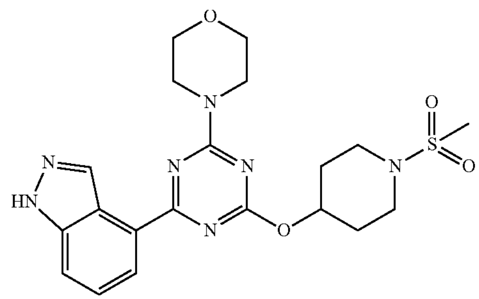 [SMILES: CS(=O)(=O)N1CCC(Oc2nc(-c3cccc4[nH]ncc34)nc(N3CCOCC3)n2)CC1] | | | | C20H25N7O4S | 459.5 | 461.0 | <5 |
| 1103 | 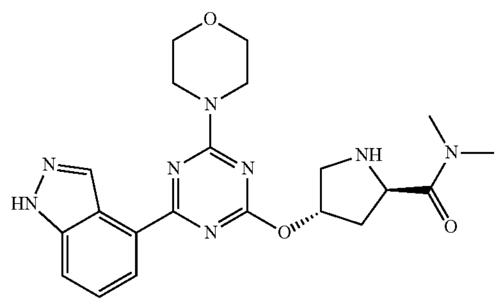 [SMILES: CN(C)C(=O)[C@H]1C[C@H](Oc2nc(-c3cccc4[nH]ncc34)nc(N3CCOCC3)n2)CN1] | | | | C21H26N8O3 | 438.5 | 439.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1104 | 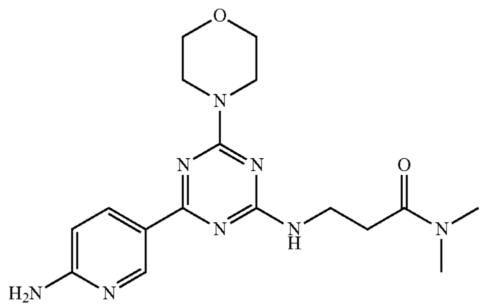 [SMILES: CN(C)C(=O)CCNc1nc(-c2ccc(N)nc2)nc(N2CCOCC2)n1] | | | | C17H24N8O2 | 372.4 | 373.0 | <5 |
| 1105 | 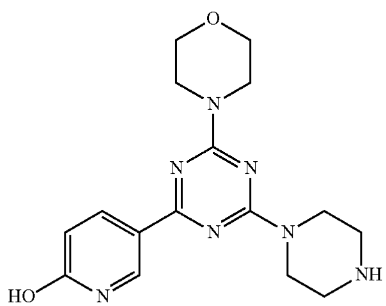 [SMILES: Oc1ccc(-c2nc(N3CCNCC3)nc(N3CCOCC3)n2)cn1] | | | | C16H21N7O2 | 343.4 | 344.0 | <5 |
| 1106 | 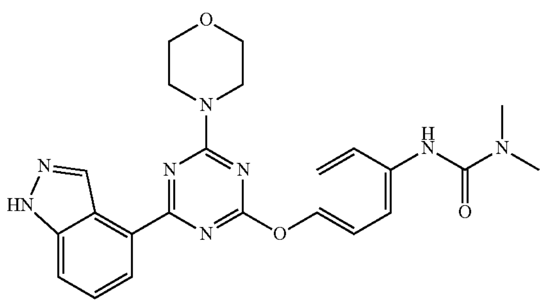 [SMILES: C=C/C(=C\C=C\Oc1nc(-c2cccc3[nH]ncc23)nc(N2CCOCC2)n1)NC(=O)N(C)C] | | | | C23H24N8O3 | 460.5 | 461.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1107 | 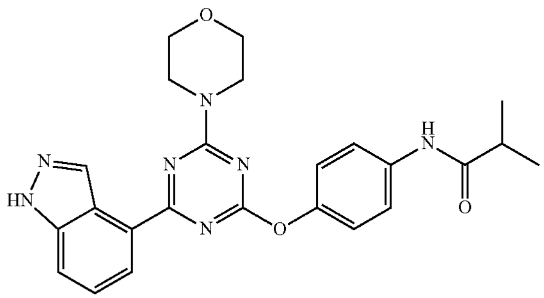 [SMILES: CC(C)C(=O)Nc1ccc(Oc2nc(-c3cccc4[nH]ncc34)nc(N3CCOCC3)n2)cc1] | | | | C24H25N7O3 | 459.5 | 460.0 | <5 |
| 1108 | 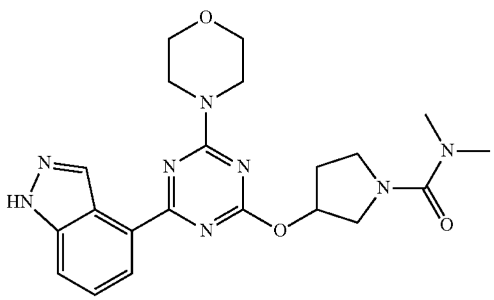 [SMILES: CN(C)C(=O)N1CCC(Oc2nc(-c3cccc4[nH]ncc34)nc(N3CCOCC3)n2)C1] | | | | C21H26N8O3 | 438.5 | 439.0 | <5 |
| 1109 | 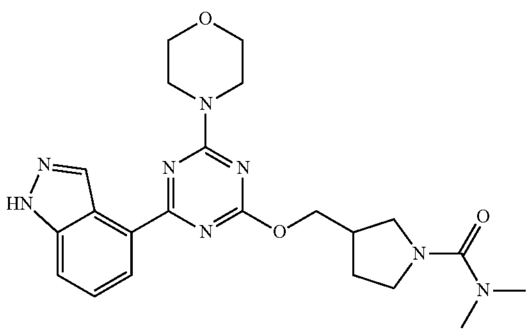 [SMILES: CN(C)C(=O)N1CCC(COc2nc(-c3cccc4[nH]ncc34)nc(N3CCOCC3)n2)C1] | | | | C22H28N8O3 | 452.5 | 453.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1110 | 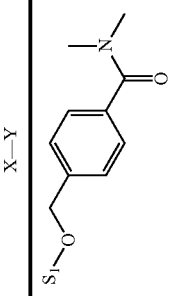 |  |  | 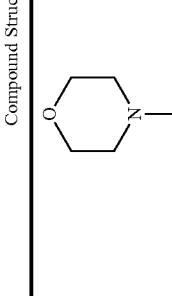 | C24H25N7O3 | 459.5 | 461.0 | <5 |
| 1111 | 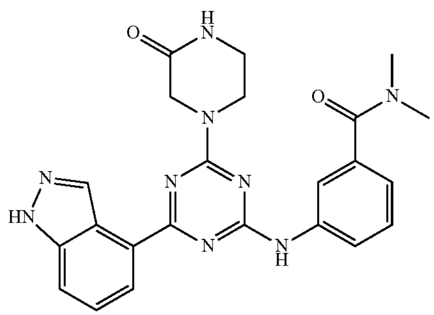 [SMILES: CN(C)C(=O)c1cccc(Nc2nc(-c3cccc4[nH]ncc34)nc(N3CCNC(=O)C3)n2)c1] | 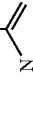 | 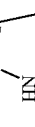 | 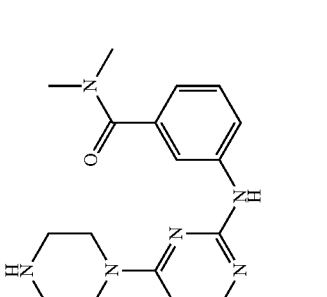 | C23H23N9O2 | 457.5 | 458.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1112 | 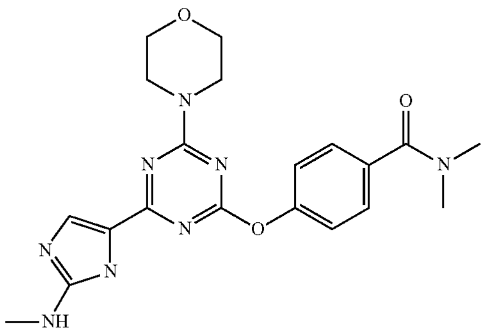 | | | | C20H23N7O3S | 441.5 | 442.0 | <5 |
| 1113 | 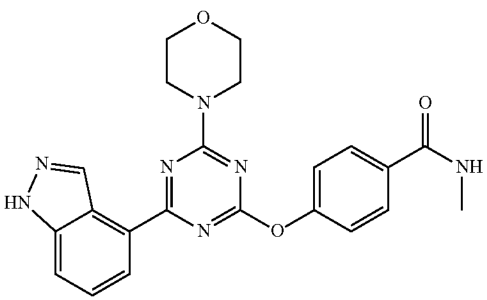 [SMILES: CNC(=O)c1ccc(Oc2nc(-c3cccc4[nH]ncc34)nc(N3CCOCC3)n2)cc1] | | | | C22H21N7O3 | 431.5 | 432.0 | <5 |
| 1114 | 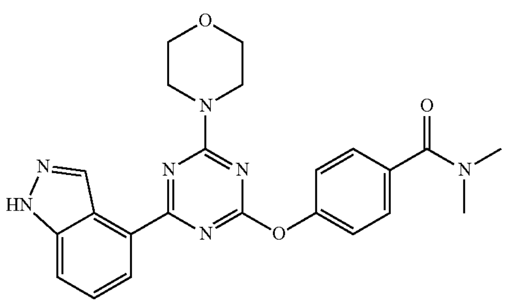 [SMILES: CN(C)C(=O)c1ccc(Oc2nc(-c3cccc4[nH]ncc34)nc(N3CCOCC3)n2)cc1] | | | | C23H23N7O3 | 445.5 | 446.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1115 | 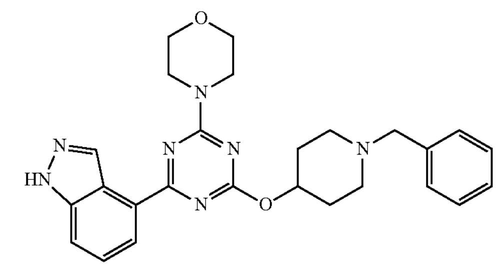 [SMILES: c1ccc(CN2CCC(Oc3nc(-c4cccc5[nH]ncc45)nc(N4CCOCC4)n3)CC2)cc1] | | | | C26H29N7O2 | 471.6 | 473.0 | <5 |
| 1116 | 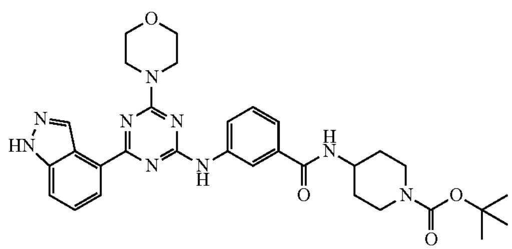 [SMILES: CC(C)(C)OC(=O)N1CCC(NC(=O)c2cccc(Nc3nc(-c4cccc5[nH]ncc45)nc(N4CCOCC4)n3)c2)CC1] | | | | C31H37N9O4 | 599.7 | 601.0 | <5 |
| 1117 | 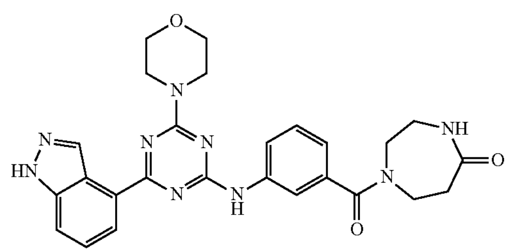 [SMILES: O=C1CCN(C(=O)c2cccc(Nc3nc(-c4cccc5[nH]ncc45)nc(N4CCOCC4)n3)c2)CCN1] | | | | C26H27N9O3 | 513.6 | 514.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1118 | 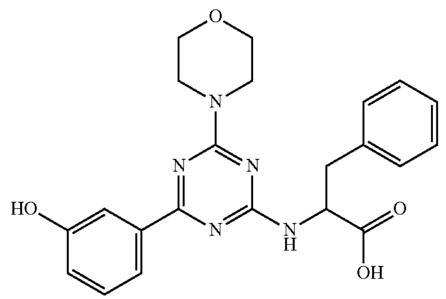 [SMILES: O=C(O)C(Cc1ccccc1)Nc1nc(-c2cccc(O)c2)nc(N2CCOCC2)n1] | | | | C22H23N5O4 | 421.5 | 422.0 | <5 |
| 1119 | 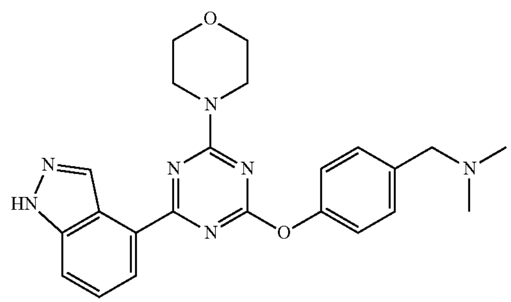 [SMILES: CN(C)Cc1ccc(Oc2nc(-c3cccc4[nH]ncc34)nc(N3CCOCC3)n2)cc1] | | | | C23H25N7O2 | 431.5 | 431.0 | <5 |
| 1120 | 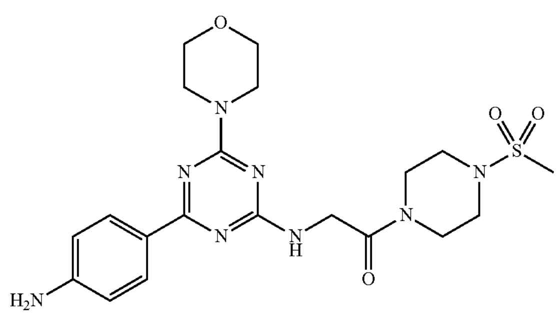 [SMILES: CS(=O)(=O)N1CCN(C(=O)CNc2nc(-c3ccc(N)cc3)nc(N3CCOCC3)n2)CC1] | | | | C20H28N8O4S | 476.6 | 478.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1121 | 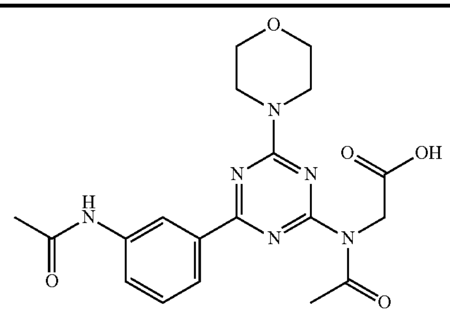 | | | | C19H22N6O5 | 414.4 | 415.0 | >5 |
| 1122 | 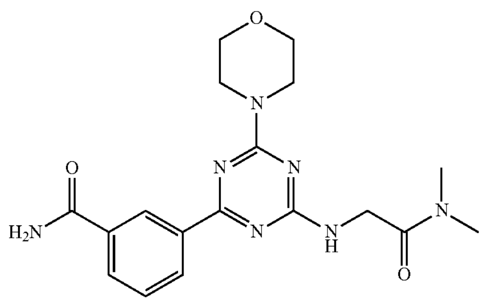 [SMILES: CN(C)C(=O)CNc1nc(-c2cccc(C(N)=O)c2)nc(N2CCOCC2)n1] | | | | C18H23N7O3 | 385.4 | 385.0 | >5 |
| 1123 | 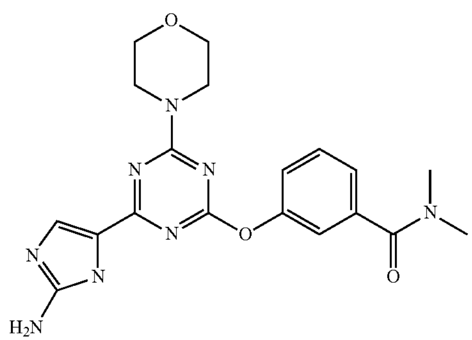 [SMILES: CN(C)C(=O)c1cccc(Oc2nc(-c3cnc(N)[nH]3)nc(N3CCOCC3)n2)c1] | | | | C19H21N7O3S | 427.5 | 428.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1124 | 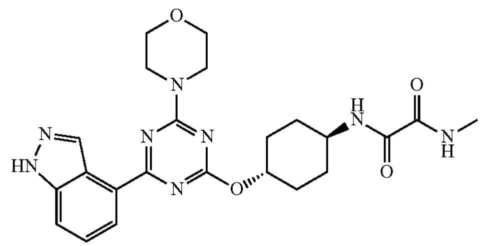 [SMILES: CNC(=O)C(=O)N[C@H]1CC[C@H](Oc2nc(-c3cccc4[nH]ncc34)nc(N3CCOCC3)n2)CC1] | | | | C23H28N8O4 | 480.5 | 481.0 | <5 |
| 1125 | 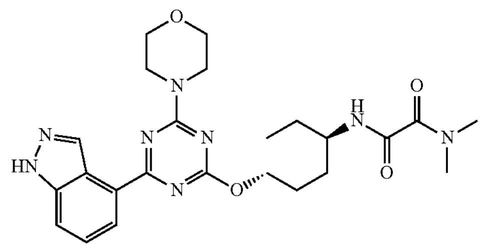 | | | | C24H30N8O4 | 494.6 | 496.0 | <5 |
| 1126 | 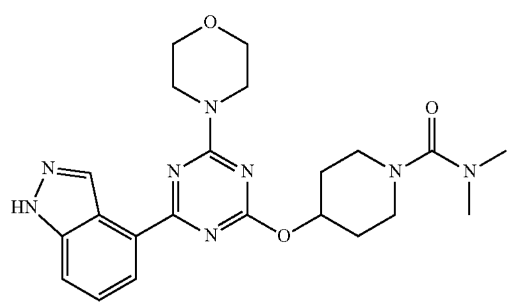 [SMILES: CN(C)C(=O)N1CCC(Oc2nc(-c3cccc4[nH]ncc34)nc(N3CCOCC3)n2)CC1] | | | | C22H28N8O3 | 452.5 | 454.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1127 | 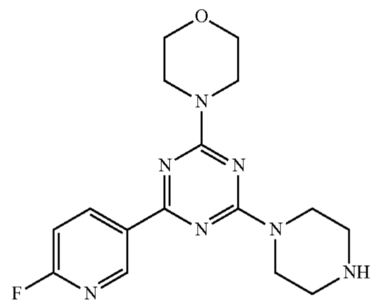 [SMILES: Fc1ccc(-c2nc(N3CCNCC3)nc(N3CCOCC3)n2)cn1] | | | | C16H20FN7O | 345.4 | 346.0 | <5 |
| 1128 | 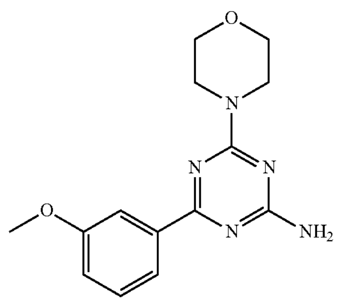 [SMILES: COc1cccc(-c2nc(N)nc(N3CCOCC3)n2)c1] | | | | C14H17N5O2 | 287.3 | 288.0 | >5 |
| 1129 | 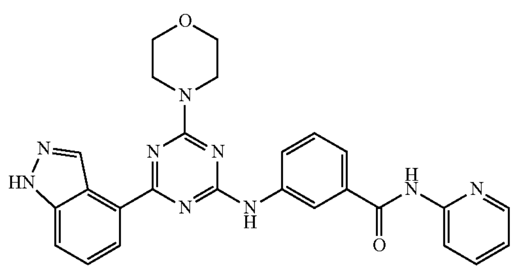 [SMILES: O=C(Nc1ccccn1)c1cccc(Nc2nc(-c3cccc4[nH]ncc34)nc(N3CCOCC3)n2)c1] | | | | C26H23N9O2 | 493.5 | 495.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1130 | 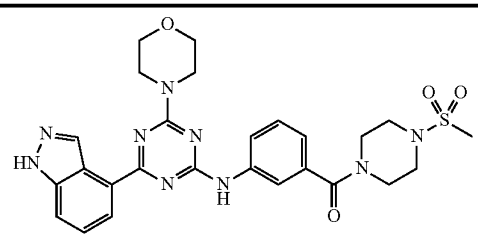 | | | | C26H29N9O4S | 563.6 | 565.0 | <5 |
| 1131 | 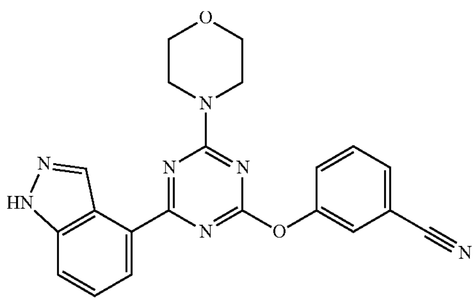 [SMILES: N#Cc1cccc(Oc2nc(-c3cccc4[nH]ncc34)nc(N3CCOCC3)n2)c1] | | | | C21H17N7O2 | 399.4 | 401.0 | >5 |
| 1132 | 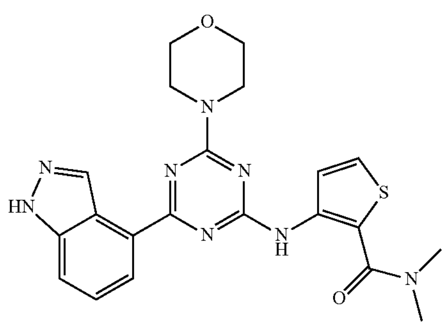 [SMILES: CN(C)C(=O)c1sccc1Nc1nc(-c2cccc3[nH]ncc23)nc(N2CCOCC2)n1] | | | | C21H22N8O2S | 450.5 | 451.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1133 | 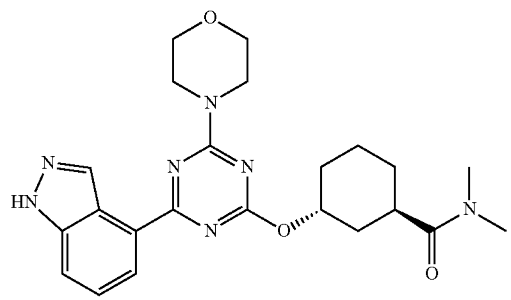 [SMILES: CN(C)C(=O)[C@@H]1CCC[C@@H](Oc2nc(-c3cccc4[nH]ncc34)nc(N3CCOCC3)n2)C1] | | | | C23H29N7O3 | 451.5 | 452.0 | <5 |
| 1134 | 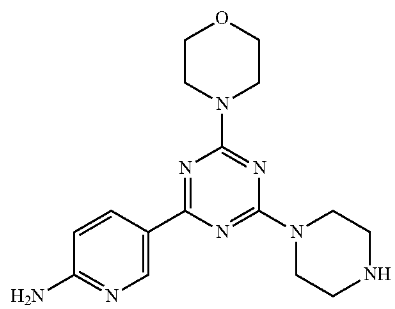 [SMILES: Nc1ccc(-c2nc(N3CCNCC3)nc(N3CCOCC3)n2)cn1] | | | | C16H22N8O | 342.4 | 343.0 | <5 |
| 1135 | 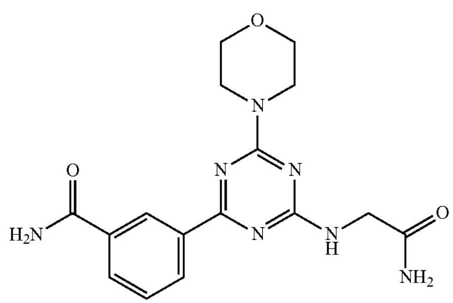 [SMILES: NC(=O)CNc1nc(-c2cccc(C(N)=O)c2)nc(N2CCOCC2)n1] | | | | C16H19N7O3 | 357.4 | 359.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1136 | 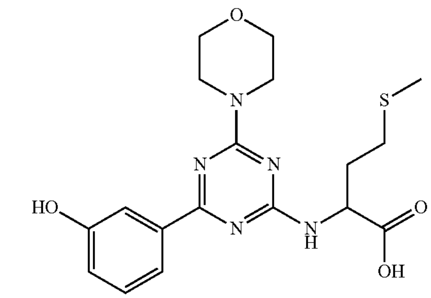 [SMILES: CSCCC(Nc1nc(-c2cccc(O)c2)nc(N2CCOCC2)n1)C(=O)O] | | | | C18H23N5O4S | 405.5 | 406.0 | <5 |
| 1137 | 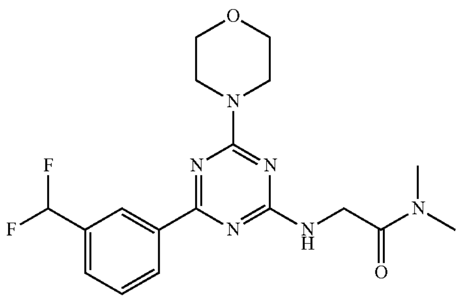 [SMILES: CN(C)C(=O)CNc1nc(-c2cccc(C(F)F)c2)nc(N2CCOCC2)n1] | | | | C18H22F2N6O2 | 392.4 | 393.0 | >5 |
| 1138 | 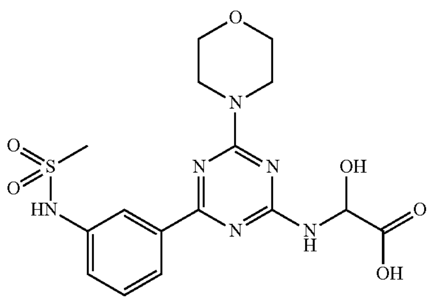 [SMILES: CS(=O)(=O)Nc1cccc(-c2nc(NC(O)C(=O)O)nc(N3CCOCC3)n2)c1] | | | | C17H22N6O5S | 422.5 | 423.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1139 | 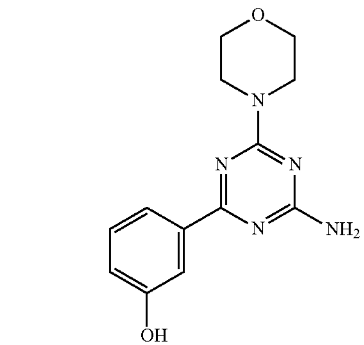 [SMILES: Nc1nc(-c2cccc(O)c2)nc(N2CCOCC2)n1] | S₁—NH₂ | morpholine-S₃ | 3-hydroxyphenyl-S₂ | C13H15N5O2 | 273.3 | 274.0 | <5 |
| 1140 | 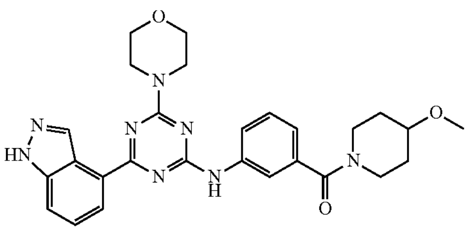 [SMILES: COC1CCN(C(=O)c2cccc(Nc3nc(-c4cccc5[nH]ncc45)nc(N4CCOCC4)n3)c2)CC1] | S₁-NH-(3-(4-methoxypiperidine-1-carbonyl)phenyl) | morpholine-S₃ | 1H-indazol-4-yl-S₂ | C27H30N8O3 | 514.6 | 516.0 | <5 |
| 1141 | 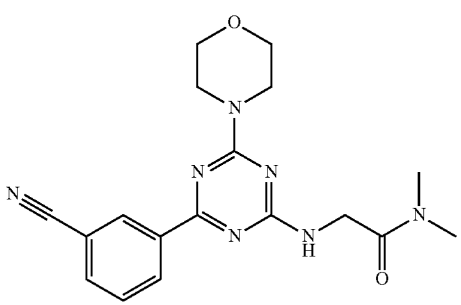 [SMILES: CN(C)C(=O)CNc1nc(-c2cccc(C#N)c2)nc(N2CCOCC2)n1] | S₁-NH-CH₂-C(O)-N(CH₃)₂ | morpholine-S₃ | 3-cyanophenyl-S₂ | C18H21N7O2 | 367.4 | 368.0 | >5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1142 | 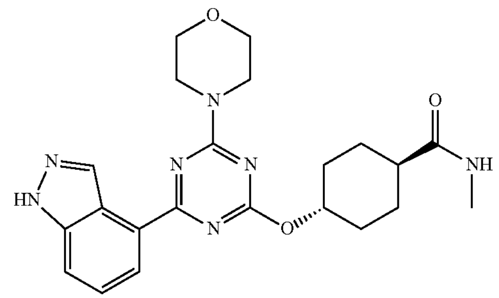 [SMILES: CNC(=O)[C@H]1CC[C@H](Oc2nc(-c3cccc4[nH]ncc34)nc(N3CCOCC3)n2)CC1] | | | | C22H27N7O3 | 437.5 | 438.0 | <5 |
| 1143 | 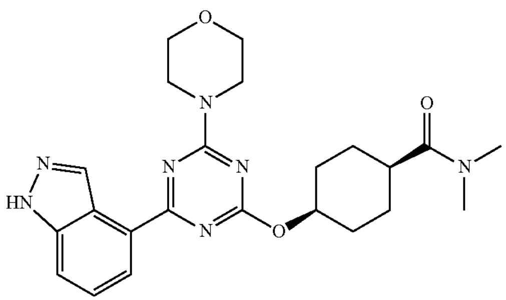 [SMILES: CN(C)C(=O)[C@H]1CC[C@@H](Oc2nc(-c3cccc4[nH]ncc34)nc(N3CCOCC3)n2)CC1] | | | | C23H29N7O3 | 451.5 | 453.0 | <5 |
| 1144 | 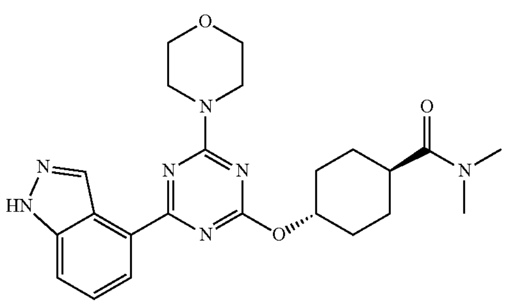 [SMILES: CN(C)C(=O)[C@H]1CC[C@H](Oc2nc(-c3cccc4[nH]ncc34)nc(N3CCOCC3)n2)CC1] | | | | C23H29N7O3 | 451.5 | 452.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1145 | 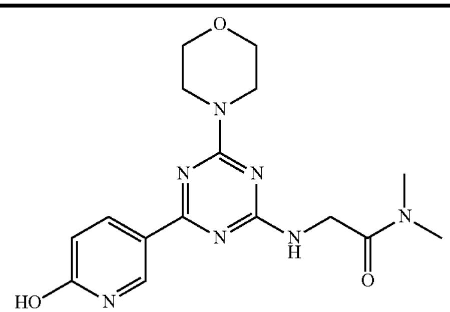 | | | | C16H21N7O3 | 359.4 | 360.0 | <5 |
| 1146 | 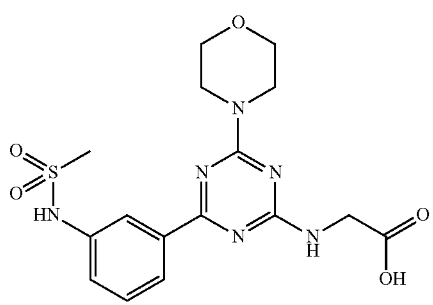 [SMILES: CS(=O)(=O)Nc1cccc(-c2nc(NCC(=O)O)nc(N3CCOCC3)n2)c1] | | | | C16H20N6O5S | 408.4 | 409.0 | >5 |
| 1147 | 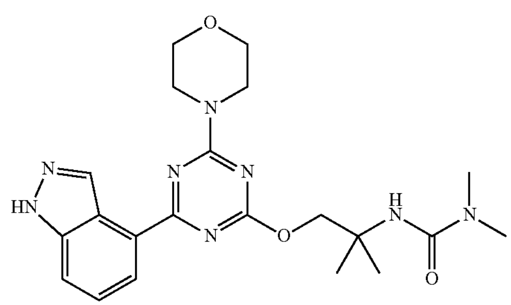 [SMILES: CN(C)C(=O)NC(C)(C)COc1nc(-c2cccc3[nH]ncc23)nc(N2CCOCC2)n1] | | | | C21H28N8O2 | 440.5 | 441.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1148 | (structure) | 3-carbamoylphenyl-NH-(S₁) | morpholine-S₃ | 1H-indazol-4-yl-S₂ | C22H21N8O2 | 416.5 | 416.0 | <5 |
| 1149 | (structure) | 1-ethylpiperidin-4-yl-O-(S₁) | morpholine-S₃ | 1H-indazol-4-yl-S₂ | C21H27N7O2 | 409.5 | 410.0 | <5 |
| 1150 | (structure) | N,N-dimethylaminocarbonylmethyl-NH-(S₁) | morpholine-S₃ | 5-hydroxypyridin-3-yl-S₂ | C16H21N7O3 | 359.4 | 361.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1151 | 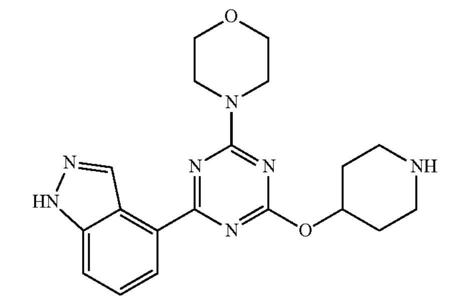 [SMILES: c1cc(-c2nc(OC3CCNCC3)nc(N3CCOCC3)n2)c2cn[nH]c2c1] | 4-piperidinyloxy (NH) | morpholine-S3 | 1H-indazol-4-yl-S2 | C19H23N7O2 | 381.4 | 382.0 | <5 |
| 1152 | 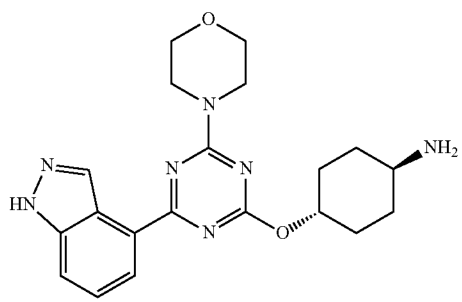 [SMILES: N[C@H]1CC[C@H](Oc2nc(-c3cccc4[nH]ncc34)nc(N3CCOCC3)n2)CC1] | trans-4-aminocyclohexyloxy | morpholine-S3 | 1H-indazol-4-yl-S2 | C20H25N7O2 | 395.5 | 396.0 | <5 |
| 1153 | 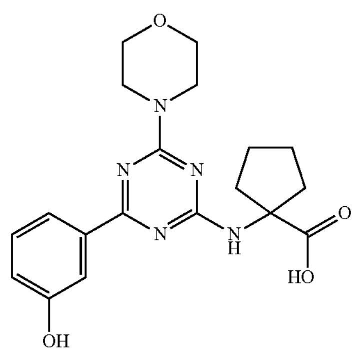 [SMILES: O=C(O)C1(Nc2nc(-c3cccc(O)c3)nc(N3CCOCC3)n2)CCCC1] | 1-aminocyclopentanecarboxylic acid | morpholine-S3 | 3-hydroxyphenyl-S2 | C19H23N5O4 | 385.4 | 386.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1154 | 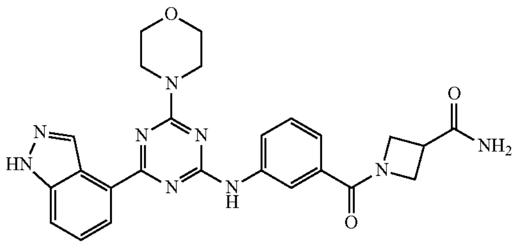 [SMILES: NC(=O)C1CN(C(=O)c2cccc(Nc3nc(-c4cccc5[nH]ncc45)nc(N4CCOCC4)n3)c2)C1] | | | | C25H25N9O3 | 499.5 | 501.0 | <5 |
| 1155 | 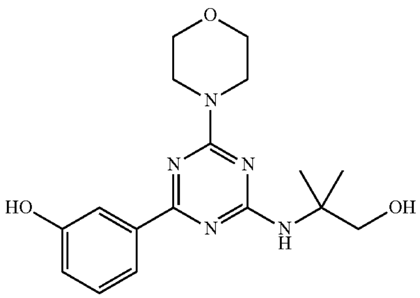 [SMILES: CC(C)(CO)Nc1nc(-c2cccc(O)c2)nc(N2CCOCC2)n1] | | | | C17H23N5O3 | 345.4 | 346.0 | <5 |
| 1156 | 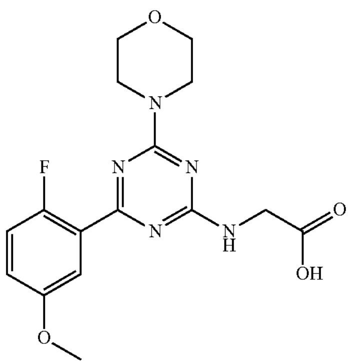 [SMILES: COc1ccc(F)c(-c2nc(NCC(=O)O)nc(N3CCOCC3)n2)c1] | | | | C16H18FN5O4 | 363.3 | 364.0 | >5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1157 | 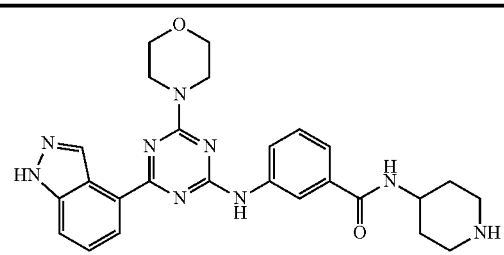 | | | | C26H29N9O2 | 499.6 | 501.0 | <5 |
| 1158 | 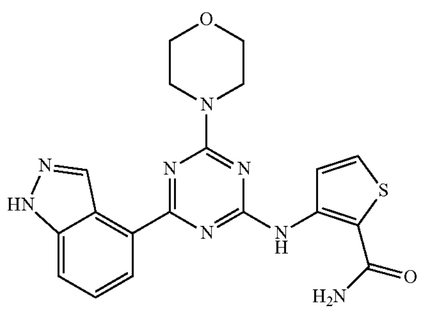 [SMILES: NC(=O)c1sccc1Nc1nc(-c2cccc3[nH]ncc23)nc(N2CCOCC2)n1] | | | | C19H18N8O2S | 422.5 | 423.0 | <5 |
| 1159 | 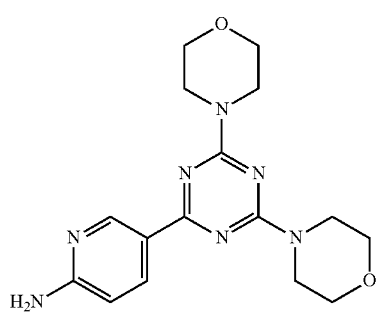 [SMILES: Nc1ccc(-c2nc(N3CCOCC3)nc(N3CCOCC3)n2)cn1] | | | | C16H21N7O2 | 343.4 | 344.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1160 | 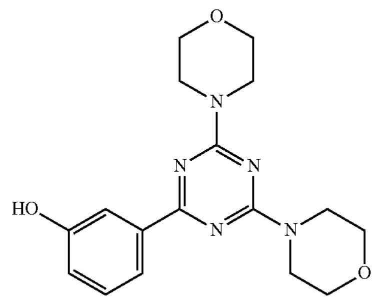 [SMILES: Oc1cccc(-c2nc(N3CCOCC3)nc(N3CCOCC3)n2)c1] | morpholine-S1 | morpholine-S3 | 3-hydroxyphenyl-S2 | C17H21N5O3 | 343.4 | 344.0 | <5 |
| 1161 | 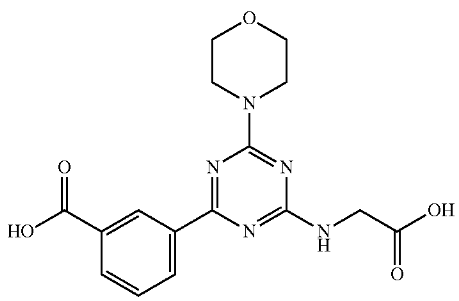 [SMILES: O=C(O)CNc1nc(-c2cccc(C(=O)O)c2)nc(N2CCOCC2)n1] | S1-NH-CH2-COOH | morpholine-S3 | 3-carboxyphenyl-S2 | C16H17N5O5 | 359.3 | 361.0 | >5 |
| 1162 | 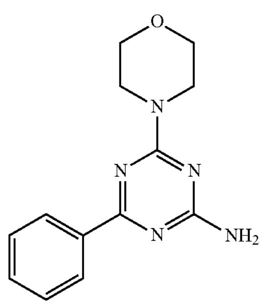 [SMILES: Nc1nc(-c2ccccc2)nc(N2CCOCC2)n1] | S1-NH2 | morpholine-S3 | phenyl-S2 | C13H15N5O | 257.3 | 258.0 | >5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1163 | 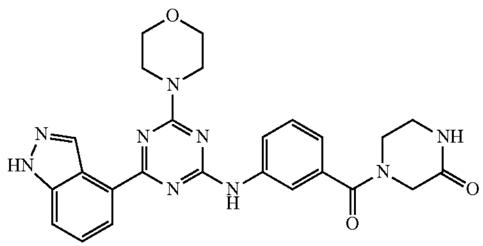 [SMILES: O=C1CN(C(=O)c2cccc(Nc3nc(-c4cccc5[nH]ncc45)nc(N4CCOCC4)n3)c2)CCN1] | | | | C25H25N9O3 | 499.5 | 501.0 | <5 |
| 1164 | 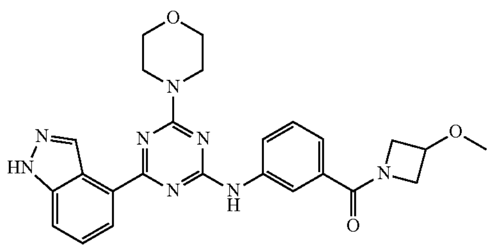 [SMILES: COC1CN(C(=O)c2cccc(Nc3nc(-c4cccc5[nH]ncc45)nc(N4CCOCC4)n3)c2)C1] | | | | C25H26N8O3 | 486.5 | 487.0 | <5 |
| 1165 | 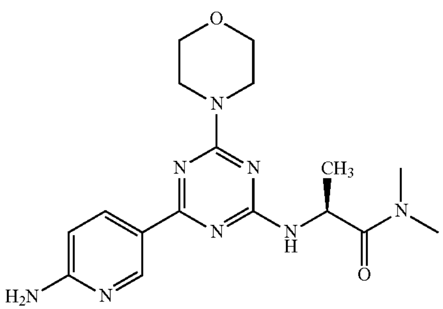 | | | | C17H24N8O2 | 372.4 | 373.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1166 | 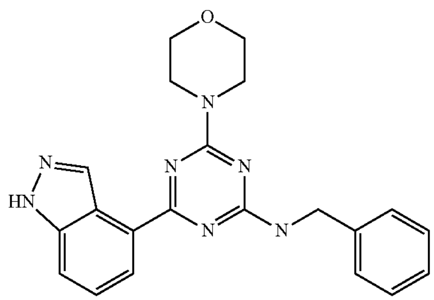 [SMILES: c1ccc(CNc2nc(-c3cccc4[nH]ncc34)nc(N3CCOCC3)n2)cc1] | | | | C21H20N6OS | 404.5 | 405.0 | <5 |
| 1167 | 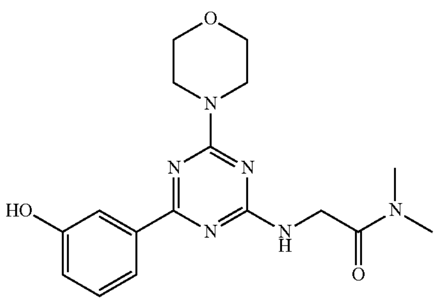 [SMILES: CN(C)C(=O)CNc1nc(-c2cccc(O)c2)nc(N2CCOCC2)n1] | | | | C17H22N6O3 | 358.4 | 359.0 | <5 |
| 1168 | 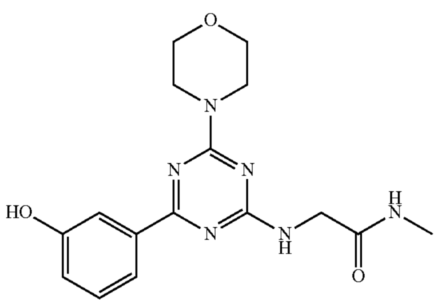 [SMILES: CNC(=O)CNc1nc(-c2cccc(O)c2)nc(N2CCOCC2)n1] | | | | C16H20N6O3 | 344.4 | 345.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1169 | 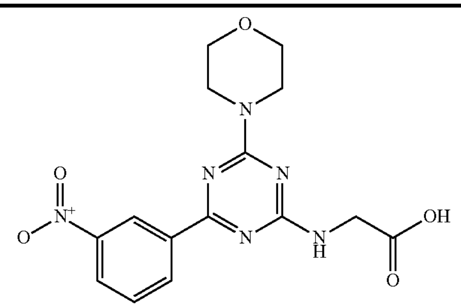 | | | | C15H16N6O5 | 360.3 | 361.0 | >5 |
| 1170 | 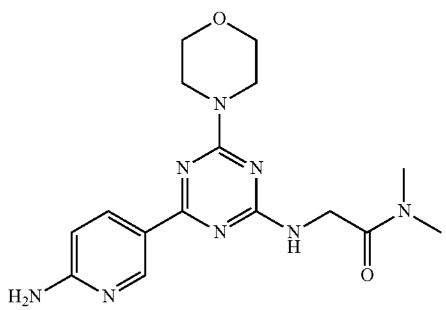 [SMILES: CN(C)C(=O)CNc1nc(-c2ccc(N)nc2)nc(N2CCOCC2)n1] | | | | C16H22N8O2 | 358.4 | 359.0 | <5 |
| 1171 | 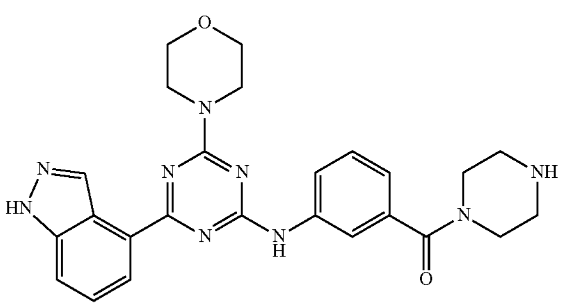 [SMILES: O=C(c1cccc(Nc2nc(-c3cccc4[nH]ncc34)nc(N3CCOCC3)n2)c1)N1CCNCC1] | | | | C25H27N9O2 | 485.5 | 487.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1172 | 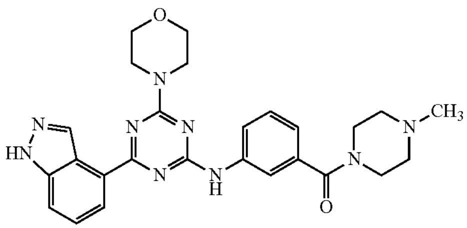 [SMILES: CN1CCN(C(=O)c2cccc(Nc3nc(-c4cccc5[nH]ncc45)nc(N4CCOCC4)n3)c2)CC1] | | | | C26H29N9O2 | 499.6 | 501.0 | <5 |
| 1173 | 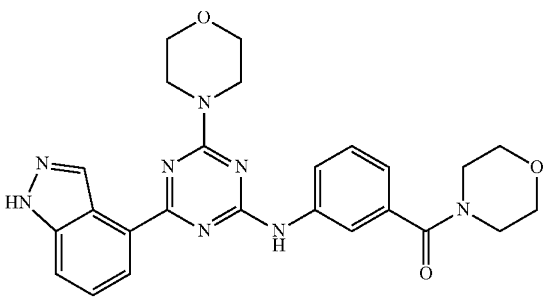 [SMILES: O=C(c1cccc(Nc2nc(-c3cccc4[nH]ncc34)nc(N3CCOCC3)n2)c1)N1CCOCC1] | | | | C25H26N8O3 | 486.5 | 488.0 | <5 |
| 1174 | 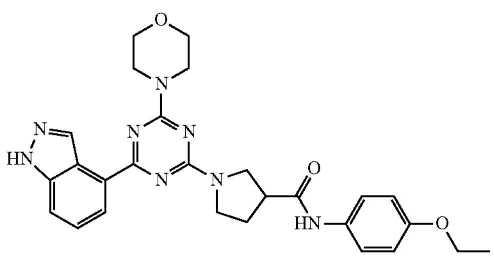 [SMILES: CCOc1ccc(NC(=O)C2CCN(c3nc(-c4cccc5[nH]ncc45)nc(N4CCOCC4)n3)C2)cc1] | | | | C27H30N8O3 | 514.6 | 516.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1175 | 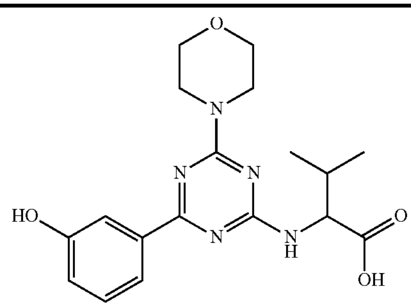 | | | | C18H23N5O4 | 373.4 | 375.0 | <5 |
| 1176 | 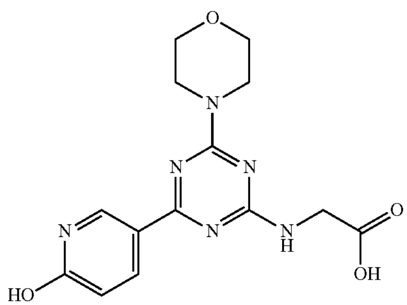 [SMILES: O=C(O)CNc1nc(-c2ccc(O)nc2)nc(N2CCOCC2)n1] | | | | C14H16N6O4 | 332.3 | 333.0 | >5 |
| 1177 | 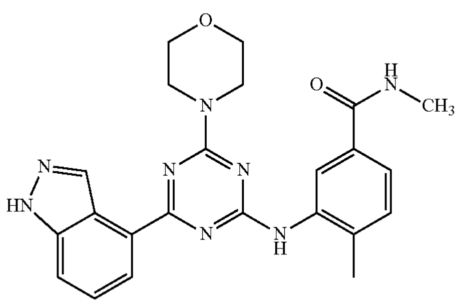 [SMILES: CNC(=O)c1ccc(C)c(Nc2nc(-c3cccc4[nH]ncc34)nc(N3CCOCC3)n2)c1] | | | | C23H24N8O2 | 444.5 | 445.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1178 | 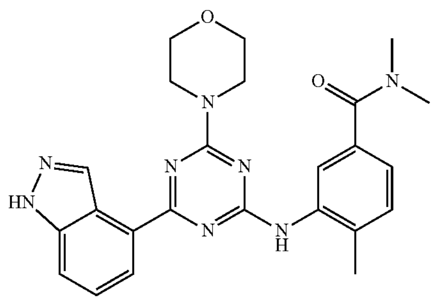 [SMILES: Cc1ccc(C(=O)N(C)C)cc1Nc1nc(-c2cccc3[nH]ncc23)nc(N2CCOCC2)n1] | | | | C24H26N8O2 | 458.5 | 459.0 | <5 |
| 1179 | 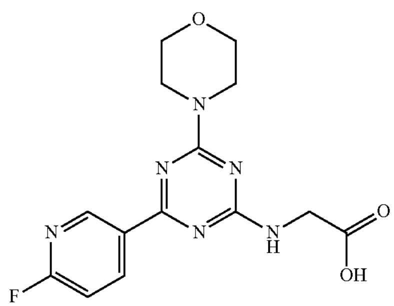 [SMILES: O=C(O)CNc1nc(-c2ccc(F)nc2)nc(N2CCOCC2)n1] | | | | C14H15FN6O3 | 334.3 | 335.0 | >5 |
| 1180 | 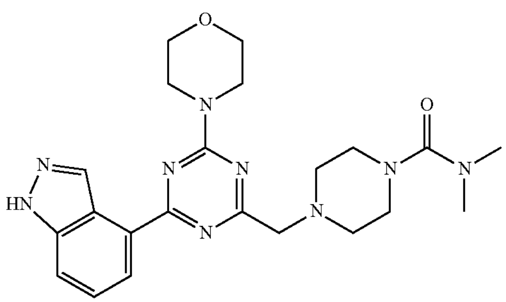 [SMILES: CN(C)C(=O)N1CCN(Cc2nc(-c3cccc4[nH]ncc34)nc(N3CCOCC3)n2)CC1] | | | | C22H29N9O2 | 451.5 | 453.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1181 | 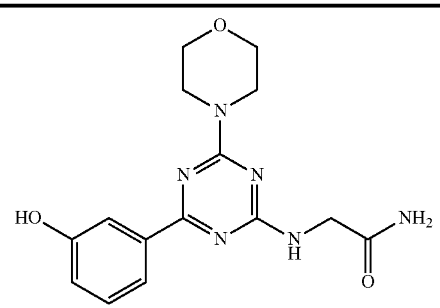 | | | | C15H18N6O3 | 330.4 | 331.0 | <5 |
| 1182 | 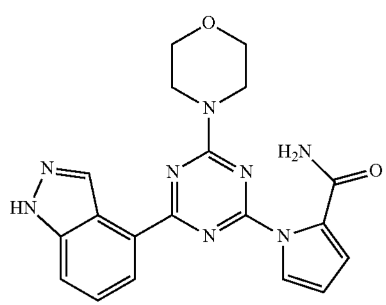 [SMILES: NC(=O)c1cccn1-c1nc(-c2cccc3[nH]ncc23)nc(N2CCOCC2)n1] | | | | C19H18N8O2 | 390.4 | 331.0 | <5 |
| 1183 | 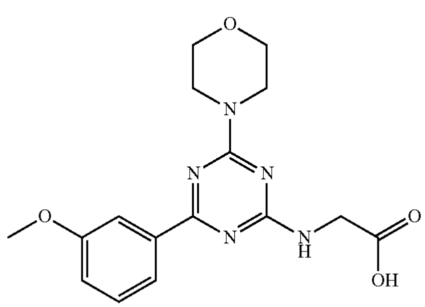 [SMILES: COc1cccc(-c2nc(NCC(=O)O)nc(N3CCOCC3)n2)c1] | | | | C16H19N5O4 | 344.4 | 345.0 | >5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1184 | 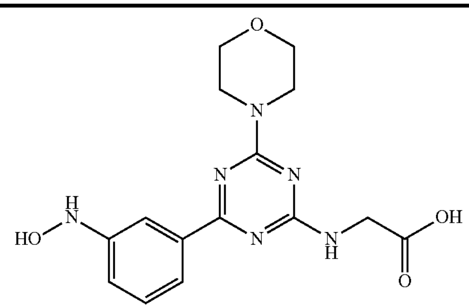 | | | | C15H18N6O4 | 345.5 | 347.0 | >5 |
| 1185 | 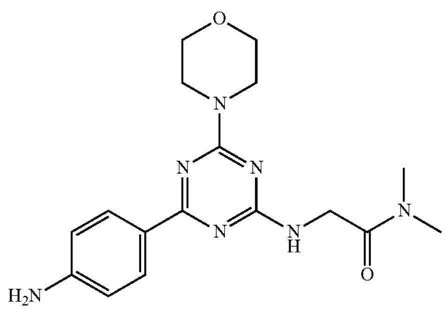 [SMILES: CN(C)C(=O)CNc1nc(-c2ccc(N)cc2)nc(N2CCOCC2)n1] | | | | C17H23N7O2 | 357.4 | 3559.0 | >5 |
| 1186 | 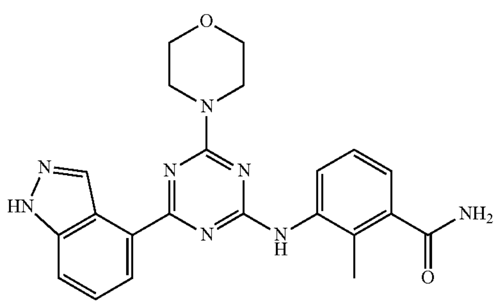 [SMILES: Cc1c(Nc2nc(-c3cccc4[nH]ncc34)nc(N3CCOCC3)n2)cccc1C(N)=O] | | | | C22H22N8O2 | 430.5 | 432.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1187 | 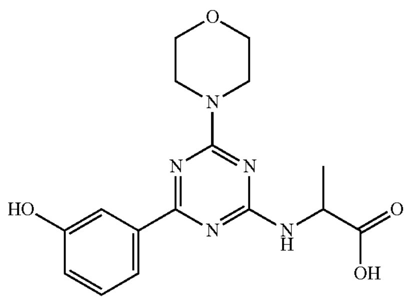 [SMILES: CC(Nc1nc(-c2cccc(O)c2)nc(N2CCOCC2)n1)C(=O)O] | | | | C16H19N5O4 | 345.5 | 346.0 | <5 |
| 1188 | 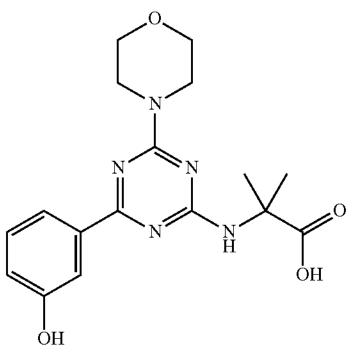 [SMILES: CC(C)(Nc1nc(-c2cccc(O)c2)nc(N2CCOCC2)n1)C(=O)O] | | | | C17H21N5O4 | 359.4 | 361.0 | <5 |
| 1189 | 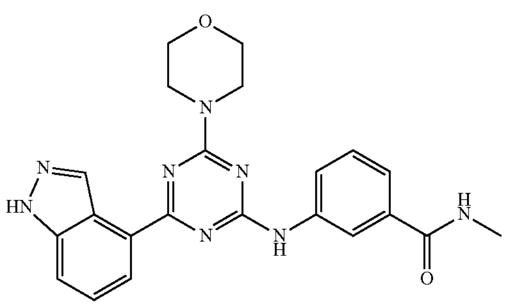 [SMILES: CNC(=O)c1cccc(Nc2nc(-c3cccc4[nH]ncc34)nc(N3CCOCC3)n2)c1] | | | | C22H22N8O2 | 430.5 | 431.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1190 | 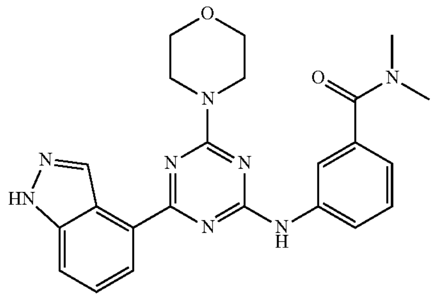 [SMILES: CN(C)C(=O)c1cccc(Nc2nc(-c3cccc4[nH]ncc34)nc(N3CCOCC3)n2)c1] | | | | C23H24N8O2 | 444.5 | 445.0 | <5 |
| 1191 | 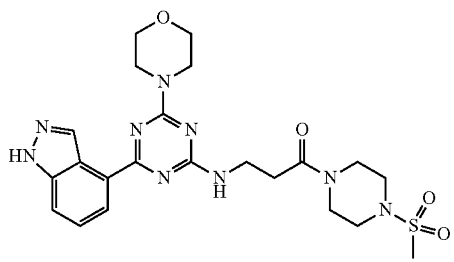 [SMILES: CS(=O)(=O)N1CCN(C(=O)CCNc2nc(-c3cccc4[nH]ncc34)nc(N3CCOCC3)n2)CC1] | | | | C22H29N9O4S | 515.6 | 517.0 | <5 |
| 1192 | 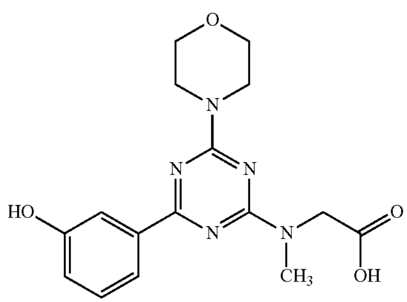 [SMILES: CN(CC(=O)O)c1nc(-c2cccc(O)c2)nc(N2CCOCC2)n1] | | | | C16H19N5O4 | 345.4 | 346.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1193 | 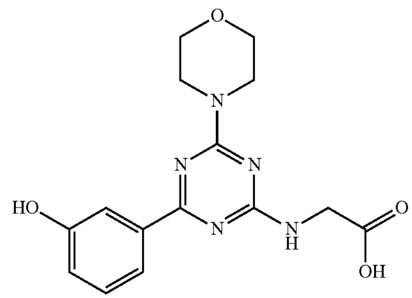 [SMILES: O=C(O)CNc1nc(-c2cccc(O)c2)nc(N2CCOCC2)n1] | | | | C15H17N5O4 | 331.3 | 333.0 | <5 |
| 1194 | 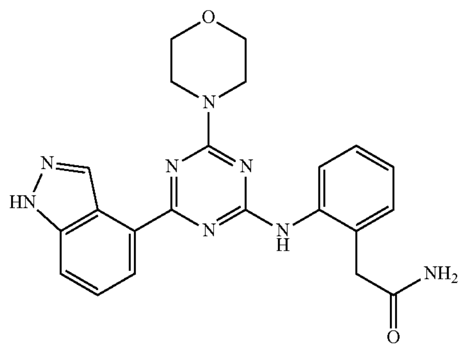 [SMILES: NC(=O)Cc1ccccc1Nc1nc(-c2cccc3[nH]ncc23)nc(N2CCOCC2)n1] | | | | C22H22N8O2 | 430.5 | 431.0 | <5 |
| 1195 | 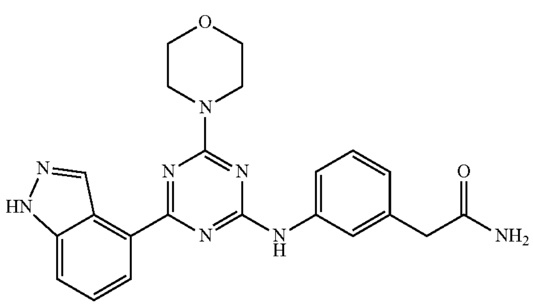 [SMILES: NC(=O)Cc1cccc(Nc2nc(-c3cccc4[nH]ncc34)nc(N3CCOCC3)n2)c1] | | | | C22H22N8O2 | 430.5 | 431.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1196 | 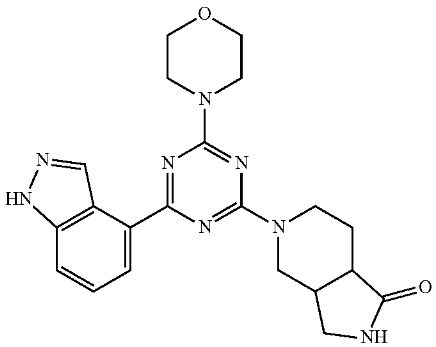 [SMILES: O=C1NCC2CN(c3nc(-c4cccc5[nH]ncc45)nc(N4CCOCC4)n3)CCC12] | | | | C12H24N8O2 | 420.5 | 421.0 | <5 |
| 1197 | 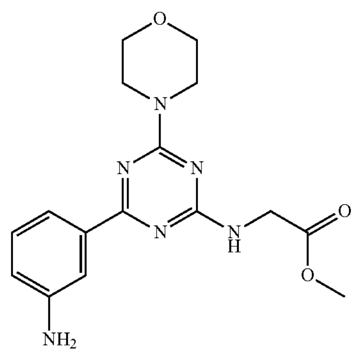 [SMILES: COC(=O)CNc1nc(-c2cccc(N)c2)nc(N2CCOCC2)n1] | | | | C16H20N6O3 | 344.4 | 345.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1198 | 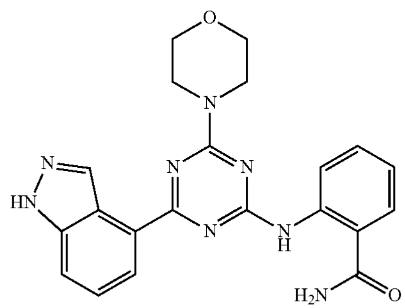 [SMILES: NC(=O)c1ccccc1Nc1nc(-c2cccc3[nH]ncc23)nc(N2CCOCC2)n1] | | | | C21H20N8O2 | 416.4 | 417.0 | >5 |
| 1199 | 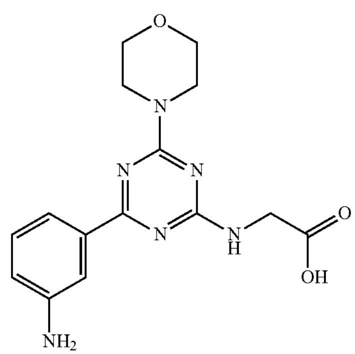 [SMILES: Nc1cccc(-c2nc(NCC(=O)O)nc(N3CCOCC3)n2)c1] | | | | C15H18N6O3 | 330.3 | 331.0 | >5 |
| 1200 | 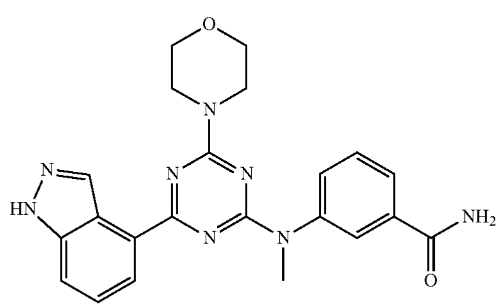 | | | | C22H22N8O2 | 430.5 | 431.0 | <5 |

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1201 | 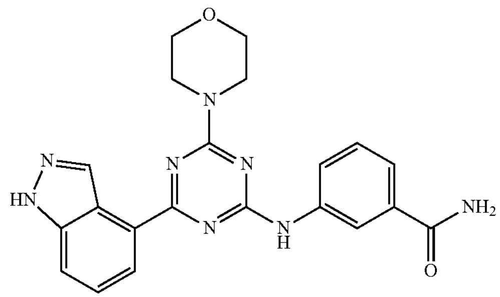 [SMILES: NC(=O)c1cccc(Nc2nc(-c3cccc4[nH]ncc34)nc(N3CCOCC3)n2)c1] | 3-(carboxamido)phenylamino | morpholine-N-S3 | 1H-indazol-4-yl | C21H20N8O2 | 416.4 | 417.0 | <5 |
| 1202 | 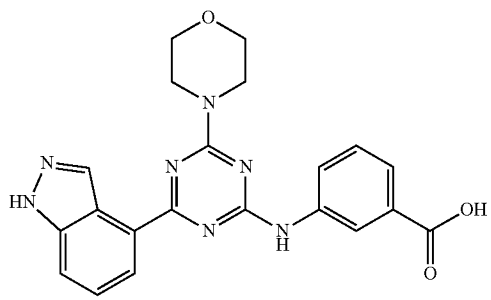 [SMILES: O=C(O)c1cccc(Nc2nc(-c3cccc4[nH]ncc34)nc(N3CCOCC3)n2)c1] | 3-(carboxy)phenylamino | morpholine-N-S3 | 1H-indazol-4-yl | C21H19N7O3 | 417.4 | 418.0 | <5 |
| 1203 | 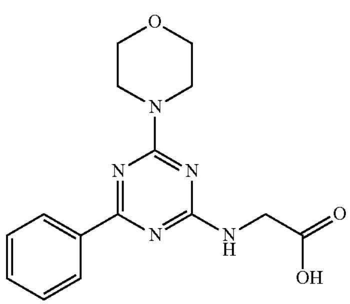 [SMILES: O=C(O)CNc1nc(-c2ccccc2)nc(N2CCOCC2)n1] | glycine-NH | morpholine-N-S3 | phenyl | C15H17N5O3 | 315.3 | 316.0 | >5 |

-continued

| Compound Number | Compound Structure | X—Y | A | Ar | Molecular Formula (Parent) | Molecular Weight (Parent) | M/Z | PI3K (WT) IC50- HTRF (IC50) (uM) |
|---|---|---|---|---|---|---|---|---|
| 1204 | 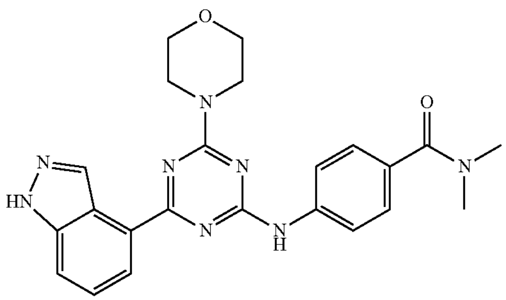 [SMILES: CN(C)C(=O)c1ccc(Nc2nc(-c3cccc4[nH]ncc34)nc(N3CCOCC3)n2)cc1] | | | | C23H24N8O2 | 444.5 | 445.0 | <5 |
| 1205 | 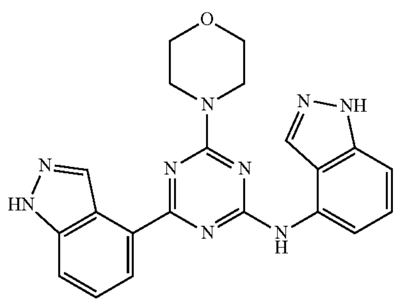 [SMILES: c1cc(Nc2nc(-c3cccc4[nH]ncc34)nc(N3CCOCC3)n2)c2cn[nH]c2c1] | | | | C21H19N9O | 413.4 | 414.0 | <5 |
| 1206 | 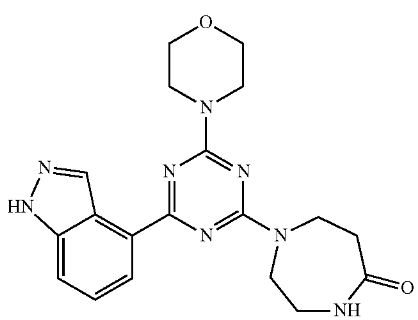 [SMILES: O=C1CCN(c2nc(-c3cccc4[nH]ncc34)nc(N3CCOCC3)n2)CCN1] | | | | C19H22N8O2 | 394.4 | 395.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1207 | 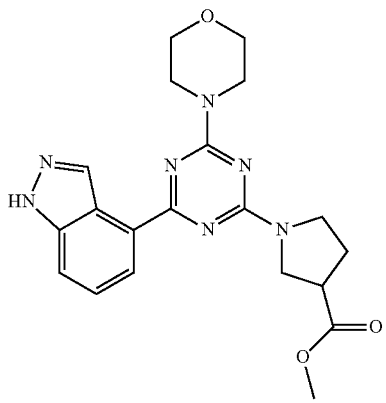 [SMILES: COC(=O)C1CCN(c2nc(-c3cccc4[nH]ncc34)nc(N3CCOCC3)n2)C1] | | | | C20H23N7O3 | 409.5 | 410.0 | <5 |
| 1208 | 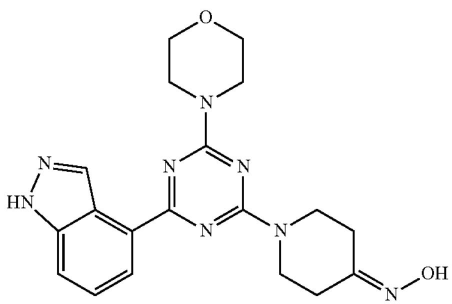 [SMILES: ON=C1CCN(c2nc(-c3cccc4[nH]ncc34)nc(N3CCOCC3)n2)CC1] | | | | C19H22N8O2 | 394.4 | 395.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1209 | 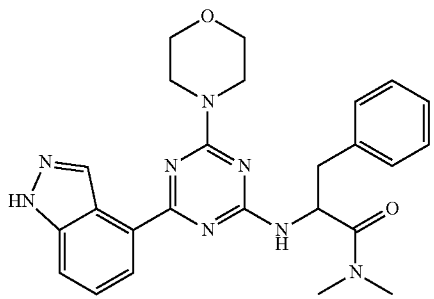 [SMILES: CN(C)C(=O)C(Cc1ccccc1)Nc1nc(-c2cccc3[nH]ncc23)nc(N2CCOCC2)n1] | | | | C25H28N8O2 | 472.5 | 473.0 | <5 |
| 1210 | 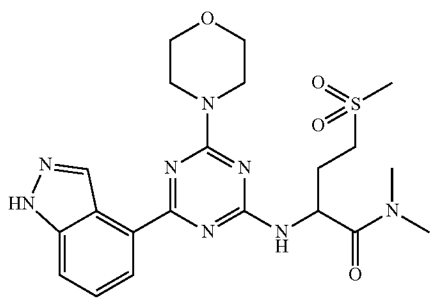 [SMILES: CN(C)C(=O)C(CCS(C)(=O)=O)Nc1nc(-c2cccc3[nH]ncc23)nc(N2CCOCC2)n1] | | | | C21H28N8O4S | 488.6 | 489.0 | <5 |
| 1211 | 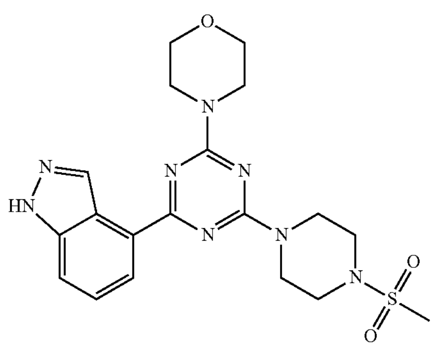 [SMILES: CS(=O)(=O)N1CCN(c2nc(-c3cccc4[nH]ncc34)nc(N3CCOCC3)n2)CC1] | | | | C19H24N8O3S | 444.5 | 445.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1212 | 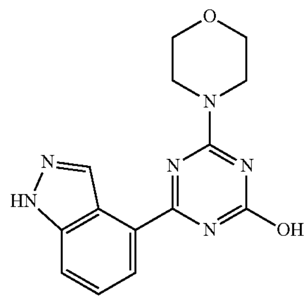 [SMILES: Oc1nc(-c2cccc3[nH]ncc23)nc(N2CCOCC2)n1] | S₁—OH | morpholine-S₃ | indazolyl-S₂ | C14H14N6O2 | 298.3 | 299.0 | <5 |
| 1213 | 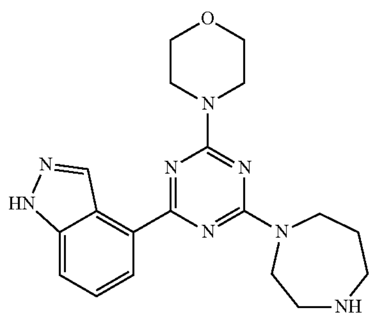 [SMILES: c1cc(-c2nc(N3CCCNCC3)nc(N3CCOCC3)n2)c2cn[nH]c2c1] | homopiperazine-S₁ | morpholine-S₃ | indazolyl-S₂ | C19H24N8O | 380.5 | 381.0 | <5 |
| 1214 | 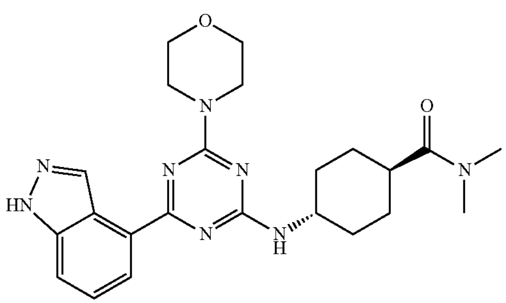 [SMILES: CN(C)C(=O)[C@H]1CC[C@H](Nc2nc(-c3cccc4[nH]ncc34)nc(N3CCOCC3)n2)CC1] | trans-4-(dimethylcarbamoyl)cyclohexylamino-S₁ | morpholine-S₃ | indazolyl-S₂ | C23H30N8O2 | 450.5 | 452.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1215 | 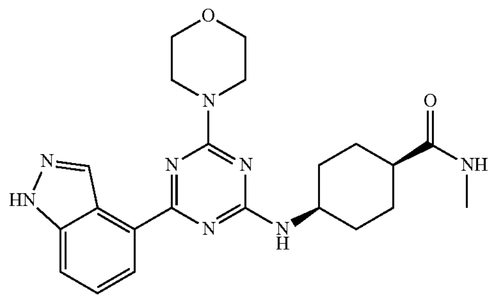 [SMILES: CNC(=O)[C@H]1CC[C@@H](Nc2nc(-c3cccc4[nH]ncc34)nc(N3CCOCC3)n2)CC1] | | | | C22H28N8O2 | 436.5 | 437.0 | <5 |
| 1216 | 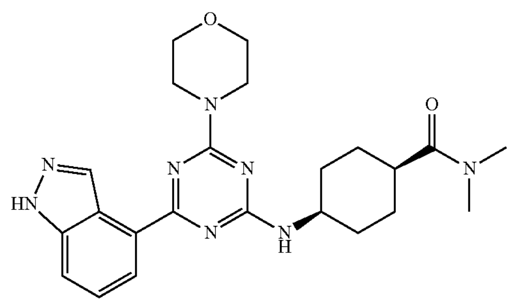 [SMILES: CN(C)C(=O)[C@H]1CC[C@@H](Nc2nc(-c3cccc4[nH]ncc34)nc(N3CCOCC3)n2)CC1] | | | | C23H30N8O2 | 450.5 | 451.0 | <5 |
| 1217 | 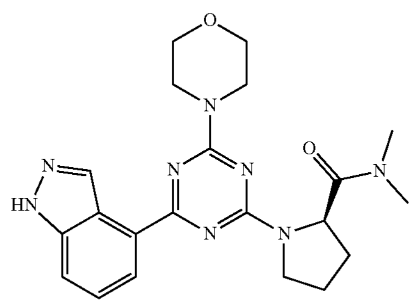 [SMILES: CN(C)C(=O)[C@H]1CCCN1c1nc(-c2cccc3[nH]ncc23)nc(N2CCOCC2)n1] | | | | C21H26N8O2 | 422.5 | 4232.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1218 | 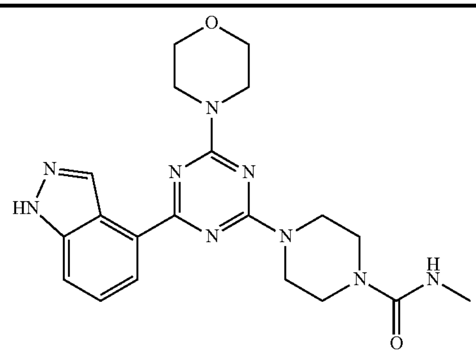 | | | | C20H25N9O2 | 423.5 | 424.0 | <5 |
| 1219 | 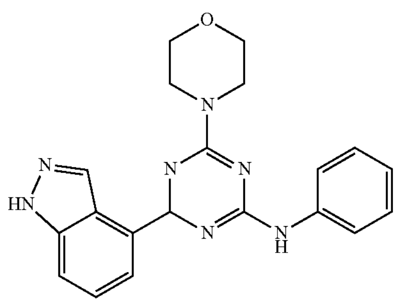 [SMILES: c1ccc(NC2=NC(c3cccc4[nH]ncc34)NC(N3CCOCC3)=N2)cc1] | | | | C20H19N7O | 373.4 | 374.0 | <5 |
| 1220 | 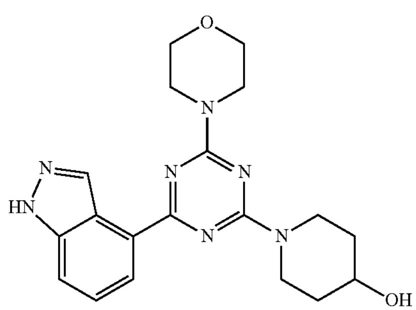 [SMILES: OC1CCN(c2nc(-c3cccc4[nH]ncc34)nc(N3CCOCC3)n2)CC1] | | | | C19H23N7O2 | 381.4 | 382.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1221 | 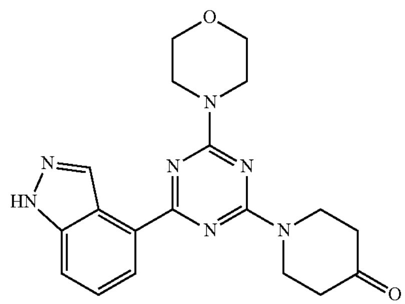 [SMILES: O=C1CCN(c2nc(-c3cccc4[nH]ncc34)nc(N3CCOCC3)n2)CC1] | | | | C19H21N7O2 | 379.4 | 381.0 | <5 |
| 1222 | 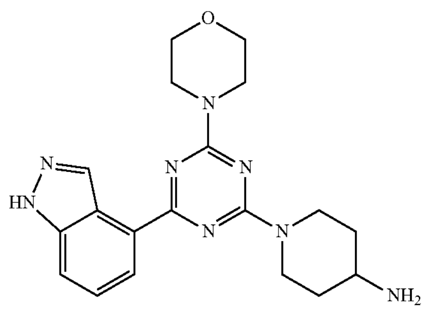 | | | | C19H24N8O | 380.5 | 381.0 | <5 |
| 1223 | 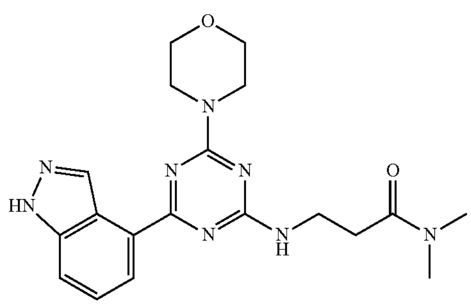 [SMILES: CN(C)C(=O)CCNc1nc(-c2cccc3[nH]ncc23)nc(N2CCOCC2)n1] | | | | C19H24N8O2 | 396.5 | 397.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1224 | 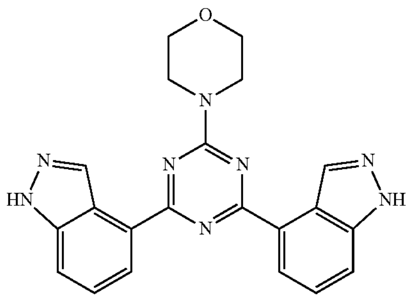 [SMILES: c1cc(-c2nc(-c3cccc4[nH]ncc34)nc(N3CCOCC3)n2)c2cn[nH]c2c1] | | | | C21H18N8O | 398.4 | 399.0 | <5 |
| 1225 | 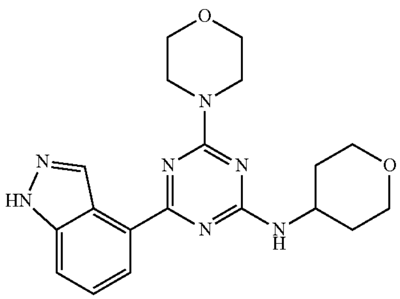 [SMILES: c1cc(-c2nc(NC3CCOCC3)nc(N3CCOCC3)n2)c2cn[nH]c2c1] | | | | C19H23N7O2 | 381.4 | 382.0 | <5 |
| 1226 | 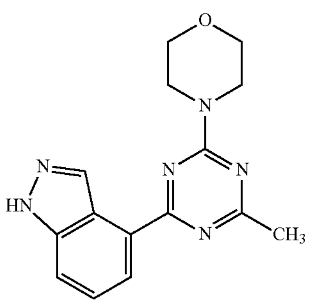 [SMILES: Cc1nc(-c2cccc3[nH]ncc23)nc(N2CCOCC2)n1] | | | | C15H16N6O | 296.3 | 297.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1227 | 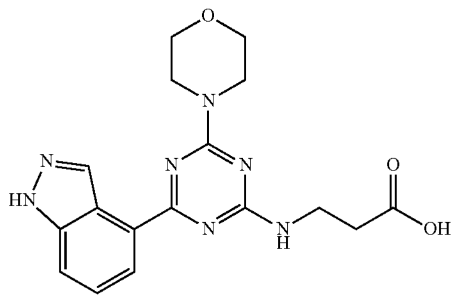 [SMILES: O=C(O)CCNc1nc(-c2cccc3[nH]ncc23)nc(N2CCOCC2)n1] | | | | C17H19N7O3 | 369.4 | 371.0 | <5 |
| 1228 | 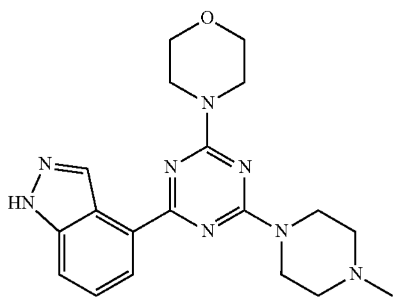 [SMILES: CN1CCN(c2nc(-c3cccc4[nH]ncc34)nc(N3CCOCC3)n2)CC1] | | | | C19H24N8O | 380.5 | 381.0 | <5 |
| 1229 | 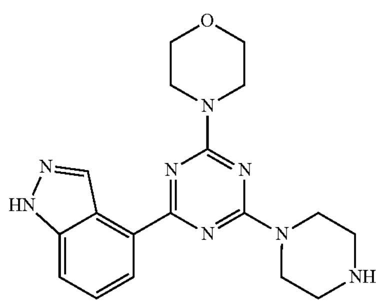 [SMILES: c1cc(-c2nc(N3CCNCC3)nc(N3CCOCC3)n2)c2cn[nH]c2c1] | | | | C18H22N8O | 366.4 | 559.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1230 | 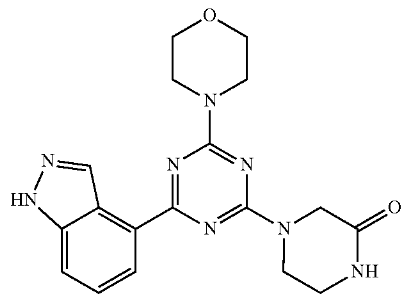 [SMILES: O=C1CN(c2nc(-c3cccc4[nH]ncc34)nc(N3CCOCC3)n2)CCN1] | | | | C18H20N8O2 | 380.4 | 381.0 | <5 |
| 1231 | 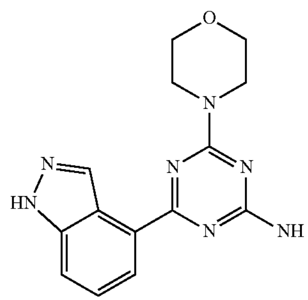 [SMILES: Nc1nc(-c2cccc3[nH]ncc23)nc(N2CCOCC2)n1] | | | | C14H15N7O | 297.3 | 298.0 | >5 |
| 1232 | 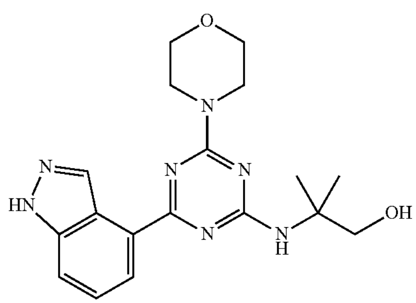 [SMILES: CC(C)(CO)Nc1nc(-c2cccc3[nH]ncc23)nc(N2CCOCC2)n1] | | | | C18H23N7O2 | 369.4 | 370.0 | <5 |

-continued

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1233 | 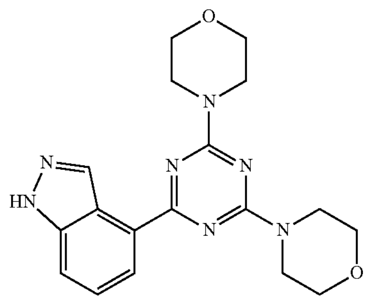 [SMILES: c1cc(-c2nc(N3CCOCC3)nc(N3CCOCC3)n2)c2cn[nH]c2c1] | morpholine-S₁ | morpholine-S₃ | 4-indazolyl-S₂ | C18H21N7O2 | 367.4 | 368.0 | <5 |
| 1234 | 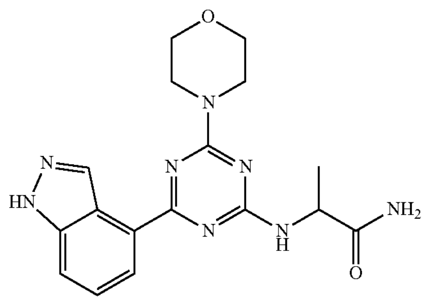 [SMILES: CC(Nc1nc(-c2cccc3[nH]ncc23)nc(N2CCOCC2)n1)C(N)=O] | S₁-NH-CH(CH₃)-C(O)NH₂ | morpholine-S₃ | 4-indazolyl-S₂ | C17H20N8O2 | 368.4 | 369.0 | <5 |
| 1235 | 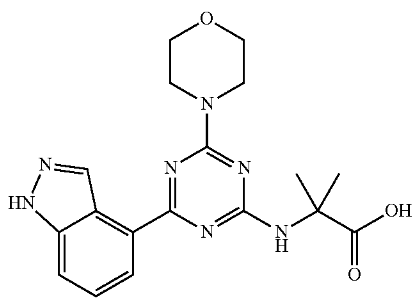 [SMILES: CC(C)(Nc1nc(-c2cccc3[nH]ncc23)nc(N2CCOCC2)n1)C(=O)O] | S₁-NH-C(CH₃)₂-C(O)OH | morpholine-S₃ | 4-indazolyl-S₂ | C18H21N7O3 | 383.4 | 384.0 | <5 |

| Compound Number | Compound Structure | X—Y | A | Ar | Molecular Formula (Parent) | Molecular Weight (Parent) | M/Z | PI3K (WT) IC50-HTRF (IC50) (uM) |
|---|---|---|---|---|---|---|---|---|
| 1236 | ![structure] | ![S1-NH-CH2-C(=O)-OH] | ![morpholine-S3] | ![indazole-S2] | C16H17N7O3 | 355.3 | 356.0 | <5 |

We claim:

1. A compound represented by formula (I), its isomer, salt and solvate thereof, wherein the isomer is a stereoisomer:

Formula (I)

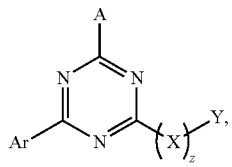

wherein
Y is

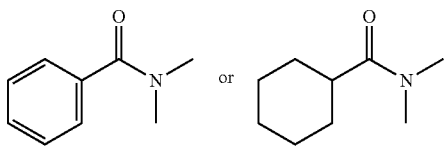

or their isomers;
A is morpholino;
X is NR or O;
Ar is

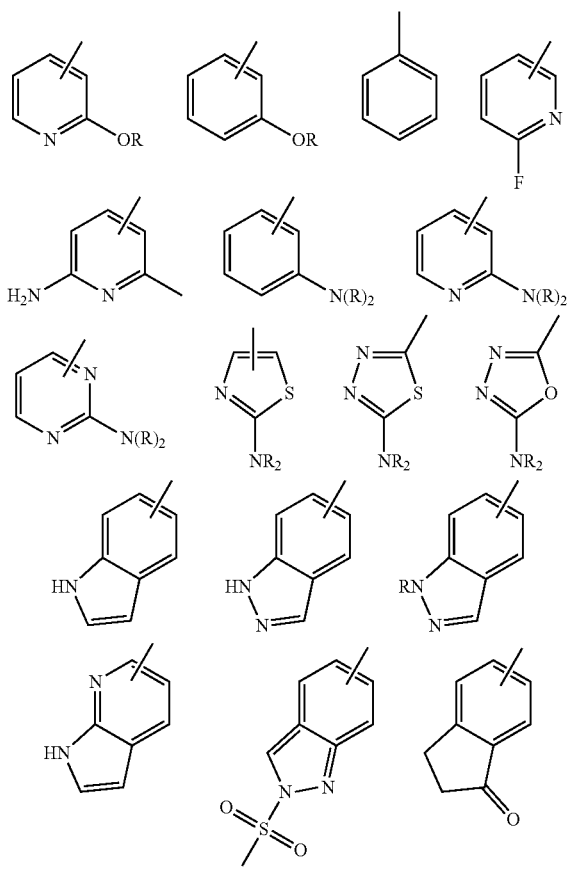

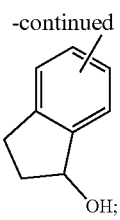

wherein $R^1$ selected from the group consisting of H, $C_1$-$C_6$ straight, branched, cycloalkyl optionally substituted $C_1$-$C_6$ alkyl, halo-$C_1$-$C_6$ alkyl, hydroxyl-$C_1$-$C_6$ alkyl, $C_1$-$C_6$ alkyloxy$C_1$-$C_6$ alkyl, cyano $C_1$-$C_6$ alkyl, amino $C_1$-$C_6$ alkyl, $C_1$-$C_6$ alkylamino $C_1$-$C_6$ alkyl, and di($C_1$-$C_6$ alkyl)amino$C_1$-$C_6$alkyl, optionally substituted $C_1$-$C_8$ heteroalkyl, optionally substituted $C_3$-$C_8$ cycloalkyl, optionally substituted $C_3$-$C_8$ heterocycloalkyl, optionally substituted $C_3$-$C_8$ heterocycloalkenyl, optionally substituted aryl, and optionally substituted heteroaryl, and wherein R is selected from the group consisting of H, F, $OR^1$, CN, $N(R^1)_2$, $COOR^1$, $CON(R^1)_2$, $N(R^1)CON(R^1)_2$, $N(R^1)COR^1$, $N(R^1)SO_2N(R^1)_2$, $SO_2N(R^1)_2$, $SO_2R^1$, $SOR^1$, $SR^1$, $N(R^1)$ $SO_2R^1$; heteroalkyl; optionally substituted monocyclic, bicyclic, fused $C_3$-$C_8$ cycloalkyl, heterocycloalkyl, heterocycloalkenyl; optionally substituted aryl, heteroaryl, arylalkyl;

wherein any two R or $R^1$ when taken together with the atoms to which they are attached may form a cyclic moiety;

wherein each R is independently selected; and
Z is 1.

2. A triazine compound, its isomer, salt and solvate thereof wherein said isomer is a stereoisomer and said compound is selected from the group comprising:

(1) 4-8-{[4-1-(2-11-amino-1,3-thiazol-5-yl)-6-5-{3-oxa-8-azabicyclo[3.2.1]octan-8-yl}-1,3,5-triazin-2-yl]oxy}-N,N-dimethylbenzamide, (2) 4-9-{[4-1-(2-17-amino-1,3-thiazol-5-yl)-6-5-(1,4-oxazepan-4-yl)-1,3,5-triazin-2-yl]oxy}-N,N-dimethylbenzamide, (3) 4-9-{[4-1-(2-22-amino-1,3-thiazol-5-yl)-6-5-(3-25-methylmorpholin-4-yl)-1,3,5-triazin-2-yl]oxy}-N,N-dimethylbenzamide, (4) 4-14-{[4-1-(2-27-amino-1,3-thiazol-5-yl)-6-5-(morpholin-4-yl)-1,3,5-triazin-2-yl]oxy}-N,N-dimethylbenzamide, (5) 5-(4-((1-(methylsulfonyl)piperidin-4-yl)methoxy)-6-morpholino-1,3,5-triazin-2-yl)pyrimidin-2-amine, (6) 2-26-(4-20-{[4-3-(2-15-aminopyrimidin-5-yl)-6-5-(morpholin-4-yl)-1,3,5-triazin-2-yl]oxy}phenyl)-N,N-dimethylacetamide, (7) N-(4-(2-aminothiazol-5-yl)-6-morpholino-1,3,5-triazin-2-yl)thiazol-2-amine, (8) 4-14-{[4-1-(2-17-aminopyrimidin-5-yl)-6-5-(morpholin-4-yl)-1,3,5-triazin-2-yl]oxy}-N,N-dimethylpiperidine-1-carboxamide, (9) 4-14-{[4-1-(5-17-aminopyrazin-2-yl)-6-5-(morpholin-4-yl)-1,3,5-triazin-2-yl]oxy}-N,N-dimethylbenzamide,

(10) 6-20-{[4-1-(6-11-aminopyridin-3-yl)-6-5-(morpholin-4-yl)-1,3,5-triazin-2-yl]oxy}-1,2,3,4-tetrahydroquinolin-2-one,

(11) 4-14-{[4-1-(2-27-aminopyrimidin-5-yl)-6-5-(morpholin-4-yl)-1,3,5-triazin-2-yl]oxy}-N,N-dimethylbenzamide,

(12) 4-9-{[4-1-(6-12-aminopyridin-3-yl)-6-5-{3-oxa-8-azabicyclo[3.2.1]octan-8-yl}-1,3,5-triazin-2-yl]oxy}-N,N-dimethylbenzamide,
(13) 2-26-(3-20-{[4-1-(6-11-aminopyridin-3-yl)-6-5-(morpholin-4-yl)-1,3,5-triazin-2-yl]oxy}phenyl)-N,N-dimethylacetamide,
(14) 4-21-{[4-1-(6-9-aminopyridin-3-yl)-6-5-(1,4-oxazepan-4-yl)-1,3,5-triazin-2-yl]oxy}-N,N-dimethylbenzamide,
(15) 3-20-{[4-1-(6-11-aminopyridin-3-yl)-6-5-(morpholin-4-yl)-1,3,5-triazin-2-yl]oxy}-N,N-dimethylbenzamide,
(16) 4-9-{[4-5-(1H-imidazol-1-yl)-6-1-(1H-indazol-4-yl)-1,3,5-triazin-2-yl]oxy}-N,N-dimethylbenzamide,
(17) 2-20-(4-9-{[4-1-(6-12-aminopyridin-3-yl)-6-5-(morpholin-4-yl)-1,3,5-triazin-2-yl]oxy}phenyl)-N,N-dimethylacetamide,
(18) 4-14-{[4-1-(6-27-amino-5-26-methylpyridin-3-yl)-6-5-(morpholin-4-yl)-1,3,5-triazin-2-yl]oxy}-N,N-dimethylbenzamide,
(19) 4-14-{[4-1-(6-26-hydrazinylpyridin-3-yl)-6-5-(morpholin-4-yl)-1,3,5-triazin-2-yl]oxy}-N,N-dimethylbenzamide,
(20) 4-14-{[4-1-(6-17-amino-2-19-methylpyridin-3-yl)-6-5-(morpholin-4-yl)-1,3,5-triazin-2-yl]oxy}-N,N-dimethylbenzamide,
(21) 4-20-{[4-1-(6-16-aminopyridin-3-yl)-6-5-(morpholin-4-yl)-1,3,5-triazin-2-yl]oxy}-N,N,2-trimethylbenzamide,
(22) 4-14-{[4-1-(6-17-amino-4-15-methylpyridin-3-yl)-6-5-(morpholin-4-yl)-1,3,5-triazin-2-yl]oxy}-N,N-dimethylbenzamide,
(23) 5-(4-((1-(methylsulfonyl)piperidin-4-yl)methoxy)-6-morpholino-1,3,5-triazin-2-yl)pyridin-2-amine,
(24) 4-9-{[4-1-(1H-indazol-4-yl)-6-5-(pyridin-4-yl)-1,3,5-triazin-2-yl]oxy}-N,N-dimethylbenzamide,
(25) 3-21-({[4-3-(6-16-aminopyridin-3-yl)-6-5-(morpholin-4-yl)-1,3,5-triazin-2-yl]oxy}methyl)-N,N-dimethylpyrrolidine-1-carboxamide,
(26) 3-19-{[4-3-(6-16-aminopyridin-3-yl)-6-5-(morpholin-4-yl)-1,3,5-triazin-2-yl]oxy}-N,N-dimethylpyrrolidine-1-carboxamide,
(27) 4-14-{[4-1-(6-17-aminopyridin-3-yl)-6-5-(morpholin-4-yl)-1,3,5-triazin-2-yl]oxy}-N,N-dimethylbenzamide,
(28) 4-20-{[4-1-(6-11-aminopyridin-3-yl)-6-5-(morpholin-4-yl)-1,3,5-triazin-2-yl]oxy}-N,N-dimethylpiperidine-1-carboxamide,
(29) 4-14-{[4-1-(6-17-fluoropyridin-3-yl)-6-5-(morpholin-4-yl)-1,3,5-triazin-2-yl]oxy}-N,N-dimethylbenzamide,
(30) 4-14-{[4-1-(3-21-hydroxyphenyl)-6-5-(morpholin-4-yl)-1,3,5-triazin-2-yl]oxy}-N,N-dimethylbenzamide,
(31) 4-14-{[4-1-(4-17-aminophenyl)-6-5-(morpholin-4-yl)-1,3,5-triazin-2-yl]oxy}-N,N-dimethylbenzamide,
(32) 4-14-{[4-1-(5-26-aminopyridin-3-yl)-6-5-(morpholin-4-yl)-1,3,5-triazin-2-yl]oxy}-N,N-dimethylbenzamide,
(33) N,N-dimethyl-4-14-{[4-5-(morpholin-4-yl)-6-1-(1-30-oxo-1,2-dihydroisoquinolin-5-yl)-1,3,5-triazin-2-yl]oxy}benzamide,
(34) N,N-dimethyl-4-14-{[4-5-(morpholin-4-yl)-6-1-(2-21-oxo-2,3-dihydro-1H-1,3-benzodiazol-4-yl)-1,3,5-triazin-2-yl]oxy}benzamide,
(35) (1r,4r)-4-9-{[4-1-(6-12-aminopyridin-3-yl)-6-5-(morpholin-4-yl)-1,3,5-triazin-2-yl]oxy}-N,N-dimethylcyclohexane-1-carboxamide,
(36) 4-14-{[4-1-(2-26-aminopyridin-4-yl)-6-5-(morpholin-4-yl)-1,3,5-triazin-2-yl]oxy}-N,N-dimethylbenzamide,
(37) 5-(4-(benzylthio)-6-morpholino-1,3,5-triazin-2-yl)pyridin-2-amine,
(38) 4-7-{[4-5-(1H-indazol-4-yl)-6-3-(5-31-oxo-1,4-diazepan-1-yl)-1,3,5-triazin-2-yl]oxy}-N,N-dimethylbenzamide,
(39) 1-27-{4-1-[4-10-(dimethylcarbamoyl)phenoxy]-6-5-(1H-indazol-4-yl)-1,3,5-triazin-2-yl}piperidine-3-carboxamide,
(40) 3-((4-(2-aminopyrimidin-5-yl)-6-morpholino-1,3,5-triazin-2-yl)amino)-N,N-dimethylbenzamide,
(41) N,N-dimethyl-4-8-{[4-5-(morpholin-4-yl)-6-1-{1H-pyrrolo[2,3-b]pyridin-5-yl}-1,3,5-triazin-2-yl]oxy}benzamide,
(42) 5-7-[4-3,6-5-bis(morpholin-4-yl)-1,3,5-triazin-2-yl]-1,3-thiazol-2-amine,
(43) 4-9-{[4-5-(3,4-dihydro-2H-1,4-benzoxazin-4-yl)-6-1-(1H-indazol-4-yl)-1,3,5-triazin-2-yl]oxy}-N,N-dimethylbenzamide,
(44) 4-8-{[4-5-(1H-indazol-4-yl)-6-3-(4-30-oxopiperidin-1-yl)-1,3,5-triazin-2-yl]oxy}-N,N-dimethylbenzamide,
(45) 2-1-methyl-4-5,6-3-bis(morpholin-4-yl)-1,3,5-triazine,
(46) 3-((4-(2-aminopyrimidin-5-yl)-6-morpholino-1,3,5-triazin-2-yl)amino)benzamide,
(47) 1-7-{4-1-[4-11-(dimethylcarbamoyl)phenoxy]-6-5-(1H-indazol-4-yl)-1,3,5-triazin-2-yl}azetidine-3-carboxamide,
(48) N-[(1S,3S)-3-14-{[4-1-(1-27-methanesulfonyl-1H-indazol-4-yl)-6-5-(morpholin-4-yl)-1,3,5-triazin-2-yl]oxy}cyclohexyl]methanesulfonamide,
(49) 4-((4-(6-aminopyridin-3-yl)-6-morpholino-1,3,5-triazin-2-yl)methyl)-N,N-dimethylpiperazine-1-carboxamide,
(50) 4-14-{[4-1-(1H-1,2,3-benzotriazol-4-yl)-6-5-(morpholin-4-yl)-1,3,5-triazin-2-yl]oxy}-N,N-dimethylbenzamide,
(51) 1-6-[4-1-(2-22-aminopyrimidin-5-yl)-6-5-(morpholin-4-yl)-1,3,5-triazin-2-yl]-1,4-diazepan-5-one,
(52) 4-14-{[4-1-(1H-indol-5-yl)-6-5-(morpholin-4-yl)-1,3,5-triazin-2-yl]oxy}-N,N-dimethylbenzamide,
(53) 4-6-[4-1-(2-16-aminopyrimidin-5-yl)-6-5-(morpholin-4-yl)-1,3,5-triazin-2-yl]piperazine-1-sulfonamide,
(54) 7-14-{[4-1-(1H-indazol-4-yl)-6-5-(morpholin-4-yl)-1,3,5-triazin-2-yl]oxy}-1,2,3,4-tetrahydroquinolin-2-one,
(55) 4-8-{[4-5-(1H-indazol-4-yl)-6-3-{2-oxa-6-azaspiro[3.3]heptan-6-yl}-1,3,5-triazin-2-yl]oxy}-N,N-dimethylbenzamide,
(56) 3-((4-(3-carbamoylcyclobutyl)-6-(1H-indazol-4-yl)-1,3,5-triazin-2-yl)amino)-N,N-dimethylbenzamide,
(57) 4-((4-(1H-indazol-4-yl)-6-((tetrahydro-2H-pyran-4-yl)amino)-1,3,5-triazin-2-yl)oxy)-N,N-dimethylbenzamide,
(58) N,N-dimethyl-4-14-{[4-5-(morpholin-4-yl)-6-1-{1H-pyrrolo[2,3-b]pyridin-4-yl}-1,3,5-triazin-2-yl]oxy}benzamide,
(59) 4-7-{[4-5-(1H-indazol-4-yl)-6-3-(3-29-oxopiperazin-1-yl)-1,3,5-triazin-2-yl]oxy}-N,N-dimethylbenzamide,
(60) 3-((4-(6-aminopyridin-3-yl)-6-morpholino-1,3,5-triazin-2-yl)amino)-N,N-dimethylbenzamide,

(61) 4-9-{[4-1-(1H-indazol-4-yl)-6-5-(4-30-methylpiperazin-1-yl)-1,3,5-triazin-2-yl]oxy}-N,N-dimethylbenzamide,
(62) 5-13-[4-3-(4-22-methanesulfonylpiperazin-1-yl)-6-5-(morpholin-4-yl)-1,3,5-triazin-2-yl]pyrimidin-2-amine,
(63) 6-14-{[4-1-(1H-indazol-4-yl)-6-5-(morpholin-4-yl)-1,3,5-triazin-2-yl]oxy}-1,2,3,4-tetrahydroquinolin-2-one,
(64) 4-14-{[4-1-(1H-indol-4-yl)-6-5-(morpholin-4-yl)-1,3,5-triazin-2-yl]oxy}-N,N-dimethylbenzamide,
(65) 4-((4-(6-aminopyridin-3-yl)-6-morpholino-1,3,5-triazin-2-yl)amino)-N,N-dimethylbenzamide,
(66) N-[3-16-(4-1-{[(2S)-1-(4-30-methanesulfonylpiperazin-1-yl)-1-oxopropan-2-yl]amino}-6-2-(morpholin-4-yl)-1,3,5-triazin-2-yl)phenyl]methanesulfonamide,
(67) 4-14-{[4-1-(1H-indazol-4-yl)-6-5-(morpholin-4-yl)-1,3,5-triazin-2-yl]oxy}-N,N-dimethylthiophene-2-carboxamide,
(68) 4-9-{[4-1-(1H-indazol-4-yl)-6-5-{3-oxa-8-azabicyclo[3.2.1]octan-8-yl}-1,3,5-triazin-2-yl]oxy}-N,N-dimethylbenzamide,
(69) 1-{1-7-[4-3-(6-16-aminopyridin-3-yl)-6-5-(morpholin-4-yl)-1,3,5-triazin-2-yl]piperidin-4-yl}-3,3-dimethylurea,
(70) 2-((4-(1-hydroxy-2,3-dihydro-1H-inden-4-yl)-6-morpholino-1,3,5-triazin-2-yl)amino)-N,N-dimethylacetamide,
(71) 1-7-[4-3-(6-16-aminopyridin-3-yl)-6-5-(morpholin-4-yl)-1,3,5-triazin-2-yl]methanol,
(72) 6-14-{[4-1-(1H-indazol-4-yl)-6-5-(morpholin-4-yl)-1,3,5-triazin-2-yl]oxy}-N,N-dimethylpyridine-3-carboxamide,
(73) 4-7-{[4-5-(1H-indazol-4-yl)-6-3-(1,4-oxazepan-4-yl)-1,3,5-triazin-2-yl]oxy}-N,N-dimethylbenzamide,
(74) 2-((4-(6-hydroxypyridin-3-yl)-6-morpholino-1,3,5-triazin-2-yl)amino)-1-(4-(methylsulfonyl)piperazin-1-yl)ethanone,
(75) 4-9-{[4-1-(1H-indazol-4-yl)-6-5-(3-29-methoxyazetidin-1-yl)-1,3,5-triazin-2-yl]oxy}-N,N-dimethylbenzamide,
(76) 2-((4-(3-hydroxyphenyl)-6-morpholino-1,3,5-triazin-2-yl)amino)-1-(4-(methylsulfonyl)piperazin-1-yl)propan-1-one,
(77) 5-13-[4-5-(morpholin-4-yl)-6-3-(piperazin-1-yl)-1,3,5-triazin-2-yl]pyrimidin-2-amine,
(78) 2-((4-morpholino-6-(1-oxo-2,3-dihydro-1H-inden-4-yl)-1,3,5-triazin-2-yl)amino)acetic acid,
(79) 2-((4-(3-methoxyphenyl)-6-morpholino-1,3,5-triazin-2-yl)amino)-1-(4-(methylsulfonyl)piperazin-1-yl)ethanone,
(80) 2-((4-(6-fluoropyridin-3-yl)-6-morpholino-1,3,5-triazin-2-yl)amino)-1-(4-(methylsulfonyl)piperazin-1-yl)ethanone,
(81) 5-13-[4-3,6-5-bis(morpholin-4-yl)-1,3,5-triazin-2-yl]pyrimidin-2-amine,
(82) 2-13-[4-1,6-6-bis(morpholin-4-yl)-1,3,5-triazin-2-yl]-2H-indazol-4-amine,
(83) N-[(1R,3R)-3-14-{[4-1-(1H-indazol-4-yl)-6-5-(morpholin-4-yl)-1,3,5-triazin-2-yl]oxy}cyclopentyl]methanesulfonamide,
(84) 4-morpholino-N-phenyl-6-(1-(tetrahydro-2H-pyran-2-yl)-1H-indazol-4-yl)-1,3,5-triazin-2-amine,
(85) 2-27-(4-14-{[4-1-(1H-indazol-4-yl)-6-5-(morpholin-4-yl)-1,3,5-triazin-2-yl]oxy}phenyl)-N,N-dimethylacetamide,
(86) 5-23-{[4-1-(1H-indazol-4-yl)-6-5-(morpholin-4-yl)-1,3,5-triazin-2-yl]oxy}-2,3-dihydro-1H-1,3-benzodiazol-2-one,
(87) 4-14-{[4-1-(1H-indazol-4-yl)-6-5-(morpholin-4-yl)-1,3,5-triazin-2-yl]oxy}-N,N-dimethylazepane-1-carboxamide,
(88) 3-22-{[4-1-(1H-indazol-4-yl)-6-5-(morpholin-4-yl)-1,3,5-triazin-2-yl]oxy}-N,N-dimethylbenzamide,
(89) 2-((4-(3-hydroxyphenyl)-6-morpholino-1,3,5-triazin-2-yl)amino)-1-(4-(methylsulfonyl)piperazin-1-yl)ethanone,
(90) 2-((4-(3-hydroxyphenyl)-6-morpholino-1,3,5-triazin-2-yl)amino)-3-phenylpropanamide,
(91) 3-22-{[4-1-(1H-indazol-4-yl)-6-5-(morpholin-4-yl)-1,3,5-triazin-2-yl]oxy}-N,N-dimethylpiperidine-1-carboxamide,
(92) N-(4-14-{[4-1-(1H-indazol-4-yl)-6-5-(morpholin-4-yl)-1,3,5-triazin-2-yl]oxy}phenyl)aminosulfonamide,
(93) N-(4-14-{[4-1-(1H-indazol-4-yl)-6-5-(morpholin-4-yl)-1,3,5-triazin-2-yl]oxy}phenyl)methanesulfonamide,
(94) N-[(1r,4r)-4-9-{[4-1-(1H-indazol-4-yl)-6-5-(morpholin-4-yl)-1,3,5-triazin-2-yl]oxy}cyclohexyl]aminosulfonamide,
(95) N-[(1r,4r)-4-9-{[4-1-(1H-indazol-4-yl)-6-5-(morpholin-4-yl)-1,3,5-triazin-2-yl]oxy}cyclohexyl]methanesulfonamide,
(96) 4-(4-(1H-indazol-4-yl)-6-((1-(methylsulfonyl)piperidin-4-yl)methoxy)-1,3,5-triazin-2-yl)morpholine,
(97) 4-9-{[4-5-(3-28,5-32-dimethylmorpholin-4-yl)-6-1-(1H-indazol-4-yl)-1,3,5-triazin-2-yl]oxy}-N,N-dimethylbenzamide,
(98) 4-9-{[4-1-(1H-indazol-4-yl)-6-5-(3-28-methylmorpholin-4-yl)-1,3,5-triazin-2-yl]oxy}-N,N-dimethylbenzamide,
(99) (2R,4S)-4-14-{[4-1-(1H-indazol-4-yl)-6-5-(morpholin-4-yl)-1,3,5-triazin-2-yl]oxy}-N,N,1-trimethylpyrrolidine-2-carboxamide,
(100) N-(4-14-{[4-1-(1H-indazol-4-yl)-6-5-(morpholin-4-yl)-1,3,5-triazin-2-yl]oxy}phenyl)-N'-methylethanediamide,
(101) N-(4-14-{[4-1-(1H-indazol-4-yl)-6-5-(morpholin-4-yl)-1,3,5-triazin-2-yl]oxy}phenyl)-N',N'-dimethylethanediamide,
(102) 4-7-{4-3-[(1-25-methanesulfonylpiperidin-4-yl)oxy]-6-5-(morpholin-4-yl)-1,3,5-triazin-2-yl}-1H-indazole,
(103) (2R,4S)-4-14-{[4-1-(1H-indazol-4-yl)-6-5-(morpholin-4-yl)-1,3,5-triazin-2-yl]oxy}-N,N-dimethylpyrrolidine-2-carboxamide,
(104) 3-((4-(6-aminopyridin-3-yl)-6-morpholino-1,3,5-triazin-2-yl)amino)-N,N-dimethylpropanamide,
(105) 5-12-[4-5-(morpholin-4-yl)-6-3-(piperazin-1-yl)-1,3,5-triazin-2-yl]pyridin-2-ol,
(106) 1-(4-14-{[4-1-(1H-indazol-4-yl)-6-5-(morpholin-4-yl)-1,3,5-triazin-2-yl]oxy}phenyl)-3,3-dimethylurea,
(107) N-(4-14-{[4-1-(1H-indazol-4-yl)-6-5-(morpholin-4-yl)-1,3,5-triazin-2-yl]oxy}phenyl)-2-30-methylpropanamide,
(108) 3-14-{[4-1-(1H-indazol-4-yl)-6-5-(morpholin-4-yl)-1,3,5-triazin-2-yl]oxy}-N,N-dimethylpyrrolidine-1-carboxamide,
(109) 3-22-({[4-1-(1H-indazol-4-yl)-6-5-(morpholin-4-yl)-1,3,5-triazin-2-yl]oxy}methyl)-N,N-dimethylpyrrolidine-1-carboxamide, (110) 4-23-({[4-1-(1H-indazol-4-yl)-6-5-(morpholin-4-yl)-1,3,5-triazin-2-yl]oxy}methyl)-N,N-dimethylbenzamide,
(111) 3-((4-(1H-indazol-4-yl)-6-(3-oxopiperazin-1-yl)-1,3,5-triazin-2-yl)amino)-N,N-dimethylbenzamide,
(112) 2-8-[4-1,6-5-bis(morpholin-4-yl)-1,3,5-triazin-2-yl]-2H-indazole,
(113) 4-14-{[4-1-(1H-indazol-4-yl)-6-5-(morpholin-4-yl)-1,3,5-triazin-2-yl]oxy}-N-methylbenzamide,
(114) 4-14-{[4-1-(1H-indazol-4-yl)-6-5-(morpholin-4-yl)-1,3,5-triazin-2-yl]oxy}-N,N-dimethylbenzamide,
(115) 4-(4-((1-benzylpiperidin-4-yl)oxy)-6-(1H-indazol-4-yl)-1,3,5-triazin-2-yl)morpholine,
(116) tert-butyl 4-(3-((4-(1H-indazol-4-yl)-6-morpholino-1,3,5-triazin-2-yl)amino)benzamido)piperidine-1-carboxylate,
(117) 1-(3-((4-(1H-indazol-4-yl)-6-morpholino-1,3,5-triazin-2-yl)amino)benzoyl)-1,4-diazepan-5-one,
(118) 2-((4-(3-hydroxyphenyl)-6-morpholino-1,3,5-triazin-2-yl)amino)-3-phenylpropanoic acid,
(119) 1-(4-((4-(1H-indazol-4-yl)-6-morpholino-1,3,5-triazin-2-yl)oxy)phenyl)-N,N-dimethylmethanamine,
(120) 2-((4-(4-aminophenyl)-6-morpholino-1,3,5-triazin-2-yl)amino)-1-(4-(methylsulfonyl)piperazin-1-yl)ethanone,
(121) 2-9-{N-[4-1-(3-14-acetamidophenyl)-6-5-(morpholin-4-yl)-1,3,5-triazin-2-yl]acetamido}acetic acid,
(122) 3-12-(4-O-{[(dimethylcarbamoyl)methyl]amino}-6-4-(morpholin-4-yl)-1,3,5-triazin-2-yl)benzamide,
(123) N-[(4E)-1-8-[4-1-(1-21-{4-24-[(4E)-4-37-(hydroxyimino)azepan-1-yl]-6-26-(morpholin-4-yl)-1,3,5-triazin-2-yl}-1H-indazol-4-yl)-6-5-(morpholin-4-yl)-1,3,5-triazin-2-yl]azepan-4-ylidene]hydroxylamine,
(124) N-methyl-N'-[(1r,4r)-4-9-{[4-1-(1H-indazol-4-yl)-6-5-(morpholin-4-yl)-1,3,5-triazin-2-yl]oxy}cyclohexyl]ethanediamide,
(125) N,N-dimethyl-N'-[(1r,4r)-4-9-{[4-1-(1H-indazol-4-yl)-6-5-(morpholin-4-yl)-1,3,5-triazin-2-yl]oxy}cyclohexyl]ethanediamide,
(126) 4-14-{[4-1-(1H-indazol-4-yl)-6-5-(morpholin-4-yl)-1,3,5-triazin-2-yl]oxy}-N,N-dimethylpiperidine-1-carboxamide,
(127) 2-1-(6-16-fluoropyridin-3-yl)-4-5-(morpholin-4-yl)-6-3-(piperazin-1-yl)-1,3,5-triazine,
(128) 4-4-(3-13-methoxyphenyl)-6-0-(morpholin-4-yl)-1,3,5-triazin-2-amine,
(129) 3-((4-(1H-indazol-4-yl)-6-morpholino-1,3,5-triazin-2-yl)amino)-N-(pyridin-2-yl)benzamide,
(130) (3-((4-(1H-indazol-4-yl)-6-morpholino-1,3,5-triazin-2-yl)amino)phenyl)(4-(methylsulfonyl)piperazin-1-yl)methanone,
(131) 3-22-{[4-1-(1H-indazol-4-yl)-6-5-(morpholin-4-yl)-1,3,5-triazin-2-yl]oxy}benzonitrile,
(132) 3-((4-(1H-indazol-4-yl)-6-morpholino-1,3,5-triazin-2-yl)amino)-N,N-dimethylthiophene-2-carboxamide,
(133) (1R,3R)-3-14-{[4-1-(1H-indazol-4-yl)-6-5-(morpholin-4-yl)-1,3,5-triazin-2-yl]oxy}-N,N-dimethylcyclohexane-1-carboxamide,
(134) 5-18-[4-5-(morpholin-4-yl)-6-3-(piperazin-1-yl)-1,3,5-triazin-2-yl]pyridin-2-amine,
(135) 3-6-{4-1-[(carbamoylmethyl)amino]-6-2-(morpholin-4-yl)-1,3,5-triazin-2-yl}benzamide,
(136) 2-((4-(3-hydroxyphenyl)-6-morpholino-1,3,5-triazin-2-yl)amino)-4-(methylthio)butanoic acid,
(137) 2-((4-(3-(difluoromethyl)phenyl)-6-morpholino-1,3,5-triazin-2-yl)amino)-N,N-dimethylacetamide,
(138) 2-((4-(3-(methylsulfonamido)phenyl)-6-morpholino-1,3,5-triazin-2-yl)amino)propanoic acid,
(139) 3-8-[4-3-amino-6-5-(morpholin-4-yl)-1,3,5-triazin-2-yl]phenol,
(140) (3-((4-(1H-indazol-4-yl)-6-morpholino-1,3,5-triazin-2-yl)amino)phenyl)(4-methoxypiperidin-1-yl)methanone,
(141) 2-((4-(3-cyanophenyl)-6-morpholino-1,3,5-triazin-2-yl)amino)-N,N-dimethylacetamide,
(142) (1r,4r)-4-21-{[4-1-(1H-indazol-4-yl)-6-5-(morpholin-4-yl)-1,3,5-triazin-2-yl]oxy}-N-methylcyclohexane-1-carboxamide,
(143) (1s,4s)-4-21-{[4-1-(1H-indazol-4-yl)-6-5-(morpholin-4-yl)-1,3,5-triazin-2-yl]oxy}-N,N-dimethylcyclohexane-1-carboxamide,
(144) (1r,4r)-4-21-{[4-1-(1H-indazol-4-yl)-6-5-(morpholin-4-yl)-1,3,5-triazin-2-yl]oxy}-N,N-dimethylcyclohexane-1-carboxamide,
(145) 2-((4-(6-hydroxypyridin-3-yl)-6-morpholino-1,3,5-triazin-2-yl)amino)-N,N-dimethylacetamide,
(146) 2-((4-(3-(methylsulfonamido)phenyl)-6-morpholino-1,3,5-triazin-2-yl)amino)acetic acid,
(147) 1-(1-14-{[4-1-(1H-indazol-4-yl)-6-5-(morpholin-4-yl)-1,3,5-triazin-2-yl]oxy}-2-15-methylpropan-2-yl)-3,3-dimethylurea,
(148) 3-((4-(1H-indol-4-yl)-6-morpholino-1,3,5-triazin-2-yl)amino)benzamide
(149) 4-7-{4-3-[(1-25-ethylpiperidin-4-yl)oxy}-6-5-(morpholin-4-yl)-1,3,5-triazin-2-yl]-1H-indazole,
(150) 2-((4-(5-hydroxypyridin-3-yl)-6-morpholino-1,3,5-triazin-2-yl)amino)-N,N-dimethylacetamide,
(151) 4-7-[4-5-(morpholin-4-yl)-6-3-(piperidin-4-yloxy)-1,3,5-triazin-2-yl]-1H-indazole,
(152) (1r,4r)-4-9-{[4-1-(1H-indazol-4-yl)-6-5-(morpholin-4-yl)-1,3,5-triazin-2-yl]oxy}cyclohexan-1-amine,
(153) 1-((4-(3-hydroxyphenyl)-6-morpholino-1,3,5-triazin-2-yl)amino)cyclopentanecarboxylic acid,
(154) 1-(3-((4-(1H-indazol-4-yl)-6-morpholino-1,3,5-triazin-2-yl)amino)benzoyl)azetidine-3-carboxamide,
(155) 3-6-{4-34(1-hydroxy-2-methylpropan-2-yl)amino]-6-5-(morpholin-4-yl)-1,3,5-triazin-2-yl}phenol,
(156) 2-((4-(2-fluoro-5-methoxyphenyl)-6-morpholino-1,3,5-triazin-2-yl)amino)acetic acid,
(157) 3-((4-(1H-indazol-4-yl)-6-morpholino-1,3,5-triazin-2-yl)amino)-N-(piperidin-4-yl)benzamide,
(158) 3-((4-(1H-indazol-4-yl)-6-morpholino-1,3,5-triazin-2-yl)amino)thiophene-2-carboxamide,
(159) 5-13-[4-0,6-8-bis(morpholin-4-yl)-1,3,5-triazin-2-yl]pyridin-2-amine,
(160) 3-6-[4-1,6-2-bis(morpholin-4-yl)-1,3,5-triazin-2-yl]phenol,
(161) 3-6-{4-1-[(carboxymethyl)amino]-6-2-(morpholin-4-yl)-1,3,5-triazin-2-yl}benzoic acid,
(162) 4-0-(morpholin-4-yl)-6-4-phenyl-1,3,5-triazin-2-amine,
(163) 4-(3-((4-(1H-indazol-4-yl)-6-morpholino-1,3,5-triazin-2-yl)amino)benzoyl)piperazin-2-one,
(164) (3-((4-(1H-indazol-4-yl)-6-morpholino-1,3,5-triazin-2-yl)amino)phenyl)(3-methoxyazetidin-1-yl)methanone,
(165) 2-((4-(6-aminopyridin-3-yl)-6-morpholino-1,3,5-triazin-2-yl)amino)-N,N-dimethylpropanamide,
(166) 4-(4-(benzylthio)-6-(1H-indazol-4-yl)-1,3,5-triazin-2-yl)morpholine,
(167) 2-((4-(3-hydroxyphenyl)-6-morpholino-1,3,5-triazin-2-yl)amino)-N,N-dimethylacetamide, (168) 2-((4-(3-hydroxyphenyl)-6-morpholino-1,3,5-triazin-2-yl)amino)-N-methylacetamide,
(169) 2-((4-morpholino-6-(3-nitrophenyl)-1,3,5-triazin-2-yl)amino)acetic acid,
(170) 2-((4-(6-aminopyridin-3-yl)-6-morpholino-1,3,5-triazin-2-yl)amino)-N,N-dimethylacetamide,
(171) (3-((4-(1H-indazol-4-yl)-6-morpholino-1,3,5-triazin-2-yl)amino)phenyl)(piperazin-1-yl)methanone,
(172) (3-((4-(1H-indazol-4-yl)-6-morpholino-1,3,5-triazin-2-yl)amino)phenyl)(4-methylpiperazin-1-yl)methanone,
(173) (3-((4-(1H-indazol-4-yl)-6-morpholino-1,3,5-triazin-2-yl)amino)phenyl)(morpholino)methanone,
(174) N-(4-23-ethoxyphenyl)-1-12-[4-1-(1H-indazol-4-yl)-6-5-(morpholin-4-yl)-1,3,5-triazin-2-yl]pyrrolidine-3-carboxamide,
(175) 2-((4-(3-hydroxyphenyl)-6-morpholino-1,3,5-triazin-2-yl)amino)-3-methylbutanoic acid,
(176) 2-((4-(6-hydroxypyridin-3-yl)-6-morpholino-1,3,5-triazin-2-yl)amino)acetic acid,
(177) 3-((4-(1H-indazol-4-yl)-6-morpholino-1,3,5-triazin-2-yl)amino)-N,4-dimethylbenzamide,
(178) 3-((4-(1H-indazol-4-yl)-6-morpholino-1,3,5-triazin-2-yl)amino)-N,N,4-trimethylbenzamide,
(179) 2-((4-(6-fluoropyridin-3-yl)-6-morpholino-1,3,5-triazin-2-yl)amino)acetic acid,
(180) 4-((4-(1H-indazol-4-yl)-6-morpholino-1,3,5-triazin-2-yl)methyl)-N,N-dimethylpiperazine-1-carboxamide,
(181) 2-((4-(3-hydroxyphenyl)-6-morpholino-1,3,5-triazin-2-yl)amino)acetamide,
(182) 1-8-[4-1-(1H-indazol-4-yl)-6-5-(morpholin-4-yl)-1,3,5-triazin-2-yl]-1H-pyrrole-2-carboxamide,
(183) 2-((4-(3-methoxyphenyl)-6-morpholino-1,3,5-triazin-2-yl)amino)acetic acid,
(184) 2-((4-(3-(hydroxyamino)phenyl)-6-morpholino-1,3,5-triazin-2-yl)amino)acetic acid,
(185) 2-((4-(4-aminophenyl)-6-morpholino-1,3,5-triazin-2-yl)amino)-N,N-dimethylacetamide,
(186) 3-((4-(1H-indazol-4-yl)-6-morpholino-1,3,5-triazin-2-yl)amino)-2-methylbenzamide,
(187) 2-((4-(3-hydroxyphenyl)-6-morpholino-1,3,5-triazin-2-yl)amino)propanoic acid,
(188) 2-((4-(3-hydroxyphenyl)-6-morpholino-1,3,5-triazin-2-yl)amino)-2-methylpropanoic acid,
(189) 3-((4-(1H-indazol-4-yl)-6-morpholino-1,3,5-triazin-2-yl)amino)-N-methylbenzamide,
(190) 3-((4-(1H-indazol-4-yl)-6-morpholino-1,3,5-triazin-2-yl)amino)-N,N-dimethylbenzamide,
(191) 3-((4-(1H-indazol-4-yl)-6-morpholino-1,3,5-triazin-2-yl)amino)-1-(4-(methylsulfonyl)piperazin-1-yl)propan-1-one,
(192) 2-((4-(3-hydroxyphenyl)-6-morpholino-1,3,5-triazin-2-yl)(methyl)amino)acetic acid,
(193) 2-((4-(3-hydroxyphenyl)-6-morpholino-1,3,5-triazin-2-yl)amino)acetic acid,
(194) 2-(2-((4-(1H-indazol-4-yl)-6-morpholino-1,3,5-triazin-2-yl)amino)phenyl)acetamide,
(195) 2-(3-((4-(1H-indazol-4-yl)-6-morpholino-1,3,5-triazin-2-yl)amino)phenyl)acetamide,
(196) 5-8-[4-1-(1H-indazol-4-yl)-6-5-(morpholin-4-yl)-1,3,5-triazin-2-yl]-octahydro-1H-pyrrolo[3,4-c]pyridin-1-one,
(197) methyl 2-((4-(3-aminophenyl)-6-morpholino-1,3,5-triazin-2-yl)amino)acetate,
(198) 2-((4-(1H-indazol-4-yl)-6-morpholino-1,3,5-triazin-2-yl)amino)benzamide,
(199) 2-((4-(3-aminophenyl)-6-morpholino-1,3,5-triazin-2-yl)amino)acetic acid,
(200) 3-((4-(1H-indazol-4-yl)-6-morpholino-1,3,5-triazin-2-yl)(methyl)amino)benzamide,
(201) 3-((4-(1H-indazol-4-yl)-6-morpholino-1,3,5-triazin-2-yl)amino)benzamide,
(202) 3-((4-(1H-indazol-4-yl)-6-morpholino-1,3,5-triazin-2-yl)amino)benzoic acid,
(203) 2-((4-morpholino-6-phenyl-1,3,5-triazin-2-yl)amino)acetic acid,
(204) 4-((4-(1H-indazol-4-yl)-6-morpholino-1,3,5-triazin-2-yl)amino)-N,N-dimethylbenz amide,
(205) N-(4-(1H-indazol-4-yl)-6-morpholino-1,3,5-triazin-2-yl)-1H-indazol-4-amine,
(206) 1-21-[4-1-(1H-indazol-4-yl)-6-5-(morpholin-4-yl)-1,3,5-triazin-2-yl]-1,4-diazepan-5-one,
(207) methyl 1-12-[4-1-(1H-indazol-4-yl)-6-5-(morpholin-4-yl)-1,3,5-triazin-2-yl]pyrrolidine-3-carboxylate,
(208) N-{1-8-[4-1-(1H-indazol-4-yl)-6-5-(morpholin-4-yl)-1,3,5-triazin-2-yl]piperidin-4-ylidene}hydroxylamine,
(209) 2-((4-(1H-indazol-4-yl)-6-morpholino-1,3,5-triazin-2-yl)amino)-N,N-dimethyl-3-phenylpropanamide,
(210) 2-((4-(1H-indazol-4-yl)-6-morpholino-1,3,5-triazin-2-yl)amino)-N,N-dimethyl-4-(methylsulfonyl)butanamide,
(211) 4-7-[4-3-(4-16-methanesulfonylpiperazin-1-yl)-6-5-(morpholin-4-yl)-1,3,5-triazin-2-yl]-1H-indazole,
(212) 4-1-(1H-indazol-4-yl)-6-5-(morpholin-4-yl)-1,3,5-triazin-2-ol,
(213) 4-12-[4-3-(1,4-diazepan-1-yl)-6-5-(morpholin-4-yl)-1,3,5-triazin-2-yl]-1H-indazole,
(214) (1 r,4r)-4-((4-(1H-indazol-4-yl)-6-morpholino-1,3,5-triazin-2-yl)amino)-N,N-dimethylcyclohexanecarboxamide,
(215) 4-((4-(1H-indazol-4-yl)-6-morpholino-1,3,5-triazin-2-yl)amino)-N-methylcyclohexanecarboxamide,
(216) 4-((4-(1H-indazol-4-yl)-6-morpholino-1,3,5-triazin-2-yl)amino)-N,N-dimethylcyclohexanecarboxamide,
(217) (2R)-1-7-[4-1-(1H-indazol-4-yl)-6-5-(morpholin-4-yl)-1,3,5-triazin-2-yl]-N,N-dimethylpyrrolidine-2-carboxamide,
(218) 4-7-[4-1-(1H-indazol-4-yl)-6-5-(morpholin-4-yl)-1,3,5-triazin-2-yl]-N-methylpiperazine-1-carboxamide,
(219) 4-(1H-indazol-4-yl)-6-morpholino-N-phenyl-1,3,5-triazin-2-amine
(220) 1-8-[4-1-(1H-indazol-4-yl)-6-5-(morpholin-4-yl)-1,3,5-triazin-2-yl]piperidin-4-ol,
(221) 1-8-[4-1-(1H-indazol-4-yl)-6-5-(morpholin-4-yl)-1,3,5-triazin-2-yl]piperidin-4-one,
(222) 1-8-[4-1-(1H-indazol-4-yl)-6-5-(morpholin-4-yl)-1,3,5-triazin-2-yl]piperidin-4-amine,
(223) 3-((4-(1H-indazol-4-yl)-6-morpholino-1,3,5-triazin-2-yl)amino)-N,N-dimethylpropanamide,
(224) 4-12-[4-3-(1H-indazol-4-yl)-6-5-(morpholin-4-yl)-1,3,5-triazin-2-yl]-1H-indazole,
(225) 4-(1H-indazol-4-yl)-6-morpholino-N-(tetrahydro-2H-pyran-4-yl)-1,3,5-triazin-2-amine,
(226) 4-7-[4-3-methyl-6-5-(morpholin-4-yl)-1,3,5-triazin-2-yl]-1H-indazole,
(227) 3-((4-(1H-indazol-4-yl)-6-morpholino-1,3,5-triazin-2-yl)amino)propanoic acid,
(228) 4-18-[4-3-(4-15-methylpiperazin-1-yl)-6-5-(morpholin-4-yl)-1,3,5-triazin-2-yl]-1H-indazole, (229) 4-17-[4-5-(morpholin-4-yl)-6-3-(piperazin-1-yl)-1,3,5-triazin-2-yl]-1H-indazole,
(230) 4-7-[4-1-(1H-indazol-4-yl)-6-5-(morpholin-4-yl)-1,3,5-triazin-2-yl]piperazin-2-one,
(231) 4-2-(1H-indazol-4-yl)-6-0-(morpholin-4-yl)-1,3,5-triazin-2-amine,
(232) 2-((4-(1H-indazol-4-yl)-6-morpholino-1,3,5-triazin-2-yl)amino)-2-methylpropan-1-ol,
(233) 4-8-[4-3,6-5-bis(morpholin-4-yl)-1,3,5-triazin-2-yl]-1H-indazole,
(234) 2-((4-(1H-indazol-4-yl)-6-morpholino-1,3,5-triazin-2-yl)amino)propanamide,
(235) 2-((4-(1H-indazol-4-yl)-6-morpholino-1,3,5-triazin-2-yl)amino)-2-methylpropanoic acid,
(236) 2-((4-(1H-indazol-4-yl)-6-morpholino-1,3,5-triazin-2-yl)amino)acetic acid,
(237) (S)-4-((4-(2-aminothiazol-5-yl)-6-(3-methylmorpholino)-1,3,5-triazin-2-yl)oxy)-N,N-dimethylbenzamide,
(238) 4-((4-(2-aminothiazol-5-yl)-6-morpholino-1,3,5-triazin-2-yl)oxy)benzamide,
(239) 4-((4-(2-aminothiazol-5-yl)-6-morpholino-1,3,5-triazin-2-yl)oxy)-N-methylbenzamide,
(240) 3-((4-(2-aminothiazol-5-yl)-6-morpholino-1,3,5-triazin-2-yl)oxy)-N,N-dimethylbenzamide,
(241) 4-((4-(2-aminothiazol-4-yl)-6-morpholino-1,3,5-triazin-2-yl)oxy)-N,N-dimethylbenzamide,
(242) 4-((4-(5-amino-1,3,4-thiadiazol-2-yl)-6-morpholino-1,3,5-triazin-2-yl)oxy)-N,N-dimethylbenzamide,
(243) 4-((4-(2-aminooxazol-5-yl)-6-morpholino-1,3,5-triazin-2-yl)oxy)-N,N-dimethylbenzamide,
(244) 4-((4-(2-amino-1H-imidazol-5-yl)-6-morpholino-1,3,5-triazin-2-yl)oxy)-N,N-dimethylbenzamide,
(245) N,N-dimethyl-4-((4-(2-(methylamino)thiazol-5-yl)-6-morpholino-1,3,5-triazin-2-yl)oxy)benzamide,
(246) 4-((4-(2-aminothiazol-5-yl)-6-morpholino-1,3,5-triazin-2-yl)amino)-N,N-dimethylbenzamide,
(247) 3-((4-(2-aminothiazol-5-yl)-6-morpholino-1,3,5-triazin-2-yl)amino)-N,N-dimethylbenzamide,
(248) 4-((4-(2-aminothiazol-5-yl)-6-morpholino-1,3,5-triazin-2-yl)oxy)-3-fluoro-N,N-dimethylbenzamide,
(249) 4-((4-(2-aminothiazol-5-yl)-6-(1,4-oxazepan-4-yl)-1,3,5-triazin-2-yl)oxy)-N,N-dimethylbenzamide,
(250) (R)-2-(4-((4-(2-aminothiazol-5-yl)-6-morpholino-1,3,5-triazin-2-yl)oxy)phenyl)-N,N-dimethylpropanamide,
(251) 4-((4-(2-amino-4-methylthiazol-5-yl)-6-morpholino-1,3,5-triazin-2-yl)oxy)-N,N-dimethylbenzamide,
(252) 5-(4-((2-(methylsulfonyl)-1,2,3,4-tetrahydroisoquinolin-5-yl)oxy)-6-morpholino-1,3,5-triazin-2-yl)thiazol-2-amine,
(253) 4-((4-(2-aminothiazol-5-yl)-6-morpholino-1,3,5-triazin-2-yl)oxy)-N,N-dimethylpiperidine-1-carboxamide,
(254) 5-(4-((1-(methylsulfonyl)piperidin-4-yl)methoxy)-6-morpholino-1,3,5-triazin-2-yl)thiazol-2-amine,
(255) 5-(4-(1-(1-(methylsulfonyl)piperidin-4-yl)ethoxy)-6-morpholino-1,3,5-triazin-2-yl)thiazol-2-amine,
(256) (1 s,4s)-4-((4-(2-aminothiazol-5-yl)-6-morpholino-1,3,5-triazin-2-yl)oxy)-N,N-dimethylcyclohexanecarboxamide,
(257) 5-(4-((1-(methylsulfonyl)pyrrolidin-3-yl)methoxy)-6-morpholino-1,3,5-triazin-2-yl)thiazol-2-amine,
(258) 5-(4-(((1-(methylsulfonyl)piperidin-3-yl)oxy)methyl)-6-morpholino-1,3,5-triazin-2-yl)thiazol-2-amine,
(259) 5-(4-(((1-(methylsulfonyl)piperidin-4-yl)oxy)methyl)-6-morpholino-1,3,5-triazin-2-yl)thiazol-2-amine,
(260) 5-(4-morpholino-6-(piperazin-1-yl)-1,3,5-triazin-2-yl)thiazol-2-amine,
(261) 5-(4-morpholino-6-(1,4-oxazepan-4-yl)-1,3,5-triazin-2-yl)thiazol-2-amine,
(262) 5-(4-morpholino-6-(piperazin-1-yl)-1,3,5-triazin-2-yl)-4-(trifluoromethyl)pyridin-2-amine,
(263) 4-(4-(6-amino-4-(trifluoromethyl)pyridin-3-yl)-6-morpholino-1,3,5-triazin-2-yl)piperazine-1-sulfonamide,
(264) 5-(4-(4-(methylsulfonyl)piperazin-1-yl)-6-morpholino-1,3,5-triazin-2-yl)-4-(trifluoromethyl)pyridin-2-amine,
(265) 5-(4-(4-methylpiperazin-1-yl)-6-morpholino-1,3,5-triazin-2-yl)-4-(trifluoromethyl)pyridin-2-amine,
(266) 5-(4,6-dimorpholino-1,3,5-triazin-2-yl)-4-(trifluoromethyl)pyridin-2-amine, and
(267) 5-(4-(4-methylpiperazin-1-yl)-6-morpholino-1,3,5-triazin-2-yl)pyrimidin-2-amine.

3. A triazine compound, its isomer, salt and solvate thereof, wherein said isomer is a stereoisomer and said compound is selected from the group comprising:

(1) 4-9-{[4-1-(2-22-amino-1,3-thiazol-5-yl)-6-5-(3-25-methylmorpholin-4-yl)-1,3,5-triazin-2-yl]oxy}-N,N-dimethylbenzamide,
(2) 2-26-(4-20-{[4-3-(2-15-aminopyrimidin-5-yl)-6-5-(morpholin-4-yl)-1,3,5-triazin-2-yl]oxy}phenyl)-N,N-dimethylacetamide,
(3) 5-(4-((1-(methylsulfonyl)piperidin-4-yl)methoxy)-6-morpholino-1,3,5-triazin-2-yl)pyridin-2-amine,
(4) 4-14-{[4-1-(2-27-amino-1,3-thiazol-5-yl)-6-5-(morpholin-4-yl)-1,3,5-triazin-2-yl]oxy}-N,N-dimethylbenzamide,
(5) 4-14-{[4-1-(1H-indol-5-yl)-6-5-(morpholin-4-yl)-1,3,5-triazin-2-yl]oxy}-N,N-dimethylbenzamide,
(6) N,N-dimethyl-4-8-{[4-5-(morpholin-4-yl)-6-1-{1H-pyrrolo [2,3-b]pyridin-5-yl}-1,3,5-triazin-2-yl]oxy}benzamide,
(7) 4-14-{[4-1-(6-17-aminopyridin-3-yl)-6-5-(morpholin-4-yl)-1,3,5-triazin-2-yl]oxy}-N,N-dimethylbenzamide
(8) (1r,4r)-4-21-{[4-1-(1H-indazol-4-yl)-6-5-(morpholin-4-yl)-1,3,5-triazin-2-yl]oxy}-N,N-dimethylcyclohexane-1-carboxamide
(9) 4-14-{[4-1-(1H-indazol-4-yl)-6-5-(morpholin-4-yl)-1,3,5-triazin-2-yl]oxy}-N,N-dimethylpiperidine-1-carboxamide
(10) 4-14-{[4-1-(2-27-aminopyrimidin-5-yl)-6-5-(morpholin-4-yl)-1,3,5-triazin-2-yl]oxy}-N,N-dimethylbenzamide
(11) 1-6-[4-1-(2-22-aminopyrimidin-5-yl)-6-5-(morpholin-4-yl)-1,3,5-triazin-2-yl]-1,4-diazepan-5-one,
(12) 4-14-{[4-1-(1H-indazol-4-yl)-6-5-(morpholin-4-yl)-1,3,5-triazin-2-yl]oxy}-N,N-dimethylbenzamide,
(13) 3-((4-(2-aminopyrimidin-5-yl)-6-morpholino-1,3,5-triazin-2-yl)amino)benzamide, or
(14) 3-((4-(6-aminopyridin-3-yl)-6-morpholino-1,3,5-triazin-2-yl)amino)-N,N-dimethylbenzamide.

* * * * *